(12) United States Patent
Gouverneur et al.

(10) Patent No.: US 12,071,390 B2
(45) Date of Patent: *Aug. 27, 2024

(54) FLUORINATION PROCESSES

(71) Applicant: Oxford University Innovation Limited, Oxford (GB)

(72) Inventors: Veronique Gouverneur, Oxford (GB); Gabriele Pupo, Oxford (GB); Duncan Browne, Biggleswade (GB); Jamie Leitch, Wallingford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/201,571

(22) Filed: May 24, 2023

(65) Prior Publication Data

US 2023/0339829 A1 Oct. 26, 2023

Related U.S. Application Data

(63) Continuation of application No. PCT/GB2022/053347, filed on Dec. 21, 2022.

(30) Foreign Application Priority Data

Dec. 22, 2021 (GB) .................................. 2118767

(51) Int. Cl.
 *C07C 17/20* (2006.01)
 *C01B 9/08* (2006.01)
(52) U.S. Cl.
 CPC .............. *C07C 17/208* (2013.01); *C01B 9/08* (2013.01); *C01P 2002/72* (2013.01); *C01P 2006/80* (2013.01)

(58) Field of Classification Search
 CPC .................................................. C07C 17/208
 See application file for complete search history.

(56) References Cited

U.S. PATENT DOCUMENTS

| 1,865,204 | A | 6/1932 | Michael et al. |
| 2,148,514 | A | 2/1939 | Swinehart |
| 2,163,232 | A | 6/1939 | Baldeschwieler |
| 2,643,226 | A | 6/1953 | White |
| 2,690,430 | A | 9/1954 | Anderson |
| 2,810,629 | A | 10/1957 | Leonard |
| 2,877,095 | A | 3/1959 | Anderson |

(Continued)

FOREIGN PATENT DOCUMENTS

| GB | 390191 A | | 3/1933 |
| GB | 1039247 | * | 8/1966 |
| WO | WO-2023118867 A1 | | 6/2023 |

OTHER PUBLICATIONS

Scholz et al., Nanocrystalline CaF2 particles obtained by high-energy ball milling, (Journal of Solid State Chemistry 179 (2006) 1119-1128.*

(Continued)

*Primary Examiner* — Jafar F Parsa
(74) *Attorney, Agent, or Firm* — Wilson Sonsini Goodrich & Rosati

(57) ABSTRACT

A process for preparing a fluorinating reagent from a calcium-containing compound is disclosed. The process bypasses the requirement to form hydrofluoric acid. The fluorinating reagent can be used to prepare high-value fluorochemicals.

20 Claims, 96 Drawing Sheets

(56) References Cited

U.S. PATENT DOCUMENTS

| | | | |
|---|---|---|---|
| 3,027,304 | A | 3/1962 | Robertson |
| 3,428,422 | A | 2/1969 | Wiesboeck |
| 3,634,034 | A | 1/1972 | Nickerson et al. |
| 4,087,475 | A | 5/1978 | Jordan |
| 4,157,377 | A | 6/1979 | Evans et al. |
| 4,174,349 | A | 11/1979 | Evans et al. |
| 4,330,419 | A | 5/1982 | Hall et al. |
| 4,802,970 | A | 2/1989 | Mamantov |
| 2005/0096251 | A1 | 5/2005 | Frankenbach et al. |
| 2024/0017996 | A1 | 1/2024 | Gouverneur et al. |

OTHER PUBLICATIONS

Ando T, et al. Silver fluoride supported on calcium fluoride. Improved fluorination and halofluorination reactions. Chemistry Letters. Nov. 5, 1988;17(11):1877-8.

Bulina NV, et al. Structure and thermal stability of fluorhydroxyapatite and fluorapatite obtained by mechanochemical method. Journal of Solid State Chemistry. Feb. 1, 2020;282:121076.

Christoffersen J, et al. Kinetics of dissolution and growth of calcium fluoride and effects of phosphate. Acta Odontol Scand. Dec. 1988;46(6):325-36.

Ebrahimi-Kahrizsangi R, et al. Characterization of single-crystal fluorapatite nanoparticles synthesized via mechanochemical method. Particuology. Oct. 1, 2011;9(5):537-44.

Ichihara J, et al. The combination of potassium fluoride and calcium fluoride: a useful heterogeneous fluorinating reagent. Journal of the Chemical Society, Chemical Communications. 1986(10):793-4.

Liu J, et al. Chloro-free synthesis of $LiPF_6$ using the fluorine-oxygen exchange technique. Chinese Chemical Letters. Aug. 1, 2022;33(8):4061-3.

Liu J, et al. Synthesis of $LiPF_6$ using $CaF_2$ as the fluorinating agent directly: an advanced industrial production process fully harmonious to the environments. Industrial & Engineering Chemistry Research. Oct. 17, 2019;58(44):20491-4.

Liu JW, et al. Preparation and characterization of lithium hexafluorophosphate for lithium-ion battery electrolyte. Transactions of Nonferrous Metals Society of China. Feb. 1, 2010;20(2):344-8.

Maier FJ. Advances in the Use of Fluorspar for Fluoridation. Journal-American Water Works Association. Jan. 1960;52(1):97-105.

Molaiyan P, Witter R. Surface defect-enhanced conductivity of calcium fluoride for electrochemical applications. Material Design & Processing Communications. Aug. 2019;1(4):e44.

Nembenna S, et al. A Well-Defined Hydrocarbon-Soluble Calcium Monofluoride, [{LCaF (thf)} 2]: The Application of Soluble Calcium Derivatives for Surface Coating. Angewandte Chemie International Edition. Mar. 26, 2007;46(14):2512-4.

Scholz G. Mechanochemistry of fluoride solids: from mechanical activation to mechanically stimulated synthesis. ChemTexts. Jun. 2021;7:1-16.

Schuhknecht D, et al. Reactivity of a Molecular Calcium Hydride Cation ([CaH]+) Supported by an NNNN Macrocycle. Inorg Chem. Jul. 6, 2020;59(13):9406-9415. Epub Jun. 16, 2020.

Sherbin, IG. A study of the reactions of fluorspar and phsophate rock with sulphur dioxide, air and water. (1969). Electronic Theses and Dissertations. 6590. https://scholar.uwindsor.ca/etd/6590/.

Aigueperse et al.: Fluorine Compounds, Inorganic in Ullmann's Encyclopedia of Industrial Chemistry (Weinheim: Wiley-VCH. 2000) https://doi.org/10.1002/14356007.a11_307.

Barrett et al.: Trifluoromethyl coordination and C-F bond activation at calcium. Angew. Chem. Int. Ed. 46(33):6339-6342 doi: 10.1002/anie.200701945 (2007).

Bennua-Skalmowski et al.: A facile conversion of primary or secondary alcohols with n-perfluorobutane-sulfonyl fluoride/1,8-diazabicyclo[5.4.0]undec-7-ene into their corresponding fluorides. Tetrahedron Lett. 36(15):2611-2614 (1995).

Bianchi et al.: Phase Transfer Catalysis, Preparation of Aliphatic and Aromatic Sulfonyl Fluorides. J Org Chem. 42(11):2031-2032 https://pubs.acs.org/doi/pdf/10.1021/jo00431a054 (1977).

Britton et al.: Contemporary Synthetic Strategies in Organofluorine Chemistry. Nat, Rev. Chem. Primers 1(1):47 (2021).

Campbell et al.: Modern Carbon-Fluorine Bond Forming Reactions for Aryl Fluoride Synthesis. Chem. Rev. 115(2):612-633 doi: 10.1021/cr500366b (2015).

Cismesia et al.: Multiple Approaches to the In Situ Generation of Anhydrous Tetraalkylammonium Fluoride Salts for SNAr Fluorination Reactions. JOC The Journal of Organic Chemistry. 82:5020-5026 (2017).

Do et al.: Mechanochemistry: A Force of Synthesis. ACS Cent. Sci. 3(1):13-19 doi: 10.1021/acscentsci.6b0027 (2017).

Dong et al.: Sulfur(VI) fluoride exchange (SuFEx): another good reaction for click chemistry. Angew. Chem. Int. Ed. 53(36):9430-9448 doi: 10.1002/anie.201309399 (2014).

Engle et al. : Coordination diversity in hydrogen-bonded homoleptic fluoride-alcohol complexes modulates reactivity. Gouverneur, Paton & Brown, Chem. Sci. 6 :5293-5302 (2015).

Feigl et al.: Analytical Use of Formation of Beryllium-Fluoride Complex. Anal. Chem. 23(2):351-353 (1951).

Feigl et al.: Chemistry of Specific, Selective and Sensitive Reactions. Anal. Chem. 685-686 (1949).

Friščić et al.: Mechanochemistry for synthesis. Angew. Chem. Int. Ed. 59(3):1018-1029 doi: 10.1002/anie.201906755 (2020).

Friščić et al.: Real-time and in situ monitoring of mechanochemical milling reactions. Nat. Chem. 5:66-73 https://doi.org/10.1038/nchem.1505 (2013).

GB2118767.9 Search Report dated Sep. 8, 2022.

Gonay et al.: Recent advances in the synthesis of acyl fluorides. Synthesis 53(4):653-665 DOI: 10.1055/s-0040-1705951 (2021).

Groult et al.: Modern Synthesis Processes and Reactivity of Fluorinated Compounds in Progress in Fluorine Science Series (Elsevier, 2016).

Halasz et al.: Quantitative in situ and real-time monitoring of mechanochemical reactions Faraday Discuss. 170:411-422 doi.org/10.1039/C4FD00013G (2014).

Harsanyi et al.: Organofluorine chemistry: applications, sources and sustainability, Green Chem. 46:2081-2086 (2015).

Ibba et al.: Impact of Multiple Hydrogen Bonds with Fluoride on Catalysis: Insight from NMR Spectroscopy. J. Am. Chem. Soc. 142(46): 19731-19744 DOI:10.1021/jacs.0c09832 (2020).

Inoue et al.: Contributions of Organofluorine Compounds to Pharmaceuticals, ACS Omega 5(19):10633-10640 doi: 10.1021/acsomega.0c00830. eCollection (2020).

Jain et al.: Direct Observation of Devect Dynamics in Nanocrystalline $CaF_2$: Results from 19F Mas NMR Spectroscopy. The Journal of Physical Chemistry Letters. 1:1126-1129 DOI:10.1021/jz100152j (2010).

Kubota et al.: Olefin-accelerated solid-state C-N cross-coupling reactions using mechanochemistry. nature communications. 10(1):111 doi: 10.1038/s41467-018-08017-9 (2019).

Laudadio et al.: Sulfonyl Fluoride Synthesis through Electrochemical Oxidative Coupling of Thiols and Potassium Floride. J. Am. Chem. Soc. 141:11832-11836 (2019).

Lukin et al.: Raman spectroscopy for real-time and in situ monitoring of mechanochemical milling reactions. Nat. Protoc. 16:3492-3521 (2021).

Narayanan et al.: Sulfonyl fluorides as privileged warheads in chemical biology. Chem. Sci. 6(5):2650-2659 doi: 10.1039/c5sc00408j (2015).

Nembenna et al.: A Well-Defined Hydrocarbon-Soluble Calcium Monofluoride, [{LCaF(thf)}2]: The Application of Soluble Calcium Derivatives for Surface Coating. Angew. Chem. Int. Ed. 46(14):2512-2514 (2007).

Nielsen et al.: PyFluor: A Low-Cost, Stable, and Selective Deoxyfluorination Reagent. J. Am. Chem. Soc. 137, 9571-9574 (2015).

Nowroozi et al.: Fluoride-ion batteries—past, present, and future. J. Mat. Chem. A 9:5980-6012 (2021).

(56) References Cited

OTHER PUBLICATIONS

Pfeifer et al.: Hydrogen-Bonded Homoleptic Fluoride-Diarylurea Complexes: Structure, Reactivity, and Coordinating Power. Gouverneur & Brown, J. Am. Chem. Soc. 138:13314-13325 (2016).
Pupo et al.: Asymmetric nucleophilic fluorination under hydrogen bonding phase-transfer catalysis. Science. 360(6389):638-642 DOI: 10.1126/science.aar7941 (2018).
Pupo et al.: Hydrogen Bonding Phase-Transfer Catalysis with Potassium Fluoride: Enantioselective Synthesis of β-Fluoroamines. J. Am. Chem. Soc. 141(7):2878-2883 DOI: 10.1021/jacs.8b12568 (2019).
Quan et al.: Preparation and application of porous calcium fluoride— a novel fluorinating reagent and support of catalyst. J. Fluor. Chem. 116(1):65-69 (2002).
Roagna et al.: Hydrogen Bonding Phase-Transfer Catalysis with Ionic Reactants: Enantioselective Synthesis of γ-Fluoroamines. J. Am. Chem. Soc. 142(33):14045-14051 DOI:10.1021/jacs.0c05131 (2020).
Schiffmann et al.: In-situ reaction monitoring of a mechanochemical ball mill reaction with solid state NMR. Solid State Nuclear Magnetic Resonance. 109(101687):1-9 (2020).
Schrenk et al.: Ind Eng Chem. 1929, 201.
See et al.: Development of SNAr Nucleophilic Fluorination: A Fruitful Academia-Industry Collaboration. Acc. Chem. Res. 53:2372-2383 (2020).
Seo et al.: Tackling Solubility Issues in Organic Synthesis: Solid-State Cross-Coupling of Insoluble Aryl Halides. J Am Chem Soc. 143(16):6165-6175 doi: 10.1021/jacs.1c00906 (2021).
Tan et al.: Main group mechanochemistry: from curiosity to established protocols. Chem. Soc. 48(8):2274-2292 https://doi.org/10.1039/C7CS00813A (2019).
Tan et al.: Towards medicinal mechanochemistry: evolution of milling from pharmaceutical solid form screening to the synthesis of active pharmaceutical ingredients (APIs). Chem. Commun. 52:7760-7781 https://doi.org/10.1039/C6CC02015A (2016).
Tarbutton et al.: Phosphorus-Halogen Compounds from Phosphorus Pentoxide and Halides. Properties of Phosphorus Trifluoride and Phosphorus Oxyfluoride. J. Am. Chem. Soc. 63(7):1782-1789 (1941).
Užarević et al.: Real-Time and In Situ Monitoring of Mechanochemical Reactions: A New Playground for All Chemists. The Journal of Physical Chemistry Letters. 6(20):4129-4140 DOI: 10.1021/acs.jpclett.5b01837 (2015).
Zhang et al.: Synthesis of 1,1,2,2,3,3,4-heptafluorocyclopentane as a new generation of green solvent. Journal of Fluorine Chemistry. 181:11-16 (2016).
U.S. Appl. No. 18/201,569 Office Action dated Mar. 11, 2024.
Co-pending U.S. Appl. No. 18/582,332, inventors Gouverneur; Veronique et al., filed on Feb. 20, 2024.

* cited by examiner

FLUORINATION PROCESSES

CROSS REFERENCE TO RELATED APPLICATIONS

This application is a continuation of International Application No. PCT/GB2022/053347, filed Dec. 21, 2022, which claims the benefit of UK Application No. GB2118767.9, filed Dec. 22, 2021, which is incorporated by reference herein in its entirety.

INTRODUCTION

The present disclosure relates to fluorination processes and fluorination reagents. In particular, the present application describes novel fluorination reagents, methods of preparation of fluorinating reagents from a salt comprising calcium and fluorine, as well as use of fluorinating reagents to prepare fluorochemicals. Fluorination process described herein can avoid a need to use hydrofluoric acid as an intermediate for fluorochemical production.

BACKGROUND OF THE INVENTION

Fluorochemicals can be present in our daily life with applications in the metallurgical industry, Li-ion batteries, electrical appliances, luminescent nanoparticles and electronics, fluoropolymers (PTFE known as Teflon or ETFE), refrigerants (HFOs), air conditioning, as well as agrochemicals, anesthetics, and pharmaceuticals. Generally fluorine atoms incorporated in organic fluorochemicals can be derived from the naturally occurring mineral fluorspar (calcium fluoride, $CaF_2$) by applying a workflow commencing with its conversion into highly toxic hydrogen fluoride (HF) (FIG. 1). Specifically, metallurgical grade Fluorspar (Metspar, 60-96% $CaF_2$, ~40% of total fluorspar production) can be employed as a flux in steelmaking, while acid grade fluorspar (Acidspar, ≥97% $CaF_2$, ~60% of total fluorspar production), can be used in the manufacture of hydrofluoric acid (HF) and/or aluminium trifluoride ($AlF_3$).

Industrial practice for the manufacture of organic fluorochemicals can rely upon energy-intensive treatment of acid grade calcium fluoride acidspar with sulfuric acid at elevated temperatures to generate hydrogen fluoride gas which can either be stored for use as liquified gas, or diluted in water for use as an aqueous solution. Safety of HF-based processes can be a concern of both producers and users, for exampled, due to HF being a highly dangerous and corrosive acid which can require extreme caution for safe handling.

Developing alternative routes for accessing value-added fluorochemicals can be extremely challenging. For example, due to the high lattice energy of $CaF_2$ (~2640 kJ·mol$^{-1}$, or ~1320 kJ·mol$^{-1}$ for each mole of fluoride generated).

SUMMARY OF THE INVENTION

According to a first aspect of the present invention there is provided a process for the preparation of a fluorinating reagent, the process comprising the step of:
  a) pulverising together a fluorine-containing compound and an ionic compound in the solid state, wherein the fluorine-containing compound is at least one of calcium fluoride and fluorapatite,
wherein the anion of said ionic compound is combinable with $Ca^{2+}$ to form a calcium salt having a lattice energy that is greater than 2450 KJ mol$^{-1}$.

According to a second aspect of the present invention there is provided a process for the preparation of a fluorochemical, the process comprising the step of:
  a) preparing a fluorinating reagent as described herein, and
  b) contacting an organic substrate with the fluorinating reagent,
wherein step b) is conducted simultaneously with, or after, step a).

According to a third aspect of the present invention there is provided a process for the preparation of a fluorochemical, the process comprising the steps of:
  a) pulverising a fluorine-containing compound in the solid state, wherein the fluorine-containing compound is at least one of calcium fluoride and fluorapatite; and
  b) contacting the product of step a) with an organic substrate;
wherein step b) is conducted simultaneously with, or after, step a).

According to a fourth aspect of the present invention there is provided a use of a fluorine-containing compound, the fluorine-containing compound being at least one of calcium fluoride and fluorapatite, as a fluorine source in a process for preparing a fluorochemical, wherein the process does not comprise a step of reacting the fluorine-containing compound with sulfuric acid to generate hydrofluoric acid.

According to a fifth aspect of the present invention there is provided a use of a fluorine-containing compound, the fluorine-containing compound being at least one of calcium fluoride and fluorapatite, as a fluorine source in a process for preparing a fluorinating reagent, wherein the process does not comprise a step of reacting the fluorine-containing compound with sulfuric acid to generate hydrofluoric acid.

In the aforementioned aspects, the fluorine-containing compound is suitably calcium fluoride (e.g., acid grade fluorspar).

According to a sixth aspect of the invention, there is provided a fluorinating reagent obtained, directly obtained or obtainable by a process of the first aspect.

According to a seventh aspect of the invention, there is provided a fluorinating reagent comprising a mixture of inorganic salts.

Calcium fluoride may be the sole fluorine source in the processes and uses of the invention.

In one aspect, described herein are activated fluorination reagents. In some embodiments, activated fluorination reagents comprise a first salt comprising calcium and fluorine. In some embodiments, the activated fluorination reagent comprises a second salt comprising an anion, which has a lattice energy greater than 2450 KJ/mol when combined with $Ca^{2+}$ to form a third salt. In some embodiments, a powder x-ray diffraction spectrum of the activated reagent comprises characteristic 2θ reflections at about 21.9°, 30.3°, 31.6°, and/or 43.4°.

In another aspect, described herein are methods of synthesizing an organo-fluorine compound. In some embodiments, the methods comprise combining a first salt, the first salt comprising calcium and fluorine, with a second salt. In some embodiments, the second salt comprises an anion, which has a lattice energy greater than 2450 KJ/mol when combined with $Ca^{2+}$ to form a third salt.

In some embodiments, the first and second salt are combined to form a salt mixture. In some embodiments, the methods comprise applying mechanical force to the salt mixture to form an activated salt-mixture. In some embodiments, the methods comprise combining the activated salt mixture with a first reactant. In some embodiments, the first reactant comprises an organic compound. In some embodiments the methods comprise fluorinating the first reactant to yield an organo-fluorine compound.

In another aspect, described herein are methods of fluorinating an organic compound. In some embodiments, the methods comprise combining an activated fluorination reagent with the organic compound and fluorinating the organic compound to produce an organo-fluorine compound. In some embodiments, the activated fluorination reagent has a powder x-ray diffraction spectrum of the activated reagent comprising characteristic 2θ reflections at about 21.9°, 30.3°, 31.6°, and/or 43.4°.

In another aspect, described herein are methods of manufacturing an activated fluorination reagent. In some embodiments, the methods comprise combining a first salt comprising calcium and fluorine, with a second salt to form a salt mixture. In some embodiments, the second salt comprises an anion, which has a lattice energy greater than 2450 KJ/mol when combined with $Ca^{2+}$ to form a third salt. In some embodiments, the methods comprise applying mechanical force to the salt mixture to yield the activated fluorination reagent.

In another aspect, described herein, are methods of recovering fluorine from a waste material to form an activated fluorination reagent. Such methods can be used for example to recover fluorine from a fluorine depleted waste material or produce a fluorination reagent from a waste stream comprising fluorine such as waste comprising $CaF_2$ or NaF. In some embodiments, the methods comprise combining a waste material comprising a first salt comprising calcium and fluorine, with a second salt to form a salt-waste mixture. In some embodiments, the second salt comprises an anion, which has a lattice energy greater than 2450 KJ/mol when combined with $Ca^{2+}$ to form a third salt. In some embodiments, the second salt combines with the first salt to form a salt-waste mixture that has a powder x-ray diffraction spectrum comprising characteristic 2θ reflections at about 21.9°, 30.3°, 31.6°, and/or 43.4°. In some embodiments, the methods comprise applying mechanical force to the salt-waste mixture to yield the activated fluorination reagent.

In some embodiments of the fluorination reagents or any of the methods described herein, the first salt is $CaF_2$. In some embodiments, the first salt is fluorapatite ($Ca_5(PO_4)_3F$). In some embodiments, the second salt is a metal hydroxide. In some embodiments the second salt is NaOH. In some embodiments the second salt is KOH. In some embodiments, the second salt is a metal sulphite. In some embodiments, the second salt is $Na_2SO_3$. In some embodiments, the second salt is $K_2SO_3$.

In some embodiments, the second salt is a metal sulphate. In some embodiments, the second salt is $KHSO_4$. In some embodiments, the second salt is an inorganic phosphate (e.g. $K_2HPO_4$, $KH_2PO_4$, $K_3PO_4$). In some embodiments, the second salt is $K_2HPO_4$. In some embodiments, the second salt is $KH_2PO_4$. In some embodiments, the second salt is $K_3PO_4$. In some embodiments, the inorganic phosphate is a pyrophosphate (e.g. $K_4P_2O_7$ or $Na_3P_2O_7$).

In some embodiments, a powder x-ray diffraction spectrum of the activated reagent comprising characteristic 2θ reflections at about 18.0°, 18.7°, 21.90, 22.6°, 24.5°, 25.4°, 26.5°, 27.0°, 28.0°, 29.2°, 30.3°, 31.6°, 33.0°, 34.8°, 36.4°, 37.7°, 39.5°, 40.4°, 41.7°, 42.4°, 43.4°, 46.1°, 48.4°, 49.4°, 52.8°, and/or 53.9°. In some embodiments, a powder x-ray diffraction spectrum of the activated reagent comprises at least two characteristic 2θ reflections selected from the group of about 18.0°, 18.7°, 21.9°, 22.6°, 24.5°, 25.4°, 26.5°, 27.0°, 28.0°, 29.2°, 30.3°, 31.6°, 33.0°, 34.8°, 36.4°, 37.7°, 39.5°, 40.4°, 41.7°, 42.4°, 43.4°, 46.1°, 48.4°, 49.4°, 52.8°, and 53.9°. In some embodiments, a powder x-ray diffraction spectrum of the activated reagent comprises at least three characteristic 2θ reflections selected from the group of about 18.0°, 18.7°, 21.9°, 22.6°, 24.5°, 25.4°, 26.5°, 27.0°, 28.0°, 29.2°, 30.3°, 31.6°, 33.0°, 34.8°, 36.4°, 37.7°, 39.5°, 40.4°, 41.7°, 42.4°, 43.4°, 46.1°, 48.4°, 49.4°, 52.8°, and 53.9°. In some embodiments, a powder x-ray diffraction spectrum of the activated reagent comprises characteristic at least four 2θ reflections selected from the group of about 18.0°, 18.7°, 21.9°, 22.6°, 24.5°, 25.4°, 26.5°, 27.0°, 28.0°, 29.2°, 30.3°, 31.6°, 33.0°, 34.8°, 36.4°, 37.7°, 39.5°, 40.4°, 41.7°, 42.4°, 43.4°, 46.1°, 48.4°, 49.4°, 52.8°, and 53.9°. In some embodiments, a powder x-ray diffraction spectrum of the activated reagent comprises characteristic 2θ reflections at about 21.9°, 30.3°, 31.6°, and 43.4°.

In some embodiments, a powder x-ray diffraction spectrum of the activated reagent comprises characteristic 2θ reflections at about 18.0°, 18.7°, 21.9°, 22.6°, 24.5°, 25.4°, 26.5°, 27.0°, 28.0°, 29.2°, 30.3°, 31.6°, 33.0°, 34.8°, 36.4°, 37.7°, 39.5°, 40.4°, 41.7°, 42.4°, 43.4°, 46.1°, 48.4°, 49.4°, 52.8°, and 53.9°.

In some embodiments, a ratio of the first salt to the second salt is about 1:0.5 to 1:100. In some embodiments, a ratio of the first salt to the second salt is about 1:1 to 1:10. In some embodiments, a ratio of the first salt to the second salt is about 1:1 to 1:5. In some embodiments, a ratio of the first salt to the second salt is about 1:1. In some embodiments, a ratio of the first salt to the second salt is about 1:2. In some embodiments, a ratio of the first salt to the second salt is about 1:3. In some embodiments, a ratio of the first salt to the second salt is about 1:5.

In some embodiments of any of the methods described herein, the mechanical force is applied using a ball mill, a mortar and pestle, a twin-screw extruder, using an ultrasonic bath, or a mechanical press.

In some embodiments, the method does not comprise reacting a strong acid with the first salt to form hydrofluoric acid. In some embodiments, the mechanical force is applied at a frequency of about 0.5 Hz-60 kHz. In some embodiments, the mechanical force is applied at a frequency of about 10 Hz-20 kHz. In some embodiments, the mechanical force is applied at a frequency of about 30 Hz. In some embodiments, the mechanical force is applied at a frequency of about 35 Hz. In some embodiments, the mechanical force is applied at a frequency of about 60 Hz.

In some embodiments, the mechanical force is applied at a temperature of about 20-300° C. In some embodiments, the mechanical force is applied at a temperature of about 20-100° C. In some embodiments, the mechanical force is applied at a temperature of about 30° C. In some embodiments, the mechanical force is applied at a temperature of about 60° C. In some embodiments, the mechanical force is applied at a temperature of about 90° C.

In some embodiments, the first and second salt are combined as solids without the addition of solvent.

In some embodiments, the organic compound is aromatic or aliphatic and comprises at least one leaving group located at a site to be fluorinated. In some embodiments, the organic compound is a sulphonyl halide, an acyl halide, an aryl halide or an alkyl halide. In some embodiments, the organic compound is an aromatic sulphonyl halide (e.g. tosyl chloride), a benzoyl halide (e.g. 4-methoxybenzoyl chloride) a halobenzene (e.g. chlorobenzene) or a benzyl halide (e.g. benzyl chloride). In some embodiments, the first salt, second salt, and the organic compound are combined in the same step. In some embodiments, the first salt, second salt are combined prior to addition of the organic compound. In some embodiments, the first salt, second salt, and the organic compound is added together with one or more solvents in which the organic compound is soluble in at least one of the one or more solvents.

In some embodiments, the one or more solvents comprise a solvent selected from the group consisting of acetonitrile, propionitrile, toluene, 1,2-dichlorobenzene, chlorobenzene, fluorobenzene, 1,2-difluorobenzene, dichloroethane, trifluorotoluene, chloroform, tert-butanol, tert-amyl alcohol and water, wherein any one or more of the aforementioned organic solvents may be in admixture with water.

In some embodiments, the one or more solvents comprise acetonitrile, chlorobenzene, tert-butanol, tert-amyl alcohol and/or water. In some embodiments, the one or more solvents comprise a cryptand, a crown ether and a hydrogen-bonding phase transfer agent.

In some embodiments, the fluorination reaction is performed at a temperature of about 20-300° C. In some embodiments, the fluorination reaction is performed at a temperature of about 20-100° C. In some embodiments, the fluorination reaction yield of the organofluorine compound is at least about 10% (measured based on a starting amount the organic compound). In some embodiments, the fluorination reaction yield is at least about 30% (measured based on a starting amount the organic compound). In some embodiments, the fluorination reaction yield is at least about 50% (measured based on a starting amount the organic compound). In some embodiments, the fluorination reaction yield is at least about 80% (measured based on a starting amount the organic compound).

In some embodiments, the fluorination reaction is a mono-fluorination reaction. In some embodiments, the fluorination reaction is a di-fluorination reaction.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 119 illustrates a general scheme according to embodiments described herein.

FIG. 120 illustrates a general scheme according to embodiments described herein.

FIG. 121 illustrates a general scheme according to embodiments described herein.

FIG. 122 illustrates a general scheme according to embodiments described herein.

FIG. 123 illustrates a general scheme according to embodiments described herein.

DETAILED DESCRIPTION OF THE INVENTION

Figure 1:
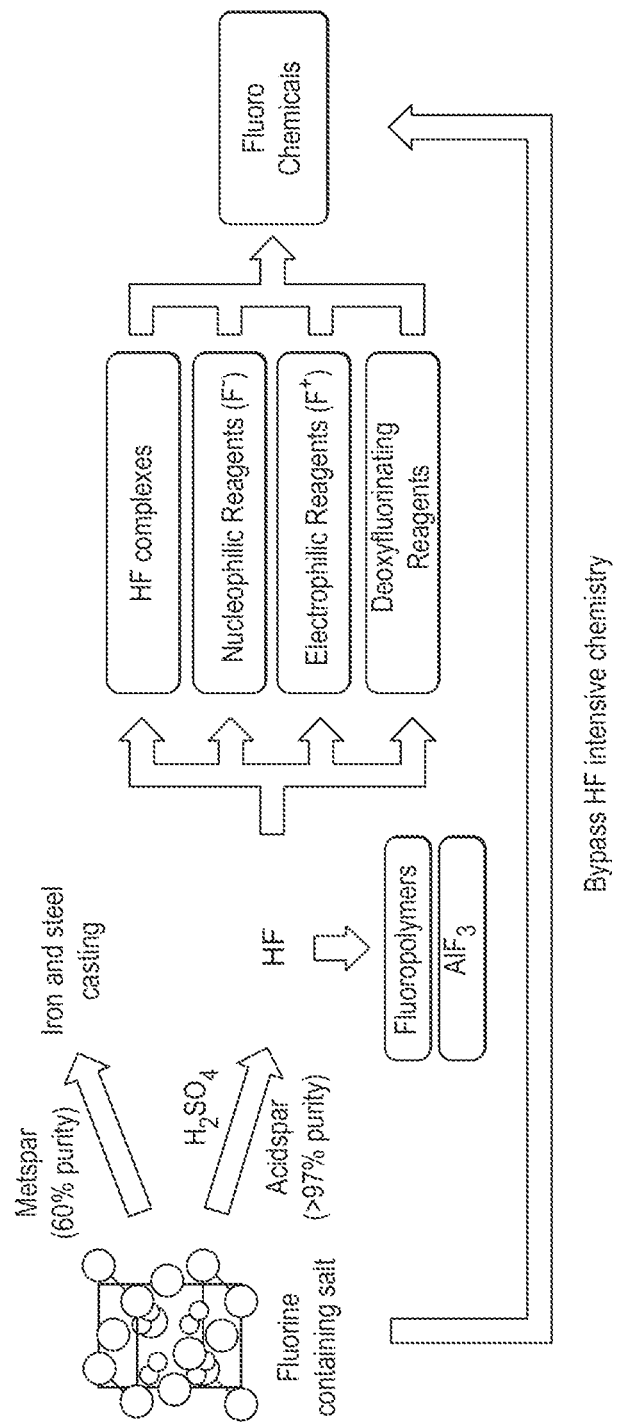
FIG. 1 shows possible manufacturing schemes of fluorochemicals from salts comprising fluorine.
Figure 2:
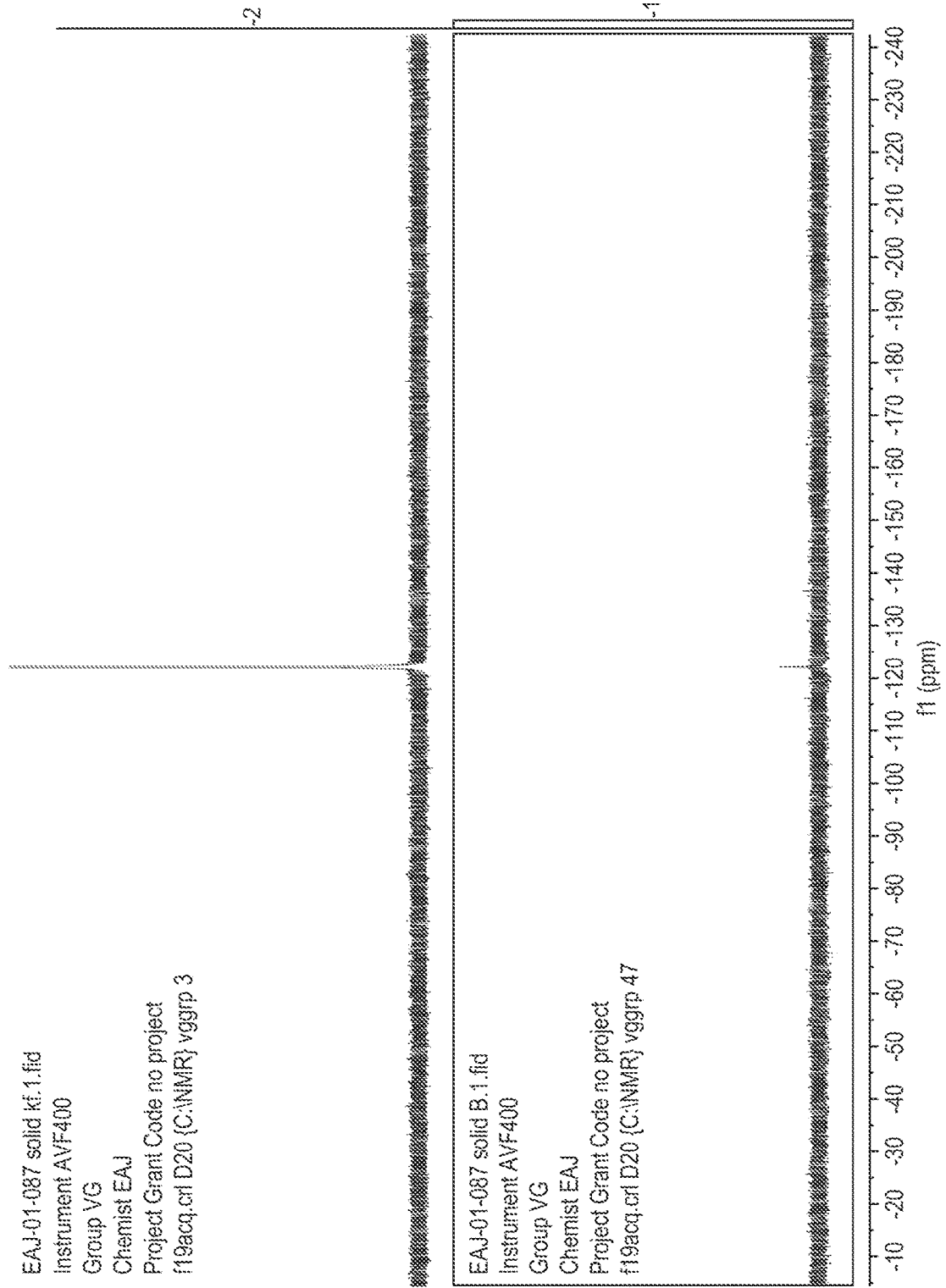
FIG. 2 shows: Top: $^{19}$F NMR in $D_2O$ of the fluorinating reagent derived from $CaF_2$ and $K_2HPO_4$ under mechanochemical conditions. Bottom: $^{19}$F NMR in $D_2O$ of the fluorinating reagent derived from $CaF_2$ and $K_2HPO_4$ under mechanochemical conditions, following spiking with KF.

Throughout the entirety of the description and claims of this specification, where subject matter is described herein using the term "comprise" (or "comprises" or "comprising"), the same subject matter instead described using the term "consist of" (or "consists of" or "consisting of") or "consist essentially of" (or "consists essentially of" or "consisting essentially of") is also contemplated.

The term "about" or "approximately" may mean within an acceptable error range for the particular value, which will depend in part on how the value is measured or determined, e.g., the limitations of the measurement system. Unless otherwise specified herein, "about" generally refers to a range of +/−10% of the stated value. In the case of X-ray diffraction reflections, however, "about" generally refers to a range of +/−0.1° of the stated value. Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Certain inventive embodiments herein contemplate numerical ranges. When ranges are present, the ranges include the range endpoints. Additionally, every sub range and value within the range is present as if explicitly written out.

Certain inventive embodiments herein contemplate characteristic x-ray diffraction reflections. In certain embodiments, the presence or absence of a characteristic x-ray diffraction reflection is determined by identification of a peak in an x-ray diffraction spectrum located at a characteristic 2θ value.

In certain embodiments, a peak is present when a 2θ signal has a signal to noise ratio of at least 3.

In certain embodiments, a peak is present when a 2θ signal has a signal to noise ratio of at least 5. In certain embodiments, a peak is present when a 2θ signal has a signal to noise ratio of at least 10.

In certain embodiments, a peak is present when a 2θ signal has a signal to noise ratio of at least 20.

In certain embodiments, peaks are identified in a raw powder x-ray diffraction spectrum. In certain embodiments, peaks are identified in a background subtracted powder x-ray diffraction spectrum. In some embodiments, peaks corresponding to a first salt are subtracted from a raw spectrum to yield a background subtracted spectrum. In some embodiments, peaks corresponding to a second salt are subtracted from a raw spectrum to yield a background subtracted spectrum. In some embodiments, one or more known contaminant peaks are subtracted from a raw spectrum to yield a background subtracted spectrum. In some embodiments, peaks corresponding to one or more of: a first salt, a second salt, and/or a known contaminant are subtracted from a raw spectrum to yield a background subtracted spectrum.

Throughout the description and claims of this specification, the singular encompasses the plural unless the context otherwise requires. In particular, where the indefinite article is used, the specification is to be understood as contemplating plurality as well as singularity, unless the context requires otherwise.

Features described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any of the specific embodiments recited herein. The invention extends to any novel one, or any novel combination, of the features disclosed in this specification (including any accompanying claims, abstract and drawings), or to any novel one, or any novel combination, of the steps of any method or process so disclosed.

Unless otherwise specified, where the quantity or concentration of a particular component of a given product is specified as a weight percentage (wt. % or % w/w), said weight percentage refers to the percentage of said component by weight relative to the total weight of the product as a whole. It will be understood by those skilled in the art that the sum of weight percentages of all components of a product will total 100 wt. %. However, where not all components are listed (e.g. where a product is said to "comprise" one or more particular components), the weight percentage balance may optionally be made up to 100 wt % by unspecified ingredients.

As described hereinbefore, in a first aspect the present invention provides a process for the preparation of a fluorinating reagent, the process comprising the step of:
  a) pulverising together a fluorine-containing compound and an ionic compound in the solid state, wherein the fluorine-containing compound is at least one of calcium fluoride and fluorapatite,
wherein the anion of said ionic compound is combinable with $Ca^{2+}$ to form a calcium salt having a lattice energy that is greater than 2450 KJ $mol^{-1}$.

Through rigorous investigations, the inventors have arrived at a solution to the long-standing problem described hereinbefore by devising a process that allows calcium fluoride and fluorapatite to be directly converted into a fluorinating reagent without the need for converting them into HF using sulfuric acid. This is achieved by reacting calcium fluoride and/or fluorapatite with particular ionic compounds according to the conditions outlined in step a) (e.g. ball milling, or other mechanochemical technique). The process of the invention therefore allows for the preparation of value-added fluorochemicals using more environmentally-friendly and sustainable techniques.

Calcium fluoride ($CaF_2$, melting point, ~1420° C.) is a white solid that is poorly soluble in water (0.016 g/L at 20° C.) and is insoluble in organic solvents. Under ambient conditions, calcium fluoride crystallizes in the fluorite structure (a, space group Fm-3m) wherein $Ca^{2+}$ ions are cubically coordinated to eight nearest-neighbor $F^-$ ions. The calcium fluoride used as part of the invention may be naturally occurring (i.e. as fluorspar) or may be synthetic (e.g. industrially produced calcium fluoride having fewer impurities). Fluorapatite is a crystalline solid having the formula $Ca_5(PO_4)_3F$.

The process of the invention involves reacting the fluorine-containing compound (i.e., calcium fluoride and/or fluorapatite) with particular ionic compounds in the solid state using a high-energy mixing technique, such as one that is sufficient to mechanically reduce the particle size of (e.g. crush) the reactants and bring them into contact with one another. Pulverising together the reactants according to step a) achieves this objective. It will, however, be appreciated that synonymous high-energy mixing techniques resulting in particle size reduction of the reactants and/or an increased surface area to volume ratio of the reactants, such as crushing together, grinding together, milling together, mashing together, macerating together and the like, are embraced by step a).

The process may be a mechanochemical process and/or step a) may be conducted under mechanochemical conditions. Mechanochemistry is a developing area of chemical synthesis and is widely understood to refer to chemical transformations that are initiated by and/or sustained by the application of a mechanical stress to one or more solid reactants.

Step a) may be conducted in a ball mill, a pestle and mortar or a twin screw extruder (TSE). Other techniques and apparatuses suitable for carrying out step a) will be familiar to one skilled in the art, e.g. those skilled in the art of mechanochemistry, including an ultrasonic bath and/or a mechanical press.

In particular embodiments, step a) is conducted in a ball mill. Exemplary ball mills include a planetary ball mill, a vibratory ball mill, an attritor ball mill or a tumbling ball mill. Most suitably, the ball mill is a vibratory ball mill.

The person skilled in the art of ball milling will be able to select appropriate conditions, including ball size and weight, and vessel size. For example, a stainless steel vessel and one or more stainless steel balls may be used. Alternatively, a zirconia vessel and one or more zirconia balls may be used. A ball, or balls, (each) weighing 2-20 g (e.g., 3 g, 4 g, 7 g or 16 g) may, for example, be used.

Step a) may be carried out for any suitable period of time. For example, step a) may be carried out for 0.5-12 hours (e.g., the fluorine-containing compound and ionic compound may be ball milled together for 0.5-12 hours).

In particular embodiments, step a) comprises ball milling the fluorine-containing compound together with the ionic compound at a frequency of 0.5-80 Hz. More suitably, step a) comprises ball milling the fluorine-containing compound together with the ionic compound at a frequency of 5-65 Hz. Even more suitably, step a) comprises ball milling the fluorine-containing compound together with the ionic compound at a frequency of 15-45 Hz. Most suitably, step a) comprises ball milling the fluorine-containing compound together with the ionic compound at a frequency of 20-40 Hz (e.g., 28-38 Hz).

Twin screw extrusion may be performed at various speeds ($S_s$), screw temperatures ($S_T$) and residence times ($T_R$), as described herein. A single pass through the extruder may be sufficient to form the fluorinating reagent. Alternatively, when step a) is conducted in a twin screw extruder, step a) may comprise collecting the product emerging from the twin screw extruder and subjecting it to one or more additional passes through the twin screw extruder.

Step a) is conducted in the solid state. In its simplest sense, step a) is conducted in the absence (or substantial absence) of any solvent. However, the use of some solvent is known to offer advantages in some solid state (e.g. mechanochemical) reactions. Examples of such techniques include solvent-assisted mechanochemistry (sometimes termed liquid-assisted mechanochemistry, e.g. liquid-assisted grinding). Suitably, the amount and type of solvent used (if any) is such that >50 wt % of the fluorine-containing compound, the ionic compound, and any reaction products derived therefrom, remain in the solid state throughout step a). More suitably, >70 wt % of the fluorine-containing compound, the ionic compound, and any reaction products derived therefrom, remain in the solid state throughout step a). Even more suitably, >90 wt % of the fluorine-containing compound, the ionic compound, and any reaction products derived therefrom, remain in the solid state throughout step a). Yet more suitably, >95 wt % of the fluorine-containing compound, the ionic compound, and any reaction products derived therefrom, remain in the solid state throughout step a).

In particular embodiments, step a) is conducted in the absence (or substantial absence) of any solvent. Suitably, step a) involves pulverising together the fluorine-containing compound and the ionic compound in a ball mill (i.e. ball milling the fluorine-containing compound and the ionic compound).

In particular embodiments, step a) is conducted in the absence (or substantial absence) of any solvent. Suitably, step a) involves pulverising together the fluorine-containing compound and the ionic compound in a twin screw extruder.

During step a), the fluorine-containing compound is reacted with an ionic compound, the anion of which is combinable with $Ca^{2+}$ to form a calcium salt having a lattice energy that is greater than 2400 KJ $mol^{-1}$. The person of skill in the art will be familiar with the term lattice energy as denoting the amount of energy required to dissociate one mole of an ionic compound into its constituent ions in the gaseous state. Calcium fluoride and fluorapatite, being only slightly soluble in certain acids, are chemically inert to nearly all organic chemicals. The stability of calcium fluoride and fluorapatite is attributed in a large part to their high lattice energy (2630 KJ $mol^{-1}$ for calcium fluoride). The inventors have, however, determined that this stability can be overcome by pulverising together (e.g. ball milling) calcium fluoride and/or fluorapatite with certain ionic compounds according to step a). Without wishing to be bound by theory, the inventors believe that the energetic bar to reactivity of calcium fluoride or fluorapatite can be overcome by the use of high-energy reaction conditions, combined with the use of a thermodynamic sink for $Ca^{2+}$. In particular, the use of ionic compounds, the anions of which (e.g. sulphate, carbonate or phosphate) are able to form calcium salts having lattice energies that are similar to, or preferably greater than, 2630 KJ $mol^{-1}$ (e.g. $CaSO_4$=2489 KJ $mol^{-1}$; $CaCO_3$=2804 KJ $mol^{-1}$; $Ca_3(PO_4)_2$=10,602 KJ $mol^{-1}$) facilitates the formation of fluorine-containing species that have improved reactivity towards organic chemicals.

The fluorine-containing compound is typically calcium fluoride or fluorapatite. Suitably, the fluorine-containing compound is calcium fluoride. Where the fluorine-containing compound is calcium fluoride, a quantity of fluorapatite may form (e.g., transiently) during the course of step a). In particular embodiments, the calcium fluoride is acid grade fluorspar.

In some instances, the fluorine-containing compound used in the first aspect may be calcium fluoride, fluorapatite and/or any other salt comprising calcium and fluorine. Such other salts may be described elsewhere herein as a first salt comprising calcium and fluorine.

Particularly suitably, the anion of the ionic compound is combinable with $Ca^{2+}$ to form a calcium salt having a lattice energy that is greater than the lattice energy of calcium fluoride (i.e. greater than 2630 KJ $mol^{-1}$).

The ionic compound is suitably inorganic. The ionic compound may be a salt. Suitably, the ionic compound is a salt of an oxoacid.

The ionic compound may be a phosphate, carbonate, sulphate, sulphite or nitrate salt. Alternatively, the ionic compound may be a phosphate, carbonate or sulphate salt. It will be understood that phosphate, carbonate, sulphate, sulphite or nitrate salts described herein are salts that contains at least one of these anions, meaning that salts such as hydrogen phosphate salts, dihydrogen phosphate salts, hydrogen sulphate salts and bicarbonate salts are also encompassed. It will be understand that phosphate salts encompass metaphosphate salts, and that phosphate salts and sulphate salts encompass pyrophosphate salts and pyrosulfate salts respectively. Alternatively, the ionic compound may be a hydroxide salt or a citrate salt. Alternatively/additionally, the ionic compound may be an alkali metal salt or an alkaline earth metal salt, for example a potassium salt, a sodium salt or a magnesium salt.

In particular embodiments, the ionic compound is a phosphate salt.

The ionic compound may be a phosphate salt of potassium, sodium or calcium, a sulphate salt of potassium, sodium or caesium, a carbonate salt of potassium or sodium, a sulphite salt of potassium or sodium, a nitrate salt of potassium or sodium, a hydroxide salt of potassium or sodium, or a citrate salt of potassium or sodium. For example, the ionic compound may be selected from the group consisting of $K_3PO_4$, $K_2HPO_4$, $KH_2PO_4$, $Na_3PO_4$, $Na_2HPO_4$, $KPO_3$, $K_4P_2O_7$, $K_5P_3O_{10}$, $Na_4P_2O_7$, $Na_5P_3O_{10}$, $(NaPO_3)_3$, $CaHPO_4$, $K_2CO_3$, $KHCO_3$, $K_2SO_4$, $KHSO_4$, $Cs_2SO_4$, $MgSO_4$, $Ag_2SO_4$, $K_2S_2O_7$, $Na_2SO_3$, $Na_2SO_4$, $Na_2CO_3$, $KNO_3$, $Na_3C_6H_5O_7$, NaOH and KOH.

Particular, non-limiting examples of the ionic compound include phosphate salts of potassium and sodium, sulphate salts of potassium and sodium, and carbonate salts of potassium and sodium. Suitably, the ionic compound is a phosphate salt of potassium or sodium. More suitably, the ionic compound is a phosphate salt of potassium. Most suitably, the ionic compound is $K_3PO_4$ or $K_2HPO_4$, of which $K_2HPO_4$ is most preferred.

Alternatively, the ionic compound may be selected from the group consisting of $K_3PO_4$, $K_2HPO_4$, $KH_2PO_4$, $KPO_3$, $Na_3PO_4$, $Na_2HPO_4$, $Cs_2SO_4$, $Na_2SO_3$, $K_4P_2O_7$, $K_5P_3O_{10}$, $Na_4P_2O_7$, $Na_5P_3O_{10}$, $Na_3C_5H_5O_7$, $K_2SO_4$, $Na_2SO_4$, $MgSO_4$, $Na_2CO_3$, $K_2CO_3$, $KHCO_3$, NaOH and KOH. Suitably, the ionic compound is selected from the group consisting of $K_3PO_4$, $K_2HPO_4$, $KPO_3$, $Na_3PO_4$, $Na_2HPO_4$, $K_4P_2O_7$, $K_5P_3O_{10}$, $Na_4P_2O_7$, $Na_5P_3O_{10}$, $K_2CO_3$, $KHCO_3$, NaOH and KOH. More suitably, the ionic compound is selected from the group consisting of $K_2HPO_4$, $KPO_3$, $Na_2HPO_4$, $K_4P_2O_7$, $K_5P_3O_{10}$ and $Na_4P_2O_7$.

In some instances, the ionic compound used in the first aspect may be described elsewhere herein as a second salt.

In particular embodiments, the ionic compound is $K_2HPO_4$, $KPO_3$, $Na_2HPO_4$, $K_4P_2O_7$, $K_5P_3O_{10}$ or $Na_4P_2O_7$ and step a) is conducted in the absence (or substantial absence) of any solvent. Suitably, step a) involves pulverising together the fluorine-containing compound and the ionic compound in a ball mill (i.e. ball milling the fluorine-containing compound and the ionic compound).

In particular embodiments, the ionic compound is a phosphate, sulphate or carbonate salt of potassium or sodium (e.g. $K_3PO_4$ or $K_2HPO_4$) and step a) is conducted in the absence (or substantial absence) of any solvent. Suitably, step a) involves pulverising together the fluorine-containing compound and the ionic compound in a ball mill (i.e. ball milling the fluorine-containing compound and the ionic compound).

It will be appreciated that ionic compounds having properties similar to those recited herein may also be suitable for use in step a).

The molar ratio of the fluorine-containing compound to the ionic compound in step a) may be (0.1-7):1 (e.g., (0.3-6):1). Suitably, the molar ratio of the fluorine-containing compound to the ionic compound in step a) may be (0.5-5):1. More suitably, the molar ratio of the fluorine-containing compound to the ionic compound in step a) is (1-2):1.

In some embodiments, the ionic compound is pulverized together with the fluorine-containing compound in portions. For example, step a) may comprise: (a-i) pulverising together the fluorine-containing compound and a first portion of the ionic compound, and (a-ii) pulverising together the product of step (a-i) and a second portion of the ionic compound. Optionally, step a) further comprises a step (a-iii) of pulverising together the product of step (a-ii) and a third portion of the ionic compound. Optionally, step a) further comprises a step (a-iv) of pulverising together the product of step (a-iii) and a fourth portion of the ionic compound. The portions of the ionic compound may be the same or different.

In some embodiments, solid $CO_2$ (i.e., dry ice) is pulverised together with the fluorine-containing compound and the ionic compound. In such embodiments, between 5 and 15 equivalents of solid $CO_2$ (relative to 1 equivalent of fluorine-containing compound) may be used in step a).

In some embodiments, the product resulting from step a) may be heat-treated. Suitably, the product resulting from step a) may be heated to a temperature of 300-700° C. (e.g., 500-600° C.).

In embodiments, essentially no HF is produced at any point during step a). For example, <1 ppm (e.g., <1 ppb) of HF may be produced at any point during step a).

The fluorinating reagent afforded by step a) can be used to prepare a fluorochemical (e.g. an organic fluorochemical). Thus, in a second aspect, the invention provides a process for the preparation of a fluorochemical, the process comprising the steps of:

a) preparing a fluorinating reagent as described herein; and
b) contacting an organic substrate with the fluorinating reagent, wherein step b) is conducted simultaneously with, or after, step a).

The organic substrate to be fluorinated may take a variety of forms. Suitably the organic substrate is an electrophile.

The organic substrate may be aliphatic (e.g. an alkyl halide) or aromatic (e.g. an aryl halide or a heteroaryl halide) in nature. The organic substrate suitably has at least one leaving group located at the site to be fluorinated. Leaving groups will be known to those of skill in the art of organic chemistry. Particular, non-limiting examples of suitable leaving groups include halide (particularly chloro or bromo), tosylate, triflate, mesylate, phosphate, nitro, ammonium and iodonium groups. Most suitably, the leaving group is halide.

The organic substrate may be any one of those organic substrates employed in the Examples outlined herein. In such Examples, the exemplified leaving group(s) may, where chemically feasible, be replaced with any one of the other aforementioned leaving groups.

In particular embodiments, the organic substrate is a sulphonyl halide, an acyl halide, an aryl halide or an alkyl halide (including alkylaryl halides, such as benzyl halides). In such embodiments, halide is suitably chloride. Sulphonyl, acyl, aryl and benzylic fluorides are among the most common fluorinated motifs in organic synthesis with broad applicability as either reagents, synthetic intermediates or biological probes. More suitably, the organic substrate is a sulphonyl halide, an acyl halide, an aryl halide or a heteroaryl halide. Particular, non-limiting examples include aromatic sulphonyl halide (e.g. tosyl chloride), benzoyl halides (e.g. 4-methoxybenzoyl chloride), halobenzenes (e.g. chlorobenzene) and benzyl halides (e.g. benzyl chloride).

In particular embodiments, the organic substrate is a sulphonyl halide, an aryl halide, an alkylaryl halide, an acyl halide, an α-halo carbonyl or an alkyl halide.

In particular embodiments, the organic substrate is ArO-$CHX_2$, wherein Ar is an aromatic group (e.g., biphenyl) and X is halide (e.g., chloro).

In particular embodiments, where the organic substrate has more than one leaving group (e.g., 2 leaving groups), the leaving groups may be attached to the same carbon atom (e.g., 2 geminal halide leaving groups).

In many instances, the organic substrate has a molecular weight of <500 g $mol^{-1}$. Suitably, the organic substrate has a molecular weight of <300 g $mol^{-1}$.

In particular embodiments, the organic substrate is a sulfonyl halide, an acyl halide, an aryl halide or an alkyl halide (e.g. where halide is bromide) and the ionic compound used in step a) is a phosphate, sulphate or carbonate salt of potassium or sodium (e.g. $K_3PO_4$ or $K_2HPO_4$). Suitably, step a) is conducted in the absence (or substantial absence) of any solvent. Alternatively/additionally, step a) involves pulverising together the fluorine-containing compound (e.g., calcium fluoride) and the ionic compound in a ball mill (i.e. ball milling calcium fluoride and the ionic compound).

In particular embodiments, the organic substrate is a sulphonyl halide, an aryl halide, an alkylaryl halide, an acyl halide, an α-halo carbonyl or an alkyl halide and the ionic compound used in step a) is a phosphate, carbonate, sulphate, sulphite, nitrate, hydroxide or citrate salt (e.g. $K_3PO_4$, $K_2HPO_4$, $KPO_3$, $Na_3PO_4$, $Na_2HPO_4$, $K_4P_2O_7$, $K_5P_3O_{10}$, $Na_4P_2O_7$, $Na_5P_3O_{10}$, $K_2CO_3$, $KHCO_3$, NaOH or KOH). Suitably, step a) is conducted in the absence (or substantial absence) of any solvent. Alternatively/additionally, step a) involves pulverising together the fluorine-containing compound (e.g., calcium fluoride) and the ionic compound in a ball mill (i.e. ball milling calcium fluoride and the ionic compound) or a twin screw extruder.

Step b) may be conducted simultaneously with step a), such that the organic substrate is available for reaction with the fluorinating reagent as soon as the latter forms during step a). Accordingly, step b) may comprise contacting the organic substrate with the fluorinating reagent under identical conditions to those used to form the fluorinating reagent. In this sense, steps a) and b) may collectively define a single step in which the fluorine-containing compound, the ionic compound and the organic substrate are pulverised together in the solid state (e.g. by ball milling).

Alternatively, step b) may be conducted after step a), such that a quantity of fluorinating reagent is allowed to form before being reacted with the organic substrate.

When step b) is conducted after step a), step b) may be conducted in the solid state. For example, step b) may comprise pulverising together the organic substrate and the fluorinating reagent formed from step a) in the solid state. Suitably, step b) is conducted in a ball mill. More suitably, step b) is conducted in the absence (or substantial absence) of a solvent. In certain embodiments, steps a) and b) are both conducted in a ball mill (e.g. the same ball mill), suitably in the absence (or substantial absence) of a solvent.

Alternatively, when step b) is conducted after step a), step b) may be conducted in solution. For example, step b) may comprise mixing together the organic substrate and the fluorinating reagent in a solvent in which the organic substrate is soluble. Any suitable solvent or combinations of solvents may be used depending on the nature of the organic substrate, including, for example, those solvents employed in the Examples outlined herein (e.g., those listed in Table 3.5). The solvent may, for example, be selected from the group consisting of tetrahydrofuran, 2-methyl tetrahydrofuran, 1, 4-dioxane, diglyme, monoglyme, acetonitrile, propionitrile, tert-butyl isocyanide, tert-butanol, tert-amyl alcohol, toluene, m-xylene, hexane, trifluorotoluene, 1,2-difluorobenzene, 1,2-dichlorobenzene, 1,3-dichlorobenzene, fluorobenzene and chlorobenzene. Particular, non-limiting examples include acetonitrile, propionitrile, toluene, 1,2-dichlorobenzene, chlorobenzene, fluorobenzene, 1,2-difluorobenzene, dichloroethane, trifluorotoluene, chloroform, tert-butanol, tert-amyl alcohol and water. Suitably, step b) is conducted in a solvent selected from the group consisting of acetonitrile, toluene, chlorobenzene, 1,2-difluorobenzene, dichloroethane, trifluorotoluene, chloroform, tert-butanol and tert-amyl alcohol. More suitably, step b) is conducted in acetonitrile, chlorobenzene, tert-butanol or tert-amyl alcohol. Most suitably, step b) is conducted in acetonitrile.

Any one or more of the aforementioned organic solvents may be in admixture with water. For example, the organic solvent may be in admixture with water at a concentration of 0.01-5M. Suitably, the organic solvent may be in admixture with water at a concentration of 0.01-1M (e.g., 0.05-0.5M).

In particular embodiments, step b) is conducted after step a), and step b) is conducted a solvent selected from the group consisting of tetrahydrofuran, 2-methyl tetrahydrofuran, 1, 4-dioxane, diglyme, monoglyme, acetonitrile, propionitrile, tert-butyl isocyanide, tert-butanol, tert-amyl alcohol, toluene, m-xylene, hexane, trifluorotoluene, 1,2-difluorobenzene, 1,2-dichlorobenzene, 1,3-dichlorobenzene, fluorobenzene and chlorobenzene, any one of which may be in admixture with water. Suitably, the organic substrate is a sulphonyl halide, an aryl halide, an alkylaryl halide, an acyl halide, an α-halo carbonyl or an alkyl halide and the ionic compound used in step a) is a phosphate, carbonate, sulphate, sulphite, nitrate, hydroxide or citrate salt (e.g. $K_3PO_4$, $K_2HPO_4$, $KPO_3$, $Na_3PO_4$, $Na_2HPO_4$, $K_4P_2O_7$, $K_5P_3O_{10}$, $Na_4P_2O_7$, $Na_5P_3O_{10}$, $K_2CO_3$, $KHCO_3$, NaOH or KOH). Step a) may involve pulverising together the fluorine-containing compound (e.g., calcium fluoride) and the ionic compound in a ball mill (i.e. ball milling calcium fluoride and the ionic compound) or a twin screw extruder.

When step b) is conducted after step a), the fluorinating reagent formed in step a) may be isolated or purified prior to reacting it with the organic substrate.

The skilled person will be able to select appropriate reaction conditions (e.g. temperature, pressure, etc) for carrying out step b) in solution. For example, when step b) is conducted in solution after step a), step b) may be performed at a temperature of 15-180° C. Suitably, step b) is performed at a temperature of 15-150° C.

Step b) may be conducted in the presence of at least one of a cryptand, a crown ether and a hydrogen-bonding phase transfer catalysts. Suitably, step b) is conducted after step a), and is performed in solution. Suitable cryptands include Kryptofix 221® and Kryptofix 222®. Suitable crown ethers include 18-crown-6, dibenzo-18-crown-6, dibenzo-30-crown-10 and dicyclohexano-18-crown-6. Suitable hydrogen-bonding phase transfer catalysts include Schreiner's urea. Amongst the aforementioned cryptands, crown ethers and hydrogen-bonding phase transfer catalysts, 18-crown-6 and dibenzo-18-crown-6 are particularly suitable.

The process may further comprise one or more additional steps in which the fluorochemical formed in step b) is isolated and/or purified.

The fluorochemical may be otherwise described herein as a fluorinated compound or an organo-fluorine compound.

As described hereinbefore, in a third aspect the present invention provides a process for the preparation of a fluorochemical, the process comprising the steps of:
 a) pulverising a fluorine-containing compound in the solid state, wherein the fluorine-containing compound is at least one of calcium fluoride and fluorapatite; and
 b) contacting the product of step a) with an organic substrate;
wherein step b) is conducted simultaneously with, or after, step a).

Through further investigations, the inventors have surprisingly determined that the formation of HF can be bypassed and calcium fluoride or fluorapatite can be directly converted into value-added fluorochemicals using a process that is similar to the process to the first aspect, albeit without the need for the fluorine-containing compound to be pulverised together with an ionic compound as defined herein.

Accordingly, it will be understood that steps a) and b) of the third aspect may have any of those definitions recited hereinbefore in relation to corresponding steps a) and b) of the first and second aspect.

In particular embodiments, step b) is conducted in solution, in the presence of an ionic compound as defined herein (e.g. $K_2HPO_4$).

As described hereinbefore, in a fourth aspect, the present invention provides a use of a fluorine-containing compound, the fluorine-containing compound being at least one of calcium fluoride and fluorapatite, as a fluorine source in a process for preparing a fluorochemical, wherein the process does not comprise a step of reacting the fluorine-containing compound with sulfuric acid to generate hydrofluoric acid.

As discussed hereinbefore, in a fifth aspect, the present invention provides a use of a fluorine-containing compound, the fluorine-containing compound being at least one of calcium fluoride and fluorapatite, as a fluorine source in a process for preparing a fluorinating reagent, wherein the process does not comprise a step of reacting the fluorine-containing compound with sulfuric acid to generate hydrofluoric acid.

It will be understood that features of the fourth and fifth aspect may have any of those definitions recited hereinbefore in relation to the first, second and third aspects.

According to a sixth aspect of the invention, there is provided a fluorinating reagent obtained, directly obtained or obtainable by a process of the first aspect.

According to a seventh aspect of the invention, there is provided a fluorinating reagent comprising a mixture of inorganic salts.

The sixth and seventh aspects of the invention may be further defined as follows.

The fluorinating reagent may be provided as a mixture of inorganic salts.

The fluorinating reagent (e.g., the mixture of inorganic salts) suitably comprises calcium, fluorine and oxygen, as well as: (i) at least one of potassium and sodium, and (ii) at least one of phosphorus, sulfur, nitrogen and carbon. More suitably, the fluorinating reagent comprises calcium, fluorine and oxygen, as well as: (i) at least one of potassium and sodium, and (ii) at least one of phosphorus, sulfur and carbon. Most suitably, the fluorinating reagent comprises calcium, fluorine, oxygen, potassium and phosphorus. The fluorinating reagent may additionally comprise hydrogen.

The mixture of inorganic salts suitably comprises a first inorganic salt and a second inorganic salt, wherein: (i) the first inorganic salt comprises $Ca^{2+}$ and at least one anion selected from phosphate, sulfate, sulfite, nitrate, carbonate and hydroxide, and (ii) the second inorganic salt comprises fluoride and at least one cation selected from $K^+$ and $Na^{2+}$. Suitably, the first inorganic salt comprises $Ca^{2+}$ and at least one anion selected from phosphate, sulfate, carbonate and hydroxide (e.g., phosphate), and/or the second inorganic salt comprises fluoride and $K^+$. The mixture of inorganic salts may further comprise one or more additional inorganic salts (i.e., in addition to the first and second inorganic salts), each comprising a cation selected from $Ca^{2+}$, $K^+$ and $Na^{2+}$, and an anion selected from fluoride, phosphate, sulfate, sulfite, nitrate, carbonate and hydroxide (e.g., fluoride, phosphate, carbonate and hydroxide).

The fluorinating reagent (e.g., the mixture of inorganic salts) may comprise calcium fluoride and/or fluorapatite. Trace quantities (i.e., those detectable by XRPD) of calcium fluoride and/or fluorapatite, originating from starting materials used in the process of the first aspect, may be present in the fluorinating reagent. Fluorapatite may be present in the fluorinating reagent even when it is not used as the fluorine-containing compound in the process of the first aspect.

The fluorinating reagent may be provided as a powder. The powder may have an average particle size, as determined by SEM or TEM analysis, of <500 μm. Suitably, the powder has an average particle size of <100 μm. More suitably, the powder has an average particle size of <50 μm.

The fluorinating reagent may be characterised by X-ray powder diffraction (XRPD) using Cu Kα1 (λ=1.5406 Å) and/or Cu Kα2 (λ=1.5444 Å). Due to differences in instruments, samples, and sample preparation, peak values are often reported with the modifier "±0.2° 2θ". This is common practice in the solid-state chemical arts because of the variation inherent in peak values.

The fluorinating reagent may have an XRPD pattern comprising peaks corresponding ±0.2° 2θ to at least 10%, at least 30%, at least 50%, at least 70%, at least 90%, or 100% of the 2-theta values reported in any one of Tables 5.7.1-5.7.13, 5.12.1, and 6.3.1-6.3.9, outlined herein. For example, the fluorinating reagent may have an XRPD pattern comprising peaks corresponding ±0.2° 2θ to at least 30% of the 25 2-theta values reported in Table 5.12.1 outlined herein, meaning that the fluorinating reagent may have an XRPD pattern comprising peaks corresponding to at least 8 of those 2-theta values reported in Table 5.12.1 (e.g., those not attributed to $CaF_2$), recognising that each 2-theta value reported in Table 5.12.1 can be modified ±0.2° 2θ. For example, the fluorinating reagent may have an XRPD pattern comprising peaks corresponding ±0.2° 2θ to at least 50% of the 33 2-theta values reported in Table 6.3.3 outlined herein, meaning that the fluorinating reagent may have an XRPD pattern comprising peaks corresponding to at least 17 of those 2-theta values reported in Table 6.3.3, recognising that each 2-theta value reported in Table 5.12.1 can be modified ±0.2° 2θ. Suitably, the fluorinating reagent has an XRPD pattern comprising peaks corresponding ±0.2° 2θ to at least 10%, at least 30%, at least 50%, at least 70%, at least 90%, or 100% of the 2-theta values reported in any one of Tables 5.7.2-5.7.11 and 5.12.1 outlined herein. More suitably, the fluorinating reagent has an XRPD pattern comprising peaks corresponding ±0.2° 2θ to at least 10%, at least 30%, at least 50%, at least 70%, at least 90%, or 100% of the 2-theta values reported in any one of Tables 5.7.7, 5.7.8 and 5.12.1 outlined herein.

The fluorinating reagent may have an XRPD pattern comprising peaks at 2-theta values of 21.9±0.2° 2θ, 30.3±0.2° 2θ, 31.6±0.2° 2θ and 43.4±0.2° 2θ. The XRPD pattern may comprise one or more additional peaks at 2-theta values of 18.0±0.2° 2θ, 18.7±0.2° 2θ, 22.6±0.2° 2θ, 24.5±0.2° 2θ, 25.4±0.2° 2θ, 26.5±0.2° 2θ, 27.0±0.2° 2θ, 28.0±0.2° 2θ, 29.2±0.2° 2θ, 33.0±0.2° 2θ, 34.8±0.2° 2θ, 36.4±0.2° 2θ, 37.7±0.2° 2θ, 39.5±0.2° 2θ, 40.4±0.2° 2θ, 41.7±0.2° 2θ, 42.4±0.2° 2θ, 46.1±0.2° 2θ, 48.4±0.2° 2θ, 49.4±0.2° 2θ, 52.8±0.2° 2θ, and 53.9±0.2° 2θ. The XRPD pattern may comprise peaks at at least five, at least ten, at least fifteen or at least twenty of the aforementioned 2-theta values. The fluorinating reagent may have an XRPD pattern substantially the same as that shown in FIG. 10. Suitably, the fluorinating reagent: (i) comprises calcium, fluorine, oxygen, potassium and phosphorus, and/or (ii) comprises a first inorganic salt and a second inorganic salt, wherein the first inorganic salt comprises $Ca^{2+}$ and phosphate, and the second inorganic salt comprises fluoride and $K^+$.

The fluorinating reagent may have an XRPD pattern comprising one or more peaks at 2-theta values of 17.5±0.2° 2θ, 21.2±0.2° 2θ, 23.5±0.2° 2θ, 24.8±0.2° 2θ, 29.4±0.2° 2θ, 29.6±0.2° 2θ, 30.5±0.2° 2θ, 31.5±0.2° 2θ, 35.4±0.2° 2θ, 36.7±0.2° 2θ, 37.4±0.2° 2θ, 39.8±0.2° 2θ, 42.9±0.2° 2θ, 47.1±0.2° 2θ, 48.1±0.2° 2θ, 51.4±0.2° 2θ, 53.2±0.2° 2θ, 54.2±0.2° 2θ, 58.2±0.2° 2θ, 60.9±0.2° 2θ and 63.4±0.2° 2θ. The XRPD pattern may at least two, at least three, at least four, at least five, at least ten, at least fifteen or at least twenty of the aforementioned 2-theta values.

Figure 26:
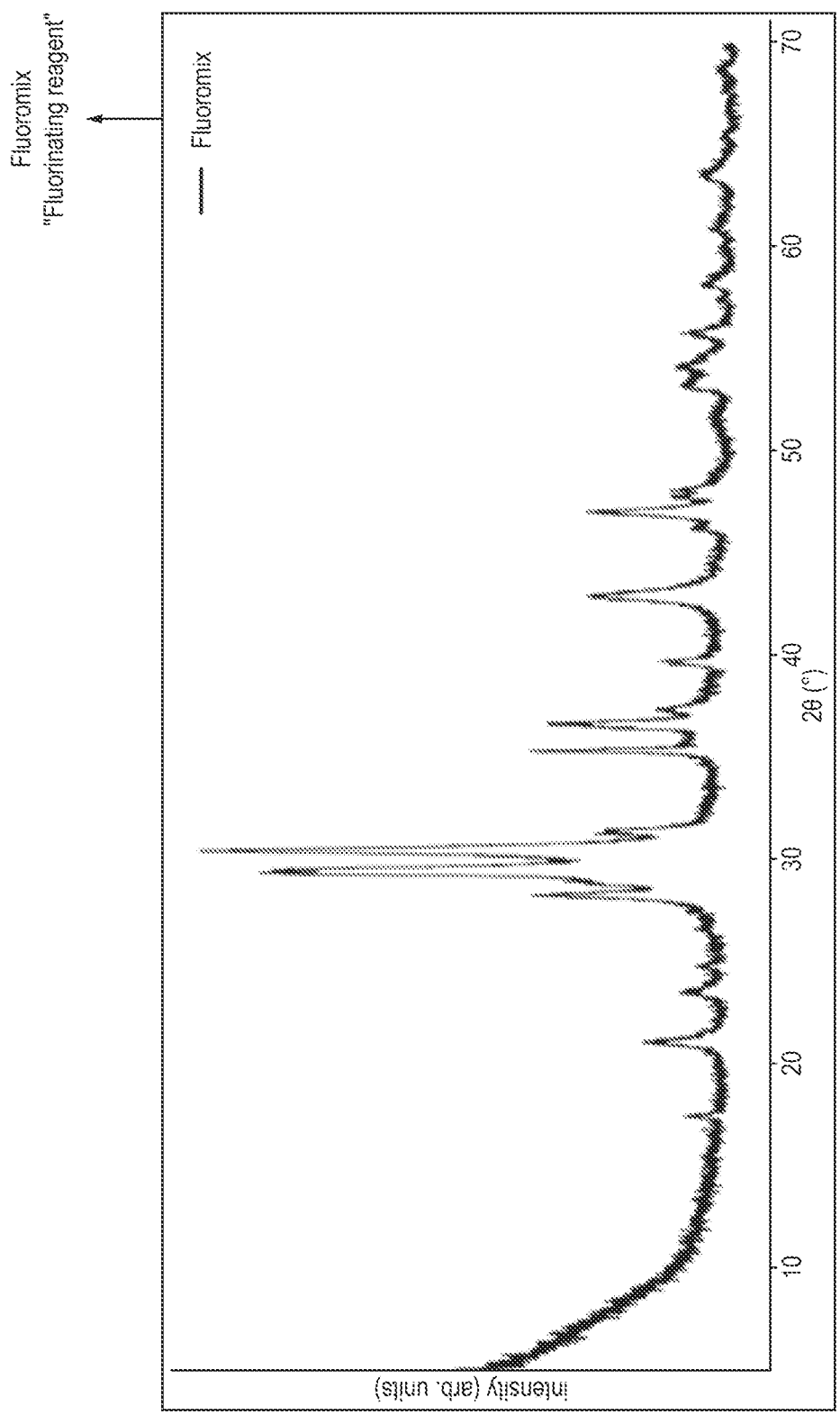
FIG. 26 shows the PXRD diffractogram of the milling product (Fluoromix) of fluorspar reacted with $K_2HPO_4$.

The fluorinating reagent may have an XRPD pattern substantially the same as that shown in FIG. 26. Suitably, the fluorinating reagent: (i) comprises calcium, fluorine, oxygen, potassium and phosphorus, and/or (ii) comprises a first inorganic salt and a second inorganic salt, wherein the first inorganic salt comprises $Ca^{2+}$ and phosphate, and the second inorganic salt comprises fluoride and $K^+$. The fluorinating reagent may comprise $K_3(HPO_4)F$.

The fluorinating reagent may comprise $K_3(HPO_4)F$ and has an XRPD pattern comprising one or more peaks at 2-theta values of 21.1±0.2° 2θ, 29.6±0.2° 2θ, 30.5±0.2° 2θ, 37.4±0.2° 2θ, 42.9±0.2° 2θ, 54.2±0.2° 2θ, 58.2±0.2° 2θ and 60.9±0.2° 2θ. Suitably, the fluorinating reagent comprises at least two, at least three, at least four, at least five, at least six, at least seven, or eight peaks at the aforementioned 2-theta values. More suitably, the fluorinating reagent comprises peaks at all eight of the aforementioned 2-theta values. The fluorinating reagent may further comprise calcium fluoride and/or fluorapatite (e.g., trace quantities of calcium fluoride and/or fluorapatite).

The fluorinating reagent may have an XRPD pattern substantially as shown in any one of FIGS. 4-16, 26, 38-46 and 52-53. Suitably, the fluorinating reagent has an XRPD pattern substantially as shown in any one of FIGS. 10, 11 and 26.

It will be understood that a fluorinating reagent is a reagent which, under those conditions described herein, is able to fluorinate an organic substrate described herein.

The fluorinating reagent of the sixth or seventh aspect may be used in the process of the second aspect. Thus, instead of preparing a fluorinating reagent, step a) of the second aspect may comprise providing a fluorinating reagent of the sixth or seventh aspect.

The following numbered statements 1 to 100 describe particular aspects and embodiments of the invention:

1. A process for the preparation of a fluorinating reagent, the process comprising the step of:
   a) pulverising together a fluorine-containing compound and an ionic compound in the solid state, wherein the fluorine-containing compound is at least one of calcium fluoride and fluorapatite,
   wherein the anion of said ionic compound is combinable with $Ca^{2+}$ to form a calcium salt having a lattice energy that is greater than 2450 KJ $mol^{-1}$.
2. The process of statement 1, wherein the fluorine-containing compound is calcium fluoride.
3. A process for the preparation of a fluorinating reagent, the process comprising the step of:
   a) pulverising together calcium fluoride and an ionic compound in the solid state,
   wherein the anion of said ionic compound is combinable with $Ca^{2+}$ to form a calcium salt having a lattice energy that is greater than 2450 KJ $mol^{-1}$.
4. The process of statement 1, 2 or 3, wherein the anion of said ionic compound is combinable with $Ca^{2+}$ to form a calcium salt having a lattice energy that is greater than 2630 KJ $mol^{-1}$.
5. The process of any one of the preceding statements, wherein the ionic compound is a salt.
6. The process of any one of the preceding statements, wherein the ionic compound is a salt of an oxoacid.
7. The process of any one of the preceding statements, wherein the ionic compound is a phosphate, carbonate, sulphate, sulphite, nitrate, hydroxide or citrate salt.
8. The process of any one of the preceding statements, wherein the ionic compound is a phosphate, carbonate or sulphate salt.
9. The process of any one of the preceding statements, wherein the ionic compound is a phosphate salt.
10. The process of any one of the preceding statements, wherein, the ionic compound is an alkali metal salt or an alkaline earth metal salt.
11. The process of any one of the preceding statements, wherein the ionic compound is a potassium salt, a sodium salt, a calcium salt, a caesium salt or a magnesium salt.
12. The process of any one of the preceding statements, wherein the ionic compound is a potassium salt, a sodium salt or a magnesium salt.
13. The process of any one of the preceding statements, wherein the ionic compound is selected from the group consisting of a phosphate, sulphate or carbonate salt of potassium or sodium.
14. The process of any one of the preceding statements, wherein the ionic compound is a phosphate salt of potassium or sodium.
15. The process of any one of the preceding statements, wherein the ionic compound is a phosphate salt of potassium.
16. The process of statement 1, 2 or 3, wherein the ionic compound is selected from the group consisting of $K_3PO_4$, $K_2HPO_4$, $KH_2PO_4$, $Na_3PO_4$, $Na_2HPO_4$, $KPO_3$, $K_4P_2O_7$, $K_5P_3O_{10}$, $Na_4P_2O_7$, $Na_5P_3O_{10}$, $(NaPO_3)_3$, $CaHPO_4$, $K_2CO_3$, $KHCO_3$, $K_2SO_4$, $KHSO_4$, $Cs_2SO_4$, $MgSO_4$, $Ag_2SO_4$, $K_2S_2O_7$, $Na_2SO_3$, $Na_2SO_4$, $Na_2CO_3$, $KNO_3$, $Na_3C_6H_5O_7$, NaOH and KOH.
17. The process of statement 16, wherein the ionic compound is selected from the group consisting of $K_3PO_4$, $K_2HPO_4$, $KPO_3$, $Na_3PO_4$, $Na_2HPO_4$, $K_4P_2O_7$, $K_5P_3O_{10}$, $Na_4P_2O_7$, $Na_5P_3O_{10}$, $K_2CO_3$, $KHCO_3$, NaOH and KOH.
18. The process of statement 16, wherein the ionic compound is selected from the group consisting of $K_2HPO_4$, $KPO_3$, $Na_2HPO_4$, $K_4P_2O_7$, $K_5P_3O_{10}$ and $Na_4P_2O_7$.
19. The process of statement 1, 2 or 3, wherein the ionic compound is $K_3PO_4$ or $K_2HPO_4$.
20. The process of any one of the preceding statements, wherein >50 wt % of the fluorine-containing compound, the ionic compound, and any reaction products derived therefrom, remain in the solid state throughout step a).
21. The process of any one of the preceding statements, wherein >70 wt % of the fluorine-containing compound, the ionic compound, and any reaction products derived therefrom, remain in the solid state throughout step a).
22. The process of any one of the preceding statements, wherein >90 wt % of the fluorine-containing compound, the ionic compound, and any reaction products derived therefrom, remain in the solid state throughout step a).
23. The process of any one of the preceding statements, wherein >95 wt % of the fluorine-containing compound, the ionic compound, and any reaction products derived therefrom, remain in the solid state throughout step a).
24. The process of any one of the preceding statements, wherein step a) is conducted in the absence of a solvent.
25. The process of any one of the preceding statements, wherein step a) is a mechanochemical process.
26. The process of any one of the preceding statements, wherein step a) is conducted in a ball mill, a pestle and mortar, a twin screw extruder, an ultrasonic bath or a mechanical press.
27. The process of any one of the preceding statements, wherein step a) is conducted in a ball mill, a pestle and mortar or a twin screw extruder.
28. The process of any one of the preceding statements, wherein step a) is conducted in a ball mill.
29. The process of statement 28, wherein the ball mill is a planetary mill, a vibratory mill, an attritor mill or a tumbling ball bill.
30. The process of statement 28, wherein the ball mill is a vibratory mill.
31. The process of statement 28, 29 or 30, wherein step a) comprises ball milling the fluorine-containing compound together with the ionic compound at a frequency of 0.5-80 Hz (e.g., 20-40 Hz).
32. The process of any one of statements 1 to 27, wherein step a) is conducted in a twin screw extruder.
33. The process of statement 32, wherein step a) comprises collecting the product emerging from the twin screw extruder and subjecting it to one or more additional passes through the twin screw extruder.

34. The process of any one of the preceding statements, wherein the molar ratio of the fluorine-containing compound to the ionic compound in step a) is (0.1-7):1 (e.g., (0.3-6):1).
35. The process of any one of the preceding statements, wherein the molar ratio of the fluorine-containing compound to the ionic compound in step a) is (0.5-5):1 (e.g., (1-2):1).
46. The process of any one of the preceding statements, wherein the ionic compound is pulverized together with the fluorine-containing compound in portions.
37. The process of statement 36, wherein step a) comprises: (a-i) pulverising together the fluorine-containing compound and a first portion of the ionic compound, and (a-ii) pulverising together the product of step (a-i) and a second portion of the ionic compound.
38. The process of statement 37, wherein step a) further comprises a step (a-iii) of pulverising together the product of step (a-ii) and a third portion of the ionic compound.
39. The process of statement 38, wherein step a) further comprises a step (a-iv) of pulverising together the product of step (a-iii) and a fourth portion of the ionic compound.
40. The process of any one of the preceding statements, wherein <1 ppm (e.g., <1 ppb) of HF is produced at any point during step a).
41. A process for the preparation of a fluorochemical, the process comprising the steps of:
   a) preparing a fluorinating reagent as described in any one of the preceding statements; and
   b) contacting an organic substrate with the fluorinating reagent,
wherein step b) is conducted simultaneously with, or after, step a).
42. The process of statement 41, wherein the organic substrate is aromatic or aliphatic.
43. The process of statement 41 or 42, wherein the organic substrate comprises at least one leaving group located at the site to be fluorinated.
44. The process of statement 43, wherein the organic substrate has more than one leaving group (e.g., 2 leaving groups), optionally wherein the leaving groups may be attached to the same carbon atom (e.g., 2 geminal halide leaving groups).
45. The process of any one of statements 41 to 44, wherein the organic substrate has a molecular weight of <500 g mol$^{-1}$.
46. The process of statement 45, wherein the organic substrate has a molecular weight of <300 g mol$^{-1}$ (e.g., <200 g mol$^{-1}$).
47. The process of any one of statements 41 to 46, wherein the organic substrate is a sulphonyl halide, an aryl halide, an alkylaryl halide, an acyl halide, an α-halo carbonyl or an alkyl halide.
48 The process of any one of statements 41 to 46, wherein the organic substrate is a sulphonyl halide, an acyl halide, a heteroaryl halide, an aryl halide or an alkyl halide.
49. The process of any one of statements 41 to 46, wherein the organic substrate is an aromatic sulphonyl halide (e.g. tosyl chloride), a benzoyl halide (e.g. 4-methoxybenzoyl chloride) a halobenzene (e.g. chlorobenzene) or a benzyl halide (e.g. benzyl chloride).
50. The process of any one of statements 41 to 49, wherein step b) is conducted simultaneously with step a) and step b) comprises contacting the organic substrate with the fluorinating reagent under identical conditions to those used to form the fluorinating reagent.
51. The process of any one of statements 41 to 49, wherein and step b) is conducted after step a) and step b) comprises pulverising together the organic substrate and the fluorinating reagent formed from step a) in the solid state.
52. The process of any one of statements 41 to 49, wherein step b) is conducted after step a) and step b) comprises mixing together the organic substrate and the fluorinating reagent in one or more solvents in which the organic substrate is soluble.
53. The process of statement 52, wherein step b) is conducted in one or more solvents selected from the group consisting of tetrahydrofuran, 2-methyl tetrahydrofuran, 1, 4-dioxane, diglyme, monoglyme, acetonitrile, propionitrile, tert-butyl isocyanide, tert-butanol, tert-amyl alcohol, toluene, m-xylene, hexane, trifluorotoluene, 1,2-difluorobenzene, 1,2-dichlorobenzene, 1,3-dichlorobenzene, fluorobenzene and chlorobenzene.
54. The process of statement 52, wherein step b) is conducted in a one or more solvents selected from the group consisting of acetonitrile, propionitrile, toluene, 1,2-dichlorobenzene, chlorobenzene, fluorobenzene, 1,2-difluorobenzene, dichloroethane, trifluorotoluene, chloroform, tert-butanol, tert-amyl alcohol and water.
55. The process of statement 52, wherein step b) is conducted in one or more solvents selected from the group consisting of acetonitrile, propionitrile, toluene, chlorobenzene, 1,2-difluorobenzene, dichloroethane, trifluorotoluene, chloroform, tert-butanol and tert-amyl alcohol.
56. The process of statement 52, wherein step b) is conducted in acetonitrile, propionitrile, chlorobenzene, tert-butanol or tert-amyl alcohol.
57. The process of any one of statements 53 to 56, wherein any one or more of the organic solvents are in admixture with water.
58. The process of statement 57, wherein the organic solvent may be in admixture with water at a concentration of 0.01-5M (e.g., 0.01-1 M, such as 0.05-0.5M).
59. The process of any one of statements 41 to 58, wherein step b) is conducted in the presence of at least one of a cryptand, a crown ether and a hydrogen-bonding phase transfer catalyst.
60. The process of statement 59, wherein step b) is conducted in the presence of a crown ether.
61. The process of 60, wherein the crown ether is 18-crown-6 or dibenzo-18-crown-6.
62. The process of any one of statements 52 to 61, wherein step b) is conducted at a temperature of 15-180° C.
63. A process for the preparation of a fluorochemical, the process comprising the steps of:
   a) pulverising a fluorine-containing compound in the solid state, wherein the fluorine-containing compound is at least one of calcium fluoride and fluorapatite; and
   b) contacting the product of step a) with an organic substrate;
wherein step b) is conducted simultaneously with, or after, step a).

64. A process for the preparation of a fluorochemical, the process comprising the steps of:
   a) pulverising a calcium fluoride in the solid state; and
   b) contacting the product of step a) with an organic substrate;
wherein step b) is conducted simultaneously with, or after, step a).

65. The process of statement 63 or 64, wherein step b) is conducted in solution, in the presence of an ionic compound as described herein (e.g., $K_2HPO_4$).

66. Use of a fluorine-containing compound, the fluorine-containing compound being at least one of calcium fluoride and fluorapatite, as a fluorine source in a process for preparing a fluorochemical or a fluorinating reagent, wherein the process does not comprise a step of reacting the calcium fluoride with sulfuric acid to generate hydrofluoric acid.

67. Use of calcium fluoride as a fluorine source in a process for preparing a fluorochemical, wherein the process does not comprise a step of reacting the calcium fluoride with sulfuric acid to generate hydrofluoric acid.

68. A fluorinating reagent obtained, directly obtained or obtainable by the process of any one of statements 1 to 40.

69. A fluorinating reagent comprising a mixture of inorganic salts.

70. The fluorinating reagent of statement 68, wherein the fluorinating reagent comprises a mixture of inorganic salts.

71. The fluorinating reagent of statement 68, 69 or 70, wherein the fluorinating reagent comprises calcium, fluorine and oxygen, as well as: (i) at least one of potassium and sodium, and (ii) at least one of phosphorus, sulfur, nitrogen and carbon.

72. The fluorinating reagent of statement 68, 69 or 70, wherein the fluorinating reagent comprises calcium, fluorine and oxygen, as well as: (i) at least one of potassium and sodium, and (ii) at least one of phosphorus, sulfur and carbon.

73. The fluorinating reagent of statement 68, 69 or 70, wherein the fluorinating reagent comprises calcium, fluorine, oxygen, potassium and phosphorus.

74. The fluorinating reagent of any one of statements 68 to 73, wherein the fluorinating reagent comprises a mixture of inorganic salts, the mixture comprising a first inorganic salt and a second inorganic salt, wherein: (i) the first inorganic salt comprises $Ca^{2+}$ and at least one anion selected from phosphate, sulfate, sulfite, nitrate, carbonate and hydroxide, and (ii) the second inorganic salt comprises fluoride and at least one cation selected from $K^+$ and $Na^{2+}$.

75. The fluorinating reagent of statement 74, wherein the first inorganic salt comprises $Ca^{2+}$ and at least one anion selected from phosphate, sulfate, carbonate and hydroxide (e.g., phosphate), and/or the second inorganic salt comprises fluoride and $K^+$.

76. The fluorinating reagent of any one of statements 68 to 75, wherein the fluorinating reagent is provided as a powder.

77. The fluorinating reagent of statements 76, wherein the powder has an average particle size, as determined by SEM or TEM analysis, of <500 μm (e.g., <100 μm).

78. The fluorinating reagent of any one of statements 68 to 77, wherein the fluorinating reagent has an XRPD pattern comprising peaks corresponding ±0.2° 2θ to at least 10%, at least 30%, at least 50%, at least 70%, at least 90%, or 100% of the 2-theta values reported in any one of Tables 5.7.1-5.7.13, 5.12.1, and 6.3.1-6.3.9, outlined herein.

79. The fluorinating reagent of any one of statements 68 to 77, wherein the fluorinating reagent has an XRPD pattern comprising peaks corresponding ±0.2° 2θ to at least 10%, at least 30%, at least 50%, at least 70%, at least 90%, or 100% of the 2-theta values reported in any one of Tables 5.7.2-5.7.11 and 5.12.1 outlined herein.

80. The fluorinating reagent of any one of statements 68 to 77, wherein the fluorinating reagent has an XRPD pattern comprising peaks corresponding ±0.2° 2θ to at least 10%, at least 30%, at least 50%, at least 70%, at least 90%, or 100% of the 2-theta values reported in any one of Tables 5.7.7, 5.7.8 and 5.12.1 outlined herein.

81. The fluorinating reagent of any one of statements 68 to 77, wherein the fluorinating reagent has an XRPD pattern comprising peaks at 2-theta values of 21.9±0.2° 2θ, 30.3±0.2° 2θ, 31.6±0.2° 2θ and 43.4±0.2° 2θ.

82. The fluorinating reagent of statement 81, wherein the XRPD pattern comprises one or more additional peaks at 2-theta values of 18.0±0.2° 2θ, 18.7±0.2° 2θ, 22.6±0.2° 2θ, 24.5±0.2° 2θ, 25.4±0.2° 2θ, 26.5±0.2° 2θ, 27.0±0.2° 2θ, 28.0±0.2° 2θ, 29.2±0.2° 2θ, 33.0±0.2° 2θ, 34.8±0.2° 2θ, 36.4±0.2° 2θ, 37.7±0.2° 2θ, 39.5±0.2° 2θ, 40.4±0.2° 2θ, 41.7±0.2° 2θ, 42.4±0.2° 2θ, 46.1±0.2° 2θ, 48.4±0.2° 2θ, 49.4±0.2° 2θ, 52.8±0.2° 2θ, and 53.9±0.2° 2θ.

83. The fluorinating reagent of statement 82, wherein the XRPD pattern comprises at least five of the additional peaks.

84. The fluorinating reagent of statement 82, wherein the XRPD pattern comprises at least ten of the additional peaks.

85. The fluorinating reagent of statement 82, wherein the XRPD pattern comprises at least fifteen of the additional peaks.

86. The fluorinating reagent of statement 82, wherein the XRPD pattern comprises at least twenty of the additional peaks.

87. The fluorinating reagent of any one of statements 68 to 77, wherein the fluorinating reagent may have an XRPD pattern comprising one or more peaks at 2-theta values of 17.5±0.2° 2θ, 21.2±0.2° 2θ, 23.5±0.2° 2θ, 24.8±0.2° 2θ, 29.4±0.2° 2θ, 29.6±0.2° 2θ, 30.5±0.2° 2θ, 31.5±0.2° 2θ, 35.4±0.2° 2θ, 36.7±0.2° 2θ, 37.4±0.2° 2θ, 39.8±0.2° 2θ, 42.9±0.2° 2θ, 47.1±0.2° 2θ, 48.1±0.2° 2θ, 51.4±0.2° 2θ, 53.2±0.2° 2θ, 54.2±0.2° 2θ, 58.2±0.2° 2θ, 60.9±0.2° 2θ and 63.4±0.2° 2θ.

88. The fluorinating reagent of statement 87, wherein the XRPD pattern comprises at least two or at least three of the peaks.

89. The fluorinating reagent of statement 87, wherein the XRPD pattern comprises at least four or at least five of the peaks.

90. The fluorinating reagent of statement 87, wherein the XRPD pattern comprises at least ten or at least fifteen of the peaks.

91. The fluorinating reagent of statement 87, wherein the XRPD pattern comprises at least twenty of the peaks.

92. The fluorinating reagent of any one of statements 87 to 91, wherein the fluorinating reagent comprises $K_3(HPO_4)F$.

93. The fluorinating reagent of any one of statements 68 to 77, wherein the fluorinating reagent comprises K$_3$(HPO$_4$)F and one or more peaks at 2-theta values of 21.1±0.2° 2θ, 29.6±0.2° 2θ, 30.5±0.2° 2θ, 37.4±0.2° 2θ, 42.9±0.2° 2θ, 54.2±0.2° 2θ, 58.2±0.2° 2θ and 60.9±0.2° 2θ. 94. The fluorinating reagent of statement 93, wherein the fluorinating reagent has an XRPD pattern comprising at least two of the peaks.
95. The fluorinating reagent of statement 93, wherein the fluorinating reagent has an XRPD pattern comprising at least four of the peaks.
96. The fluorinating reagent of statement 93, wherein the fluorinating reagent has an XRPD pattern comprising at least six of the peaks.
97. The fluorinating reagent of statement 93, wherein the fluorinating reagent has an XRPD pattern comprising all eight of the peaks.
98. The fluorinating reagent of any one of statements 68 to 97, wherein the fluorinating reagent comprises calcium fluoride and/or fluorapatite (e.g., a trace quantity of calcium fluoride and/or fluorapatite).
99. The fluorinating reagent of any one of statements 68 to 98, wherein the fluorinating reagent has an XRPD pattern substantially as shown in any one of FIGS. 4-16, 26, 38-46 and 52-53.
100. The fluorinating reagent of any one of statements 68 to 98, wherein the fluorinating reagent has an XRPD pattern substantially as shown in any one of FIGS. 10, 11 and 26.

In some embodiments, provided herein is an activated fluorinated reagent. In some embodiments, the activated fluorinated reagent comprises a first salt, the first salt comprising calcium and fluorine, and a second salt. In some embodiments, the second salt comprises an anion. The first salt and second salt are described elsewhere herein.

In some embodiments, provided herein is a method of synthesizing a fluoro compound. In some embodiments, provided herein is a method of synthesizing an organofluorine compound. In some embodiments, the method comprises combining a first salt, the first salt comprising calcium and fluorine, with a second salt to form a salt mixture.

Provided herein, in some embodiments, are compositions and methods that use a first salt. In any composition or method provided herein, any suitable first salt is used. In some embodiments, the first salt comprises calcium and fluorine. In some embodiments, the first salt comprises fluorine. In some embodiments, the first salt comprises calcium. In some embodiments, the first salt is CaF$_2$. In some embodiments, the first salt is fluorspar. In some embodiments, the first salt is fluorapatite (Ca$_5$(PO$_4$)$_3$F). In some embodiments, waste material comprises the first salt. In some embodiments, the first salt is added in an amount necessary to provide an activated fluorination reagent.

In some embodiments, the methods and compositions described herein do not comprise reacting a strong acid with the first salt to form hydrofluoric acid. In some embodiments, essentially no HF is produced during the reaction. In some embodiments, <1 ppm of HF is observable in a mixture at any point during the reaction. In some embodiments, <1 ppb of HF is observable in a mixture at any point during the reaction.

In some embodiments, provided herein are compositions and methods that use a second salt. In some embodiments, any suitable second salt is used in any composition or method provided herein. In some embodiments, the second salt comprises an anion. In some embodiments, the second salt comprises an anion, which has a lattice energy greater than 2450 kJ/mol when combined with Ca$^{2+}$ to form a third salt. In some embodiments, the second salt comprises a cation and anion.

In some embodiments, any composition or method herein comprises a second salt, the second salt comprising an anion, which has a lattice energy greater than 2450 kJ/mol when combined with Ca$^{2+}$ to form a third salt. In some embodiments, the anion and Ca$^{2+}$ can form a third salt which has a lattice energy greater than 2450 kJ/mol when combined. In some embodiments, the fluorinating reagent comprises a salt which has a lattice energy greater than 2450 kJ/mol.

In some embodiments, the second salt is a metal hydroxide. In some embodiments, the second salt is NaOH and/or KOH. In some embodiments, the second salt is NaOH. In some embodiments the second salt is KOH. In some embodiments, the second salt is a metal sulphite.

In some embodiments, the second salt comprises Na$_2$SO$_3$ and/or K$_2$SO$_3$. In some embodiments, the second salt is Na$_2$SO$_3$. In some embodiments, the second salt is K$_2$SO$_3$. In some embodiments, the second salt is a metal sulphate. In some embodiments, the second salt comprises KHSO$_4$. In some embodiments, the second salt is an inorganic phosphate.

In some embodiments, the second salt comprises K$_2$HPO$_4$, KH$_2$PO$_4$, and/or K$_3$PO$_4$. In some embodiments, the second salt is K$_2$HPO$_4$. In some embodiments, the second salt is KH$_2$PO$_4$. In some embodiments, the second salt is K$_3$PO$_4$. In some embodiments, the inorganic phosphate is a pyrophosphate. In some embodiments, the inorganic phosphate comprises K$_4$P$_2$O$_7$ and/or Na$_3$P$_2$O$_7$.

In some embodiments, an inorganic phosphate is K$_4$P$_2$O$_7$. In some embodiments, an inorganic phosphate is Na$_3$P$_2$O$_7$. In some embodiments, the second salt is Na$_3$PO$_4$, Na$_2$HPO$_4$, NaH$_2$PO$_4$, K$_2$SO$_4$, Na$_2$SO$_4$, MgSO$_4$, Ag$_2$SO$_4$, Na$_2$CO$_3$, and/or KHCO$_3$. In some embodiments, the second salt comprises Na$_3$PO$_4$. In some embodiments, the second salt comprises Na$_2$HPO$_4$. In some embodiments, the second salt comprises NaH$_2$PO$_4$.

In some embodiments, the second salt comprises K$_2$SO$_4$. In some embodiments, the second salt comprises Na$_2$SO$_4$. In some embodiments, the second salt comprises MgSO$_4$. In some embodiments, the second salt comprises Ag$_2$SO$_4$. In some embodiments, the second salt comprises Na$_2$CO$_3$. In some embodiments, the second salt comprises KHCO$_3$.

In some embodiments, any suitable ratio of first salt to second is used in any composition or method provided herein. In some embodiments, any suitable ratio of first salt to second is used in any composition or method provided herein. In some embodiments, the ratio of the first salt to the second salt is about 1:0.5 to 1:150 or any range therein. In some embodiments, the ratio of first salt to second salt is about 2:1 to 150:1 or any range therein. In some embodiments, the ratio of the first salt to the second salt is about 1:0.5 to 1:100. In some embodiments, the ratio of the first salt to the second salt is about 1:1 to 1:10. In some embodiments, the ratio of first salt to second salt is about 1:0.5 to 1:2. In some embodiments, the ratio of first salt to second salt is about 1:0.5 to 1:4. In some embodiments, the ratio of first salt to second salt is about 1:0.5 to 1:8. In some embodiments, the ratio of first salt to second salt is about 1:0.5 to 1:10. In some embodiments, the ratio of first salt to second salt is about 1:0.5 to 1:20. In some embodiments, the ratio of the first salt to the second salt is about 1:1 to 1:5. In some embodiments, the ratio of the first salt to the second salt is about 1:0.5, 1:1, 1:2, 1:3, 1:4, 1:5, 1:6, 1:7, 1:8, 1:9, 1:10, 1:15, 1:20, 1:25, 1:30, 1:40, 1:50, 1:60, 1:70, 1:80, 1:90, or 1:100. In some embodiments, the range of first salt to second salt is about 1:2, 1:1, 2:1, 3:1, 4:1, 5:1, 6:1, 7:1, 8:1, 9:1, 10:1, 15:1, 20:1, 25:1, 30:1, 40:1, 50:1, 60:1, 70:1, 80:1, 90:1, or 100:1. In some embodiments, the ratio of the first salt to the second salt is about 1:1. In some embodiments, the ratio of the first salt to the second salt is about 1:2. In some embodiments, the ratio of the first salt to the second salt is about 1:3. In some embodiments, the ratio of the first salt to the second salt is about 1:5. In some embodiments, the range of first salt to second salt is 1:8. In some embodiments, the ratio of first salt to second salt is 2:1.

In some embodiments, the method comprises applying mechanical force to the salt mixture to form an activated salt-mixture. In some embodiments, the activated salt mixture is the fluorinating reagent. In some embodiments, the activated salt mixture is the activated fluorinated reagent.

In some embodiments, mechanical force is applied to the salt mixtures provided in any of the compositions or methods herein. In some embodiments, mechanical force is applied to the salt-waste mixtures provided herein. In some embodiments, mechanical force is applied to the salt mixtures provided herein to yield activated fluorinated reagents.

In some embodiments, mechanical force is applied to the salt-waste mixtures provided herein to yield activated fluorinated reagents. In some embodiments, the mechanical force is applied using a ball mill, a mortar and pestle, a twin-screw extruder, using an ultrasonic bath, or a mechanical press.

In some embodiments, the mechanical force is applied using a ball mill. In some embodiments, the mechanical force is applied using a mortar and pestle. In some embodiments, the mechanical force is applied using a twin-screw extruder. In some embodiments, the mechanical force is applied using an ultrasonic bath. In some embodiments, the mechanical force is applied using a mechanical press.

In some embodiments, mechanical frequency is applied at any suitable frequency in any composition or method provided herein. In some embodiments, the mechanical force is applied at a frequency of about 0.5 Hz-60 kHz or any range therein. In some embodiments, the mechanical force is applied at a frequency of about 0.5 Hz-60 kHz. In some embodiments, the mechanical force is applied at a frequency of about 0.5 Hz-10 Hz. In some embodiments, the mechanical force is applied at a frequency of about 0.5 Hz-100 Hz. In some embodiments, the mechanical force is applied at a frequency of about 0.5-1 kHz. In some embodiments, the mechanical force is applied at a frequency of about 0.5-10 kHz. In some embodiments, the mechanical force is applied at a frequency of about 0.5-20 kHz. In some embodiments, the mechanical force is applied at a frequency of about 0.5-30 kHz. In some embodiments, the mechanical force is applied at a frequency of about 0.5-50 kHz. In some embodiments, the mechanical force is applied at a frequency of about 0.5-60 kHz. In some embodiments, the mechanical force is applied at a frequency of about 10 Hz-20 kHz. In some embodiments, the mechanical force is applied at a frequency of about 0.5 Hz, 1 Hz, 5 Hz, 10 Hz, 15 Hz, 20 Hz, 25 Hz, 30 Hz, 35 Hz, 40 Hz, 45 Hz, 50 Hz, 55 Hz, or 60 Hz. In some embodiments, the mechanical force is applied at a frequency of about 1 kHz, 5 kHz, 10 kHz, 15 kHz, 20 kHz, 25 kHz, 30 kHz, 35 kHz, 40 kHz, 45 kHz, 50 kHz, 55 kHz, or 60 kHz. In some embodiments, the mechanical force is applied at a frequency of about 30 Hz. In some embodiments, the mechanical force is applied at a frequency of about 35 Hz. In some embodiments, the mechanical force is applied at a frequency of about 60 Hz.

In some embodiments, the mechanical frequency is applied at any suitable temperature in any composition or method provided herein. In some embodiments, the mechanical force is applied at a temperature of about 20° C. to about 300° C. In some embodiments, the mechanical force is applied at a temperature of about 20° C. to about 30° C., about 20° C. to about 40° C., about 20° C. to about 60° C., about 20° C. to about 90° C., about 20° C. to about 100° C., about 20° C. to about 130° C., about 20° C. to about 150° C., about 20° C. to about 200° C., about 20° C. to about 250° C., about 20° C. to about 280° C., about 20° C. to about 300° C., about 30° C. to about 40° C., about 30° C. to about 60° C., about 30° C. to about 90° C., about 30° C. to about 100° C., about 30° C. to about 130° C., about 30° C. to about 150° C., about 30° C. to about 200° C., about 30° C. to about 250° C., about 30° C. to about 280° C., about 30° C. to about 300° C., about 40° C. to about 60° C., about 40° C. to about 90° C., about 40° C. to about 100° C., about 40° C. to about 130° C., about 40° C. to about 150° C., about 40° C. to about 200° C., about 40° C. to about 250° C., about 40° C. to about 280° C., about 40° C. to about 300° C., about 60° C. to about 90° C., about 60° C. to about 100° C., about 60° C. to about 130° C., about 60° C. to about 150° C., about 60° C. to about 200° C., about 60° C. to about 250° C., about 60° C. to about 280° C., about 60° C. to about 300° C., about 90° C. to about 100° C., about 90° C. to about 130° C., about 90° C. to about 150° C., about 90° C. to about 200° C., about 90° C. to about 250° C., about 90° C. to about 280° C., about 90° C. to about 300° C., about 100° C. to about 130° C., about 100° C. to about 150° C., about 100° C. to about 200° C., about 100° C. to about 250° C., about 100° C. to about 280° C., about 100° C. to about 300° C., about 130° C. to about 150° C., about 130° C. to about 200° C., about 130° C. to about 250° C., about 130° C. to about 280° C., about 130° C. to about 300° C., about 150° C. to about 200° C., about 150° C. to about 250° C., about 150° C. to about 280° C., about 150° C. to about 300° C., about 200° C. to about 250° C., about 200° C. to about 280° C., about 200° C. to about 300° C., about 250° C. to about 280° C., about 250° C. to about 300° C., or about 280° C. to about 300° C. In some embodiments, the mechanical force is applied at a temperature of about 20° C., about 30° C., about 40° C., about 60° C., about 90° C., about 100° C., about 130° C., about 150° C., about 200° C., about 250° C., about 280° C., or about 300° C. In some embodiments, the mechanical force is applied at a temperature of at least about 20° C., about 30° C., about 40° C., about 60° C., about 90° C., about 100° C., about 130° C., about 150° C., about 200° C., about 250° C., or about 280° C. In some embodiments, the mechanical force is applied at a temperature of at most about 30° C., about 40° C., about 60° C., about 90° C., about 100° C., about 130° C., about 150° C., about 200° C., about 250° C., about 280° C., or about 300° C. In some embodiments, the mechanical force is applied at a temperature of about 30° C. In some embodiments, the mechanical force is applied at a temperature of about 60° C. In some embodiments, the mechanical force is applied at a temperature of about 90° C.

In any of the compositions or methods provided herein, the mechanical force may be applied to the first and second salt together. In any of the compositions or methods provided herein, the mechanical force may be applied to the first salt alone. In some embodiments, the mechanical force may be applied for any suitable time period.

In some embodiments, the mechanical force may be applied for about 0.5 hours to about 12 hours. In some embodiments, the mechanical force may be applied for 0.5-1 hour. In some embodiments, the mechanical force may be applied for 0.5-4 hours. In some embodiments, the mechanical force may be applied for 0.5-8 hours. In some embodiments, the mechanical force may be applied for 4-8 hours. In some embodiments, the mechanical force may be applied for 4-12 hours. In some embodiments, the mechanical force may be applied for about 0.5, 1, 2, 3, 4, 5, 6, 7, 8, 9, 10, 11, or 12 hours. In some embodiments, the mechanical force is applied for about 1 hour. In some embodiments, the mechanical force is applied for about 2 hours. In some embodiments, the mechanical force is applied for about 3 hours. In some embodiments, the mechanical force is applied for about 4 hours. In some embodiments, the mechanical force is applied for about 6 hours. In some embodiments, the mechanical force is applied for about 9 hours. In some embodiments, longer mechanical force times may be associated with higher yields of fluorinated product.

In some embodiments, provided herein are salt mixtures produced by ball milling in any composition or method provided herein. In some embodiments, ball milling is completed by combining said salts into jars and adding balls. In some embodiments, the jars and balls comprise stainless steel.

In some embodiments, the jar has a volume of 15 mL. In some embodiments, the jar has a volume of 30 mL. In some embodiments, multiple balls are used. In some embodiments, 2-20 balls are used. In some embodiments, 1 ball is used. In some embodiments, the ball weight is 1-20 g or any range therein. In some embodiments, the ball weight is 1-2 g. In some embodiments, the ball weight is 1-3 g. In some embodiments, the ball weight is 1-5 g. In some embodiments, the ball weight is 1-10 g. In some embodiments, the ball weight is 1-13 g. In some embodiments, the ball weight is 1-18 g. In some embodiments, the ball weight is 1-3 g. In some embodiments, the ball weight is 3-5 g. In some embodiments, the ball weight is 3-10 g. In some embodiments, the ball weight is 5-10 g. In some embodiments, the ball weight is 5-18 g. In some embodiments, the ball weight is 5-20 g. In some embodiments, the ball weight is about 1, 2, 3, 4, 5, 6, 7, 8, 9, 10, 11, 12, 13, 14, 15, 16, 17, 18, 19, or 20 g. In some embodiments, the ball weight is 2 g. In some embodiments, the ball weight is 3 g. In some embodiments, the ball weight is 4 g. In some embodiments, the ball weight is 7 g. In some embodiments, the ball weight is 9 g. In some embodiments, 2 balls were used and the ball weights were 3 g. In some embodiments, the ball weight is 16 g. In some instances, ball weight is used as an analog of ball size. In some embodiments, the ball size may affect the fluorination reaction yield.

Figure 54:
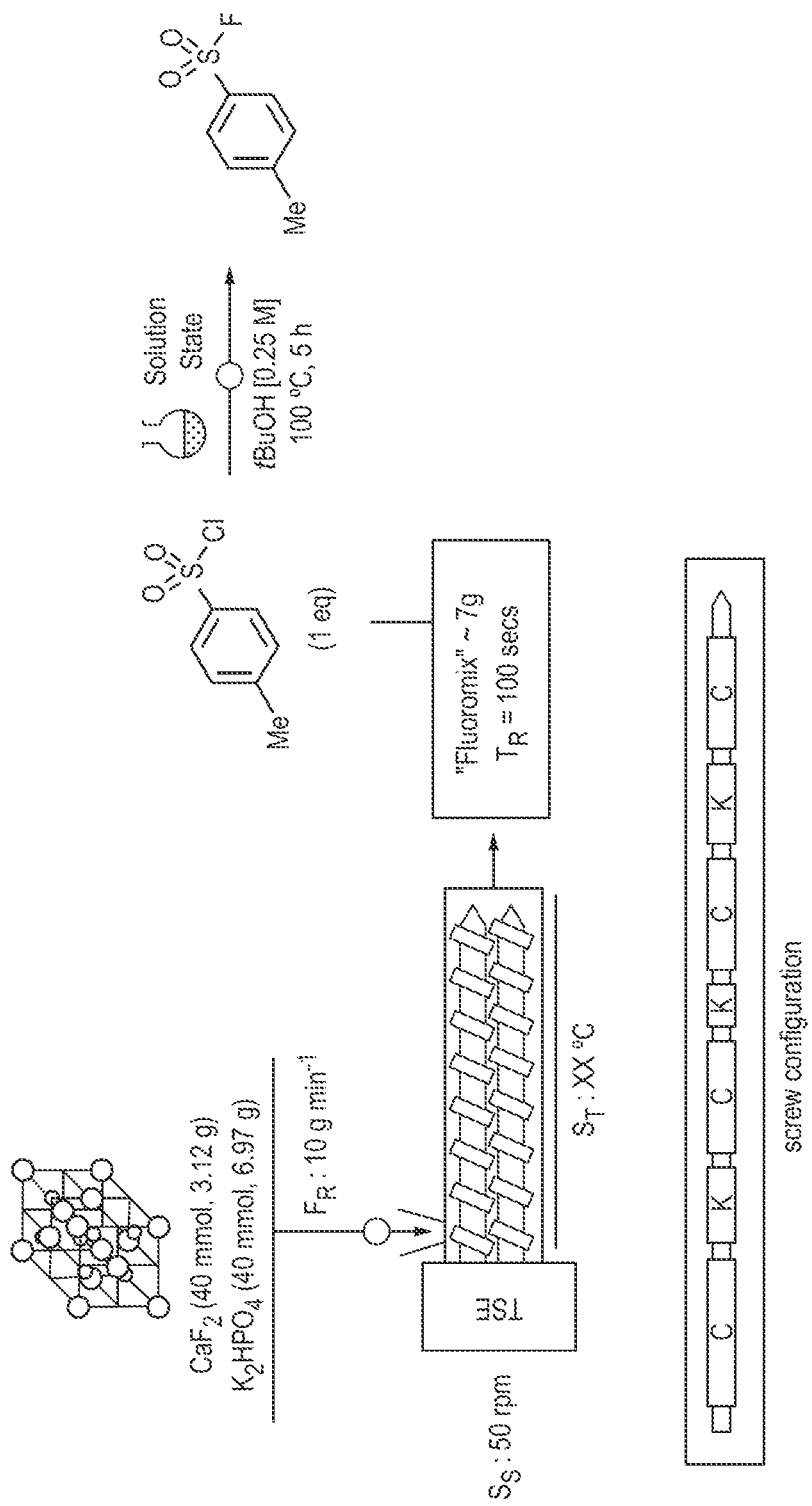
FIG. 54 shows a general scheme for which the effect of the variation of screw temperature on the generation of active fluorination material was tested.

In some embodiments, mechanical force is applied in the compositions or methods herein using a twin-screw extruder. In some embodiments, a twin-screw extruder may be fixed with a gravimetric single screw feeder (e.g., hopper) for programmed addition of solids. FIG. 54 shows a schematic of a twin-screw extruder (TSE) wherein the first and second salts may be added into the TSE at a rate of $F_R$, followed by extruding of the salts at varying screw speeds ($S_s$), screw temperatures ($S_T$), and residence times ($T_R$), providing the fluorinating reagent (e.g., fluoromix). In some embodiments, the screw configuration may be modified wherein C indicates conveying, K indicates kneading, and R indicates reverse elements.

In some embodiments, the screw temperature ($S_T$) in a twin-screw extruder is applied at any suitable temperature in any composition or method provided herein. In some embodiments, the screw temperature is about 0° C. to about 300° C. In some embodiments, the screw temperature is about 0° C. to about 25° C., about 0° C. to about 50° C., about 0° C. to about 100° C., about 0° C. to about 150° C., about 0° C. to about 200° C., about 0° C. to about 250° C., about 0° C. to about 300° C., about 25° C. to about 50° C., about 25° C. to about 100° C., about 25° C. to about 150° C., about 25° C. to about 200° C., about 25° C. to about 250° C., about 25° C. to about 300° C., about 50° C. to about 100° C., about 50° C. to about 150° C., about 50° C. to about 200° C., about 50° C. to about 250° C., about 50° C. to about 300° C., about 100° C. to about 150° C., about 100° C. to about 200° C., about 100° C. to about 250° C., about 100° C. to about 300° C., about 150° C. to about 200° C., about 150° C. to about 250° C., about 150° C. to about 300° C., about 200° C. to about 250° C., about 200° C. to about 300° C., or about 250° C. to about 300° C. In some embodiments, the screw temperature is about 0° C., about 25° C., about 50° C., about 100° C., about 150° C., about 200° C., about 250° C., or about 300° C. In some embodiments, the screw temperature is 50° C. In some embodiments, the screw temperature is 100° C. In some embodiments, the screw temperature is 150° C. In some embodiments, the screw temperature is 200° C.

In some embodiments, the screw speed ($S_s$) in a twin-screw extruder is applied at any suitable speed in any composition or method provided herein. In some embodiments, the screw speed is set at a range of about 1 rpm to about 80 rpm. In some embodiments, the screw speed is set at a range of about 1 rpm to about 5 rpm, about 1 rpm to about 10 rpm, about 1 rpm to about 15 rpm, about 1 rpm to about 25 rpm, about 1 rpm to about 40 rpm, about 1 rpm to about 50 rpm, about 1 rpm to about 60 rpm, about 1 rpm to about 70 rpm, about 1 rpm to about 75 rpm, about 1 rpm to about 80 rpm, about 5 rpm to about 10 rpm, about 5 rpm to about 15 rpm, about 5 rpm to about 25 rpm, about 5 rpm to about 40 rpm, about 5 rpm to about 50 rpm, about 5 rpm to about 60 rpm, about 5 rpm to about 70 rpm, about 5 rpm to about 75 rpm, about 5 rpm to about 80 rpm, about 10 rpm to about 15 rpm, about 10 rpm to about 25 rpm, about 10 rpm to about 40 rpm, about 10 rpm to about 50 rpm, about 10 rpm to about 60 rpm, about 10 rpm to about 70 rpm, about 10 rpm to about 75 rpm, about 10 rpm to about 80 rpm, about 15 rpm to about 25 rpm, about 15 rpm to about 40 rpm, about 15 rpm to about 50 rpm, about 15 rpm to about 60 rpm, about 15 rpm to about 70 rpm, about 15 rpm to about 75 rpm, about 15 rpm to about 80 rpm, about 25 rpm to about 40 rpm, about 25 rpm to about 50 rpm, about 25 rpm to about 60 rpm, about 25 rpm to about 70 rpm, about 25 rpm to about 75 rpm, about 25 rpm to about 80 rpm, about 40 rpm to about 50 rpm, about 40 rpm to about 60 rpm, about 40 rpm to about 70 rpm, about 40 rpm to about 75 rpm, about 40 rpm to about 80 rpm, about 50 rpm to about 60 rpm, about 50 rpm to about 70 rpm, about 50 rpm to about 75 rpm, about 50 rpm to about 80 rpm, about 60 rpm to about 70 rpm, about 60 rpm to about 75 rpm, about 60 rpm to about 80 rpm, about 70 rpm to about 75 rpm, about 70 rpm to about 80 rpm, or about 75 rpm to about 80 rpm. In some embodiments, the screw speed is set at a range of about 1 rpm, about 5 rpm, about 10 rpm, about 15 rpm, about 25 rpm, about 40 rpm, about 50 rpm, about 60 rpm, about 70 rpm, about 75 rpm, or about 80 rpm. In some embodiments, the screw speed is 10 rpm. In some embodiments, the screw speed is 25 rpm. In some embodiments, the screw speed is 75 rpm.

In some embodiments, the residence time ($T_R$) in a twin-screw extruder is set to any suitable time in any composition or method provided herein. In some embodiments, the residence time is about 1 seconds to about 420 seconds. In some embodiments, the residence time is about 1 seconds to about 20 seconds, about 1 seconds to about 40 seconds, about 1 seconds to about 60 seconds, about 1 seconds to about 80 seconds, about 1 seconds to about 120 seconds, about 1 seconds to about 140 seconds, about 1 seconds to about 165 seconds, about 1 seconds to about 220 seconds, about 1 seconds to about 300 seconds, about 1 seconds to about 420 seconds, about 20 seconds to about 40 seconds, about 20 seconds to about 60 seconds, about 20 seconds to about 80 seconds, about 20 seconds to about 120 seconds, about 20 seconds to about 140 seconds, about 20 seconds to about 165 seconds, about 20 seconds to about 220 seconds, about 20 seconds to about 300 seconds, about 20 seconds to about 420 seconds, about 40 seconds to about 60 seconds, about 40 seconds to about 80 seconds, about 40 seconds to about 120 seconds, about 40 seconds to about 140 seconds, about 40 seconds to about 165 seconds, about 40 seconds to about 220 seconds, about 40 seconds to about 300 seconds, about 40 seconds to about 420 seconds, about 60 seconds to about 80 seconds, about 60 seconds to about 120 seconds, about 60 seconds to about 140 seconds, about 60 seconds to about 165 seconds, about 60 seconds to about 220 seconds, about 60 seconds to about 300 seconds, about 60 seconds to about 420 seconds, about 80 seconds to about 120 seconds, about 80 seconds to about 140 seconds, about 80 seconds to about 165 seconds, about 80 seconds to about 220 seconds, about 80 seconds to about 300 seconds, about 80 seconds to about 420 seconds, about 120 seconds to about 140 seconds, about 120 seconds to about 165 seconds, about 120 seconds to about 220 seconds, about 120 seconds to about 300 seconds, about 120 seconds to about 420 seconds, about 140 seconds to about 165 seconds, about 140 seconds to about 220 seconds, about 140 seconds to about 300 seconds, about 140 seconds to about 420 seconds, about 165 seconds to about 220 seconds, about 165 seconds to about 300 seconds, about 165 seconds to about 420 seconds, about 220 seconds to about 300 seconds, about 220 seconds to about 420 seconds, or about 300 seconds to about 420 seconds. In some embodiments, the residence time is about 1 seconds, about 20 seconds, about 40 seconds, about 60 seconds, about 80 seconds, about 120 seconds, about 140 seconds, about 165 seconds, about 220 seconds, about 300 seconds, or about 420 seconds. In some embodiments, the residence time is 80 seconds. In some embodiments, the residence time is 165 seconds. In some embodiments, the residence time is 420 seconds.

In some embodiments, the fluorinated reagent is recycled through the twin-screw extruder (e.g., twin-screw extruder) any suitable number of times in any composition or method provided herein. In some embodiments, the fluorinated reagent was recycled through the extruder 1 time. In some embodiments, the fluorinated reagent was recycled through the extruder 2 times. In some embodiments, the fluorinated reagent was recycled through the extruder 3 times.

In some embodiments, the activated fluorinating reagent or third salt described in any of the compositions or methods herein is characterized with Powder X-ray diffraction. The powder x-ray diffraction spectrum of the activated fluorinating reagent described herein may exhibit one or more characteristic reflections at about 18.0°, 18.7°, 21.9°, 22.6°, 24.5°, 25.4°, 26.5°, 27.0°, 28.0°, 29.2°, 30.3°, 31.6°, 33.0°, 34.8°, 36.4°, 37.7°, 39.5°, 40.4°, 41.7°, 42.4°, 43.4°, 46.1°, 48.4°, 49.4°, 52.8°, and/or 53.9°.

In some embodiments, a powder x-ray diffraction spectrum of the activated reagent comprises characteristic 2θ reflections at about 18.0°, 18.7°, 21.9°, 22.6°, 24.5°, 25.4°, 26.5°, 27.0°, 28.0°, 29.2°, 30.3°, 31.6°, 33.0°, 34.8°, 36.4°, 37.7°, 39.5°, 40.4°, 41.7°, 42.4°, 43.4°, 46.1°, 48.4°, 49.4°, 52.8°, and/or 53.9°.

In some embodiments, a powder x-ray diffraction spectrum of the activated reagent comprises at least two characteristic 2θ reflections at about 18.0°, 18.7°, 21.9°, 22.6°, 24.5°, 25.4°, 26.5°, 27.0°, 28.0°, 29.2°, 30.3°, 31.6°, 33.0°, 34.8°, 36.4°, 37.7°, 39.5°, 40.4°, 41.70, 42.4°, 43.4°, 46.1°, 48.4°, 49.4°, 52.8°, and/or 53.9°.

In some embodiments, a powder x-ray diffraction spectrum of the activated reagent comprises at least three characteristic 2θ reflections selected from the group of about 18.0°, 18.7°, 21.9°, 22.6°, 24.5°, 25.4°, 26.5°, 27.0°, 28.0°, 29.2°, 30.3°, 31.6°, 33.0°, 34.8°, 36.4°, 37.7°, 39.5°, 40.4°, 41.7°, 42.4°, 43.4°, 46.1°, 48.4°, 49.4°, 52.8°, and 53.9°.

In some embodiments, a powder x-ray diffraction spectrum of the activated reagent comprises characteristic at least four 2θ reflections selected from the group of about 18.0°, 18.7°, 21.9°, 22.6°, 24.5°, 25.4°, 26.5°, 27.0°, 28.0°, 29.2°, 303, 31.6°, 33.0°, 34.8°, 36.4°, 37.7°, 39.5°, 40.4°, 41.7°, 42.4°, 43.4°, 46.10, 48.4°, 49.4°, 52.8°, and 53.9°. In some embodiments, a powder x-ray diffraction spectrum of the activated reagent comprises characteristic 2θ reflections at about 21.9°, 30.3°, 31.6°, and 43.4°.

In some embodiments, a powder x-ray diffraction spectrum of the activated reagent comprises characteristic 2θ reflections at about 18.0°, 18.70, 21.90, 22.6°, 24.5°, 25.4°, 26.5°, 27.0°, 28.0°, 29.20, 30.3°, 31.6°, 33.0°, 34.8°, 36.4°, 37.7°, 39.5°, 40.40, 41.7°, 42.40, 43.4°, 46.1°, 48.4°, 49.4°, 52.80, and 53.9°.

In some embodiments, a powder x-ray diffraction spectrum of the activated reagent comprises 1, 2, 3, 4, 5, 6, 7, 8, 9, or 10 characteristic 2θ reflections.

In some embodiments, a powder x-ray diffraction spectrum of the activated reagent comprises relative peak intensities of characteristic reflections which are at least 0.1%, at least 1%, or at least 5% relative to the tallest peak in a raw spectrum. In some embodiments, a powder x-ray diffraction spectrum of the activated reagent comprises relative peak intensities of characteristic reflections which are at least 0.1%, at least 1%, or at least 5% relative to the tallest peak in a background subtracted spectrum. In some embodiments, a powder x-ray diffraction spectrum of the activated reagent comprises relative peak intensities of characteristic reflections which are at least 10%, at least 15%, or at least 20% relative to the tallest peak in a background subtracted spectrum.

In some embodiments, a powder x-ray diffraction spectrum of the activated reagent comprises relative peak integrations of characteristic reflections which are at least 0.1%, at least 1%, or at least 5% relative to the peak with the largest integration in a raw spectrum. In some embodiments, a powder x-ray diffraction spectrum of the activated reagent comprises relative peak integrations of characteristic reflections which are at least 0.1%, at least 1%, or at least 5% relative to the peak with the largest integration in a background subtracted spectrum. In some embodiments, a powder x-ray diffraction spectrum of the activated reagent comprises relative peak integrations of characteristic reflections which are at least 10%, at least 15%, or at least 20% relative to the peak with the largest integration in a background subtracted spectrum.

In some embodiments, a powder x-ray diffraction spectrum of the activated reagent comprises relative peak integrations of characteristic reflections which are about one or more values independently selected from those described in any one of the Tables provided herein, e.g. Tables 5.7.1, 5.7.2, 5.7.3, 5.7.4, 5.7.5, 5.7.6, 5.7.7, 5.7.8, 5.7.9, 5.7.10, 5.7.11, 5.7.12, 5.7.13, 5.12.1, 5.12.2, 5.12.3, 5.12.4, 5.12.5, 5.13.1, 5.13.2, 5.14.1, 5.14.2, 5.14.3, 5.14.4, 6.3.1, 6.3.2, 6.3.3, 6.3.4, 6.3.5, 6.3.6, 6.3.7, 6.3.8, 6.3.9, 7.7.1, 7.7.2, and/or combinations thereof.

In some embodiments, a powder x-ray diffraction spectrum of the activated reagent comprises relative peak intensities of characteristic reflections which are about one or more values independently selected from those described in any one of the Tables provided herein, e.g. Tables 5.7.1, 5.7.2, 5.7.3, 5.7.4, 5.7.5, 5.7.6, 5.7.7, 5.7.8, 5.7.9, 5.7.10, 5.7.11, 5.7.12, 5.7.13, 5.12.1, 5.12.2, 5.12.3, 5.12.4, 5.12.5, 5.13.1, 5.13.2, 5.14.1, 5.14.2, 5.14.3, 5.14.4, 6.3.1, 6.3.2, 6.3.3, 6.3.4, 6.3.5, 6.3.6, 6.3.7, 6.3.8, 6.3.9, 7.7.1, 7.7.2, and/or combinations thereof.

In some embodiments, a powder x-ray diffraction spectrum of the activated reagent comprises d-spacing values of characteristic reflections which are about one or more values independently selected from those described in any one of the Tables provided herein, e.g.

Tables 5.7.1, 5.7.2, 5.7.3, 5.7.4, 5.7.5, 5.7.6, 5.7.7, 5.7.8, 5.7.9, 5.7.10, 5.7.11, 5.7.12, 5.7.13, 5.12.1, 5.12.2, 5.12.3, 5.12.4, 5.12.5, 5.13.1, 5.13.2, 5.14.1, 5.14.2, 5.14.3, 5.14.4, 6.3.1, 6.3.2, 6.3.3, 6.3.4, 6.3.5, 6.3.6, 6.3.7, 6.3.8, 6.3.9, 7.7.1, 7.7.2, and/or combinations thereof.

In some embodiments, a powder x-ray diffraction spectrum of the activated reagent comprises absolute peak intensities of characteristic reflections which are about one or more values independently selected from those described in any one of the Tables provided herein, e.g. Tables 5.7.1, 5.7.2, 5.7.3, 5.7.4, 5.7.5, 5.7.6, 5.7.7, 5.7.8, 5.7.9, 5.7.10, 5.7.11, 5.7.12, 5.7.13, 5.12.1, 5.12.2, 5.12.3, 5.12.4, 5.12.5, 5.13.1, 5.13.2, 5.14.1, 5.14.2, 5.14.3, 5.14.4, 6.3.1, 6.3.2, 6.3.3, 6.3.4, 6.3.5, 6.3.6, 6.3.7, 6.3.8, 6.3.9, 7.7.1, 7.7.2, and/or combinations thereof.

In some embodiments, a powder x-ray diffraction spectrum of the activated reagent comprises a ratio of any spectral property of any characteristic reflection to the same spectral property of another characteristic reflection which is about a ratio of the spectral properties of the corresponding characteristic reflections described in any one of the Tables provided herein, e.g.

Tables 5.7.1, 5.7.2, 5.7.3, 5.7.4, 5.7.5, 5.7.6, 5.7.7, 5.7.8, 5.7.9, 5.7.10, 5.7.11, 5.7.12, 5.7.13, 5.12.1, 5.12.2, 5.12.3, 5.12.4, 5.12.5, 5.13.1, 5.13.2, 5.14.1, 5.14.2, 5.14.3, 5.14.4, 6.3.1, 6.3.2, 6.3.3, 6.3.4, 6.3.5, 6.3.6, 6.3.7, 6.3.8, 6.3.9, 7.7.1, 7.7.2.

In some embodiments, the spectral property can include an absolute intensity, a relative intensity, an absolute area, a relative area, an estimated d-spacing, a full-width at half max peak resolution, and/or combinations thereof. In some embodiments, the method comprises combining the activated salt mixture with a first reactant, the first reactant, and fluorinating the first reactant to yield a fluorinated compound. In some embodiments, the first reactant is an organic compound. In some embodiments, the fluorinated compound is an organo-fluorine compound. In some embodiments, the first reactant is an inorganic compound.

In any of the compositions or methods described herein, fluorinating is performed at any suitable temperature. In some embodiments, the fluorination reaction is performed at a temperature of about 0° C. to about 400° C. In some embodiments, the fluorination reaction is performed at a temperature of about 0° C. to about 20° C., about 0° C. to about 50° C., about 0° C. to about 100° C., about 0° C. to about 150° C., about 0° C. to about 200° C., about 0° C. to about 250° C., about 0° C. to about 300° C., about 0° C. to about 350° C., about 0° C. to about 400° C., about 20° C. to about 50° C., about 20° C. to about 100° C., about 20° C. to about 150° C., about 20° C. to about 200° C., about 20° C. to about 250° C., about 20° C. to about 300° C., about 20° C. to about 350° C., about 20° C. to about 400° C., about 50° C. to about 100° C., about 50° C. to about 150° C., about 50° C. to about 200° C., about 50° C. to about 250° C., about 50° C. to about 300° C., about 50° C. to about 350° C., about 50° C. to about 400° C., about 100° C. to about 150° C., about 100° C. to about 200° C., about 100° C. to about 250° C., about 100° C. to about 300° C., about 100° C. to about 350° C., about 100° C. to about 400° C., about 150° C. to about 200° C., about 150° C. to about 250° C., about 150° C. to about 300° C., about 150° C. to about 350° C., about 150° C. to about 400° C., about 200° C. to about 250° C., about 200° C. to about 300° C., about 200° C. to about 350° C., about 200° C. to about 400° C., about 250° C. to about 300° C., about 250° C. to about 350° C., about 250° C. to about 400° C., about 300° C. to about 350° C., about 300° C. to about 400° C., or about 350° C. to about 400° C. In some embodiments, the fluorination reaction is performed at a temperature of about 0° C., about 20° C., about 50° C., about 100° C., about 150° C., about 200° C., about 250° C., about 300° C., about 350° C., or about 400° C. In some embodiments, the fluorination reaction is performed at a temperature of at least about 0° C., about 20° C., about 50° C., about 100° C., about 150° C., about 200° C., about 250° C., about 300° C., or about 350° C. In some embodiments, the fluorination reaction is performed at a temperature of at most about 20° C., about 50° C., about 100° C., about 150° C., about 200° C., about 250° C., about 300° C., about 350° C., or about 400° C. In some embodiments, the fluorination is performed at a temperature of about 100° C.

In some embodiments, the fluorination reaction yield is measured. The fluorination reaction yield is for example, measured by $^{19}$F NMR using 4-fluoroanisole as an internal standard. In some embodiments, the reaction yield of the organo-fluorine compound is about 0.1% to about 95%. In some embodiments, the reaction yield of the organo-fluorine compound is about 0.1% to about 1%, about 0.1% to about 10%, about 0.1% to about 20%, about 0.1% to about 30%, about 0.1% to about 40%, about 0.1% to about 50%, about 0.1% to about 60%, about 0.1% to about 70%, about 0.1% to about 80%, about 0.1% to about 90%, about 0.1% to about 95%, about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, about 1% to about 95%, about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, or about 90% to about 95%. In some embodiments, the reaction yield of the organo-fluorine compound is about 0.1%, about 1%, about 10%, about 20%, about 30%, about 40%, about 50%, about 60%, about 70%, about 80%, about 90%, or about 95%. In some embodiments the reaction yield of the organo-fluorine compound is measured based on a starting amount of the organic compound.

In some embodiments, the organic compound in any of the compositions or methods provided herein comprises an aromatic or aliphatic and comprises at least one leaving group located at a site to be fluorinated. In some embodiments, the leaving group comprises a halogen.

In some embodiments, the organic compound comprises an aromatic. In some embodiments, the organic compound comprises an aliphatic. In some embodiments, the organic compound comprises an aromatic and comprises at least one leaving group located at a site to be fluorinated. In some embodiments, the organic compound comprises an aliphatic and comprises at least one leaving group at a site to be fluorinated. In some embodiments, the fluorination occurs at the same site of the leaving group as described in Scheme 0.1.

Scheme 0.1.

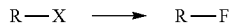

In some embodiments, R is an aromatic. In some embodiments, R is an aliphatic. In some embodiments, X is a leaving group. In some embodiments, X is a halogen. In some embodiments, X is a bromide. In some embodiments, X is a chloride.

In some embodiments, the organic compound is a sulphonyl halide, an acyl halide, an aryl halide, and/or an alkyl halide. In some embodiments, the organic compound comprises a sulphonyl halide. In some embodiments, the organic compound comprises an acyl halide. In some embodiments, the organic compound comprises an aryl halide. In some embodiments, the organic compound comprises an alkyl halide.

In some embodiments, the organic compound is an aromatic sulphonyl halide, a benzoyl halide, a halobenzene, or a benzyl halide. In some embodiments, the organic compound is an aromatic sulphonyl halide. In some embodiments, the organic compound comprises tosyl chloride. In some embodiments, the organic compound is a benzoyl halide. In some embodiments, the organic compound comprises 4-methoxybenzoyl chloride. In some embodiments, the organic compound is a halobenzene. In some embodiments, the organic compound comprises chlorobenzene. In some embodiments, the organic compound is a benzyl halide. In some embodiments, the organic compound is benzyl chloride. In some embodiments, the organic compound is an α-halo carbonyl. In some embodiments, the organic compound is a α-bromo carbonyl. In some embodiments, the organic compound is an alkyl halide. In some embodiments, the organic compound is an alkyl bromide. In some embodiments, the compound is a (hetero)aryl halide. In some embodiments, the compound is a (hetero)aryl chloride.

In some embodiments, the fluorination reaction is a mono-fluorination reaction. In some embodiments, the fluorination reaction is a poly-fluorination reaction. In some embodiments, the fluorination reaction is a di-fluorination reaction. In some embodiments, the fluorinated product is stable to reaction against the second salt after formation.

In some embodiments, the inorganic compound of any of the compositions or methods provided herein comprises a salt. In some embodiments, the inorganic compound comprises a cation and an anion. In some embodiments, the anion is a halogen. In some embodiments, the halogen is a chlorine. In some embodiments, the halogen is a bromine. In some embodiments, the halogen is an iodine. In some embodiments, the anion is exchangeable with fluorine, providing the fluoro compound. In some embodiments, the fluoro compound is NaF. In some embodiments, the fluoro compound is KF.

In any of the methods or compositions provided herein, in some embodiments, the first salt, second salt, and the organic compound are combined in the same step. In any of the methods or compositions provided herein, in other embodiments, the first salt and second salt are combined prior to addition of the organic compound.

In some embodiments, a solvent is used in the fluorination of an organic compound in any of the compositions or methods provided herein. In some embodiments, the first and second salt are combined as solids without the addition of solvent. In other embodiments, the first salt, second salt, and the organic compound is added together with one or more solvents in which the organic compound is soluble in at least one of the one or more solvents. In some embodiments, the first salt and second salt are combined prior to addition of the organic compound.

In some embodiments, a solvent is used in the fluorination of an organic compound in any of the compositions or methods provided herein. In some embodiments, the solvent is an aqueous solvent. In some embodiments, the solvent is a polar aprotic solvent.

In some embodiments, the solvent is a polar aprotic solvent with a polarity index of less than 6.3. In some embodiments, the solvent is an organic solvent with a polarity index of 6.3 or less. In some instances, an organic solvent is a carbon containing solvent. In some embodiments, the first salt is soluble in the solvent. In some embodiments, the second salt is soluble in the solvent. In some embodiments, the organic compound is soluble in the solvent. In some embodiments, the first salt, second salt, and the organic compound are soluble in the solvent.

In some embodiments, the one or more solvents comprise a solvent selected from the group consisting of acetonitrile, propionitrile, toluene, 1,2-dichlorobenze, chlorobenzene fluorobenzene, 1,2-difluorobenze, dichloroethane, trifluorotoluene, chloroform, tert-butanol, tert-amyl alcohol, and/or water. In some embodiments, the one or more solvents comprise acetonitrile, chlorobenzene, tert-butanol, tert-amyl alcohol, and/or water. In some embodiments, the solvent may comprise acetonitrile. In some embodiments, the solvent may comprise propionitrile. In some embodiments, the solvent may comprise toluene. In some embodiments, the solvent may comprise 1,2-dichlorobenzene. In some embodiments, the solvent may comprise fluorobenzene. In some embodiments, the solvent may comprise 1,2-difluorobenze. In some embodiments, the solvent may comprise dichloroethane. In some embodiments, the solvent may comprise trifluorotoluene. In some embodiments, the solvent may comprise chloroform. In some embodiments, the solvent may comprise tert-butanol. In some embodiments, the solvent may comprise tert-amyl alcohol.

In some embodiments, the solvent may comprise water. In some embodiments, the solvent may comprise tetrahydrofuran, 2-methyltetrahydrofuran, 1,4-dioxane, tert-butyl isocyanide, m-xylene, hexane, diglyme, and/or monoglyme. In some embodiments, the solvent may comprise tetrahydrofuran. In some embodiments, the solvent may comprise 2-methyltetrahydrofuran. In some embodiments, the solvent may comprise 1,4-dioxane. In some embodiments, the solvent may comprise tert-butyl isocyanide. In some embodiments, the solvent may comprise m-xylene. In some embodiments, the solvent may comprise hexane. In some embodiments, the solvent may comprise diglyme. In some embodiments, the solvent may comprise monoglyme. In some embodiments, any one or more of the aforementioned organic solvents may be in admixture with water.

In some embodiments, in any composition or method herein, the organic solvent may be in admixture with water at a concentration of about 0.01 M to about 5M or any range therein. In some embodiments, the organic solvent may be in admixture with water at a concentration of about 0.01 M to about 1 M. In some embodiments, the organic solvent may be in admixture with water at a concentration of about 0.01 M to about 0.05 M, about 0.01 M to about 0.1 M, about 0.01 M to about 0.2 M, about 0.01 M to about 0.3 M, about 0.01 M to about 0.4 M, about 0.01 M to about 0.6 M, about 0.01 M to about 0.8 M, about 0.01 M to about 1 M, about 0.05 M to about 0.1 M, about 0.05 M to about 0.2 M, about 0.05 M to about 0.3 M, about 0.05 M to about 0.4 M, about 0.05 M to about 0.6 M, about 0.05 M to about 0.8 M, about 0.05 M to about 1 M, about 0.1 M to about 0.2 M, about 0.1 M to about 0.3 M, about 0.1 M to about 0.4 M, about 0.1 M to about 0.6 M, about 0.1 M to about 0.8 M, about 0.1 M to about 1 M, about 0.2 M to about 0.3 M, about 0.2 M to about 0.4 M, about 0.2 M to about 0.6 M, about 0.2 M to about 0.8 M, about 0.2 M to about 1 M, about 0.3 M to about 0.4 M, about 0.3 M to about 0.6 M, about 0.3 M to about 0.8 M, about 0.3 M to about 1 M, about 0.4 M to about 0.6 M, about 0.4 M to about 0.8 M, about 0.4 M to about 1 M, about 0.6 M to about 0.8 M, about 0.6 M to about 1 M, or about 0.8 M to about 1 M. In some embodiments, the organic solvent may be in admixture with water at a concentration of about 0.01 M, about 0.05 M, about 0.1 M, about 0.2 M, about 0.3 M, about 0.4 M, about 0.6 M, about 0.8 M, or about 1 M. In some embodiments, the organic solvent may be in admixture with water at a concentration of about 0.25 M. In some instances, the inclusion of water may increase the yield of organo-fluorine product.

In other embodiments, in any composition or method herein, the one or more solvents may comprise an additive. In some embodiments, in any composition or method herein, the one or more solvents may comprise a cryptand, a crown ether, and a hydrogen-bonding phase transfer agent. In some embodiments, the one or more solvents comprise a cryptand. In some embodiments, the one or more solvents comprise a crown ether. In some embodiments, the one or more solvents comprise a hydrogen-bonding phase transfer agent. In some embodiments, the crown ether is 18-crown-6. In some embodiments, the crown ether is 30-crown-6. In some embodiments, the crown ether is a dibenzo derivative of a crown ether. In some embodiments the dibenzo derivative of the crown ether is dibenzo 18-crown-6 ether. In some embodiments the dibenzo derivative of the crown ether is dibenzo-30-crown-6-ether. In some embodiments, the crown ether is dicyclohexano-18-crown-6-ether. In some embodiments, the cryptand is [2.2.2]cryptand. In some embodiments, the cryptand is [2.2.1]cryptand. In some embodiments, the one or more solvents may comprise schreiner's urea.

In some embodiments, the cryptand, crown ether, or hydrogen-bond phase transfer agent is added in any suitable amount to any composition or method provided herein. In some embodiments, the cryptand, crown ether, or hydrogen-bond phase transfer agent, are added in amount of about 0.01 equivalents to about 5 equivalents. In some embodiments, the cryptand, crown ether, or hydrogen-bond phase transfer agent, are added in amount of about 0.01 equivalents to about 0.1 equivalents, about 0.01 equivalents to about 1 equivalents, about 0.01 equivalents to about 2 equivalents, about 0.01 equivalents to about 3 equivalents, about 0.01 equivalents to about 4 equivalents, about 0.01 equivalents to about 5 equivalents, about 0.1 equivalents to about 1 equivalents, about 0.1 equivalents to about 2 equivalents, about 0.1 equivalents to about 3 equivalents, about 0.1 equivalents to about 4 equivalents, about 0.1 equivalents to about 5 equivalents, about 1 equivalents to about 2 equivalents, about 1 equivalents to about 3 equivalents, about 1 equivalents to about 4 equivalents, about 1 equivalents to about 5 equivalents, about 2 equivalents to about 3 equivalents, about 2 equivalents to about 4 equivalents, about 2 equivalents to about 5 equivalents, about 3 equivalents to about 4 equivalents, about 3 equivalents to about 5 equivalents, or about 4 equivalents to about 5 equivalents. In some embodiments, the cryptand, crown ether, or hydrogen-bond phase transfer agent, are added in amount of about 0.01 equivalents, about 0.1 equivalents, about 1 equivalent, about 2 equivalents, about 3 equivalents, about 4 equivalents, or about 5 equivalents. In some embodiments, the cryptand, crown ether, or hydrogen-bond phase transfer agent is added in amount to increase the yield of the organo-fluorine product.

In any composition or method herein, in some embodiments, fluorinating may take place for any suitable amount of time. In some embodiments, fluorinating may take place for about 0.5 hrs to about 24 hrs. In some embodiments, fluorinating may take place for about 0.5 hrs to about 1 hr, about 0.5 hrs to about 3 hrs, about 0.5 hrs to about 5 hrs, about 0.5 hrs to about 12 hrs, about 0.5 hrs to about 16 hrs, about 0.5 hrs to about 24 hrs, about 1 hr to about 3 hrs, about 1 hr to about 5 hrs, about 1 hr to about 12 hrs, about 1 hr to about 16 hrs, about 1 hr to about 24 hrs, about 3 hrs to about 5 hrs, about 3 hrs to about 12 hrs, about 3 hrs to about 16 hrs, about 3 hrs to about 24 hrs, about 5 hrs to about 12 hrs, about 5 hrs to about 16 hrs, about 5 hrs to about 24 hrs, about 12 hrs to about 16 hrs, about 12 hrs to about 24 hrs, or about 16 hrs to about 24 hrs. In some embodiments, fluorinating may take place for about 0.5 hrs, about 1 hr, about 3 hrs, about 5 hrs, about 12 hrs, about 16 hrs, or about 24 hrs. In some embodiments, fluorinating may take place for at least about 0.5 hrs, about 1 hr, about 3 hrs, about 5 hrs, about 12 hrs, or about 16 hrs. In some embodiments, fluorinating may take place for 3 hours. In some embodiments, fluorinating may take place for 5 hrs. In some embodiments, fluorinating may take place for 12 hrs. In some embodiments, fluorinating may take place for 16 hrs.

In further embodiments, provided herein is a method of fluorinating an organic compound. In some embodiments, the method comprises combining an activated fluorinating reagent with the organic compound, wherein the activated fluorinating reagent and the organic compound are described elsewhere herein. In some embodiments, the method comprises fluorinating the organic compound to produce an organo-fluorine compound.

In some embodiments, provided herein is a method of manufacturing an activated fluorination reagent. In some embodiments, the method comprises combining a first salt, the first salt comprising calcium and fluorine, with a second salt to form a salt mixture, wherein the first salt and second salt are described elsewhere herein. In some embodiments, the method comprises applying mechanical force to the salt mixture to form an activated salt mixture, wherein the mechanical force is described elsewhere herein. In some embodiments, the method comprises combining the activated salt mixture with a first reactant. In some embodiments, the first reactant is an organic compound, wherein the organic compound is described elsewhere herein. In some embodiments, the method comprises fluorinating the first reactant to yield an organo-fluorine compound.

In other embodiments, provided herein is a method of recovering fluorine from a water material to form an activated fluorination reagent. In some embodiments, the method comprises combining a waste material comprising a first salt comprising calcium and fluorine with a second salt to form a salt-waste mixture, wherein the first salt and second salt are described elsewhere herein. In some embodiments, the method comprises applying mechanical force to the salt-waste mixture to yield the activated fluorination reagent, wherein the mechanical force is described elsewhere herein.

EXAMPLES

Materials and Methods

Unless otherwise stated, all reagents were purchased from commercial suppliers (Sigma-Aldrich, Alfa Aesar, Fluorochem, Apollo Scientific and Fisher Chemicals) and used without further purification. Dry solvents were purchased from commercial suppliers or dried on a column of alumina. Reagent grade calcium fluoride ($CaF_2$, ≥97.0%, Alfa Aesar), potassium phosphate ($K_3PO_4$, >98%, Sigma Aldrich, CAS 7778-53-2), dipotassium hydrogen phosphate ($K_2HPO_4$, ≥98.0%, Alfa Aesar), potassium dihydrogen phosphate ($KH_2PO_4$, ≥99.0%, Alfa Aesar), sodium phosphate ($Na_3PO_4$, ≥96.0%, Sigma Aldrich), disodium hydrogen phosphate ($Na_2HPO_4$, 98%, Fisher Scientific), sodium dihydrogen phosphate ($NaH_2PO_4$, 96%, Fisher Scientific), potassium tripolyphosphate ($K_5P_3O_{10}$, >94%, Strem Chemicals), sodium pyrophosphate tetrabasic decahydrate ($Na_4P_2O_7 \cdot 10H_2O$, ≥99%, Sigma Aldrich, CAS 13472-36-1), sodium tripolyphosphate ($Na_5P3_{O10}$, Alfa Aesar), sodium trimetaphosphate ($Na_3P_3O_9$, Alfa Aesar), sodium hexametaphosphate (Graham's salt, 65-70% $P_2O_5$ basis, Sigma Aldrich), potassium metaphosphate ($KPO_3$, 98%, Strem Chemicals), anhydrous calcium hydrogen phosphate ($CaHPO_4$, 98.0-105.0%, Sigma Aldrich) were used without drying and stored under ambient conditions.

Potassium pyrophosphate ($K_4P_2O_7$, 97.0%, Sigma Aldrich), anhydrous potassium fluoride (KF, 99%, Alfa Aesar), were used without drying and stored in a dessicator.

Fluorspar (acid grade) was purchased from Mistral Industrial Chemicals (UK), produced by Minersa group (Asturias region, Spain) and contains $CaF_2$ (>97%), total carbonates (<1.50%), $SiO_2$ (<1.00%), $BaSO_4$ (<0.50%), Pb (<0.10%), $Fe_2O_3$ (<0.10%), S (<0.15%), $H_2O$ (<1.0%). Fluorspar (acid grade) was used without drying and stored under ambient conditions.

Unless otherwise stated, all reagents were purchased from commercial suppliers (Sigma-Aldrich, Alfa Aesar, Fluorochem, Minersa Group (Fluorspar), Apollo Scientific and Fisher Chemicals) and used without further purification. Unless otherwise specified, $CaF_2$ used was purchased from Alfa Aesar (>97%, reagent grade), and $K_2HPO_4$ was acquired from Fisher Chemical (anhydrous, crystalline powder). Dry solvents were purchased from commercial suppliers or dried on a column of alumina. Column chromatography was performed on Merck silica gel (60, particle size 0.040-0.063 mm).

NMR experiments were recorded on Bruker AVIIIHD 400, AVIIIHD 500, AVII 500, or AV NEO 600 NMR Spectrometers. $^1H$ and $^{13}C$ NMR spectral data are reported as chemical shifts (δ) in parts per million (ppm) relative to the solvent peak using the Bruker internal referencing procedure (edlock). Chemical shifts are reported using the internal standard residual $CDCl_3$ (δ=7.26 ppm for 1H NMR spectra and δ=77.16 ppm for $^{13}C$ NMR spectra). $^{19}F$ NMR spectra are referenced relative to $CFCl_3$. Data are reported as follows: chemical shift, multiplicity (s=singlet, d=doublet, t=triplet, q=quartet, pent=pentet, sept=septet, br=broad, m=multiplet), coupling constants (Hz) and integration. NMR spectra were processed with MestReNova 14.2.1 or Topspin 3.5 or 4.0. $^{19}F$ NMR yields were determined using 4-fluoroanisole (−123.7 ppm) as an internal standard. The standard was added to the crude residue after solvent evaporation, dissolved in $CDCl_3$, and an aliquot was taken to be analyzed by $^{19}F$ NMR.

Powder X-ray diffraction (PXRD) data was collected using a Bruker D8 Advance X-Ray diffractometer with Bragg-Brentano geometry. Cu K α1 and 2 were used and measurements were performed at room temperature unless otherwise stated. All PXRD data was collected at room temperature. For simulated structures a Rietveld refinement of powder diffraction data was performed using the TOPAS Academic (V6).

Ball milling experiments were performed using a Retsch MM 400 mixer mill. Mechanochemical reactions were performed in 15 mL, 30 mL or 50 mL stainless steel jars with either two stainless steel balls of mass 2 g, or one stainless steel ball of various mass (2 g, 3 g, 4 g, 7 g, or 9 g). No precaution was taken to exclude air and moisture.

1. One-Pot Solid State Reactions

General Procedure 1 (GP1): To a 15 mL (or 50 mL) stainless steel milling jar was added a 4 g stainless-steel ball (or 2×2 g), $CaF_2$ (5.0 mmol), $K_2HPO_4$ (2.0 mmol) and the corresponding sulfonyl chloride (1.0 equiv). The jar was then closed and securely fitted to the mill which was set for 60 minutes at the frequency of 30 Hz. After that time, the jar was opened and the solid residue was scratched out with a spatula and collected in a beaker. The jar was rinsed with EtOAc (3×5 mL) and transferred to the beaker. The resulting suspension was stirred at room temperature for 5 minutes, filtered over a short plug of silica gel (washed with ~20 mL EtOAc); the solvent was removed in vacuo and the crude mixture purified by silica gel chromatography if required.

1.1. Varying Salt

Figure 59:
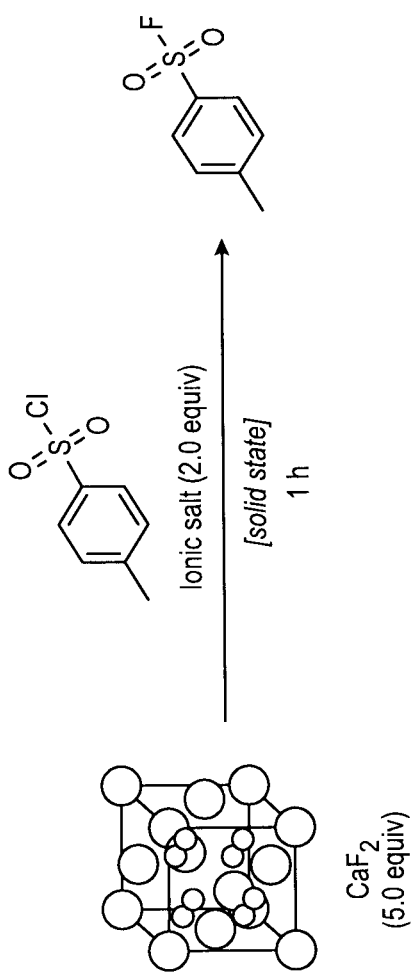
FIG. 59 illustrates a general scheme according to embodiments described herein.

Following GP1 outlined above, and having regard to FIG. 59, the effect of varying the nature of the salt was investigated. The results are outlined in Table 1.1.

TABLE 1.1

Effect of varying the salt on product yield

| Entry | Salt | TsF | TsCl | pTSA | MB |
|---|---|---|---|---|---|
| 1 | $K_3PO_4$ | 7% | 18% | 0% | 25% |
| 2 | $K_2HPO_4$ | 17% | 62% | 0% | 79% |
| 3 | $KH_2PO_4$ | <1% | 97% | 0% | 80% |
| 4 | $Na_3PO_4$ | 6% | 74% | 0% | 80% |
| 5 | $Na_2HPO_4$ | 2% | 97% | 0% | 99% |
| 6 | $NaH_2PO_4$ | <1% | >99% | 0% | >99% |
| 7 | $K_2SO_4$ | 1% | 92% | 0% | 95% |
| 8 | $Na_2SO_4$ | 3% | 92% | 0% | 95% |
| 9 | $MgSO_4$ | 1% | 97% | 0% | 98% |
| 10 | $Ag_2SO_4$ | <1% | 4% | 25% | 30% |

TABLE 1.1-continued

Effect of varying the salt on product yield

Figure 60:
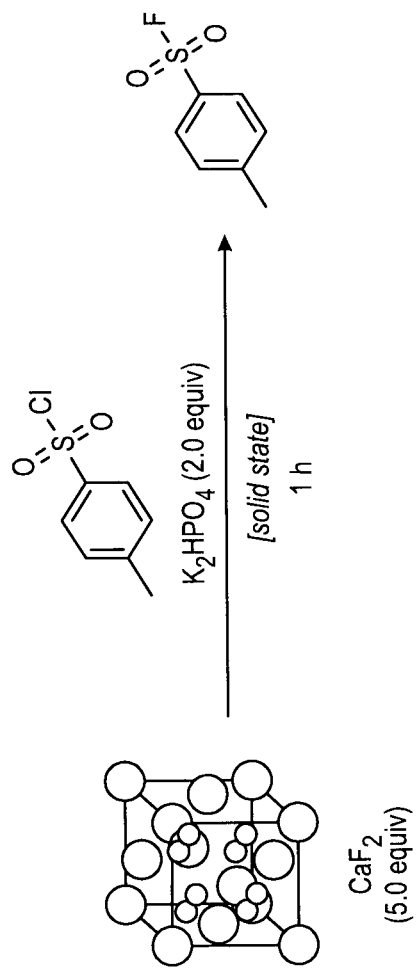
FIG. 60 illustrates a general scheme according to embodiments described herein.

| Entry | Salt | TsF | TsCl | pTSA | MB |
|---|---|---|---|---|---|
| 11 | Na$_2$CO$_3$ | 3% | 93% | 0% | 93% |
| 12 | KHCO$_3$ | 5% | 80% | 0% | 85% | with TsF = pTolSO$_2$F;
TsCl = pTolSO$_2$Cl;
MB = Mass Balance 1.2. Varying Ball Size Following GP1 outlined above, and having regard to FIG. 60, the effect of varying the ball size was investigated. The results are outlined in Table 1.2. The ball size used may have an effect on the resulting fluorinated product (TsF) yield. Exemplary ball sizes may include 7 and 9 g based on organo-fluorine product (TsF) yield.

TABLE 1.2

Effect of varying ball size on product yield

| Entry | Ball size (g) | TsF | TsCl | pTSA | MB |
|---|---|---|---|---|---|
| 1 | 2 | 18% | 45% | 0% | 63% |
| 2 | 3 | 23% | 55% | 0% | 78% |
| 3 | 4 | 25% | 40% | 0% | 65% |
| 4 | 7 | 30% | 9% | 2% | 41% |
| 5 | 9 | 31% | 6% | 4% | 41% |
| 6 | 2 × 3 | 19% | 46% | 0% | 65% |

1.3. Varying ratio of CaF$_2$ to K$_2$HPO$_4$

Figure 61:
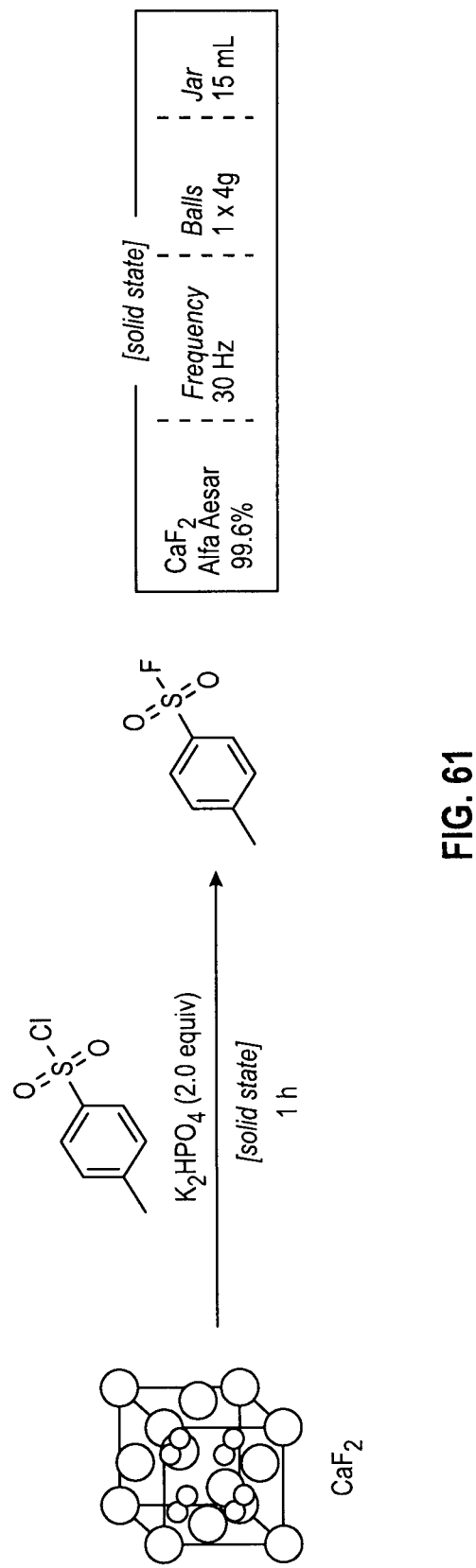
FIG. 61 illustrates a general scheme according to embodiments described herein.

Following GP1 outlined above, and having regard to FIG. 61, the effect of varying the relative amounts of CaF$_2$ and K$_2$HPO$_4$ was investigated. The results are outlined in Table 1.3. The data may support that higher ratios of CaF$_2$ to K$_2$HPO$_4$ may be beneficial for product yield.

TABLE 1.3

Effect of varying ratio of CaF$_2$ to K$_2$HPO$_4$ on product yield

| Entry | CaF$_2$ (equiv) | TsF | TsCl | pTSA | MB |
|---|---|---|---|---|---|
| 1 | 6 | 23% | 51% | 1% | 75% |
| 2 | 5 | 25% | 40% | 0% | 65% |
| 3 | 4 | 30% | 35% | 2% | 67% |
| 4 | 3 | 17% | 56% | 1% | 74% |
| 5 | 2 | 12% | 67% | 1% | 80% |
| 6 | 1 | 13% | 37% | 0% | 50% |
| 7 | 1* | 13% | 51% | 0% | 64% |

Figure 62:
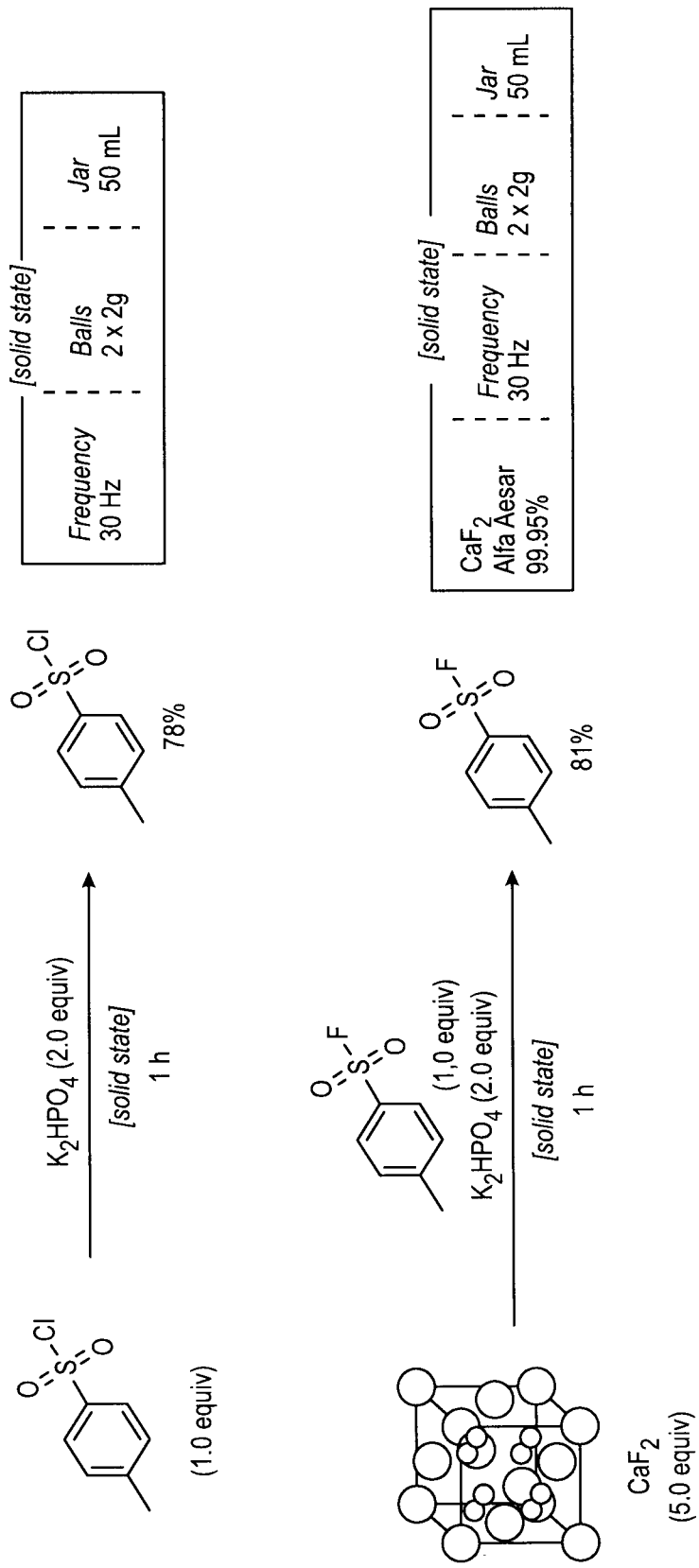
FIG. 62 illustrates a general scheme according to embodiments described herein.

*using 0.5 equiv of K$_2$HPO$_4$ 1.4. Assessing the Stability of p-Toluenesulphonyl Chloride and p-Toluenesulphonyl Fluoride Under Mechanical Forces To investigate the stability of p-toluenesulphonyl chloride and p-toluenesulphonyl fluoride under solid state, ball milling conditions, the reactions depicted FIG. 62 were performed.

In the first reaction, a 50 mL stainless steel milling jar was charged with stainless-steel balls (2×2 g), p-toluenesulfonyl chloride (1.0 equiv) and K$_2$HPO$_4$ (2.0 mmol). The jar was then closed and securely fitted to the mill which was set for 60 minutes at the frequency of 30 Hz. The jar was then opened and the solid residue was scratched out with a spatula and collected in a beaker. The jar was rinsed with EtOAc (3×5 mL) and transferred in a beaker. The resulting suspension was stirred at room temperature for 5 minutes, filtered over a short plug of silica gel (washed with ~20 mL EtOAc), and the solvent was removed in vacuo. NMR yield was determined using 4-fluoroanisole as an internal standard. The standard was added to the crude residue, which dissolved in CDCl$_3$ by swirling, and analysed by $^1$H NMR.

In the second reaction, a 50 mL stainless steel milling jar was charged with stainless-steel balls (2×2 g), p-toluenesulfonyl fluoride (1.0 equiv), CaF$_2$ (5.0 equiv) and K$_2$HPO$_4$ (2.0 mmol). The jar was then closed and securely fitted to the mill which was set for 60 minutes at the frequency of 30 Hz. The jar was then opened and the solid residue was scratched out with a spatula and collected in a beaker. The jar was rinsed with EtOAc (3×5 mL) and transferred in a beaker. The resulting suspension was stirred at room temperature for 5 minutes, filtered over a short plug of silica gel (washed with ~20 mL EtOAc), and the solvent was removed in vacuo. NMR yield was determined using 4-fluoroanisole as an internal standard. The standard was added to the crude residue, which was dissolved in CDCl$_3$ by swirling, and analysed by $^{19}$F NMR.

Under mechanical forces, the instability of both p-toluenesulphonyl chloride and p-toluenesulphonyl fluoride was assessed with 22% and 19% loss of material, respectively.

1.5. Assessing Fluoride Leaching from p-Toluenesulphonyl Fluoride

Figure 63:
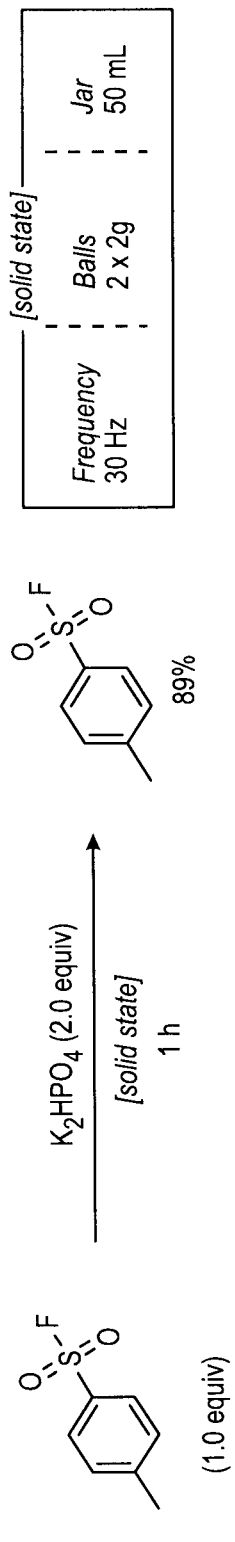
FIG. 63 illustrates a general scheme according to embodiments described herein.

To investigate the leaching of any fluoride from p-toluenesulphonyl fluoride under solid state, ball milling conditions, the reaction depicted in FIG. 63 was performed.

To a 50 mL stainless steel milling jar was added stainless-steel balls (2×2 g), p-toluenesulfonyl fluoride (1.0 equiv) and K$_2$HPO$_4$ (2.0 mmol). The jar was then closed and securely fitted to the mill which was set for 60 minutes at the frequency of 30 Hz. The jar was then opened and the solid residue was scratched out with a spatula and collected in a beaker. The jar was rinsed with EtOAc (3×5 mL) and transferred in a beaker. The resulting suspension was stirred at room temperature for 5 minutes, filtered over a short plug of silica gel (washed with ~20 mL EtOAc), and the solvent was removed in vacuo. NMR yield was determined using 4-fluoroanisole as an internal standard. The standard was added to the crude residue, dissolved in CDCl$_3$ by swirling, and analysed by $^{19}$F NMR.

Under mechanical forces and in presence of K$_2$HPO$_4$, fluoride leaching from p-toluenesulfonyl fluoride was assessed through identification of fluoride anion by $^{19}$F NMR, along with 11% loss of the fluorinated compound.

2. Two-Stage Reactions—Solid State/Solid State

General Procedure 2 (GP2): To a 15 mL stainless steel milling jar was added a stainless-steel ball (3 g), CaF$_2$ (4.0 mmol) and K$_2$HPO$_4$ (2.0 mmol). The jar was then closed and securely fitted to the mill which was set for 2×90 minutes at the frequency of 30 Hz (termed "pre-milling" step). The jar was then opened and the corresponding sulfonyl chloride (1.0 equiv) was added to the resulting white residue. The jar was then closed and securely fitted to the mill which was set for another 2×90 minutes at the frequency of 30 Hz (termed "fluorination" step). Once the reaction was complete, the jar was opened and the white solid residue was scratched out with a spatula and collected in a beaker. The jar was rinsed with EtOAc (3×5 mL) and transferred to the beaker. The resulting suspension was stirred at room temperature for 5 minutes, filtered over a short plug of silica gel (washed with ~20 mL EtOAc), and the solvent was removed in vacuo and the crude mixture purified by silica gel chromatography if required.

2.1. Varying Pre-Milling and Fluorination Duration

Figure 64:
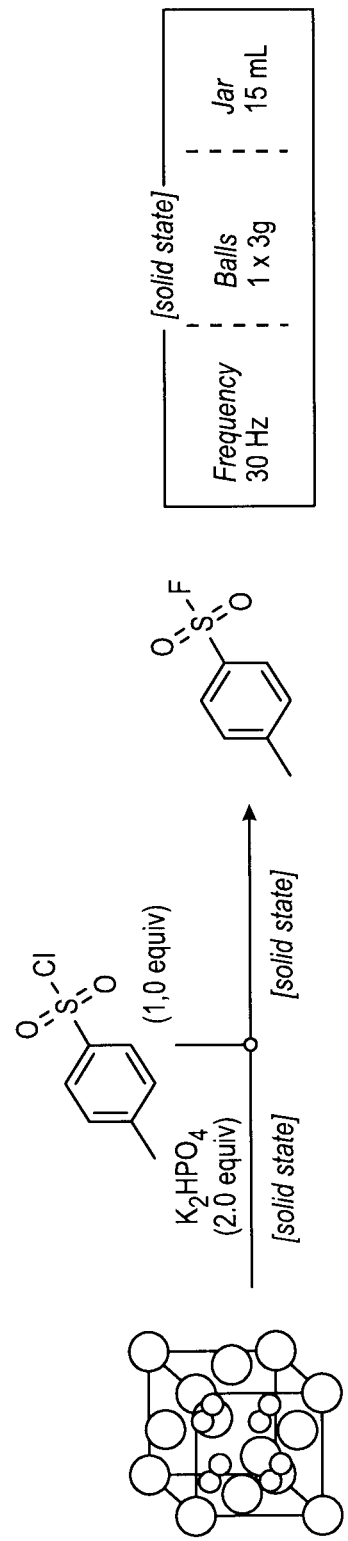
FIG. 64 illustrates a general scheme according to embodiments described herein.

Following GP2 outlined above, and, having regard to FIG. 64, the effect of varying the duration of the pre-milling and fluorination steps was investigated. The results are outlined in Table 2.1. Longer pre-milling times lead to higher yields of organofluorine products (e.g., TsF). Longer fluorination times may also lead to higher yields of organofluorine products.

TABLE 2.1

Effect of varying the duration of pre-milling and fluorination on product yield

| Entry | Pre-milling (h) | Fluorination (h) | TsF | TsCl | pTSA | MB |
|---|---|---|---|---|---|---|
| 1 | 0 | 3 | 31% | 4% | 0% | 35% |
| 2 | 1 | 1 | 29% | 47% | 0% | 76% |
| 3 | 2 | 1 | 41% | 22% | 0% | 63% |
| 4 | 3 | 3 | 66% | 0% | 0% | 66% |

Figure 65:
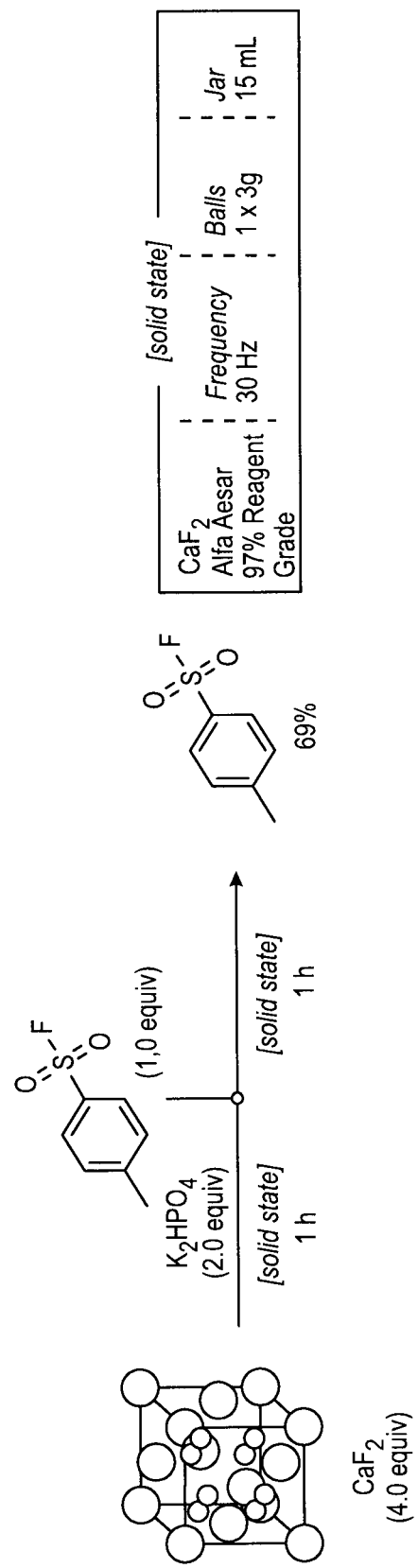
FIG. 65 illustrates a general scheme according to embodiments described herein.

2.2. Assessing the Stability of p-Toluenesulphonyl Fluoride Under Mechanical Forces Following GP2 outlined above, and having regard to FIG. 65, the stability of p-toluenesulphonyl fluoride under two-stage, solid state, ball milling conditions was investigated by replacing p-toluenesulphonyl chloride with p-toluenesulphonyl fluoride.

The partial instability of p-toluenesulfonyl fluoride under ball milling conditions was assessed. A stability experiment of p-toluenesulfonyl fluoride under mechanical forces and after pre-milling of $CaF_2$ and $K_2HPO_4$ showed that 31% of the fluorinated product is lost.

2.3. Varying Organic Substrate

Figure 66:
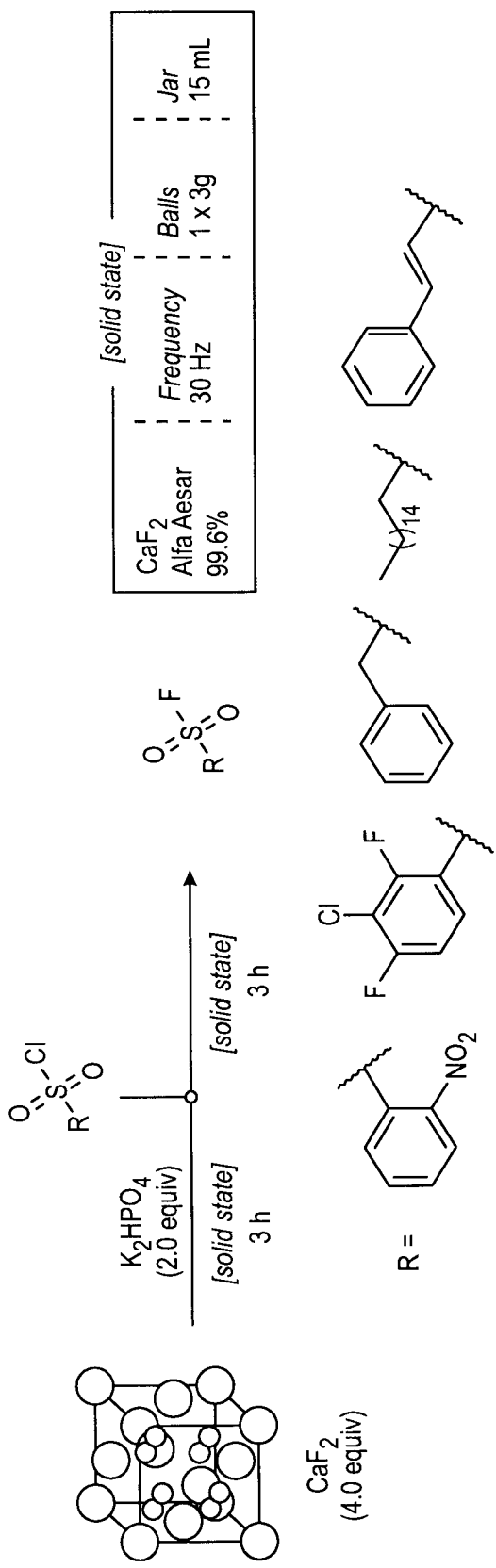
FIG. 66 illustrates a general scheme according to embodiments described herein.
Figure 67:
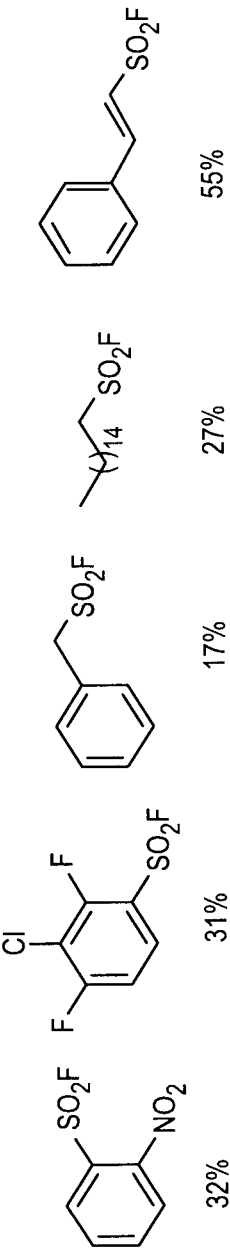
FIG. 67 illustrates a general scheme according to embodiments described herein.

Following GP2 outlined above, and having regard to FIG. 66, the effect of varying the organic substrate was investigated. FIG. 67 outlines the product yield obtained for each substrate.

2.4. Varying Organic Substrate

Figure 68:
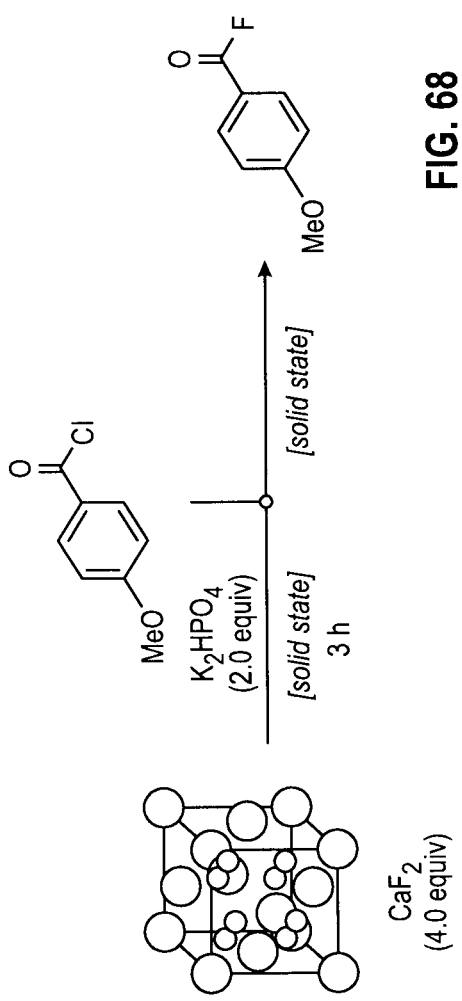
FIG. 68 illustrates a general scheme according to embodiments described herein.

Following GP2 outlined above, and having regard to FIG. 68 the effect of replacing the p-toluenesulphonyl chloride substrate with 4-methylbenzoyl chloride was investigated. The results are outlined in Table 2.2.

TABLE 2.2

Effect of varying organic substrate on product yield

| Entry | Fluorination | ArC(O)F | ArC(O)Cl | $ArCO_2H$ | $(ArCO)_2O$ |
|---|---|---|---|---|---|
| 1 | 1 | 5% | 63% | 23% | 0% |
| 2 | 0.25 | 20% | 34% | 0% | 19% |

3. Two-Stage Reactions—Solid State/Solution Phase

General Procedure 3 (GP3): To a 15 mL stainless steel milling jar was added a stainless-steel ball (7 g), $CaF_2$ (4.0 mmol) and $K_2HPO_4$ (2.0 mmol). The jar was then closed and securely fitted to the mill which was set for 2×90 minutes at the frequency of 30 Hz (termed "pre-milling" step). Once the reaction was complete, the jar was opened and the white solid residue was collected. A 7 mL vial was charged with the milled solid residue, the corresponding electrophile (1.0 equiv) and MeCN (0.25 M), and then closed with a screw cap. After stirring at 100° C. for 5 to 16 hours (termed "fluorination" step), the resulting suspension was cooled to rt, filtered over a short plug of silica gel (washed with ~20 mL EtOAc), and the solvent was removed in vacuo and the crude mixture purified by silica gel chromatography if required.

3.1. Inclusion of Additives

Figure 69:
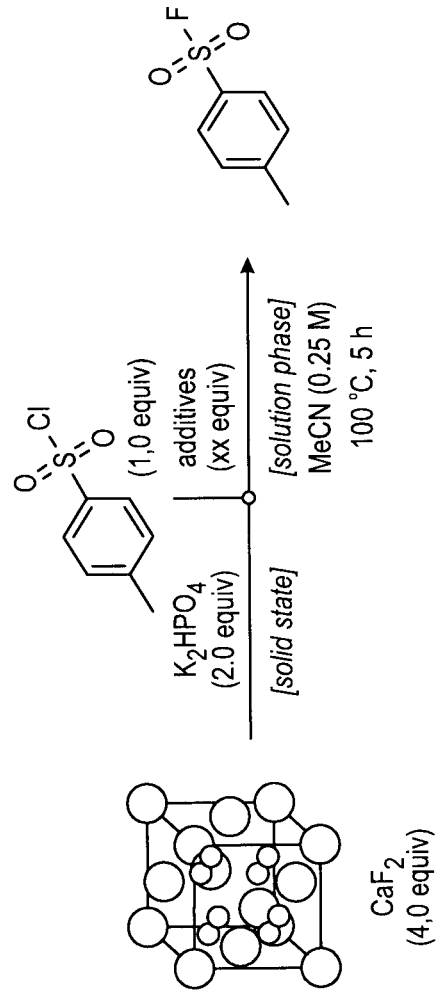
FIG. 69 illustrates a general scheme according to embodiments described herein.

Following GP3 outlined above, and having regard to FIG. 69, the effect of including one or more additives during the fluorination step was investigated. The results are outlined in Table 3.1. The addition of additives such as 18-crown-6 or Schreiner's urea may increase the yield of organofluorine product.

TABLE 3.1

Effect of including various additives on product yield

| Entry | Pre-milling (h) | Additives (equiv) | TsF | TsCl | pTSA |
|---|---|---|---|---|---|
| 1 | 1 | — | 62% | 15% | 0% |
| 2 | 1 | 18-crown-6 (1) | 70% | 0% | 0% |
| 3 | 3 | Kryptofix [2.2.2] (1) | 59% | 0% | ≈50% |
| 4 | 3 | Kryptofix [2.2.1] (1) | 52% | 0% | ≈50% |
| 5 | 3 | Schreiner's Urea (0.1) | 64% | 8% | 0% |
| 6 | 3 | Schreiner's Urea (0.1) + 18-crown-6 (1) | 79% | 0% | ≈20% |

3.2. Varying Pre-Milling Duration

Figure 70:
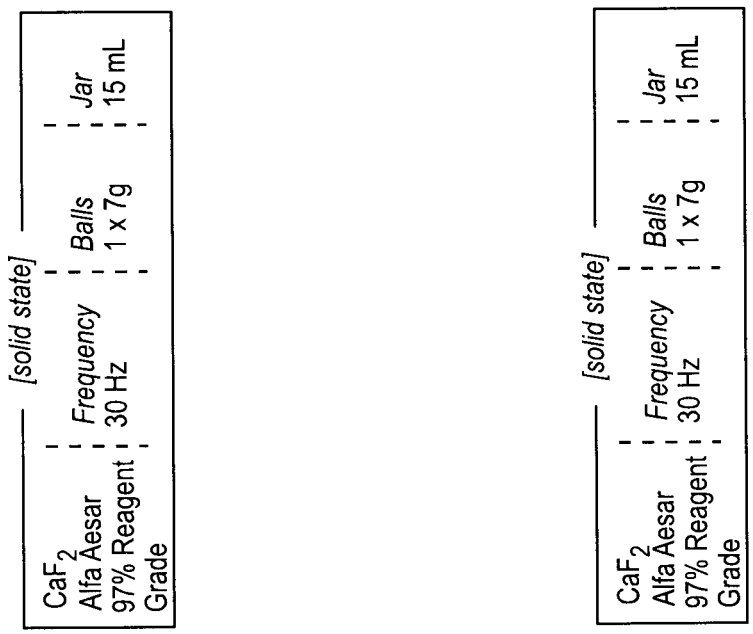
FIG. 70 illustrates a general scheme according to embodiments described herein.

Following GP3 outlined above, and having regard to FIG. 70, the effect of varying the pre-milling duration was investigated. The results are outlined in Table 3.2. Longer pre-milling duration may increase the yield of organofluorine product (e.g., TsF) and decrease resulting yields of the starting material (e.g., TsCl).

TABLE 3.2

Effect of varying pre-milling duration on product yield

| Entry | Pre-milling (h) | TsF | TsCl | pTSA |
|---|---|---|---|---|
| 1 | 1 | 62% | 15% | 0% |
| 2 | 3 | 79% | 0% | ≈20% |
| 3 | 6 | 69% | 0% | 23% |

3.3. Varying Pre-Milling Duration and Inclusion of Additives

Figure 71:
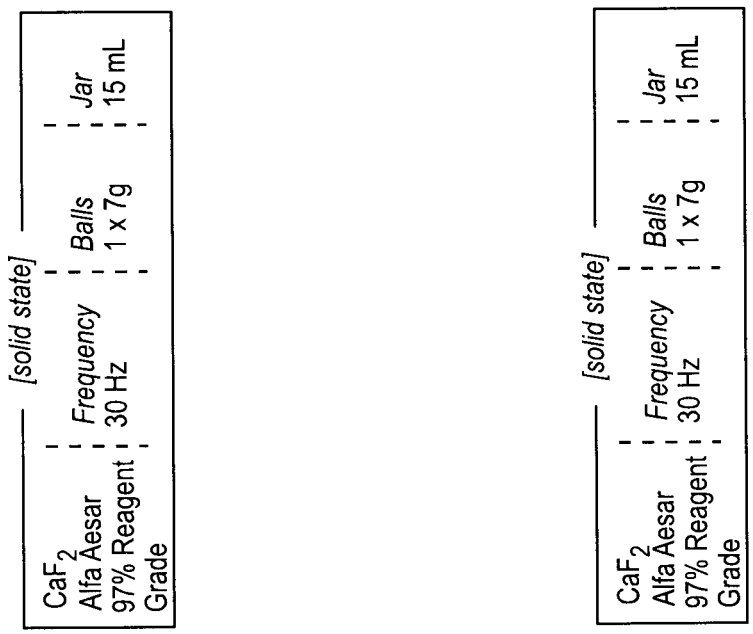
FIG. 71 illustrates a general scheme according to embodiments described herein.

Following GP3 outlined above, and having regard to FIG. 71, the effect of varying pre-milling duration and including one or more additives during the fluorination step was investigated. The results are outlined in Table 3.3. The addition of crown ethers and/or schreiner's urea may increase the yield of organofluorine product (e.g., TsF).

TABLE 3.3

Effect of varying pre-milling duration and the inclusion of various additives on product yield

| Entry | Pre-milling (h) | Additive | TsF | TsCl | pTSA |
|---|---|---|---|---|---|
| 1 | 1 | — | 62% | 15% | 0% |
| 2 | 1 | 18-crown-6 | 70% | 0% | 0% |
| 3 | 3 | Kryptofix [2.2.2] | 59% | 0% | ≈50% |
| 4 | 3 | Kryptofix [2.2.1] | 52% | 0% | ≈50% |
| 5 | 3 | Schreiner's Urea | 64% | 8% | 0% |
| 6 | 3 | Urea + 18-crown-6 | 79% | 0% | ≈20% |

3.4. Varying Ratio of $CaF_2$ to $K_2HPO_4$

Figure 72:
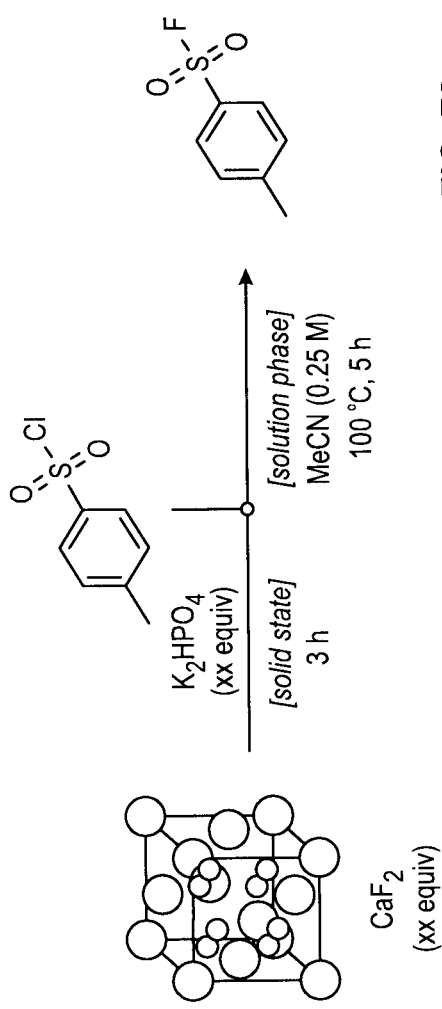
FIG. 72 illustrates a general scheme according to embodiments described herein.

Following GP3 outlined above, and having regard to FIG. 72, the effect of varying the amount of $CaF_2$ and $K_2HPO_4$ introduced during pre-milling and then added in the fluorination step was investigated. The results are outlined in Table 3.4.

TABLE 3.4

Effect of varying the amount of CaF$_2$ and K$_2$HPO$_4$ on product yield

| Entry | CaF$_2$:K$_2$HPO$_4$ | CaF$_2$ | K$_2$HPO$_4$ (equiv) | Additive (equiv) | TsF | TsCl |
|---|---|---|---|---|---|---|
| 1 | 1:0 | 4 | 0 | — | 7% | 70% |
| 2 | 2:1 | 4 | 2 | — | 62% | 15% |
| 3 | 2:1 | 4 | 2 | 18-crown-6(1) | 70% | 0% |
| 4 | 1:1 | 4 | 4 | — | 76% | 0% |
| 5 | 1:8 | 2 | 16 | — | 30% | 8% |

From the results outlined in Table 3.4, the use of a 2:1 ratio of ball milled CaF$_2$ and K$_2$HPO$_4$ (4 and 2 equivalents, respectively) in the fluorination reaction in the presence of 18-crown-6 ether may give similar yield as a 1:1 ratio of ball milled CaF$_2$ and K$_2$HPO$_4$ (4 equivalents each) without additive. The results also indicate that addition of 1 equivalent of 18-crown-6 ether may result in higher yields of organofluorine product and lower yields of organochlorine starting material. The results also indicate that addition of the second salt, K$_2$HPO$_4$ in any amount may increase the yield of organofluorine product in comparison to reactions where no K$_2$HPO$_4$ is added.

3.5. Varying Solvent

Figure 73:
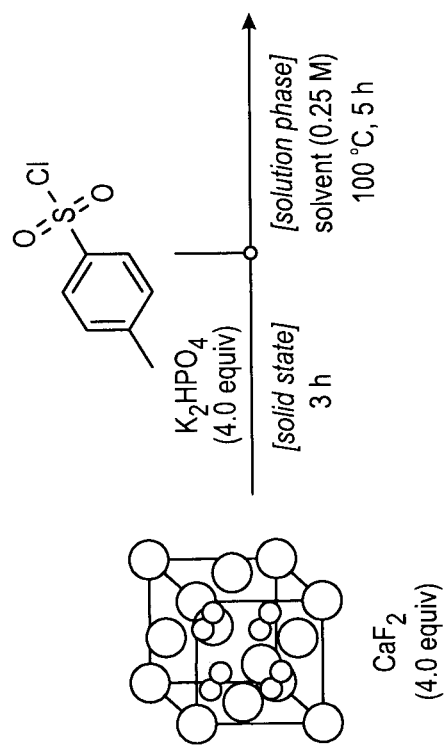
FIG. 73 illustrates a general scheme according to embodiments described herein.

Following GP3 outlined above, and having regard to FIG. 73, the effect of varying the solvent used during the fluorination step was investigated. The results are outlined in Table 3.5. The results indicate that some the use of some solvents may lead to higher yields of organofluorine product. Solvents such as DMF, DMA, and DMSO may not be effective as they yields of TsF are in trace amounts, where as other solvents such as 1,2-dichlorobenzene, chlorobenzene, t-amylOH, and t-buOH may be more effective solvents with organofluorine product (e.g., TsF) yields of over 70%. Solvents which have a polar aprotic polarity index of 6.4 or greater may be particularly suitable for use in fluorination of organic compounds using fluorination reagents (e.g. as shown in FIG. 73).

TABLE 3.5

Effect of varying solvent on product yield

| Entry | Solvent | TsF | TsCl |
|---|---|---|---|
| 1 | DMF | trace | 8% |
| 2 | DMA | trace | 43% |
| 3 | DMSO | trace | 0% |
| 4 | THF | 27% | 64% |
| 5 | 2-MeTHF | 65% | 0% |
| 6 | 1,4-dioxane | 56% | 16% |
| 7 | MeCN | 76% | 0% |
| 8 | EtCN | 80% | 4% |
| 9 | tBuCN | 57% | 31% |
| 10 | toluene | 50% | 50% |
| 11 | 1,2-difluorobenzene | 34% | 62% |
| 12 | 1,2-dichlorobenzene | 84% | 2% |
| 13 | trifluorotoluene | 69% | 17% |
| 14 | fluorobenzene | 33% | 55% |
| 15 | chlorobenzene | 92% | 0% |
| 16 | m-xylene | 68% | 31% |
| 17 | hexane | 28% | 62% |
| 18 | tBuOH | 82% | 0% |
| 19 | t-amylOH | 73% | 0% |
| 20 | H$_2$O | 32% | 4% |
| 21 | Diglyme | 46% | 0% |
| 22 | Monoglyme | 37% | 0% |

Figure 74:
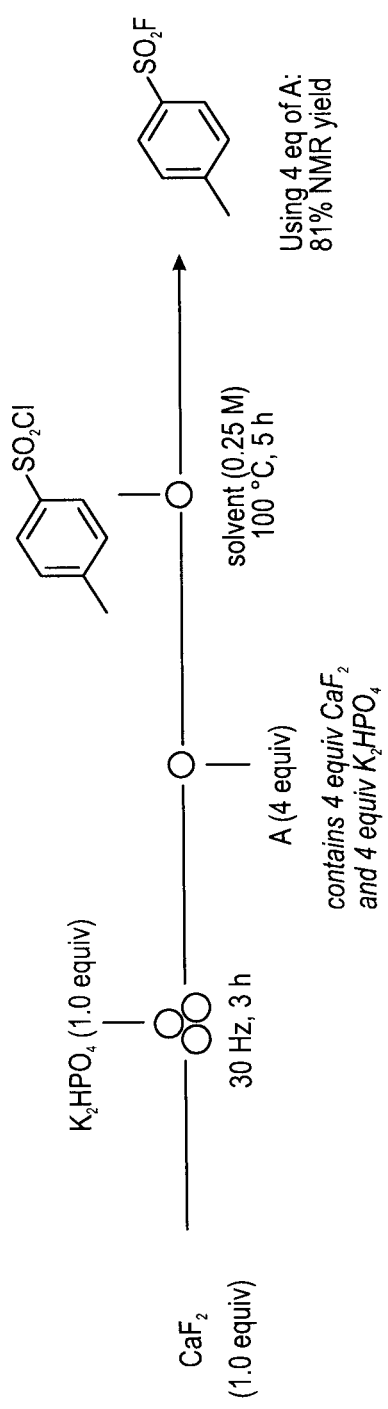
FIG. 74 illustrates a general scheme according to embodiments described herein.
Figure 75:
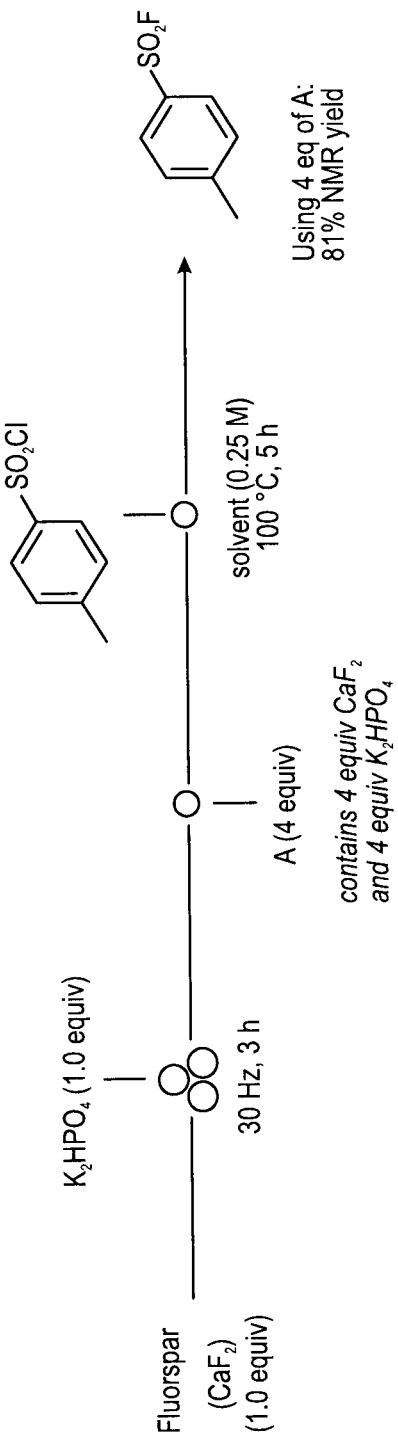
FIG. 75 illustrates a general scheme according to embodiments described herein.
Figure 76:
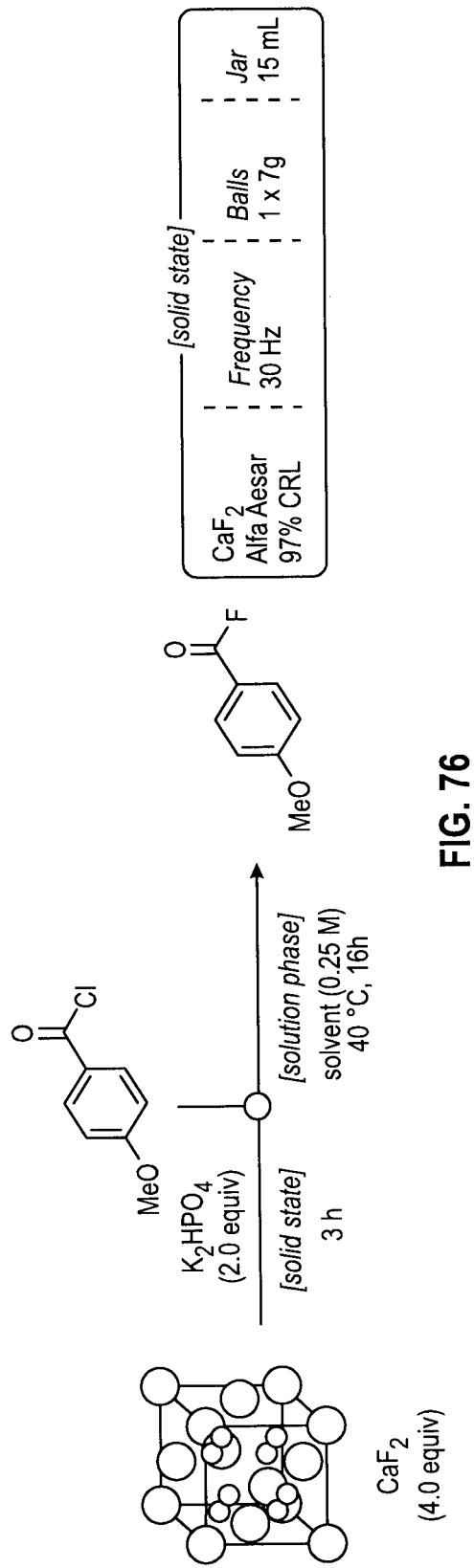
FIG. 76 illustrates a general scheme according to embodiments described herein.
Figure 77:
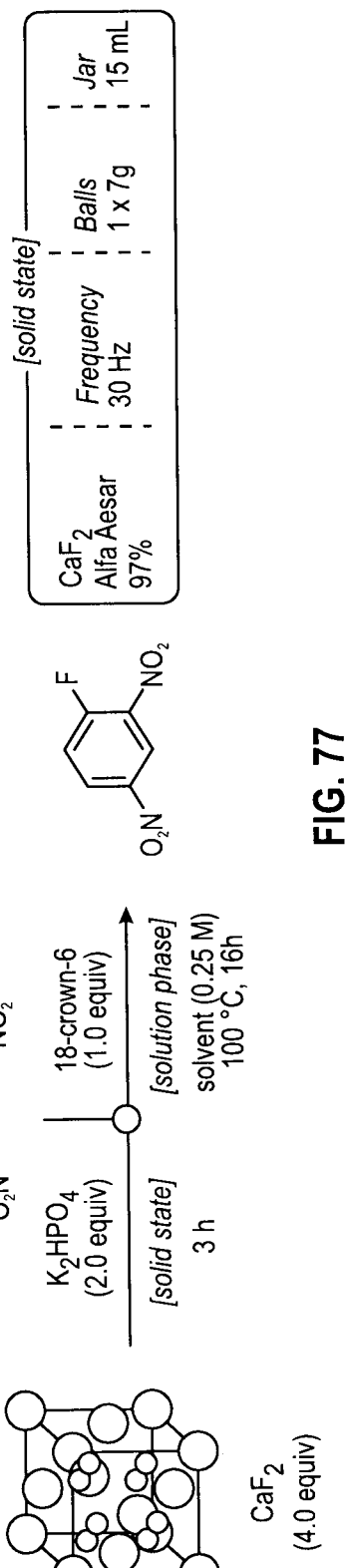
FIG. 77 illustrates a general scheme according to embodiments described herein.
Figure 78:
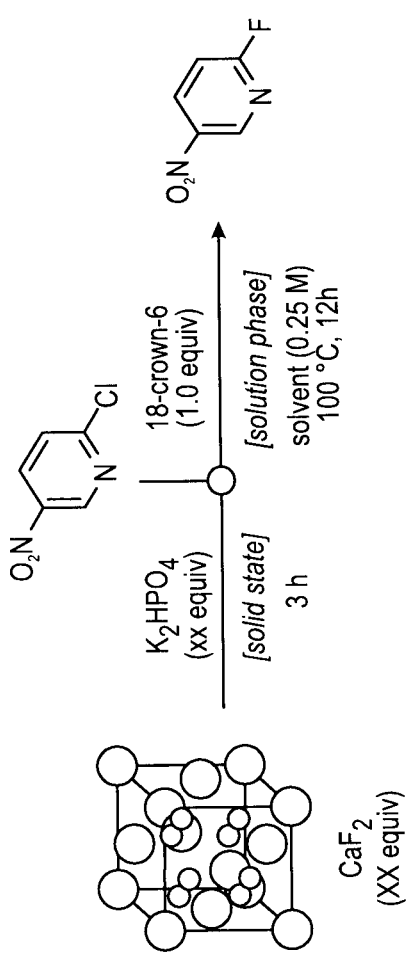
FIG. 78 illustrates a general scheme according to embodiments described herein.
Figure 79:
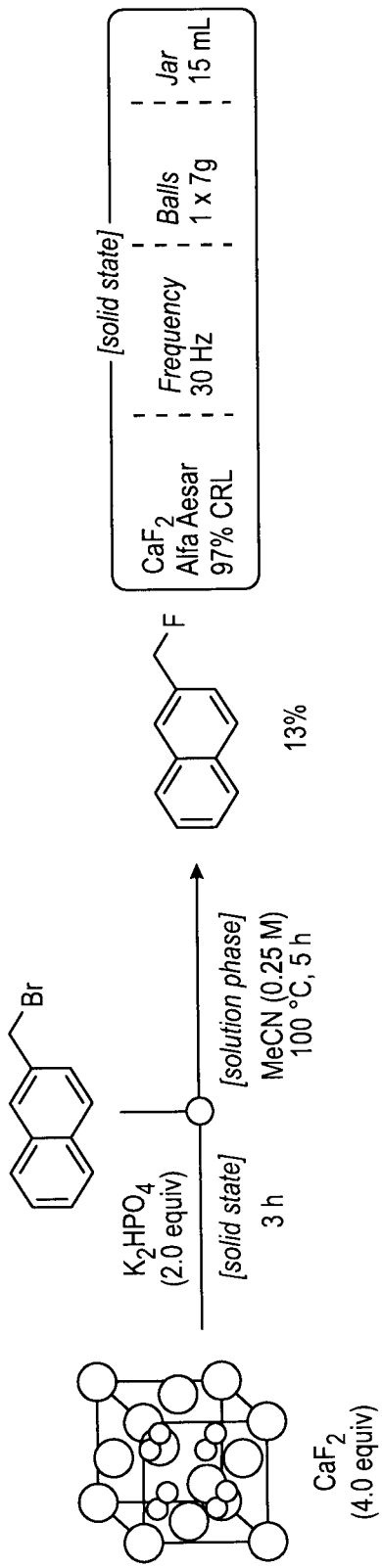
FIG. 79 illustrates a general scheme according to embodiments described herein.

In some instances, reagent grade CaF$_2$ is milled with 1 equivalent of K$_2$HPO$_4$ for 3 hours at 30 Hz before 4 equivalents of the resulting reagent is reacted with TsCl in a solvent according to FIG. 74 to achieve the resulting TsF. In some instances, 1 equivalent of acid grade fluorspar is milled with 1 equivalent of K$_2$HPO$_4$ for 3 hours at 30 Hz according to FIGS. 75 and 4 equivalents of the resulting fluorination reagent is reacted in a solvent with TsCl to achieve the fluorinated TsF. The resulting fluorinated TsF product yields resulting from reagent grade CaF$_2$ and acid grade fluorspar (81% and 82% respectively by NMR) may support the conclusion that either starting material can be used to synthesize the fluorinating reagent.

3.6. Varying Organic Substrate

Following GP3 outlined above, and having regard to FIGS. 76, 77, 78, and 79, the effect of replacing the p-toluenesulphonyl chloride substrate with 4-methylbenzoyl chloride, 2,4-dinitrochlorobenzene, 2-chloro-5-nitropyridine or 2-(bromomethyl)naphthalene was investigated. The results are outlined in Tables 3.6a, 3.6b, 3.6c and Scheme 3.6d. The results may support that the fluorination reagent can sufficiently fluorinate various chlorinated aromatic compounds. The fluorination of toluene (40% yield), may indicate that the fluorination reagent can fluorinate non-halogenated compounds.

TABLE 3.6a

Effect of varying the organic substrate on product yield

| Entry | Solvent | ArC(O)F | Arc(O)Cl | ArCO$_2$H |
|---|---|---|---|---|
| 1 | EtCN | 46% | 65% | 0% |
| 2 | PhCl | 44% | 45% | 10% |

TABLE 3.6b

Effect of varying the organic substrate on product yield

| Entry | Solvent | ArF | ArCl |
|---|---|---|---|
| 1 | Toluene | 40% | 0% |
| 2 | 1,2-dichlorobenzene | 60% | 23% |
| 3 | Chlorobenzene | 49% | 44% |
| 4 | 1,2-difluorobenzene | 49% | 26% |

TABLE 3.6c

Effect of varying the organic substrate on product yield

| Entry | Solvent | CaF$_2$ (equiv) | K$_2$HPO$_4$ (equiv) | ArF | ArCl |
|---|---|---|---|---|---|
| 1 | MeCN | 4 | 2 | 18% | 41% |
| 2 | MeCN | 6 | 4 | 20% | 16% |
| 3 | Toluene | 4 | 2 | 14% | 63% |

3.7. Removal of Salt

Figure 80:
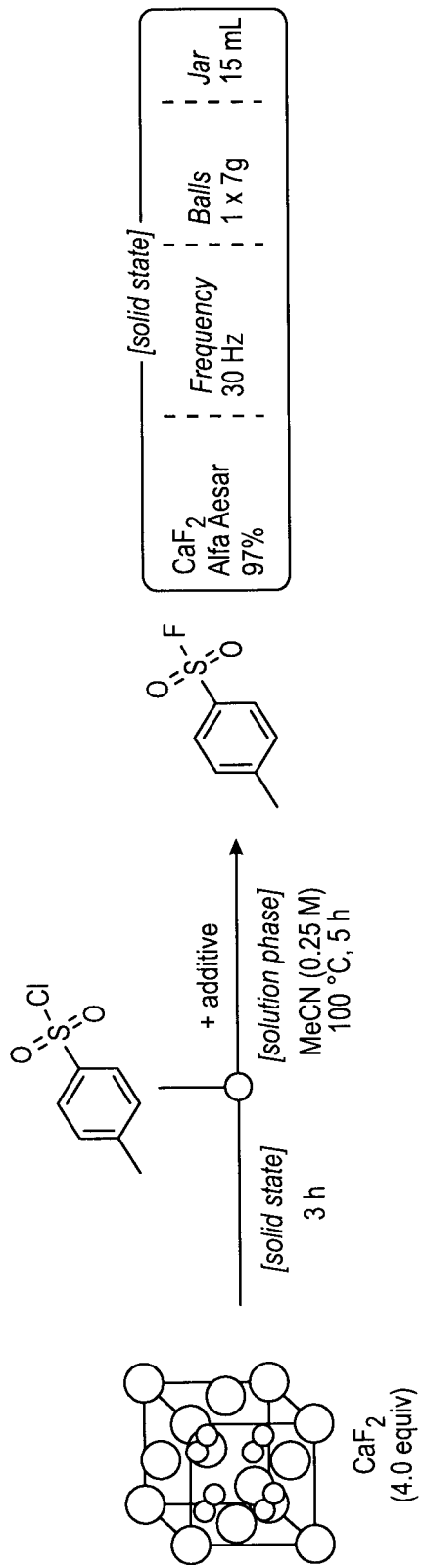
FIG. 80 illustrates a general scheme according to embodiments described herein.

To investigate the effect of removing the salt on the ability of CaF$_2$ to fluorinate p-toluenesulphonyl chloride, the reaction depicted in FIG. 80 was performed according to a similar procedure to GP3, in which the salt was removed from the pre-milling step. The results are outlined in Table 3.7. These results highlight the importance that the pre-milling of additive with CaF$_2$ has on the yield of the organofluorine product (e.g., TsF), wherein yields without the addition of the additive in the pre-milling step were less than 8%.

TABLE 3.7

Effect of removing the salt on product yield

| Additive (equiv) | TsF | TsCl | pTSA |
|---|---|---|---|
| — | 7% | 70% | trace |
| $K_2HPO_4$ (2) | <2% | 91% | 0% |
| 18-crown-6 (1) | 4% | 49% | 0% |
| Krypt [2.2.2] (1) | 4% | 1% | trace |
| Krypt [2.2.1] (1) | 2% | 0% | trace |
| Dibenzo-18-crown-6 (1) | 4% | 96% | 0% |
| Dibenzo-30-crown-10 (1) | 5% | 91% | 0% |
| Dicyclohexano-18-crown-6 (1) | 4% | 84% | 0% |
| 18-crown-6 (1) + Schreiner's Urea (0.1) | 4% | 63% | 0% |

3.8. Varying Salt

Figure 81:
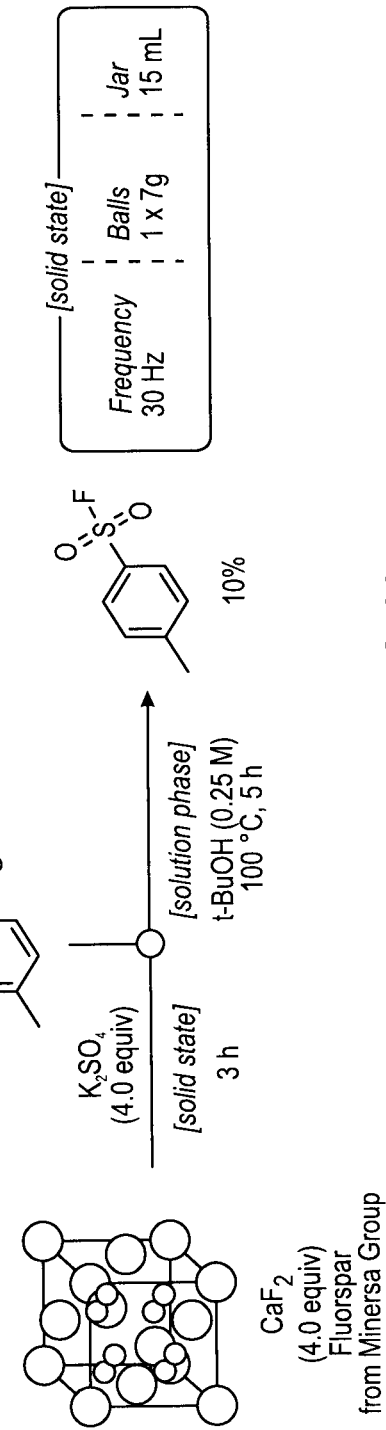
FIG. 81 illustrates a general scheme according to embodiments described herein.
Figure 82:
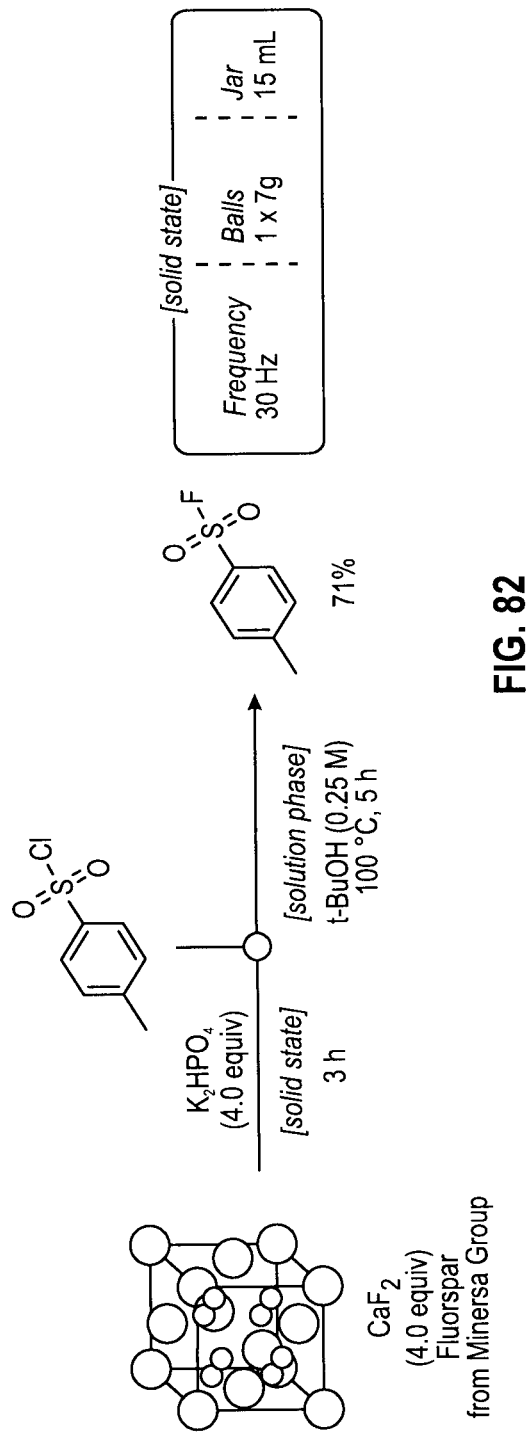
FIG. 82 illustrates a general scheme according to embodiments described herein.

Following GP3 outlined above, and having regard to FIG. 81 and FIG. 82, the effect of varying the nature of the salt was investigated. The results are outlined in FIG. 81 and FIG. 82. The variation of the salt from $K_2SO_4$ to $K_2HPO_4$ led to yields of 10% and 71% respectively in otherwise similar conditions. These results highlight the role the second salt may play in the formation of the fluorinating agent, and the resulting fluorinating agents ability to fluorinate the organic substrate. Specifically, the results highlight $K_2HPO_4$ as an exemplary salt additive.

4. Nucleophilic Fluorination with $CaF_2$

Figure 83:
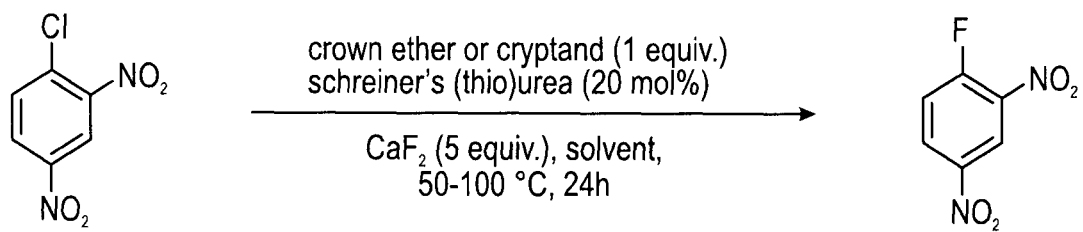
FIG. 83 illustrates a general scheme according to embodiments described herein.

To investigate the efficacy of nucleophilic fluorination with $CaF_2$ in solution, several reactions detailed in Table 4.1 were attempted according to reaction FIG. 83.

Briefly, a crown ether or cryptand (1 equiv.) described in Table 4.1 was dissolved with Schreiner's thio(urea) (20 mol %) with $CaF_2$ (5 equiv.). In some instances, an additive selected from $K_3PO$ or Schreiner's urea was added to the reaction. In all cases, the yield of the fluorinated product was 0% or found in trace amounts as determined by $^{19}F$-NMR using 4-fluoroanisole as an internal standard. In all instances, solvents used were anhydrous. In some cases, the side product formed was 1-(2,4-dinitrophenoxy)-4-nitro-2-nitrosobenzene and urea degradation occurred. In other cases, no reaction occurred. The low to zero NMR yields of fluorinated product associated with these reactions may highlight the role of the pre-milling (mechanical force) step discussed herein between $CaF_2$ (first salt) and the second salt to form the fluorinating reagent.

TABLE 4.1

| Entry | Solvent | Crown ether or Cryptand | Additive | NMR Yield |
|---|---|---|---|---|
| 1 | | Kryptofix 221 | — | 0% |
| 2 | | Kryptofix 222 | — | 0% |
| 3 | DMF | 18-crown-6 | — | 0% |
| 4 | | (Dibenzo)18-crown-6 (or dicyclo) | — | 0% |
| 5 | | 18-crown-6 | $K_3PO_4$ | Traces |
| 6 | | Kryptofix 221 | — | 0% |
| 7 | | Kryptofix 222 | — | 0% |
| 8 | Toluene | (Dibenzo)18-crown-6 (or dicyclo) | — | 0% |
| 9 | | Kryptofix 221 | Schreiner's urea | 0% |
| 10 | | Kryptofix 221 | — | 0% |
| 11 | | Kryptofix 222 | — | 0% |
| 12 | 1,2-DCE | 18-crown-6 | — | 0% |
| 13 | | Kryptofix 221 | Schreiner's urea | 0% |
| 14 | | 18-crown-6 | $K_3PO_4$ | traces |

Figure 84:
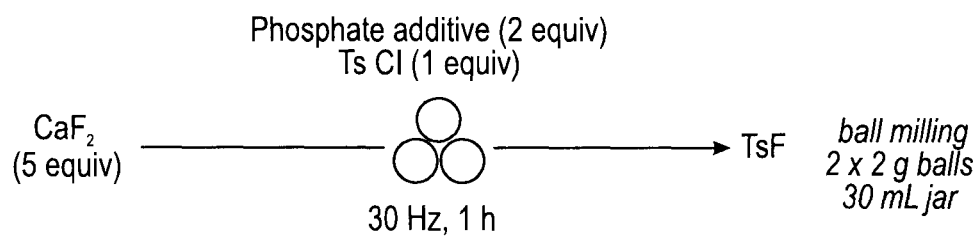
FIG. 84 illustrates a general scheme according to embodiments described herein.

5. Fluorination of 4-Toluenesulfonyl Chloride with $CaF_2$ Using Ball Milling 5.1. Use of Phosphate Additives The effect of phosphate additives on the reaction of $CaF_2$ and TsCl as seen in FIG. 84.

$CaF_2$ (1.00 mmol, 5 equiv.), the phosphate additive (2 equiv., see Table 5.1), and TsCl (1 equiv.) were added to a 30 mL stainless steel jar with 2×2 g balls (316 SS grade) to undergo ball milling using a Retsch MM400 Ball Mill. The ball milling conditions were 30 Hz for 1 hour. The resulting products were examined for starting material (TsCl %), product (TsF %), and side product (TsOH %), as seen in Table 5.1 The yields were determined by $^1H$ and $^{19}F$-NMR with 4-fluoroanisole as an internal standard. In some instances, the phosphate additive was a carbonate additive or a sulfate additive. The experimental results indicate that the $K_2HPO_4$ and $K_2CO_3$ additives may be exemplary additives, increasing yields of organofluorine product (e.g., TsF).

TABLE 5.1.

| Entry | Phosphate Additive | TsCl (%) | TsF (%) | TsOH (%) | Mass Balance (%) |
|---|---|---|---|---|---|
| 1 | $K_3PO_4$ | 12 | 7 | 0 | 25 |
| 2 | $K_2HPO_4$ | 62 | 17 | 0 | 79 |
| 3* | $K_2HPO_4$ | 40 | 25 | 0 | 65 |
| 4 | $KH_2PO_4$ | 97 | 1 | 0 | 97 |
| 5 | $Na_3PO_4$ | 74 | 6 | 0 | 80 |
| 6 | $Li_3PO_4$ | 100 | 0 | 0 | 100 |
| 7 | $Na_2HPO_4$ | 97 | 2 | 0 | 99 |
| 8 | $NaH_2PO_4$ | 99 | 1 | 0 | 100 |
| 9 | $K_2SO_4$ | 92 | 1 | 0 | 93 |
| 10 | $Na_2SO_4$ | 92 | 3 | 0 | 95 |
| 11 | $MgSO_4$ | 97 | 1 | 0 | 98 |
| 12 | $Ag_2SO_4$ | 4 | <1 | 25 | 30 |
| 13 | $Na_2CO_3$ | 93 | 3 | 0 | 93 |
| 14 | $KHCO_3$ | 80 | 5 | 0 | 85 |
| 15* | $K_2CO_3$ | 10 | 24 | 0 | 34 |

*Using 1 × 4 g ball, 15 mL jar 5.2. $CaF_2$ to $K_2HPO_4$ Ratio

Figure 85:
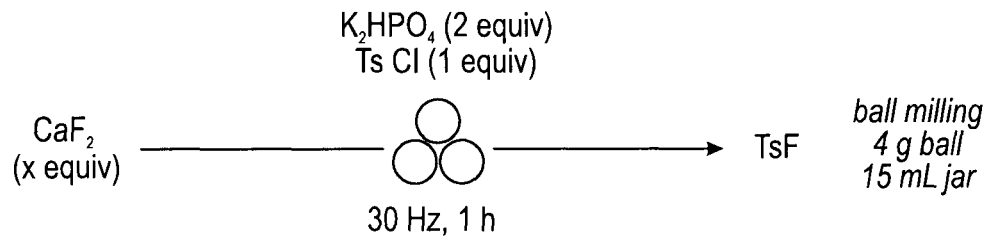
FIG. 85 illustrates a general scheme according to embodiments described herein.

Given the benefit that $K_2HPO_4$ may have as an additive in the reaction of $CaF_2$ and TsCl ball milling fluorination experiments, the ratio of $CaF_2$ and the $K_2HPO_4$ ratio was probed via FIG. 85.

Briefly, $CaF_2$ (varying equiv.) was added to a stainless steel jar with a 4 g ball (316 SS grade) along with $K_2HPO_4$ (2 equiv) and TsCl (1 equiv). The ball milling was completed with a Retsch MM400 Ball Mill at 30 Hz for 1 hour. The TsCl yield (%), TsF yield (%), and TsOH side product yield (%), were determined by $^1H$ and $^{19}F$-NMR with 4-fluoroanisole as an internal standard. The results can be seen in Table 5.2. The increased yield with increased ratio of $CaF_2:K_2HPO_4$ indicates that the ratio of the two salts may play an a role in optimizing the resulting yield of organofluorine product and a ratio of 2:1 may provide the highest yield of organofluorine product (e.g., TsF).

TABLE 5.2.

| Entry | Equivalents of $CaF_2$ | TsCl (%) | TsF (%) | TsOH (%) | Mass balance (%) |
|---|---|---|---|---|---|
| 1 | 6 | 51 | 23 | 1 | 75 |
| 2 | 5 | 40 | 25 | 0 | 65 |
| 3 | 4 | 35 | 30 | 2 | 67 |
| 4 | 3 | 56 | 17 | 1 | 74 |
| 5 | 2 | 67 | 12 | 1 | 80 |
| 6 | 1 | 37 | 13 | 0 | 50 |

5.3. Product and Starting Material Stability

Figure 86:
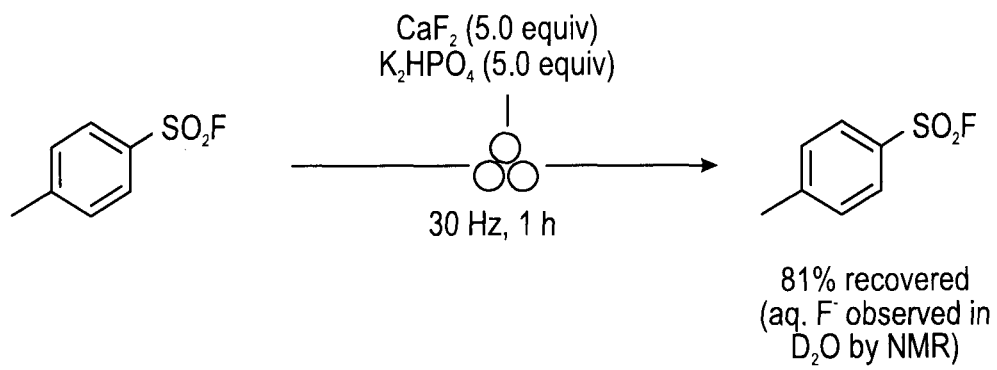
FIG. 86 illustrates a general scheme according to embodiments described herein.
Figure 86:
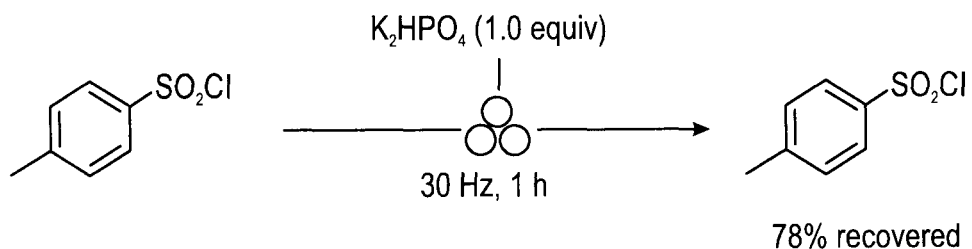

The stability of the product (TsF) and starting material (TsCl) were probed in the presence of $CaF_2$ and $K_2HPO_4$ for TsF and in the presence of $K_2HPO_4$ for TsCl as in FIG. 86.

In the case of the product (TsF), upon ball milling in stainless steel jars with a Retsch MM400 ball mill at 30 Hz for 1 hour in the presence of $CaF_2$ (5.0 equiv.) and $K_2HPO_4$ (5.0 equiv), 81% of the product (TsF) was recovered. Some aqueous fluoride ion was observed in $D_2O$ by NMR. The 81% recovery of the starting material, TsF, highlight the stability of the fluorinated material in the presence of the fluorinating reagent under milling conditions.

In the case of the starting material (TsCl), upon ball milling under similar conditions in the presence of $K_2HPO_4$ (1.0 equiv), 78% of the TsCl was recovered.

5.4. Step-Wise Addition in the Solid State

Figure 87:
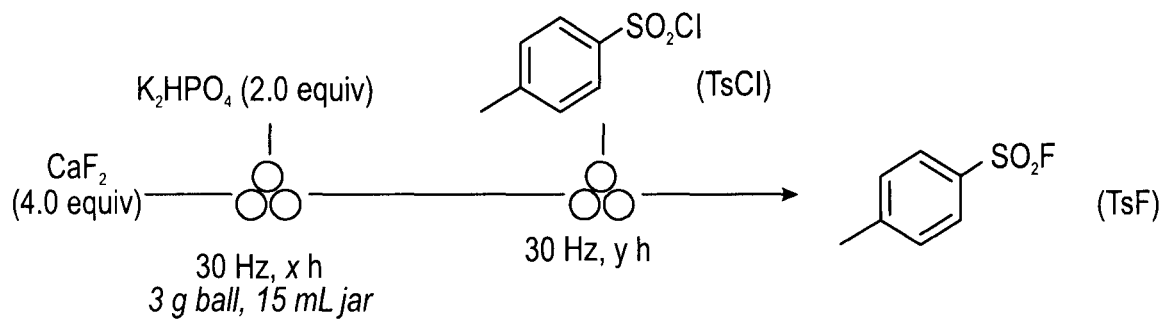
FIG. 87 illustrates a general scheme according to embodiments described herein.

The effect on product yield when step-wise addition of starting materials was examined as seen in FIG. 87.

Ball milling was completed using a Retsch MM400 Ball Mill using 15 mL stainless steel jars and 3 g balls. Briefly, $CaF_2$ (4.0 equiv.) was added to the stainless steel jar with $K_2HPO_4$ (2.0 equiv.) and ball milling took place at 30 Hz (varying times seen in Table 5.4. In the second step, TsCl (1 mmol) was added to the stainless steel jar and fluorination via ball milling took place at 30 Hz (varying times seen in Table 5.4. Yields of TsCl and TsF (%) were determined by $^1H$ and $^{19}F$-NMR with 4-fluoroanisole as an internal standard. The results show that the combination of pre-milling of the $CaF_2$ and $K_2HPO_4$ followed by longer fluorination times may lead to higher yields of organofluorine product (e.g., 66% yield of TsF with 3 hrs of pre-milling followed by 3 hours of fluorination).

TABLE 5.4.

| Entry | Pre-milling (x h) | Fluorination (y h) | TsCl (%) | TsF (%) | Mass balance |
|---|---|---|---|---|---|
| 1 | 0 | 3 | 4 | 31 | 35 |
| 2 | 1 | 1 | 47 | 29 | 76 |
| 3 | 2 | 1 | 22 | 41 | 63 |
| 4 | 3 | 3 | 0 | 66 | 66 |

5.5. Step-Wise Addition in the Solid State to Solution State

Figure 88:
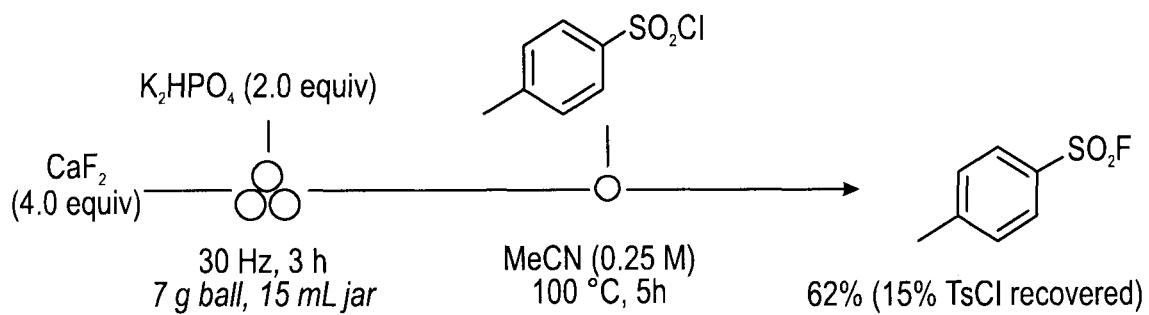
FIG. 88 illustrates a general scheme according to embodiments described herein.

The effect on product yield was examined when $K_2HPO_4$ (2.0 equiv.) was first milled with $CaF_2$ (4.0 equiv.) at 30 Hz for 3 hours followed by a second step, solution state reaction with TsCl in acetonitrile (0.25 M) for 5 hours at 100° C. as seen in FIG. 88.

When adding $CaF_2$ (4 equiv.) and $K_2HPO_4$ (2.0 equiv.) to a stainless steel jar for ball milling at 30 Hz for 3 hours as seen in FIG. 88, followed by adding TsCl in the solution state (1.00 mmol, 0.25 M) and reacting the solution at 100° C. for 5 hours in acetonitrile, the yield of TsF was determined to be 62% with 15% of the TsCl recovered. The 62% yield of TsF may highlight the importance of pre-milling $CaF_2$ with the phosphate activator, $K_2HPO_4$ before the solution fluorination reaction with TsCl.

5.6. Step-Wise Addition in the Solid State to Solution State

Figure 89:
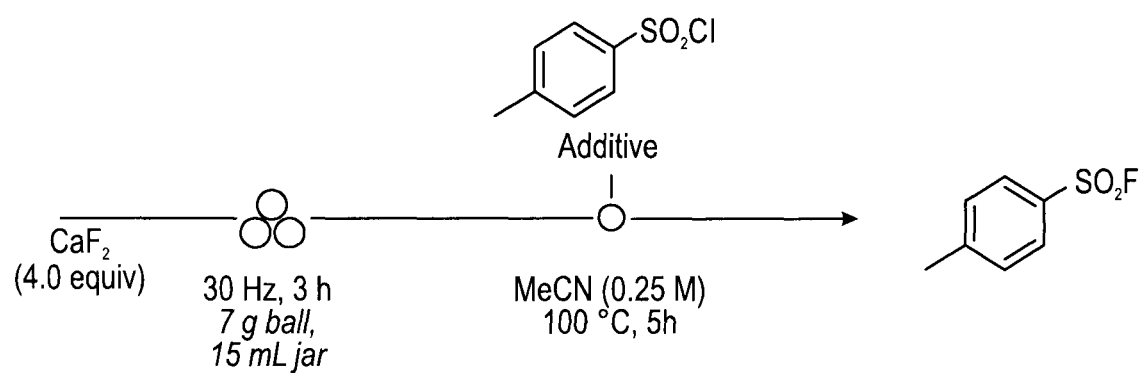
FIG. 89 illustrates a general scheme according to embodiments described herein.

Several control experiments were completed using ball milled $CaF_2$, as seen in FIG. 89, where the $CaF_2$ is not ball milled with the additive before addition of the TsCl.

In summary, $CaF_2$ (4.0 equiv.) is added to a 15 mL stainless steel jar and ball milled alone at 30 Hz for 3 hours before being added to an additive (see Table 5.6) and TsCl (1 mmol) in acetonitrile (0.25 M) and reacted for 5 hours at 100° C. This method may result in lower yields of fluorinated product than when the additive is milled with the $CaF_2$.

TABLE 5.6

| Entry | Additive | Additive Equiv | TsCl (%) | TsF (%) | TsOH (%) | Mass Balance (%) |
|---|---|---|---|---|---|---|
| 1 | — | — | 70 | 7 | <1 | 77 |
| 2 | $K_2HPO_4$ | 2 | 91 | 2 | 0 | 93 |
| 3 | 18-crown-6 | 1 | 49 | 4 | 0 | 53 |
| 4 | Krypt [2.2.2] | 1 | 1 | 4 | <1 | 5 |
| 5 | Krypt [2.2.1] | 1 | 0 | 2 | <1 | 3 |
| 6 | Dibenzo-18-crown-6 | 1 | 96 | 4 | 0 | 100 |
| 7 | Dibenzo-30-crown-6 | 1 | 91 | 5 | 0 | 96 |
| 8 | Dicyclohexano-18-crown-6 | 1 | 84 | 4 | 0 | 88 |
| 9 | 18-crown-6 + Schreiner's Urea | 1 + 0.1 | 63 | 4 | 0 | 67 |

5.7. Replacement of Reagent Grade $CaF_2$ with Acid Grade Fluorspar

Figure 90:
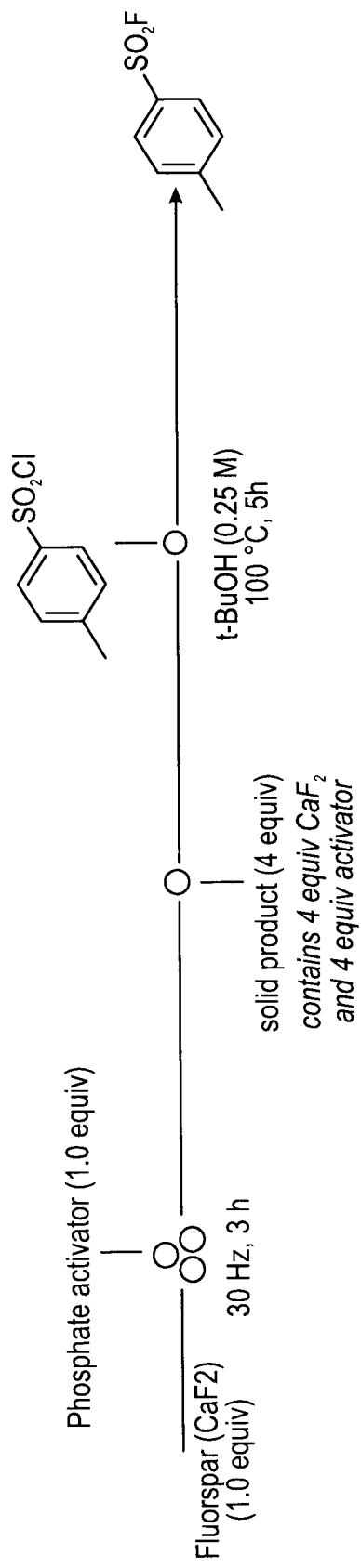
FIG. 90 illustrates a general scheme according to embodiments described herein.

In some instances, reagent grade $CaF_2$ was replaced with acid grade Fluorspar and screening of the various phosphate activators was completed as described in FIG. 90. The various phosphate activators included $K_3PO_4$, $K_2HPO_4$, $KH_2PO_4$, $Na_3PO_4$, $Na_2HPO_4$, $KPO_3$, $K_4P_2O_7$, $K_5P_3O_{10}$, $Na_4P_2O_7$, $Na_5P_3O_{10}$, $(NaPO_3)_3$, $CaHPO_4$, and $\alpha$-$Ca_3(PO_4)_2$.

Figure 3:
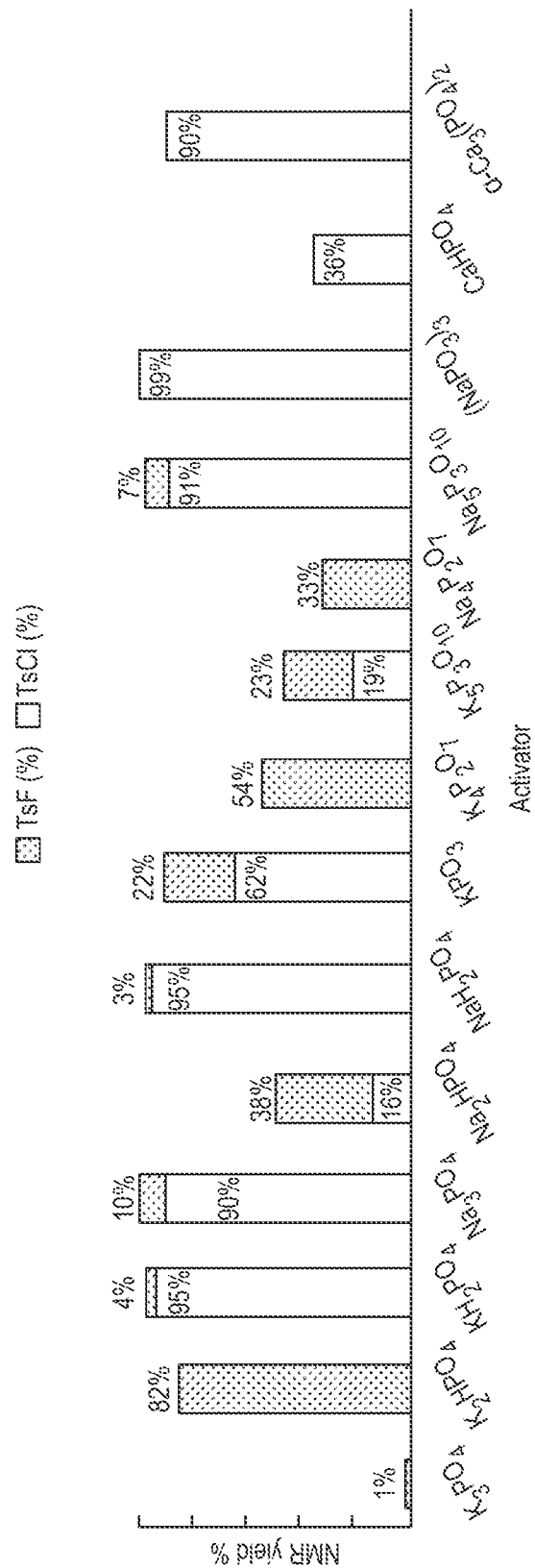
FIG. 3 shows the NMR yields (%) of TsF and TsCl when various phosphates were used as activators of Fluorspar.

The Fluorspar (1.0 equiv.) was added to the stainless steel jar and milled for 3 hours at 30 Hz with a phosphate activator (1 equiv.) (see FIG. 3). Subsequently, the solid product is added, containing $CaF_2$ (4 equiv.) and phosphate activator (4 equiv.), to t-butanol (0.25 M) with TsCl (1.00 mmol) and reacted for 5 hours at 100° C. to obtain the fluorinated product (TsF). The yields of the reaction (TsF(%), TsCl (%)) can be seen in FIG. 3. Corresponding sulfonyl bromide and tosylate as substrates afforded the sulfonyl fluoride in 71%, and 26% respectively (using $K_2HPO_4$ as the additive, compared with 82% using the sulfonyl chloride). Using $K_4P_2O_7$ resulted in yields of 54% TsF. In some instances, the phosphate activators (e.g., $CaHPO_4$, $(NaPO_3)_3$, $\alpha$-$Ca_3(PO_4)_2$) led to trace amounts or 0% of TsF product yield. In brief, the results indicate that the selection of the activator salt (second salt) may play a significant role in the resulting fluorinating reagent's ability to fluorinate the substrate. The results highlight potential exemplary additives including $K_2HPO_4$, $Na_2HPO_4$, $K_4P_2O_7$ and $Na_4P_2O_7$.

Figure 4:
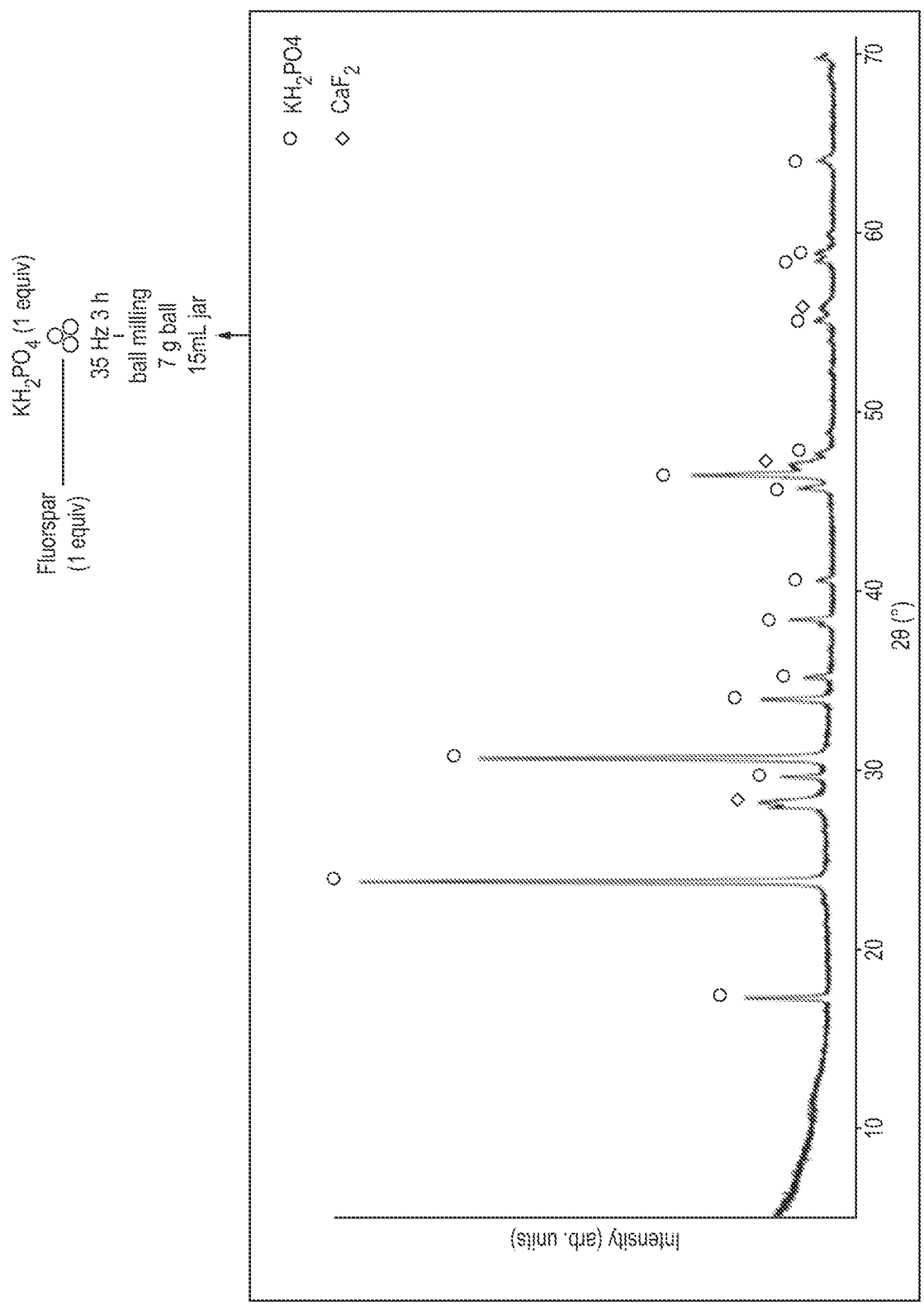
FIG. 4 shows a PXRD diffractogram of the milling product of fluorspar and $KH_2PO_4$ after 3 hours at 35 Hz.

PXRD data was obtained for each of the solid products obtained from Fluorspar activation by various phosphate activators included $K_3PO_4$, $K_2HPO_4$, $KH_2PO_4$, $Na_3PO_4$, $Na_2HPO_4$, $KPO_3$, $K_4P_2O_7$, $K_5P_3O_{10}$, $Na_4P_2O_7$, $Na_5P_3O_{10}$, $(NaPO_3)_3$, $CaHPO_4$, and $\alpha$-$Ca_3(PO_4)_2$. FIG. 4 shows the PXRD pattern resulting from milling of Fluorspar with $KH_2PO_4$ at 35 Hz for 3 hours. Table 5.7.1 shows the PXRD data from the milling of Fluorspar with $KH_2PO_4$ represented in FIG. 4. Labels on the diffraction pattern indicate crystalline phase of $CaF_2$ and $KH_2PO_4$.

TABLE 5.7.1.

| Pos. [°2Th.] | Height [cts] | FWHM [°2Th.] | d-spacing [Å] | Rel. Int. [%] |
|---|---|---|---|---|
| 17.4503 | 686.27 | 0.0528 | 5.07796 | 16.95 |
| 17.5072 | 731.34 | 0.0541 | 5.06577 | 18.06 |
| 23.9279 | 4049.59 | 0.1299 | 3.71901 | 100.00 |

TABLE 5.7.1.-continued

| Pos. [°2Th.] | Height [cts] | FWHM [°2Th.] | d-spacing [Å] | Rel. Int. [%] |
|---|---|---|---|---|
| 28.0696 | 487.06 | 0.0433 | 3.17898 | 12.03 |
| 28.3647 | 574.15 | 0.1515 | 3.14657 | 14.18 |
| 29.8125 | 339.33 | 0.0866 | 2.99698 | 8.38 |
| 30.7783 | 2994.59 | 0.1407 | 2.90510 | 73.95 |
| 34.0483 | 591.48 | 0.0649 | 2.63321 | 14.61 |
| 35.2759 | 216.71 | 0.1732 | 2.54434 | 5.35 |
| 38.5033 | 368.10 | 0.0758 | 2.33817 | 9.09 |
| 40.6969 | 138.12 | 0.1299 | 2.21706 | 3.41 |
| 45.8277 | 299.07 | 0.1082 | 1.98008 | 7.39 |
| 46.5419 | 1217.04 | 0.0974 | 1.95135 | 30.05 |
| 47.1639 | 370.38 | 0.1515 | 1.92705 | 9.15 |
| 47.7466 | 132.31 | 0.1732 | 1.90488 | 3.27 |
| 48.9681 | 32.23 | 0.2598 | 1.86019 | 0.80 |
| 52.3336 | 26.58 | 0.3464 | 1.74821 | 0.66 |
| 54.0701 | 27.15 | 0.2598 | 1.69610 | 0.67 |
| 55.1283 | 170.76 | 0.0866 | 1.66602 | 4.22 |
| 55.7911 | 105.97 | 0.3031 | 1.64779 | 2.62 |
| 58.4622 | 159.43 | 0.1082 | 1.57871 | 3.94 |
| 58.8671 | 151.82 | 0.1082 | 1.56882 | 3.75 |
| 59.8709 | 40.85 | 0.2598 | 1.54489 | 1.01 |
| 64.0433 | 146.25 | 0.0866 | 1.45394 | 3.61 |
| 69.7452 | 120.73 | 0.1320 | 1.34726 | 2.98 |

Figure 5:
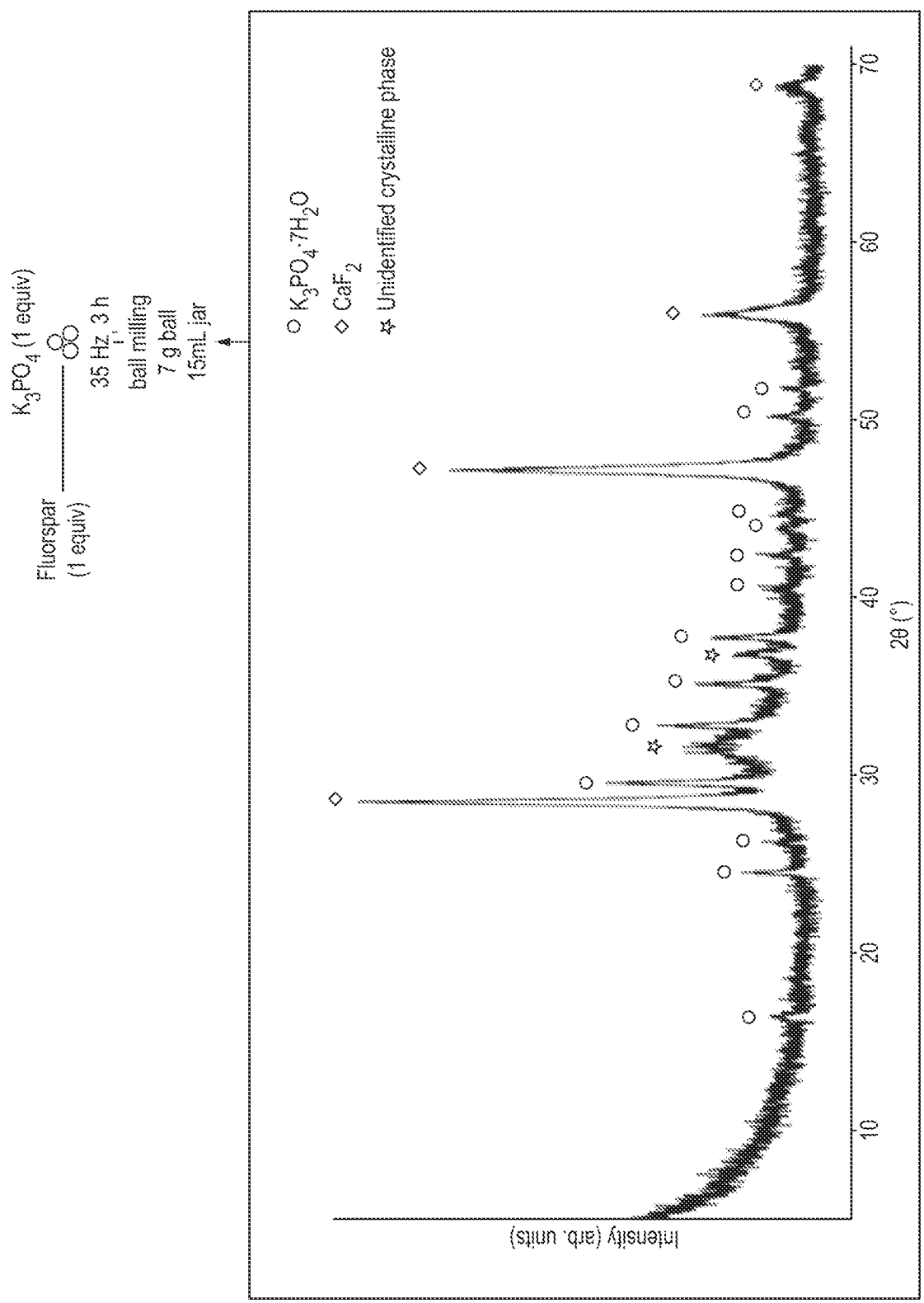
FIG. 5 shows a PXRD diffractogram of the milling product of fluorspar and $K_3PO_4$ after 3 hours at 35 Hz.

FIG. 5 shows the PXRD pattern resulting from milling of Fluorspar with $K_3PO_4$ at 35 Hz for 3 hours. Table 5.7.2 shows the PXRD data from the milling of Fluorspar with $K_3PO_4$ represented in FIG. 5. Labels in FIG. 5 indicate crystalline phases of $K_3PO_4 \cdot 7H_2$, $CaF_2$, and an unidentified crystalline phase.

TABLE 5.7.2.

| Pos. [°2Th.] | Height [cts] | FWHM [°2Th.] | d-spacing [Å] | Rel. Int. [%] |
|---|---|---|---|---|
| 5.1808 | 76.50 | 0.5196 | 17.05776 | 13.83 |
| $K_3PO_4$ 16.3622 | 31.25 | 0.2598 | 5.41759 | 5.65 |
| $K_3PO_4$ 24.4974 | 60.81 | 0.1732 | 3.63384 | 11.00 |
| $K_3PO_4$ 26.1679 | 28.97 | 0.2598 | 3.40552 | 5.24 |
| $CaF_2$ 28.4848 | 552.97 | 0.3031 | 3.13357 | 100.00 |
| $K_3PO_4$ 29.5428 | 228.67 | 0.2598 | 3.02372 | 41.35 |
| new phase 31.5443 | 118.01 | 0.8659 | 2.83628 | 21.34 |
| $K_3PO_4$ 32.7690 | 166.82 | 0.2165 | 2.73303 | 30.18 |
| $K_3PO_4$ 35.1033 | 117.05 | 0.1732 | 2.55645 | 21.17 |
| new phase 36.7972 | 77.63 | 0.2165 | 2.44256 | 14.04 |
| $K_3PO_4$ 37.7484 | 99.72 | 0.2165 | 2.38318 | 18.03 |
| $K_3PO_4$ 40.5069 | 24.30 | 0.3464 | 2.22702 | 4.39 |
| $K_3PO_4$ 42.3931 | 25.64 | 0.2165 | 2.13220 | 4.64 |
| $CaF_2$ 47.1921 | 403.01 | 0.2381 | 1.92597 | 72.88 |
| $K_3PO_4$ 50.2093 | 39.46 | 0.1732 | 1.81708 | 7.14 |
| $K_3PO_4$ 51.7624 | 19.86 | 0.2598 | 1.76615 | 3.59 |
| $CaF_2$ 55.9692 | 111.97 | 0.2598 | 1.64297 | 20.25 |
| $CaF_2$ 68.9523 | 30.23 | 0.8448 | 1.36080 | 5.47 |

Figure 6:
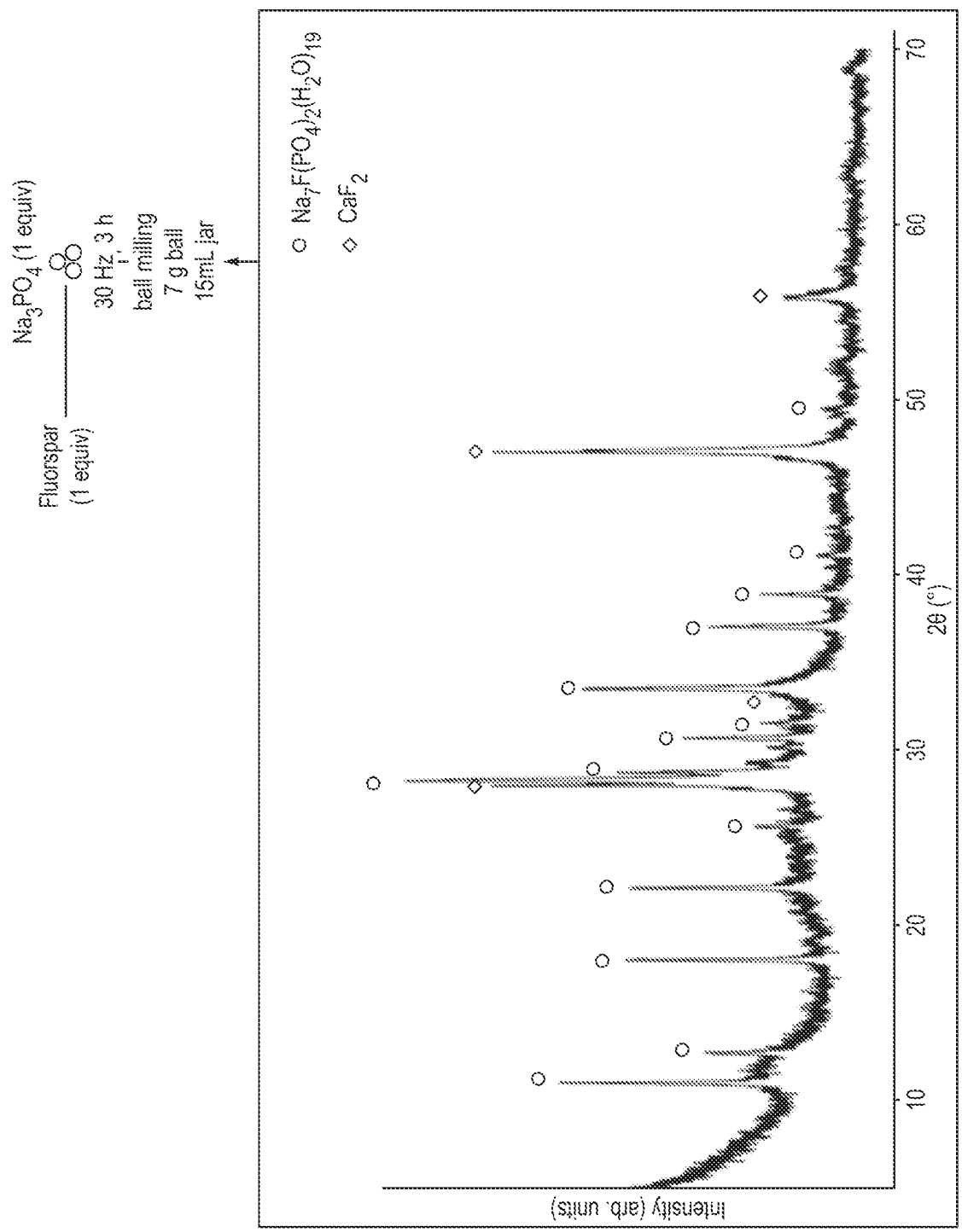
FIG. 6 shows a PXRD diffractogram of the milling product of fluorspar with $Na_3PO_4$ after 3 hours at 30 Hz.

FIG. 6 shows the PXRD pattern resulting from milling of Fluorspar with $Na_3PO_4$ at 30 Hz for 3 hours. Table 5.7.3 shows the PXRD data from the milling of Fluorspar with $Na_3PO_4$ represented in FIG. 6. Labels in FIG. 6 indicate crystalline phases of $Na_7F(PO_4)_2(H_2O)_{19}$ and $CaF_2$.

TABLE 5.7.3.

| Pos. [°2Th.] | Height [cts] | FWHM [°2Th.] | d-spacing [Å] | Rel. Int. [%] |
|---|---|---|---|---|
| 11.0987 | 575.32 | 0.0758 | 7.97217 | 55.68 |
| 12.8527 | 230.21 | 0.1082 | 6.88791 | 22.28 |
| 18.1294 | 481.00 | 0.1299 | 4.89331 | 46.55 |
| 22.2114 | 429.50 | 0.0866 | 4.00239 | 41.57 |
| 25.7262 | 114.34 | 0.1515 | 3.46298 | 11.07 |
| 28.0698 | 819.87 | 0.0433 | 3.17896 | 79.35 |
| $CaF_2$ 28.3394 | 1033.22 | 0.0758 | 3.14932 | 100.00 |

TABLE 5.7.3.-continued

| Pos. [°2Th.] | Height [cts] | FWHM [°2Th.] | d-spacing [Å] | Rel. Int. [%] |
|---|---|---|---|---|
| 28.7953 | 453.13 | 0.1515 | 3.10049 | 43.86 |
| 29.3760 | 147.60 | 0.2165 | 3.04051 | 14.29 |
| 30.2262 | 90.55 | 0.1299 | 2.95690 | 8.76 |
| 30.7564 | 308.53 | 0.1299 | 2.90712 | 29.86 |
| $CaF_2$ 31.6106 | 121.58 | 0.1515 | 2.83049 | 11.77 |
| 33.5540 | 611.75 | 0.0541 | 2.67086 | 59.21 |
| 37.0842 | 313.50 | 0.1082 | 2.42432 | 30.34 |
| 38.9278 | 168.51 | 0.1515 | 2.31365 | 16.31 |
| 41.1692 | 55.41 | 0.1732 | 2.19272 | 5.36 |
| $CaF_2$ 47.0750 | 894.37 | 0.0528 | 1.92889 | 86.56 |
| 47.2052 | 643.97 | 0.0649 | 1.92546 | 62.33 |
| 49.4533 | 52.13 | 0.2598 | 1.84307 | 5.04 |
| 52.0627 | 30.14 | 0.8659 | 1.75667 | 2.92 |
| $CaF_2$ 55.8334 | 157.23 | 0.2165 | 1.64664 | 15.22 |
| 57.5195 | 25.10 | 0.3464 | 1.60232 | 2.43 |
| $CaF_2$ 68.8110 | 33.78 | 0.5280 | 1.36325 | 3.27 |

Figure 7:
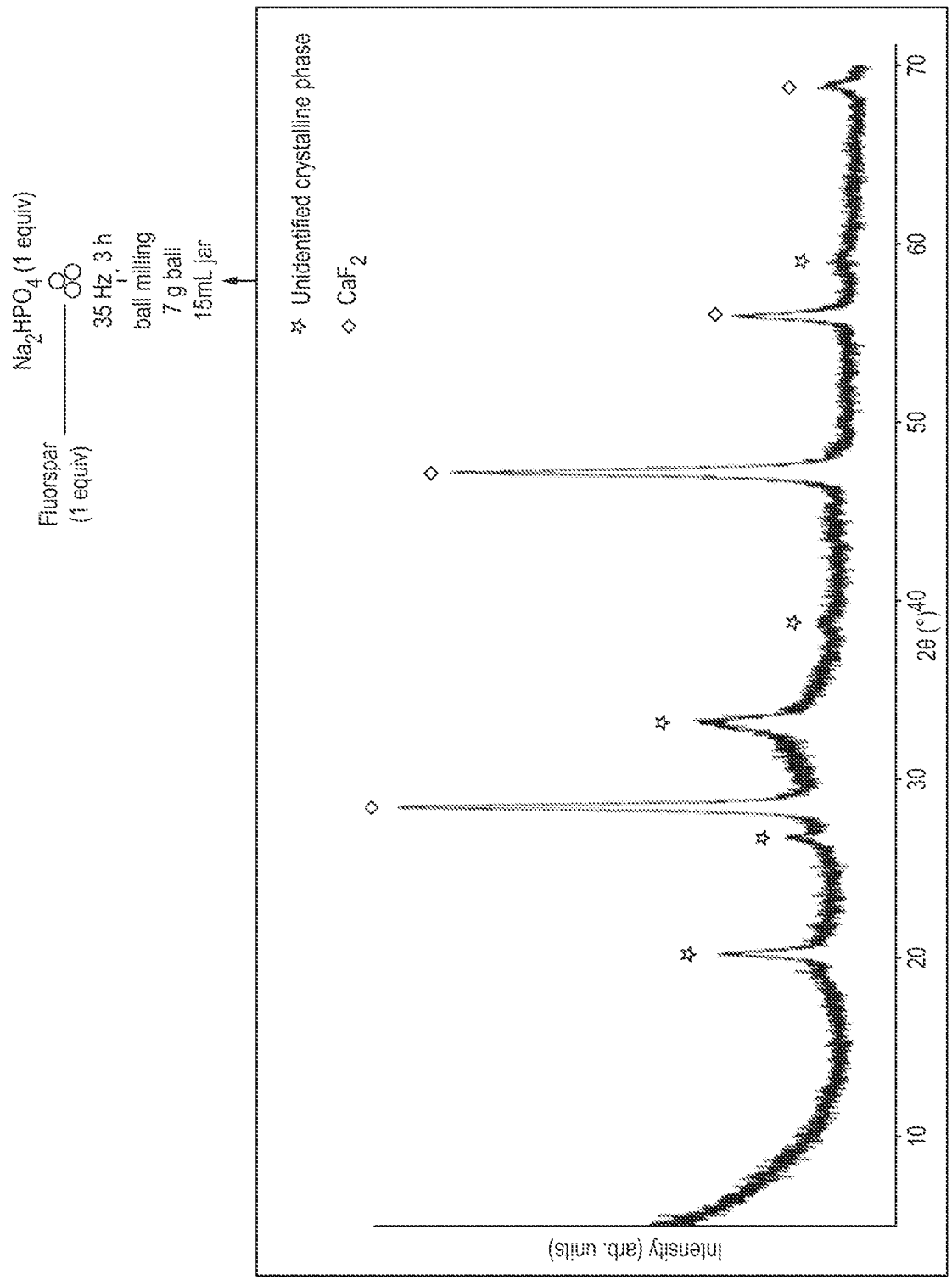
FIG. 7 shows a PXRD diffractogram of the milling product of fluorspar with $Na_2HPO_4$ after 3 hours at 35 Hz.

FIG. 7 shows the PXRD pattern resulting from milling of Fluorspar with $Na_2HPO_4$ at 35 Hz for 3 hours. Table 5.7.4 shows the PXRD data from the milling of Fluorspar with $Na_2HPO_4$ represented in FIG. 7. Labels in FIG. 7 indicate crystalline phases of $CaF_2$ and an unidentified crystalline phase.

TABLE 5.7.4.

| Pos. [°2Th.] | Height [cts] | FWHM [°2Th.] | d-spacing [Å] | Rel. Int. [%] |
|---|---|---|---|---|
| 20.1820 | 170.30 | 0.2598 | 4.40001 | 23.76 |
| 26.6900 | 46.47 | 0.2598 | 3.34008 | 6.48 |
| $CaF_2$ 28.4541 | 716.88 | 0.2814 | 3.13689 | 100.00 |
| 33.2761 | 170.13 | 0.3031 | 2.69253 | 23.73 |
| 38.7654 | 18.81 | 0.5196 | 2.32296 | 2.62 |
| $CaF_2$ 47.1554 | 663.65 | 0.2814 | 1.92738 | 92.57 |
| $CaF_2$ 55.9176 | 188.00 | 0.3031 | 1.64436 | 26.22 |
| $CaF_2$ 68.8390 | 51.16 | 0.4224 | 1.36276 | 7.14 |

Figure 8:
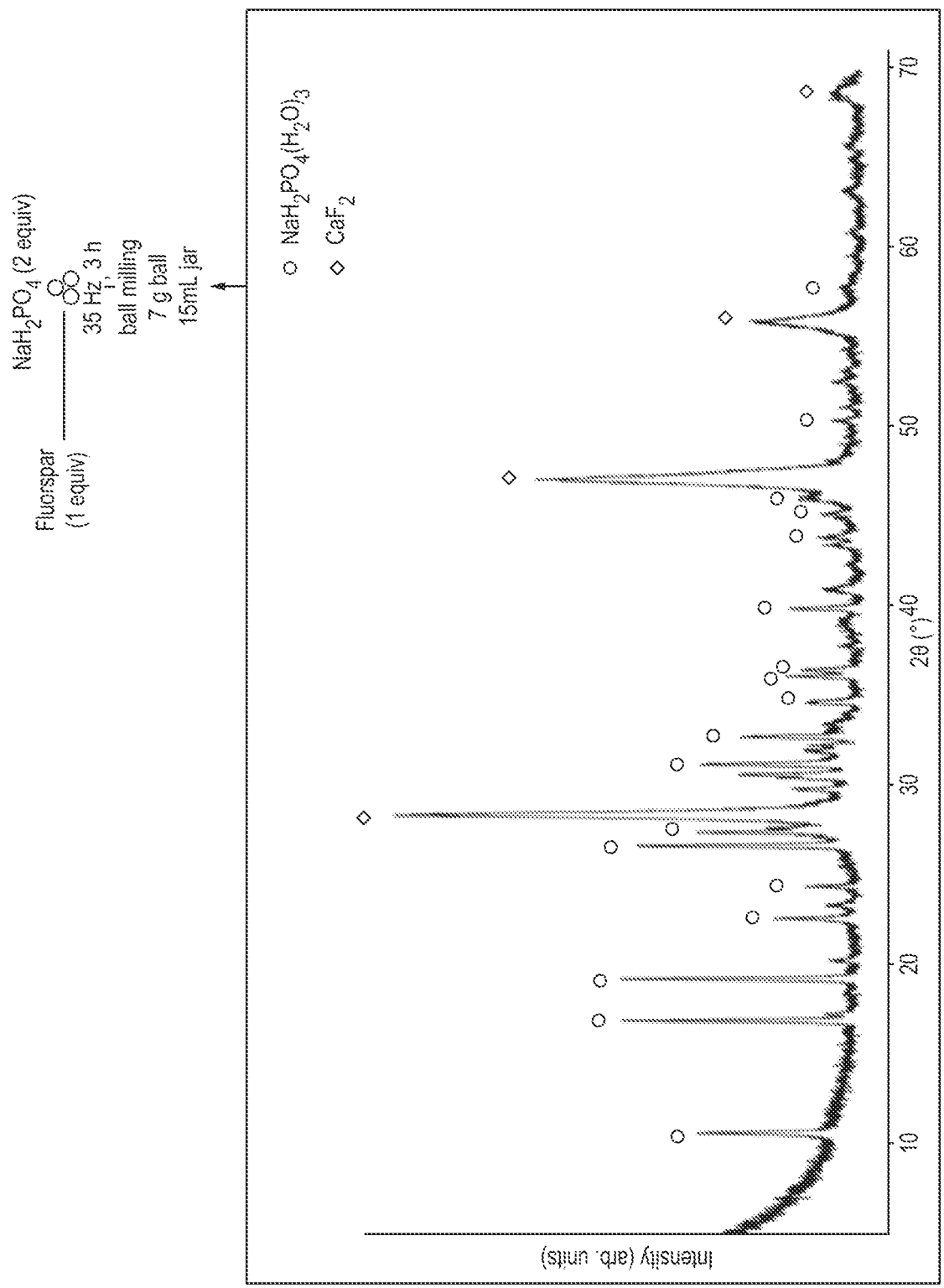
FIG. 8 shows a PXRD diffractogram of the milling product of fluorspar with $NaH_2PO_4$ after 3 hours at 35 Hz.

FIG. 8 shows the PXRD pattern resulting from milling of Fluorspar with $NaH_2PO_4$ at 35 Hz for 3 hours. Table 5.7.5 shows the PXRD data from the milling of Fluorspar with $NaH_2PO_4$ represented in FIG. 8. Labels in FIG. 8 indicate crystalline phases of $CaF_2$ and $NaH_2PO_4(H_2O)_3$.

TABLE 5.7.5.

| Pos. [°2Th.] | Height [cts] | FWHM [°2Th.] | d-spacing [Å] | Rel. Int. [%] |
|---|---|---|---|---|
| 5.1628 | 111.00 | 0.5196 | 17.11719 | 10.75 |
| 10.6534 | 324.58 | 0.1515 | 8.30443 | 31.42 |
| 16.9107 | 580.27 | 0.0758 | 5.24309 | 56.18 |
| 17.2912 | 68.53 | 0.1299 | 5.12858 | 6.63 |
| 19.2624 | 595.57 | 0.0974 | 4.60795 | 57.66 |
| 20.2745 | 49.87 | 0.1515 | 4.38016 | 4.83 |
| 22.6340 | 196.21 | 0.1082 | 3.92860 | 18.99 |
| 23.3705 | 59.97 | 0.1732 | 3.80644 | 5.81 |
| 24.4355 | 101.84 | 0.1515 | 3.64289 | 9.86 |
| 26.6815 | 527.64 | 0.1299 | 3.34113 | 51.08 |
| 27.4363 | 400.96 | 0.0866 | 3.25090 | 38.82 |
| 28.3572 | 1032.95 | 0.1732 | 3.14738 | 100.00 |
| 29.8795 | 149.68 | 0.1515 | 2.99041 | 14.49 |
| 30.6959 | 268.41 | 0.1082 | 2.91271 | 25.98 |
| 31.2197 | 391.71 | 0.1515 | 2.86502 | 37.92 |
| 32.0102 | 118.51 | 0.1299 | 2.79606 | 11.47 |
| 32.7605 | 292.25 | 0.1732 | 2.73371 | 28.29 |
| 34.6523 | 115.42 | 0.1082 | 2.58868 | 11.17 |
| 36.1761 | 149.25 | 0.1299 | 2.48306 | 14.45 |
| 36.5045 | 135.17 | 0.1515 | 2.46148 | 13.09 |
| 37.8231 | 25.18 | 0.1732 | 2.37864 | 2.44 |
| 39.0272 | 36.90 | 0.4330 | 2.30798 | 3.57 |
| 39.9166 | 161.17 | 0.1299 | 2.25859 | 15.60 |

TABLE 5.7.5.-continued

| Pos. [°2Th.] | Height [cts] | FWHM [°2Th.] | d-spacing [Å] | Rel. Int. [%] |
|---|---|---|---|---|
| 40.9910 | 67.01 | 0.3464 | 2.20183 | 6.49 |
| 42.3863 | 15.91 | 0.2598 | 2.13253 | 1.54 |
| 43.5308 | 53.93 | 0.2598 | 2.07908 | 5.22 |
| 43.9368 | 83.86 | 0.1732 | 2.06081 | 8.12 |
| 45.2239 | 81.41 | 0.1299 | 2.00510 | 7.88 |
| 46.0782 | 112.69 | 0.2598 | 1.96990 | 10.91 |
| 47.1350 | 786.79 | 0.1515 | 1.92817 | 76.17 |
| 49.5339 | 19.28 | 0.3031 | 1.84026 | 1.87 |
| 50.4606 | 41.62 | 0.2165 | 1.80862 | 4.03 |
| 51.1946 | 26.58 | 0.1732 | 1.78440 | 2.57 |
| 52.5781 | 49.03 | 0.1299 | 1.74066 | 4.75 |
| 55.9901 | 237.76 | 0.3897 | 1.64241 | 23.02 |
| 57.7920 | 25.50 | 0.5196 | 1.59541 | 2.47 |
| 59.7053 | 9.88 | 0.5196 | 1.54878 | 0.96 |
| 60.9672 | 20.31 | 0.3464 | 1.51971 | 1.97 |
| 63.2931 | 31.33 | 0.3464 | 1.46935 | 3.03 |
| 65.7834 | 24.71 | 0.2598 | 1.41963 | 2.39 |
| 68.4277 | 51.66 | 1.0560 | 1.36995 | 5.00 |

Figure 9:
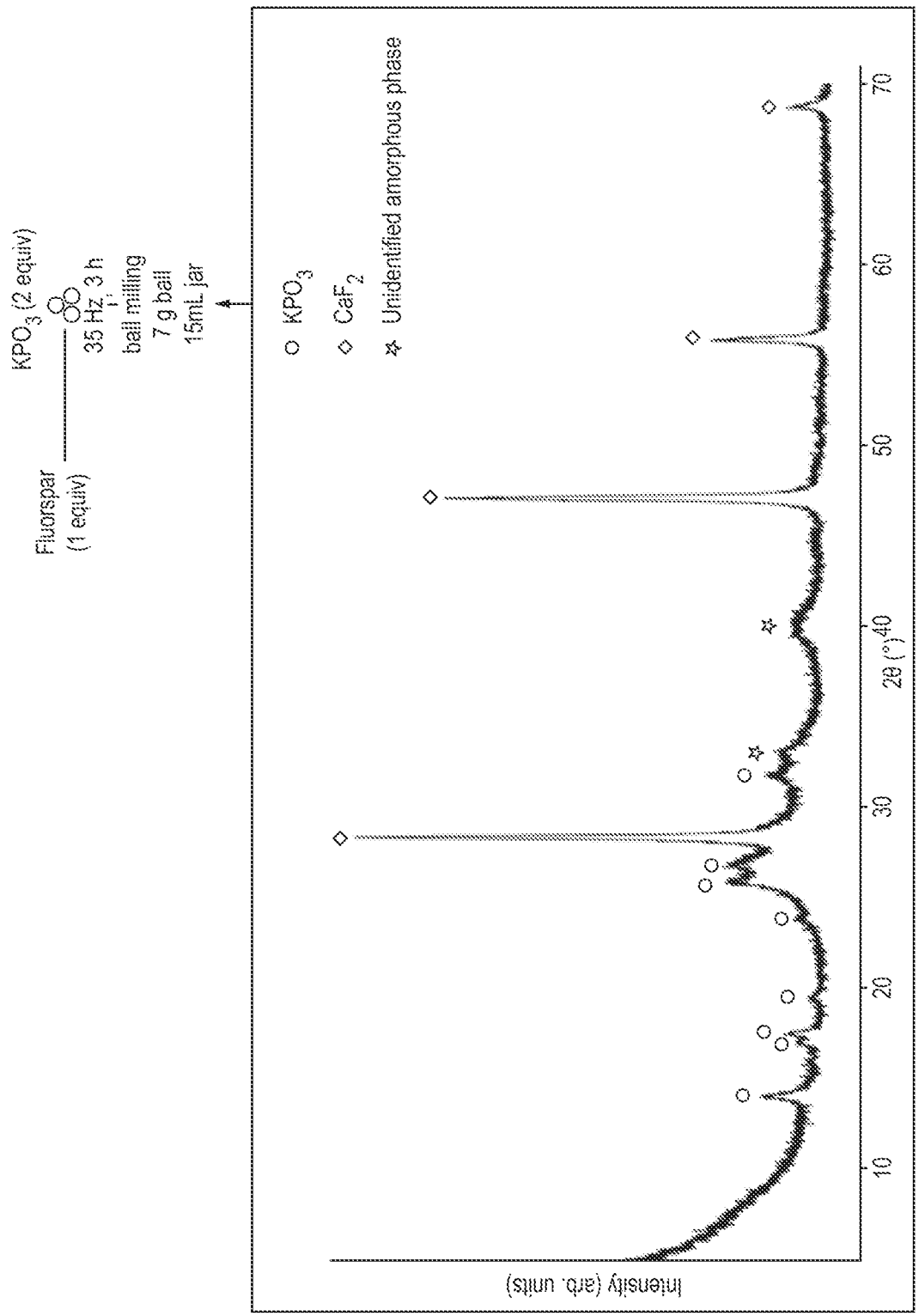
FIG. 9 shows a PXRD diffractogram of the milling product of fluorspar with $KPO_3$ after 3 hours at 35 Hz.

FIG. 9 shows the PXRD pattern resulting from milling of Fluorspar with $KPO_3$ at 35 Hz for 3 hours. Table 5.7.6 shows the PXRD data from the milling of Fluorspar with $KPO_3$ represented in FIG. 9. Labels in FIG. 9 indicate crystalline phases of $CaF_2$, $KPO_3$, and an unidentified amorphous phase.

TABLE 5.7.6.

| Pos. [°2Th.] | Height [cts] | FWHM [°2Th.] | d-spacing [Å] | Rel. Int. [%] |
|---|---|---|---|---|
| $KPO_3$ 14.0459 | 162.80 | 0.2165 | 6.30536 | 9.79 |
| $KPO_3$ 17.5192 | 108.65 | 0.2598 | 5.06233 | 6.53 |
| $KPO_3$ 19.5372 | 32.72 | 0.3464 | 4.54377 | 1.97 |
| $KPO_3$ 23.8310 | 52.28 | 0.3464 | 3.73391 | 3.14 |
| $KPO_3$ 25.9074 | 266.00 | 0.3464 | 3.43917 | 15.99 |
| $KPO_3$ 26.7862 | 254.20 | 0.3464 | 3.32830 | 15.28 |
| $CaF_2$ 28.3520 | 1663.57 | 0.0866 | 3.14795 | 100.00 |
| $KPO_3$ 31.7224 | 85.00 | 0.2598 | 2.82077 | 5.11 |
| new phase 33.1713 | 75.46 | 0.4330 | 2.70079 | 4.54 |
| $CaF_2$ 47.0642 | 1381.50 | 0.0660 | 1.92930 | 83.04 |
| $CaF_2$ 55.8027 | 400.25 | 0.1082 | 1.64748 | 24.06 |
| $CaF_2$ 68.7042 | 122.83 | 0.2112 | 1.36511 | 7.38 |

Figure 10:
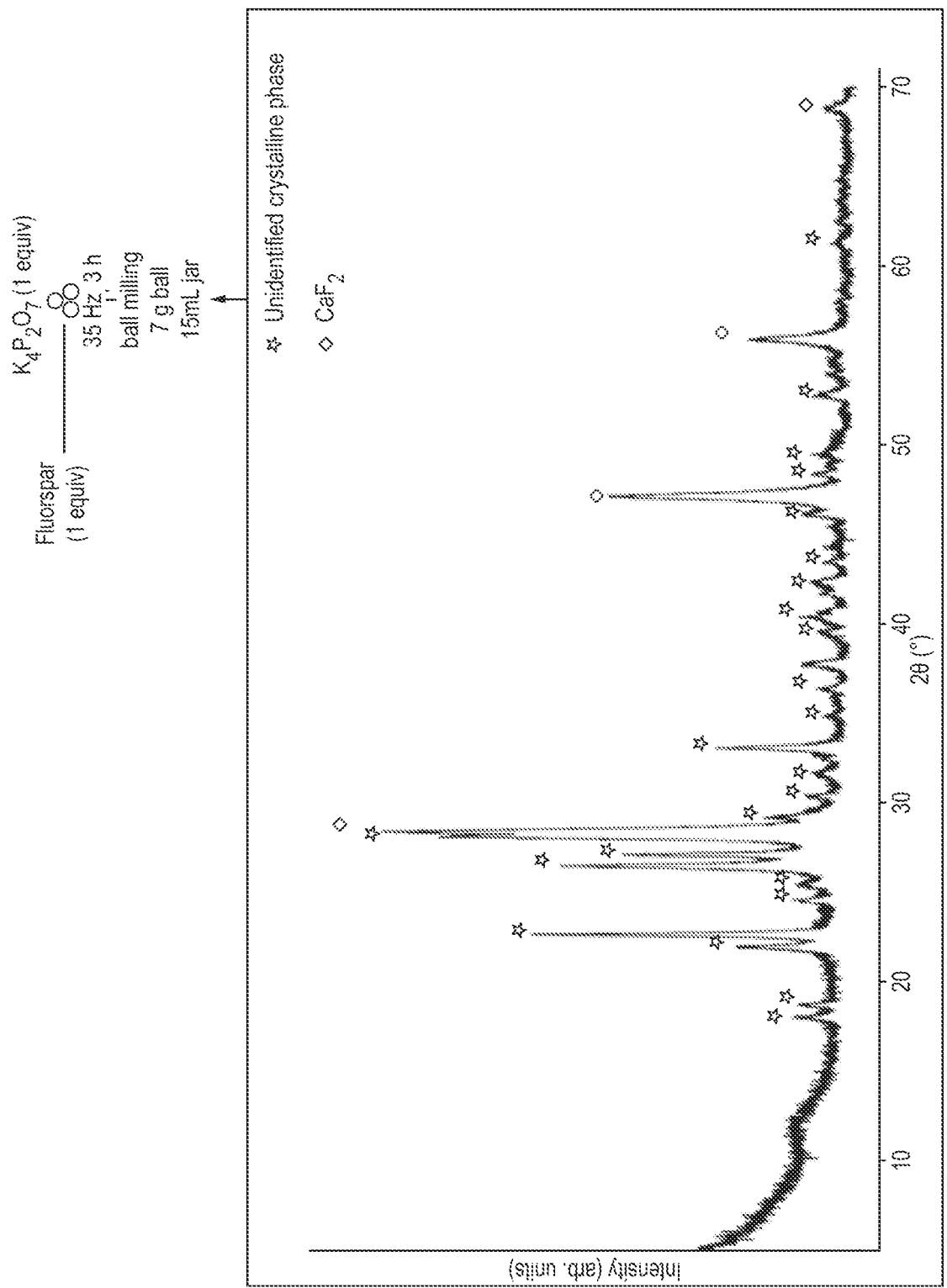
FIG. 10 shows a PXRD diffractogram of the milling product of fluorspar with $K_4P_2O_7$ after 3 hours at 35 Hz.

FIG. 10 shows the PXRD pattern resulting from milling of Fluorspar with $K_4P_2O_7$ at 35 Hz for 3 hours. Table 5.7.7 shows the PXRD data from the milling of Fluorspar with $K_4P_2O_7$ represented in FIG. 10. Labels in FIG. 10 indicate crystalline phases of $CaF_2$ and an unidentified crystalline phase.

TABLE 5.7.7.

| Pos. [°2Th.] | Height [cts] | FWHM [°2Th.] | d-spacing [Å] | Rel. Int. [%] |
|---|---|---|---|---|
| 5.1444 | 130.15 | 0.2598 | 17.17830 | 10.54 |
| 17.9889 | 94.86 | 0.1732 | 4.93120 | 7.68 |
| 18.7323 | 79.36 | 0.1732 | 4.73714 | 6.43 |
| 21.8984 | 254.80 | 0.1732 | 4.05888 | 20.64 |
| 22.6004 | 826.97 | 0.0541 | 3.93436 | 66.98 |
| 24.4977 | 89.59 | 0.2165 | 3.63379 | 7.26 |
| 25.3643 | 87.27 | 0.2598 | 3.51157 | 7.07 |
| 26.4568 | 735.97 | 0.1948 | 3.36898 | 59.61 |
| 27.0316 | 509.38 | 0.1732 | 3.29864 | 41.26 |
| 28.0638 | 1053.98 | 0.1948 | 3.17962 | 85.37 |
| $CaF_2$ 28.3868 | 1234.61 | 0.1732 | 3.14417 | 100.00 |
| 29.1860 | 173.05 | 0.1732 | 3.05987 | 14.02 |
| 30.3572 | 76.33 | 0.1732 | 2.94443 | 6.18 |
| 31.6322 | 61.17 | 0.2598 | 2.82860 | 4.95 |
| 33.0425 | 312.45 | 0.1082 | 2.71103 | 25.31 |

TABLE 5.7.7.-continued

| Pos. [°2Th.] | Height [cts] | FWHM [°2Th.] | d-spacing [Å] | Rel. Int. [%] |
|---|---|---|---|---|
| 34.8349 | 30.59 | 0.3464 | 2.57553 | 2.48 |
| 36.3748 | 54.35 | 0.2165 | 2.46996 | 4.40 |
| 37.6922 | 100.83 | 0.3031 | 2.38660 | 8.17 |
| 39.5079 | 62.17 | 0.2598 | 2.28100 | 5.04 |
| 40.3630 | 108.66 | 0.1299 | 2.23463 | 8.80 |
| 41.6540 | 56.14 | 0.2598 | 2.16831 | 4.55 |
| 42.3742 | 83.32 | 0.2165 | 2.13311 | 6.75 |
| 43.4426 | 48.03 | 0.2598 | 2.08309 | 3.89 |
| 46.0690 | 102.39 | 0.2598 | 1.97027 | 8.29 |
| $CaF_2$ 47.1347 | 647.18 | 0.1299 | 1.92818 | 52.42 |
| 48.3579 | 85.22 | 0.2165 | 1.88223 | 6.90 |
| 49.4397 | 67.00 | 0.3031 | 1.84354 | 5.43 |
| 52.7532 | 64.11 | 0.3464 | 1.73529 | 5.19 |
| 53.9036 | 38.86 | 0.2598 | 1.70094 | 3.15 |
| $CaF_2$ 55.8878 | 248.87 | 0.2598 | 1.64517 | 20.16 |
| 61.3555 | 21.45 | 0.4330 | 1.51102 | 1.74 |
| 62.4719 | 17.97 | 0.2598 | 1.48668 | 1.46 |
| $CaF_2$ 68.7998 | 53.55 | 0.4224 | 1.36344 | 4.34 |

Figure 11:
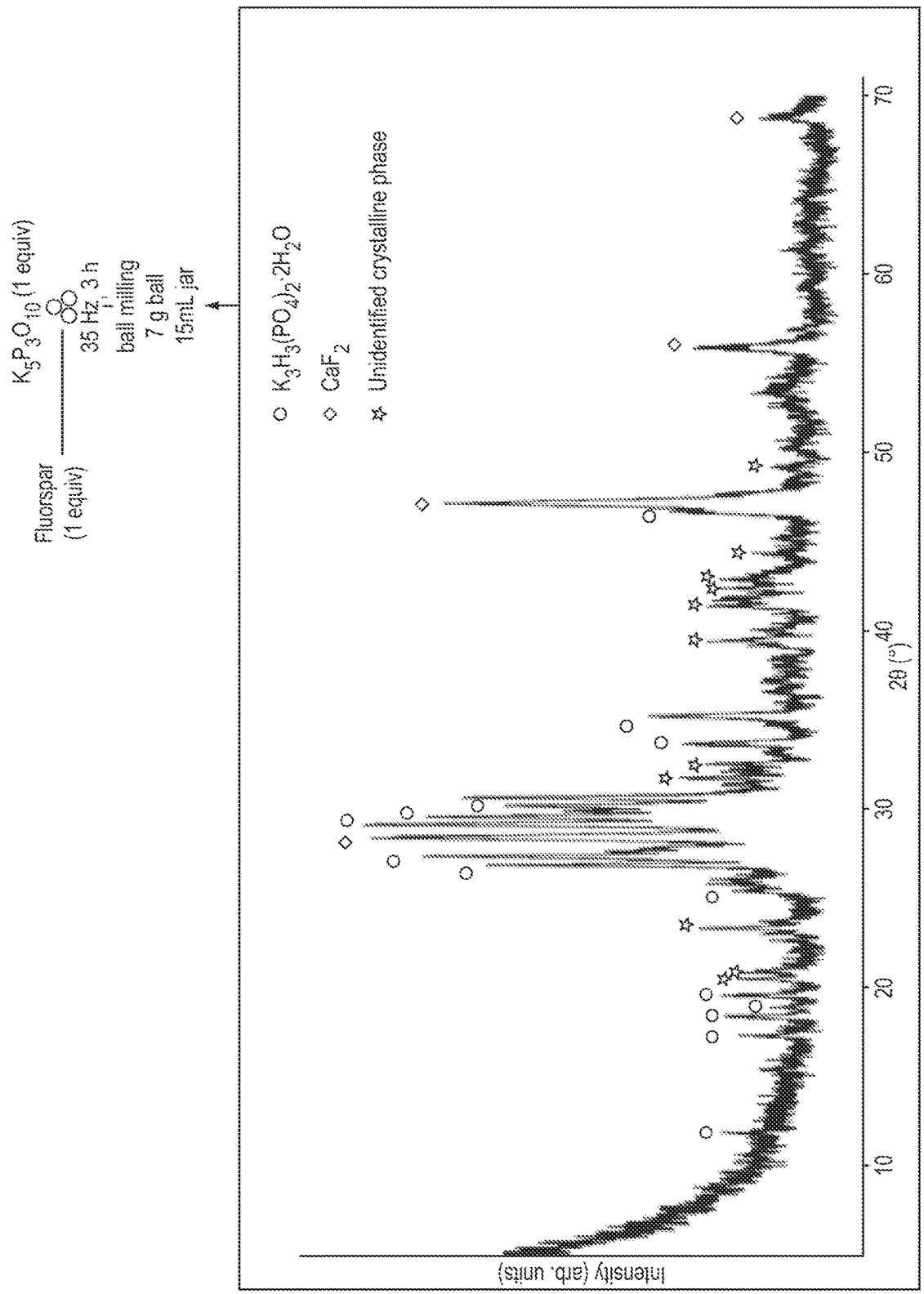
FIG. 11 shows a PXRD diffractogram of the milling product of fluorspar with $K_5P_3O_{10}$ after 3 hours at 35 Hz.

FIG. 11 shows the PXRD pattern resulting from milling of Fluorspar with $K_5P_3O_{10}$ at 35 Hz for 3 hours. Table 5.7.8 shows the PXRD data from the milling of Fluorspar with $K_5P_3O_{10}$ represented in FIG. 11. Labels in FIG. 11 indicate crystalline phases of $CaF_2$ and $K_3H3(PO_4)_2 \cdot 2H_2O$ and an unidentified crystalline phase.

TABLE 5.7.8.

| Pos. [°2Th.] | Height [cts] | FWHM [°2Th.] | d-spacing [Å] | Rel. Int. [%] |
|---|---|---|---|---|
| 5.2732 | 114.29 | 0.5196 | 16.75922 | 27.96 |
| 17.2799 | 39.30 | 0.1732 | 5.13189 | 9.62 |
| 18.3993 | 55.60 | 0.1948 | 4.82211 | 13.60 |
| 19.5241 | 58.21 | 0.1299 | 4.54679 | 14.24 |
| 20.4719 | 53.71 | 0.1299 | 4.33836 | 13.14 |
| 20.8963 | 39.65 | 0.2165 | 4.25120 | 9.70 |
| 23.2997 | 88.92 | 0.1299 | 3.81784 | 21.76 |
| 25.3934 | 53.09 | 0.1299 | 3.50760 | 12.99 |
| 25.9552 | 58.44 | 0.3464 | 3.43294 | 14.30 |
| 26.8517 | 251.68 | 0.1299 | 3.32033 | 61.58 |
| 27.3606 | 340.00 | 0.1299 | 3.25972 | 83.19 |
| $CaF_2$ 28.3670 | 375.75 | 0.3031 | 3.14632 | 91.94 |
| 29.0963 | 408.69 | 0.1732 | 3.06910 | 100.00 |
| 29.5586 | 337.62 | 0.1299 | 3.02214 | 82.61 |
| 30.2354 | 251.36 | 0.1515 | 2.95602 | 61.50 |
| 30.6491 | 301.67 | 0.1299 | 2.91705 | 73.81 |
| 31.7495 | 106.23 | 0.1732 | 2.81842 | 25.99 |
| 32.5474 | 69.78 | 0.1299 | 2.75113 | 17.08 |
| 33.6613 | 105.09 | 0.1299 | 2.66259 | 25.71 |
| 35.2089 | 141.22 | 0.1732 | 2.54903 | 34.56 |
| 36.5470 | 35.78 | 0.2598 | 2.45871 | 8.75 |
| 39.4710 | 71.52 | 0.2165 | 2.28305 | 17.50 |
| 40.0449 | 41.44 | 0.3464 | 2.25165 | 10.14 |
| 41.3836 | 75.03 | 0.1732 | 2.18185 | 18.36 |
| 41.8761 | 70.61 | 0.2598 | 2.15732 | 17.28 |
| 42.3942 | 65.61 | 0.1732 | 2.13215 | 16.05 |
| 42.8791 | 74.72 | 0.1299 | 2.10916 | 18.28 |
| 44.3482 | 31.39 | 0.3464 | 2.04264 | 7.68 |
| 46.6089 | 101.65 | 0.1732 | 1.94869 | 24.87 |
| $CaF_2$ 47.1154 | 307.91 | 0.1732 | 1.92892 | 75.34 |
| 49.1345 | 20.31 | 0.3464 | 1.85428 | 4.97 |
| 50.2219 | 22.27 | 0.2598 | 1.81665 | 5.45 |
| 53.5032 | 26.67 | 0.5196 | 1.71272 | 6.53 |
| $CaF_2$ 55.8875 | 78.51 | 0.4330 | 1.64518 | 19.21 |
| 56.9644 | 15.27 | 0.2598 | 1.61661 | 3.74 |
| 59.2874 | 12.50 | 0.5196 | 1.55869 | 3.06 |
| 61.4948 | 15.16 | 0.5196 | 1.50793 | 3.71 |
| 64.1902 | 14.04 | 0.5196 | 1.45097 | 3.43 |
| $CaF_2$ 68.7999 | 38.69 | 0.4224 | 1.36344 | 9.47 |

Figure 12:
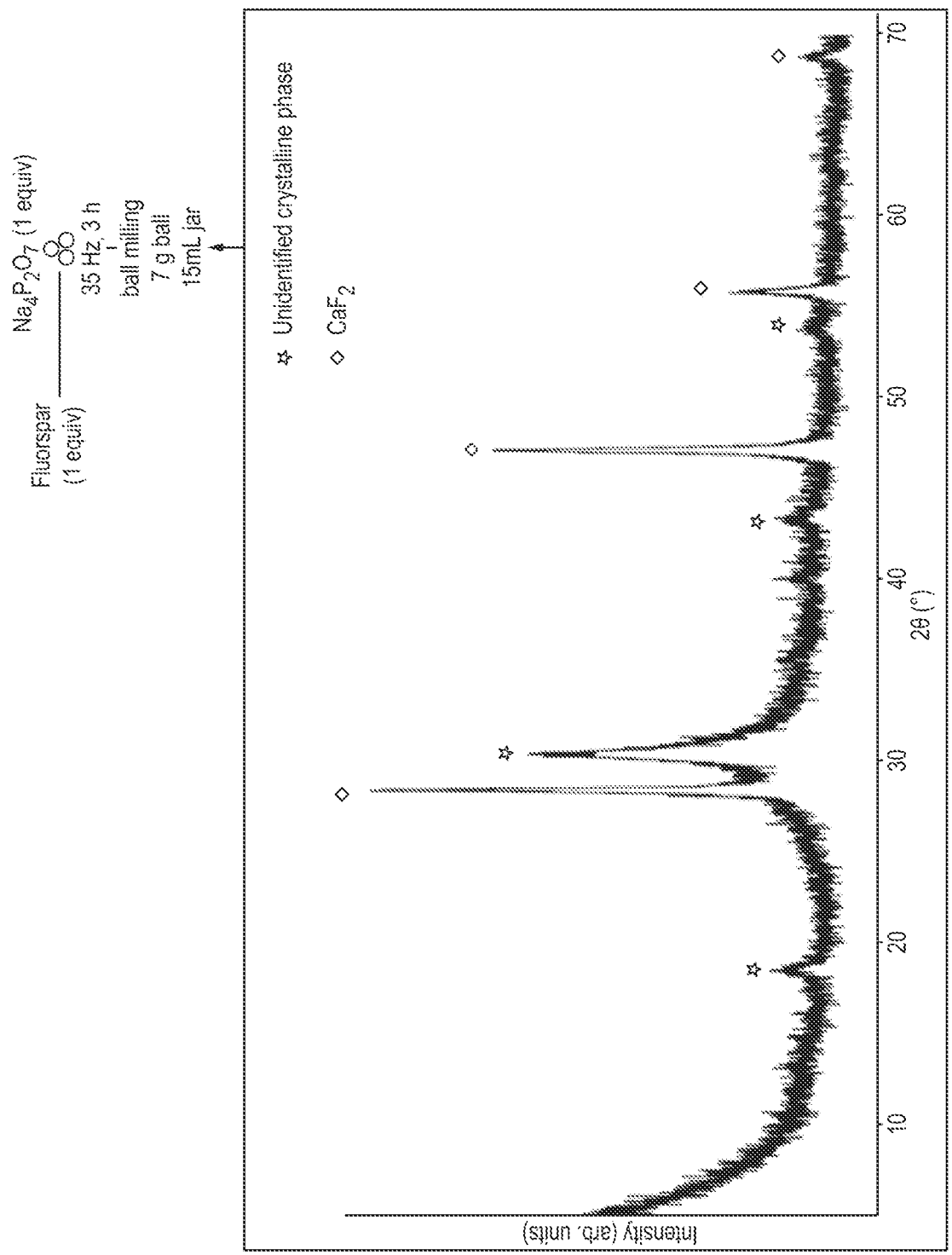
FIG. 12 shows a PXRD diffractogram of the milling product of fluorspar with $Na_4P_2O_7$ after 3 hours at 35 Hz.

FIG. 12 shows the PXRD pattern resulting from milling of Fluorspar with $Na_4P_2O_7$ at 35 Hz for 3 hours. Table 5.7.9 shows the PXRD data from the milling of Fluorspar with Na$_4$P$_2$O$_7$ represented in FIG. 12. Labels in FIG. 12 indicates a crystalline phase of CaF$_2$ and an unidentified crystalline phase.

TABLE 5.7.9.

| Pos. [°2Th.] | Height [cts] | FWHM [°2Th.] | d-spacing [Å] | Rel. Int. [%] |
|---|---|---|---|---|
| 18.5302 | 32.30 | 0.4330 | 4.78835 | 8.95 |
| CaF$_2$ 28.3978 | 360.72 | 0.0758 | 3.14297 | 100.00 |
| 30.4726 | 184.31 | 0.3464 | 2.93354 | 51.10 |
| 40.0968 | 13.45 | 0.5196 | 2.24885 | 3.73 |
| 43.2966 | 15.99 | 0.5196 | 2.08978 | 4.43 |
| CaF$_2$ 47.1173 | 295.61 | 0.1515 | 1.92885 | 81.95 |
| 54.0107 | 13.24 | 0.6927 | 1.69782 | 3.67 |
| CaF$_2$ 55.8334 | 76.55 | 0.2598 | 1.64664 | 21.22 |
| CaF$_2$ 68.8257 | 22.49 | 0.5280 | 1.36299 | 6.24 |

Figure 13:
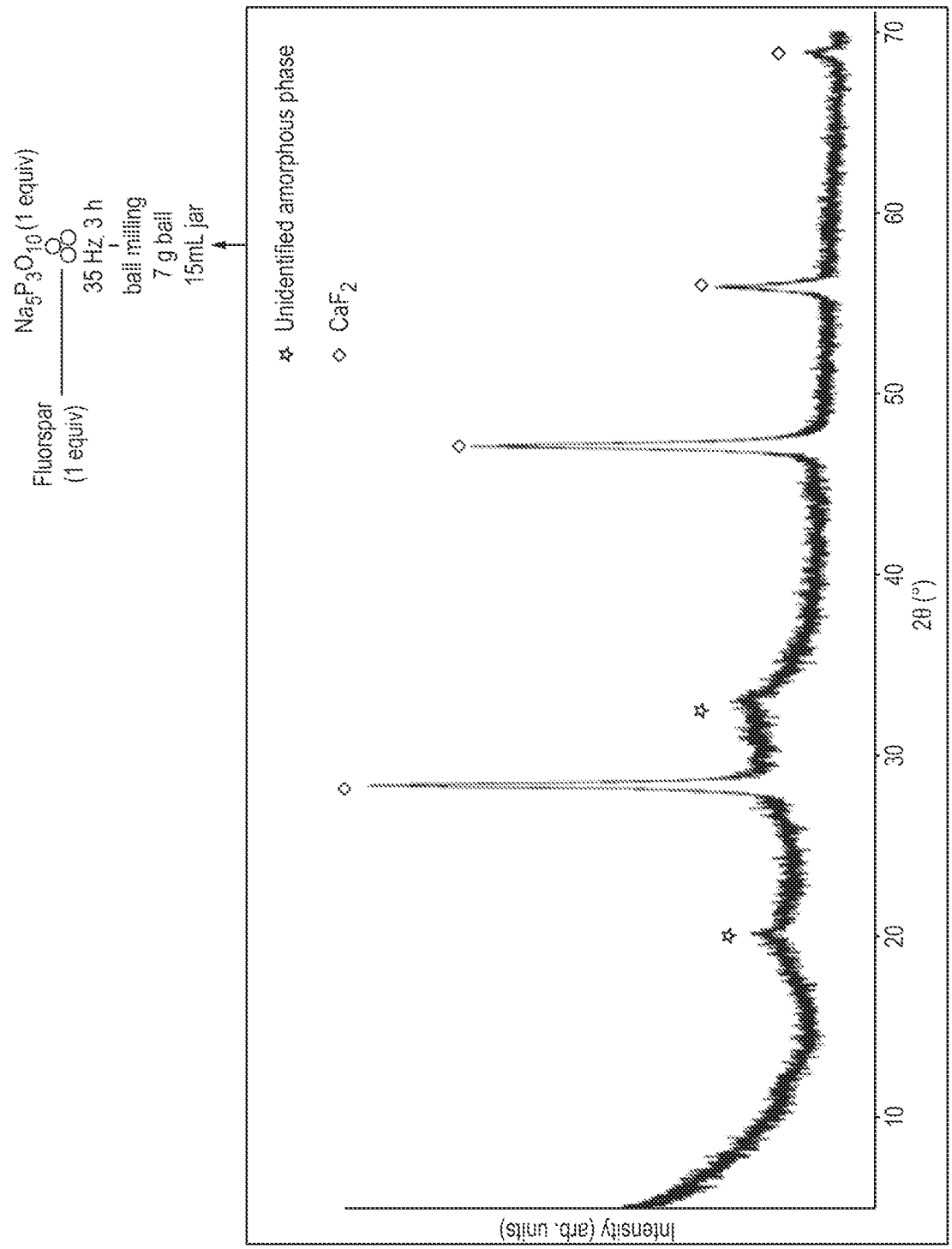
FIG. 13 shows a PXRD diffractogram of the milling product of fluorspar with $Na_5P_3O_{10}$ after 3 hours at 35 Hz.

FIG. 13 shows the PXRD pattern resulting from milling of Fluorspar with Na$_5$P$_3$O$_{10}$ at 35 Hz for 3 hours. Table 5.7.10 shows the PXRD data from the milling of Fluorspar with Na$_5$P$_3$O$_{10}$ represented in FIG. 13. Labels in FIG. 13 indicates a crystalline phase of CaF$_2$ and an unidentified amorphous phase.

TABLE 5.7.10.

| Pos. [°2Th.] | Height [cts] | FWHM [°2Th.] | d-spacing [Å] | Rel. Int. [%] |
|---|---|---|---|---|
| 28.2976 | 1396.75 | 0.1632 | 3.15126 | 100.00 |
| 47.0169 | 926.02 | 0.4896 | 1.93113 | 66.30 |
| 55.8035 | 259.77 | 0.4896 | 1.64609 | 18.60 |
| 68.6839 | 70.90 | 0.8160 | 1.36546 | 5.08 |

Figure 14:
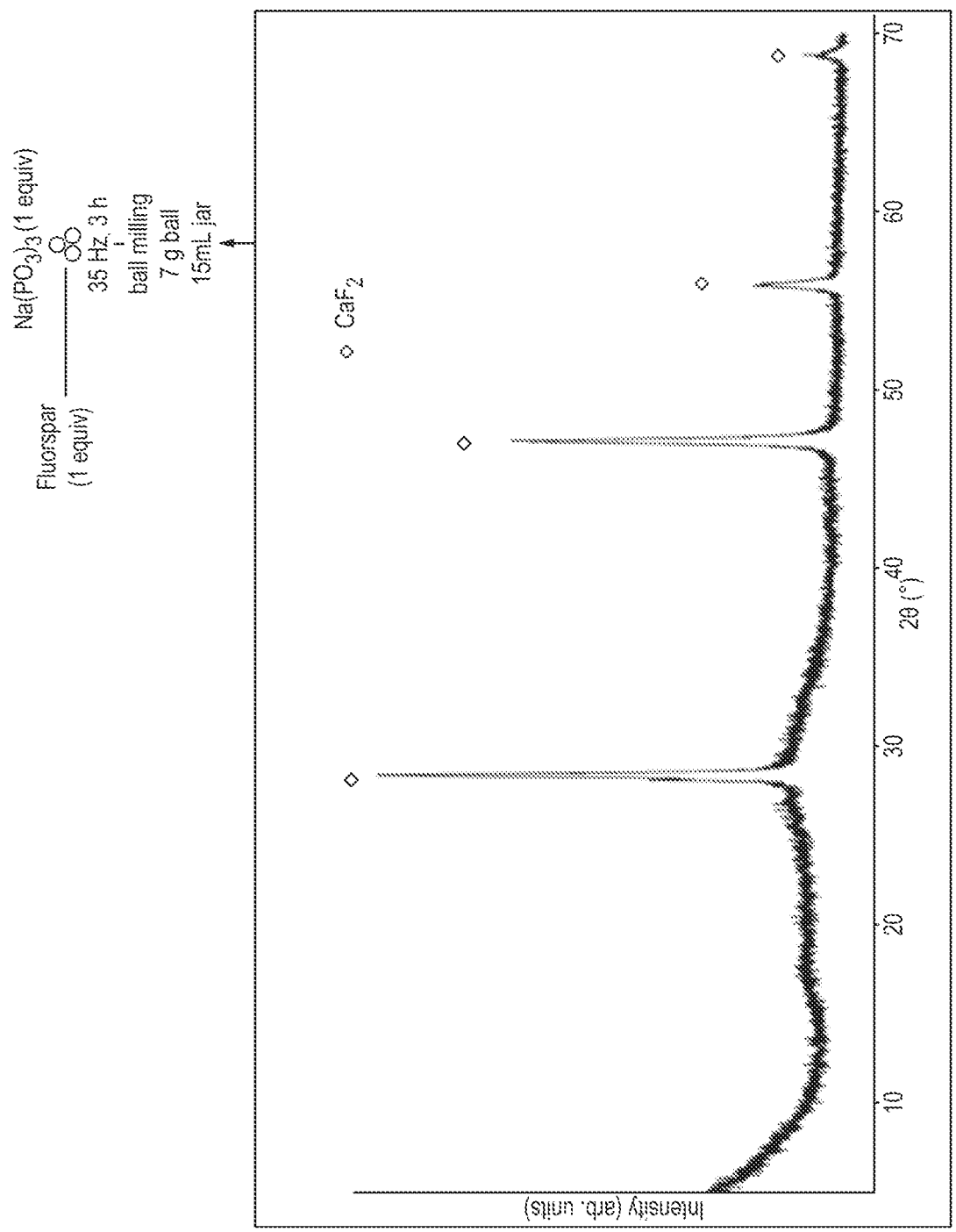
FIG. 14 shows a PXRD diffractogram of the milling product of fluorspar with $Na(PO_3)_3$ after 3 hours at 35 Hz.

FIG. 14 shows the PXRD pattern resulting from milling of Fluorspar with Na(PO$_3$)$_3$ at 35 Hz for 3 hours. Table 5.7.11 shows the PXRD data from the milling of Fluorspar with Na(PO$_3$)$_3$ represented in FIG. 14. Labels in FIG. 14 indicates a crystalline phase of CaF$_2$.

TABLE 5.7.11.

| Pos. [°2Th.] | Height [cts] | FWHM [°2Th.] | d-spacing [Å] | Rel. Int. [%] |
|---|---|---|---|---|
| 28.2976 | 1396.75 | 0.1632 | 3.15126 | 100.00 |
| 47.0169 | 926.02 | 0.4896 | 1.93113 | 66.30 |
| 55.8035 | 259.77 | 0.4896 | 1.64609 | 18.60 |
| 68.6839 | 70.90 | 0.8160 | 1.36546 | 5.08 |

Figure 15:
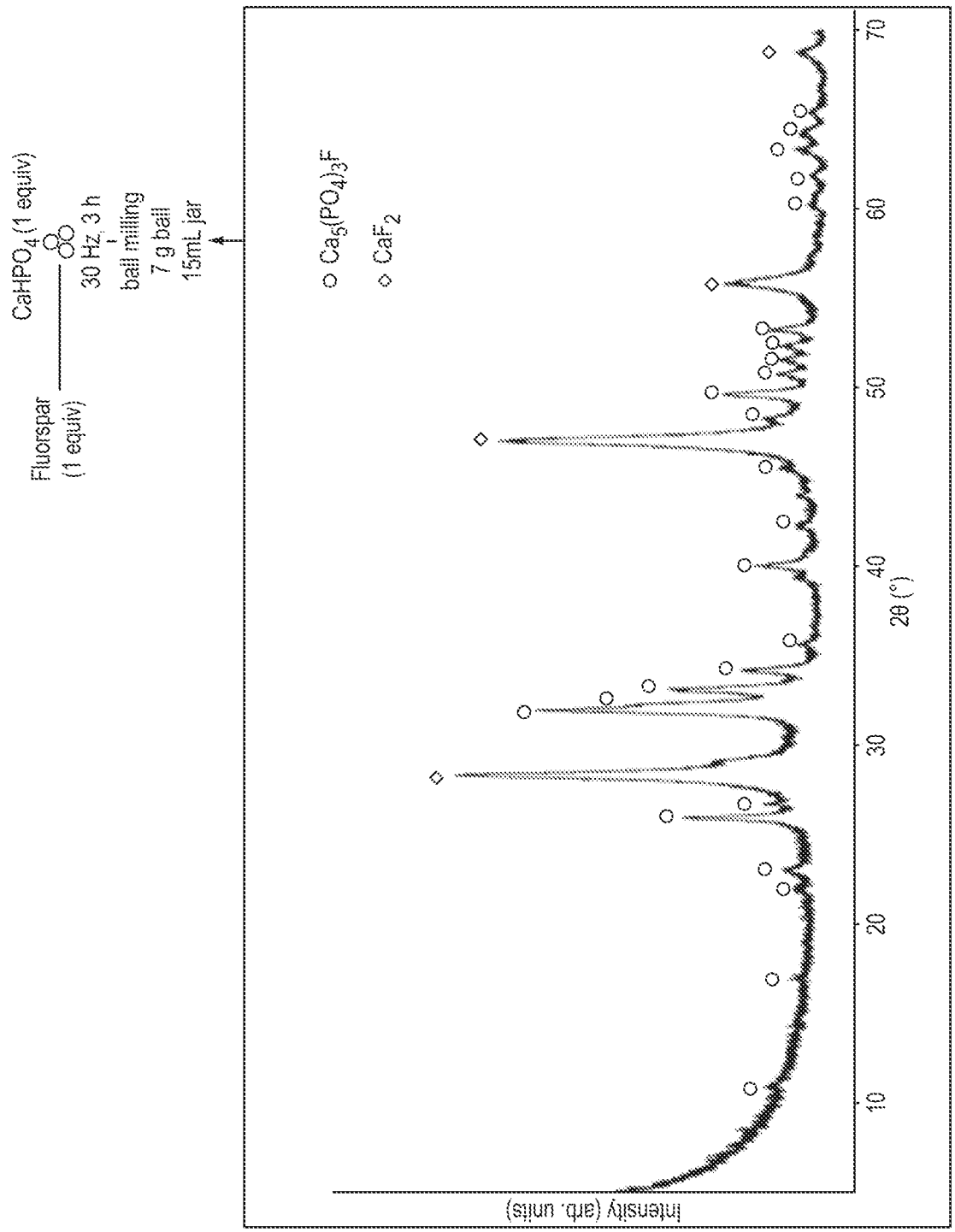
FIG. 15 shows a PXRD diffractogram of the milling product of fluorspar with $CaHPO_4$ after 3 hours at 30 Hz.

FIG. 15 shows the PXRD pattern resulting from milling of Fluorspar with CaHPO$_4$ at 30 Hz for 3 hours. Table 5.7.12 shows the PXRD data from the milling of Fluorspar with CaHPO$_4$ represented in FIG. 15. Labels in FIG. 15 indicates crystalline phases of CaF$_2$ and Ca$_5$(PO$_4$)$_3$F.

TABLE 5.7.12.

| Pos. [°2Th.] | Height [cts] | FWHM [°2Th.] | d-spacing [Å] | Rel. Int. [%] |
|---|---|---|---|---|
| 10.8159 | 22.19 | 0.3464 | 8.18003 | 1.71 |
| 16.9988 | 27.36 | 0.3464 | 5.21612 | 2.11 |
| 21.9471 | 44.50 | 0.2598 | 4.04997 | 3.43 |
| 22.9223 | 87.66 | 0.3031 | 3.87984 | 6.76 |
| 25.9108 | 464.01 | 0.1515 | 3.43873 | 35.79 |
| 26.7231 | 164.61 | 0.1299 | 3.33602 | 12.70 |
| CaF$_2$ 28.3972 | 1296.45 | 0.2165 | 3.14305 | 100.00 |
| 29.1216 | 365.28 | 0.1732 | 3.06649 | 28.18 |
| 31.9522 | 1014.39 | 0.1515 | 2.80100 | 78.24 |
| 32.3833 | 548.05 | 0.1948 | 2.76469 | 42.27 |

TABLE 5.7.12.-continued

| Pos. [°2Th.] | Height [cts] | FWHM [°2Th.] | d-spacing [Å] | Rel. Int. [%] |
|---|---|---|---|---|
| 33.1624 | 541.34 | 0.0866 | 2.70150 | 41.76 |
| 34.1845 | 268.43 | 0.2598 | 2.62303 | 20.71 |
| 35.6375 | 53.32 | 0.1732 | 2.51934 | 4.11 |
| 39.3033 | 78.45 | 0.1732 | 2.29241 | 6.05 |
| 40.0474 | 226.94 | 0.1515 | 2.25151 | 17.50 |
| 42.2195 | 64.59 | 0.3031 | 2.14056 | 4.98 |
| 43.9611 | 61.89 | 0.2598 | 2.05972 | 4.77 |
| 45.4737 | 106.84 | 0.2598 | 1.99467 | 8.24 |
| CaF$_2$ 46.9114 | 1075.26 | 0.1515 | 1.93683 | 82.94 |
| 49.6178 | 342.27 | 0.3031 | 1.83734 | 26.40 |
| 50.7543 | 131.19 | 0.2165 | 1.79884 | 10.12 |
| 51.5785 | 118.41 | 0.2598 | 1.77201 | 9.13 |
| 52.3593 | 105.86 | 0.2598 | 1.74741 | 8.17 |
| 53.2237 | 143.52 | 0.1732 | 1.72106 | 11.07 |
| CaF$_2$ 55.7559 | 291.37 | 0.4330 | 1.64875 | 22.47 |
| 60.1404 | 30.48 | 0.3464 | 1.53861 | 2.35 |
| 61.8997 | 32.01 | 0.3897 | 1.49904 | 2.47 |
| 63.2828 | 70.58 | 0.3464 | 1.46957 | 5.44 |
| 64.2073 | 72.79 | 0.6061 | 1.45062 | 5.61 |
| 65.5460 | 30.47 | 0.5196 | 1.42420 | 2.35 |
| CaF$_2$ 68.7224 | 84.83 | 0.6336 | 1.36479 | 6.54 |

Figure 16:
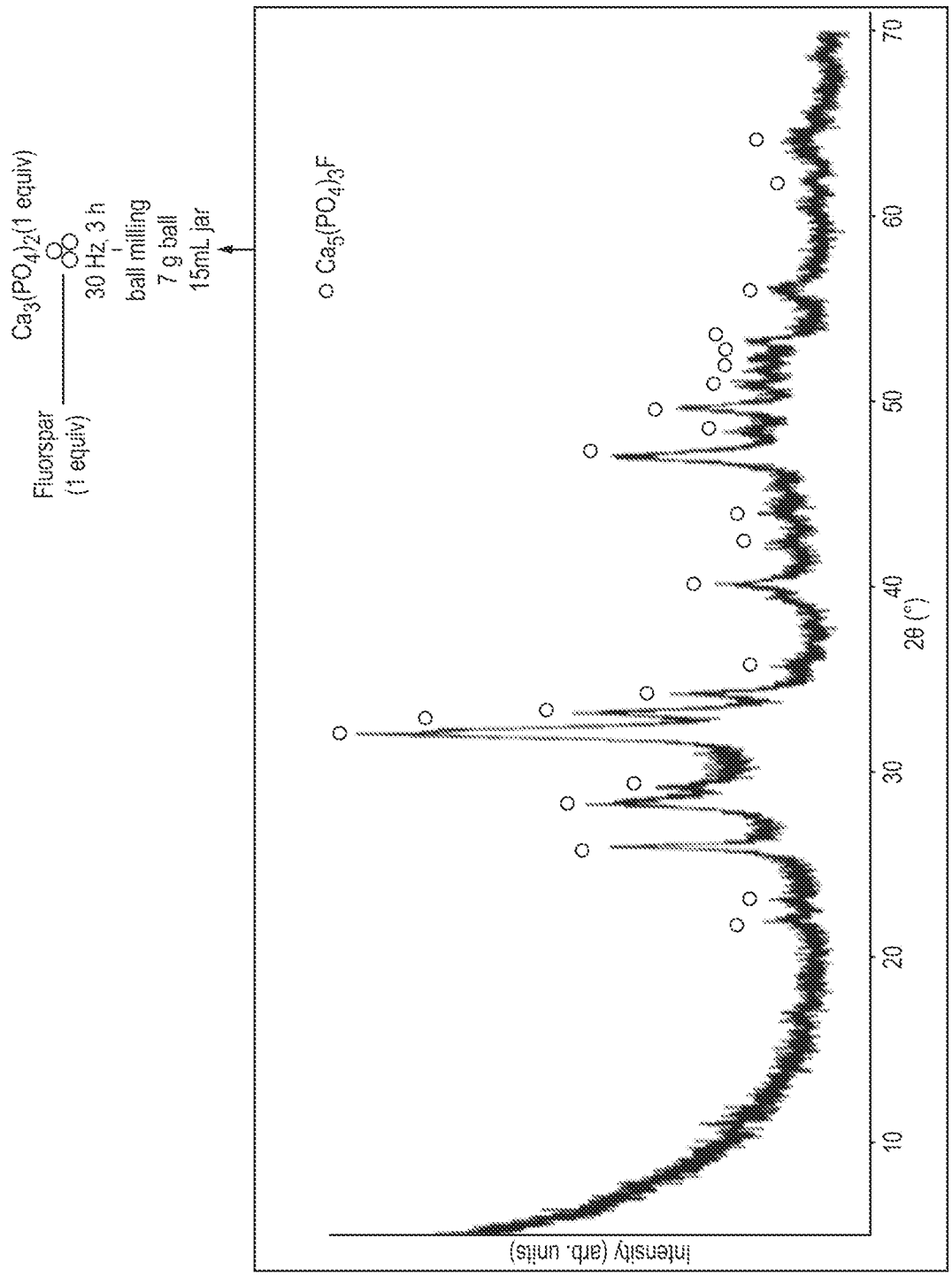
FIG. 16 shows a PXRD diffractogram of the milling product of fluorspar with $Ca_3(PO_4)_2$ after 3 hours at 30 Hz.

FIG. 16 shows the PXRD pattern resulting from milling of Fluorspar with Ca$_3$(PO$_4$)$_2$ at 35 Hz for 3 hours. Table 5.7.13 shows the PXRD data from the milling of Fluorspar with Ca$_3$(PO$_4$)$_2$ represented in FIG. 16. Labels in FIG. 16 indicates a crystalline phase of Ca$_5$(PO$_4$)$_3$F.

TABLE 5.7.13.

| Pos. [°2Th.] | Height [cts] | FWHM [°2Th.] | d-spacing [Å] | Rel. Int. [%] |
|---|---|---|---|---|
| 22.0434 | 15.65 | 0.5196 | 4.03250 | 3.25 |
| 26.0518 | 184.78 | 0.1948 | 3.42044 | 38.31 |
| 28.3091 | 213.59 | 0.3031 | 3.15262 | 44.28 |
| 29.2225 | 140.14 | 0.2598 | 3.05613 | 29.05 |
| 32.0450 | 482.35 | 0.2598 | 2.79310 | 100.00 |
| 33.1785 | 229.57 | 0.2598 | 2.70022 | 47.59 |
| 34.2570 | 111.95 | 0.2165 | 2.61764 | 23.21 |
| 40.1975 | 87.58 | 0.2165 | 2.24345 | 18.16 |
| 42.3548 | 16.81 | 0.5196 | 2.13404 | 3.49 |
| 43.9319 | 15.64 | 0.5196 | 2.06102 | 3.24 |
| 46.9721 | 173.42 | 0.3464 | 1.93447 | 35.95 |
| 48.4374 | 53.81 | 0.3464 | 1.87932 | 11.16 |
| 49.6795 | 132.95 | 0.2165 | 1.83521 | 27.56 |
| 50.9224 | 56.80 | 0.3464 | 1.79330 | 11.78 |
| 53.3052 | 60.24 | 0.3464 | 1.71862 | 12.49 |
| 56.2117 | 34.73 | 0.6061 | 1.63645 | 7.20 |
| 61.9102 | 13.34 | 0.5196 | 1.49881 | 2.77 |
| 64.2938 | 23.96 | 0.8448 | 1.44768 | 4.97 |

Figure 91:
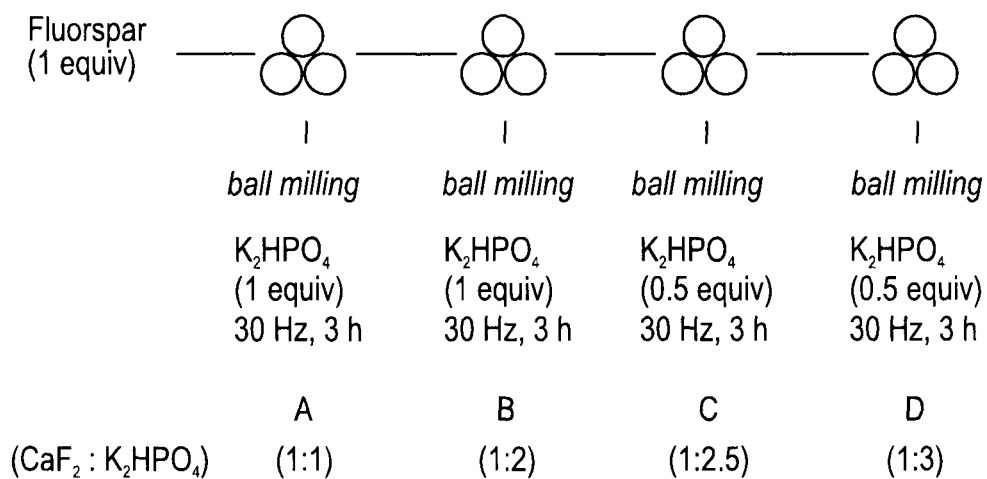
FIG. 91 illustrates a general scheme according to embodiments described herein.

5.8. Milling Frequency and Consumption of Crystalline CaF$_2$ in Solid State Reactions An increased consumption of crystalline CaF$_2$ may be achieved by successively spiking the milled mixtures (A to D in FIG. 91) with additional K$_2$HPO$_4$ and milling for additional 3 hour periods until all of the crystalline CaF$_2$ was consumed as detailed in FIG. 91.

Figure 17:
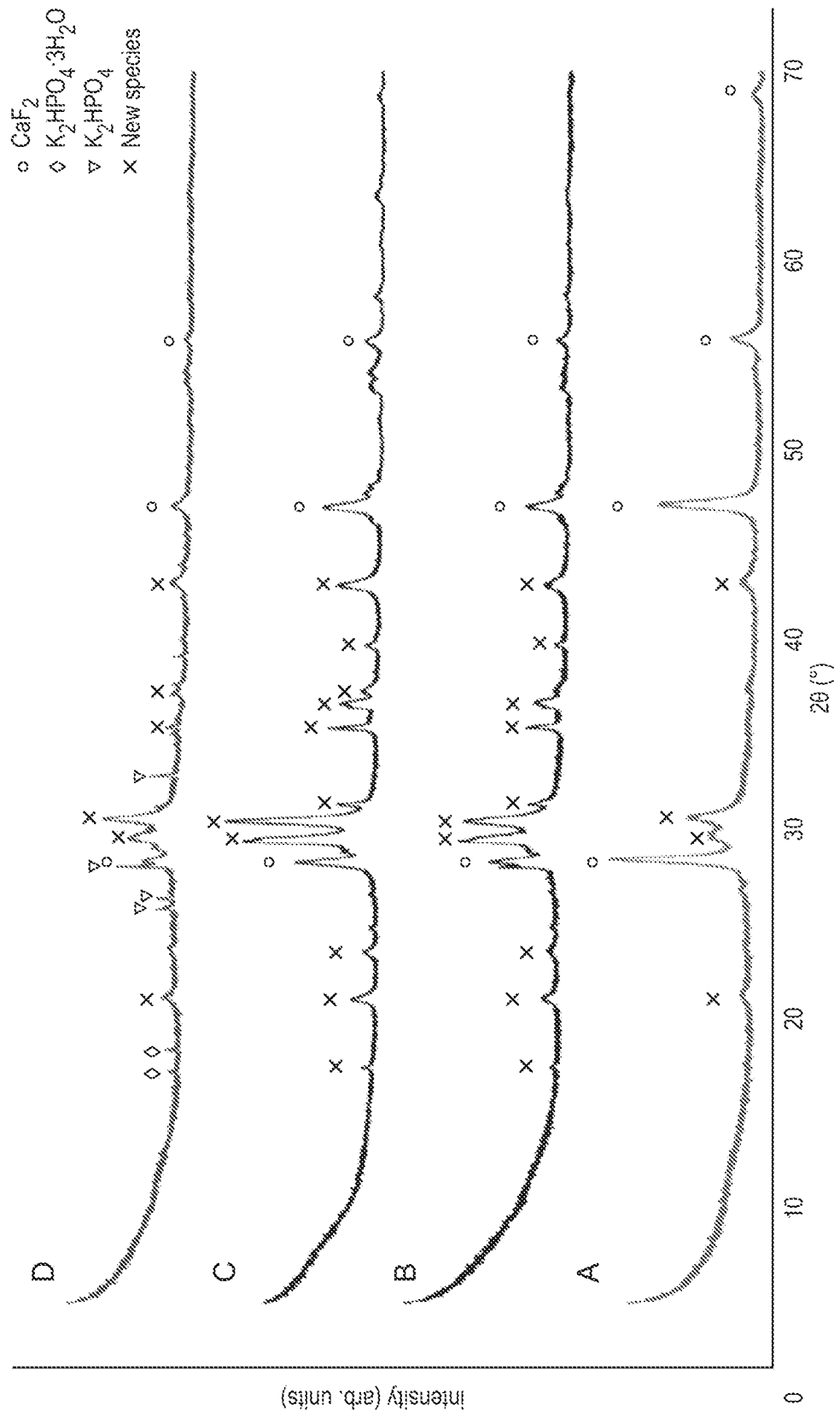
FIG. 17 shows stacked PXRD diffractograms of the milling products of fluorspar after subsequent addition and milling at 30 Hz for 3 hours of $K_2HPO_4$ resulting in $CaF_2$:$K_2HPO_4$ ratios of 1:1, 1:2, 1:2.5, and 1:3.

In this reaction, Fluorspar (1 equiv.) was added to a stainless steel container with 1 equivalent of K$_2$HPO$_4$ the mixture was milled for 3 hours at 30 Hz, followed by successive additions of 1 additional equivalent of K$_2$HPO$_4$, 0.5 equiv. K$_2$HPO$_4$, and 0.5 equiv. K$_2$HPO$_4$ each accompanied by 3 hours of milling at 30 Hz. FIG. 17 shows Powder X-Ray Diffraction patterns of each of these mixtures, labelled to show the appearance of the new species. The PXRD was obtained on a Bruker Eco D8 Diffractometer.

Figure 92:
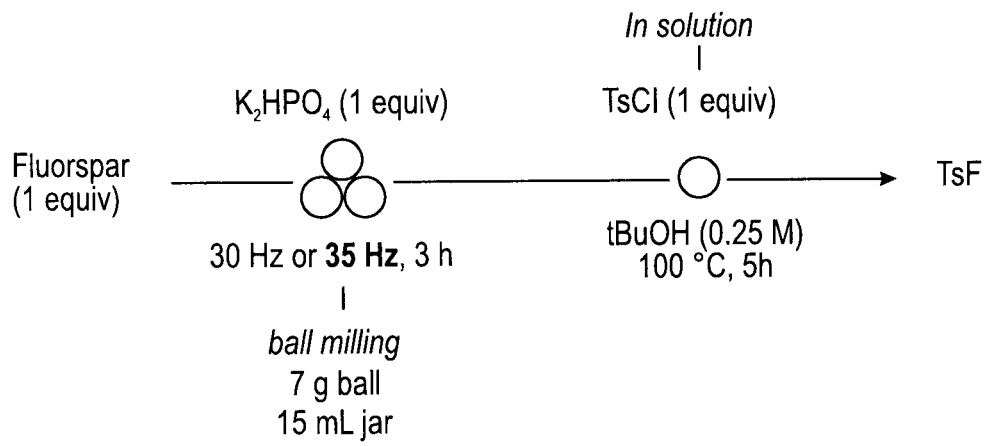
FIG. 92 illustrates a general scheme according to embodiments described herein.

The effect of milling intensity was investigated as shown in FIG. 92. Acid grade Fluorspoar (1 equiv.) was milled with K₂HPO₄ (1 equiv.) at 30 Hz or 35 Hz for 3 hours and the powder reagent (A) was used in the fluorination of TsCl at 0.125 mmol scale and yields were determined by $^1$H NMR and $^{19}$F NMR with 4-fluoroaniosole as an internal standard. Milling was completed using a Retsch MM400 ball mill and stainless steel jars (15 mL) and a 7 g ball.

Figure 18:
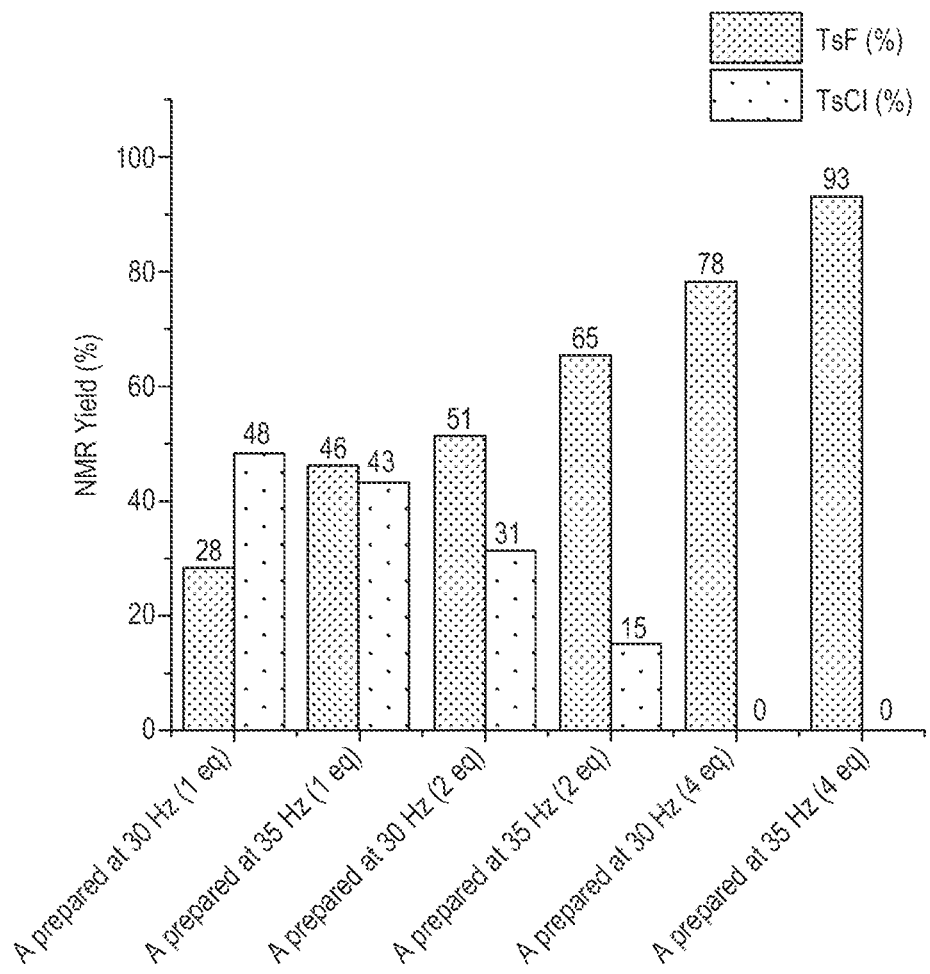
FIG. 18 shows the NMR yields of TsF from TsCl using fluorspar and $K_2HPO_4$ as an activator wherein the fluorspar and $K_2HPO_4$ are milled at different frequencies.

FIG. 18 shows the results of the experiment, when the powder reagent is reacted in solution with TsCl in tBuOH (0.25 M) at 100° C. for 5 hours, showing that higher frequency milling may result in powder reagents, that when used for fluorination, may lead to higher fluorination yields. Additionally, when higher equivalents of the fluorination reagent (A) are used, higher fluorinations yields may be exhibited.

5.9. Varying Stoichiometry of CaF₂ (Fluorpar)

Figure 93:
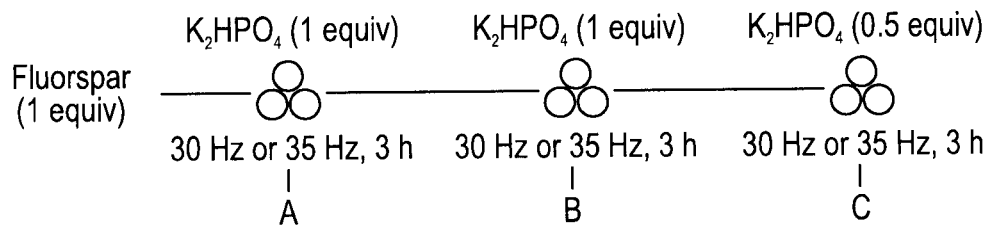
FIG. 93 illustrates a general scheme according to embodiments described herein.

Milled mixtures A to C as seen in FIG. 93 were investigated as fluorinating reagents, in turn allowing for fluorination of TsCl at high yield using fewer equivalents of CaF₂ (Fluorspar).

Figure 19:
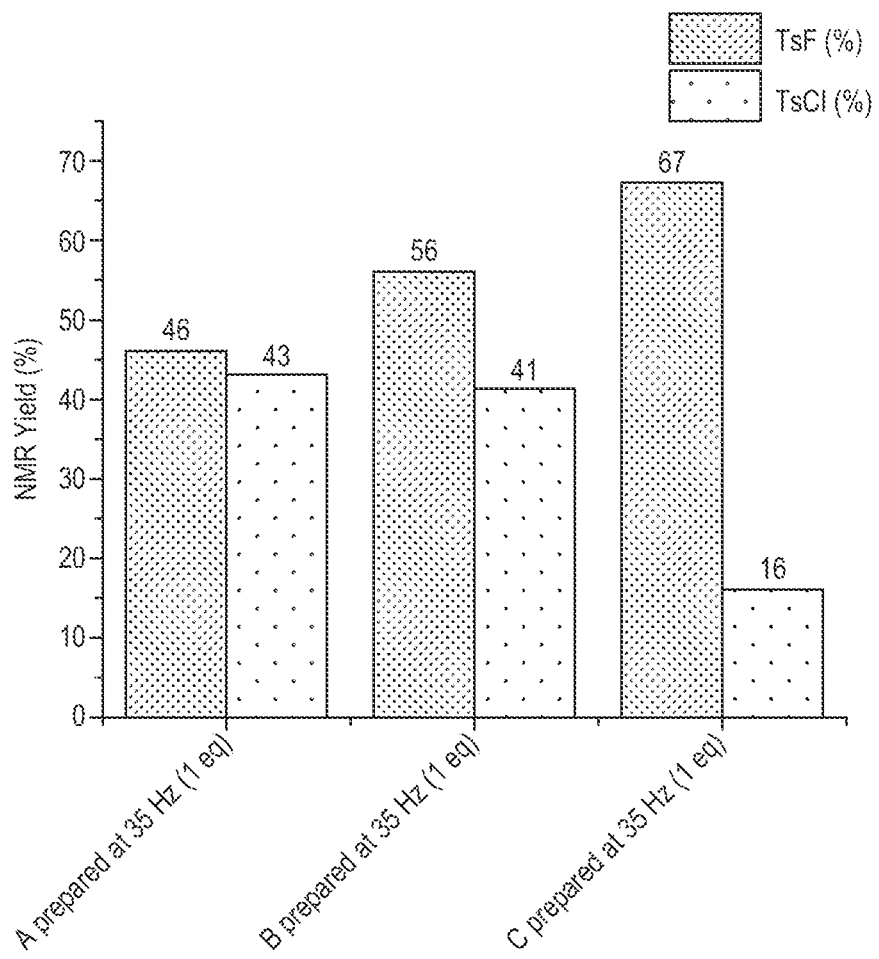
FIG. 19 shows the NMR yields of TsF from TsCl using fluorspar and varying amounts of $K_2HPO_4$ activator resulting in the use of different ratios of $CaF_2$:$K_2HPO_4$. In A, 1 equivalent of $K_2HPO_4$ was added to fluorspar, in B, 2 equivalents total are added, and in C, 2.5 total equivalents of $K_2HPO_4$ are added.
Figure 94:
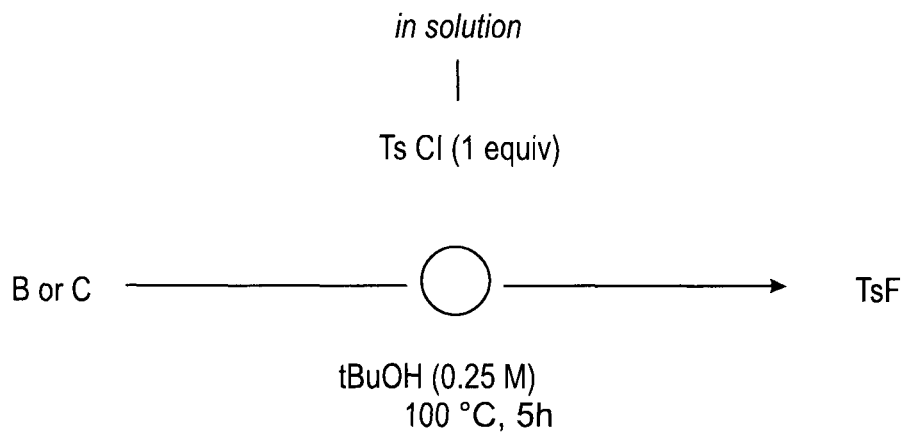
FIG. 94 illustrates a general scheme according to embodiments described herein.

In A, 1 equivalent of Fluorspar was milled with 1 equivalent of K₂HPO₄ at 30 or 35 Hz for 3 hours. In B, 1 additional equivalent of K₂HPO₄ was added and milled for 3 hours at 30 or 35 Hz. In C, 0.5 additional equivalent of K₂HPO₄ was added and milled for 3 hours at 30 or 35 Hz. The powder reagents were reacted with TsCl (1 equiv., 0.125-0.25 mmol) in solution as seen in FIG. 94 in tBuOH (0.25 M) at 100° C. for 5 hours. FIG. 19 shows the experimental results which indicate that lower equivalents of CaF₂ can lead to higher fluorination yields of organofluorine product (e.g., TsF).

Figure 20:
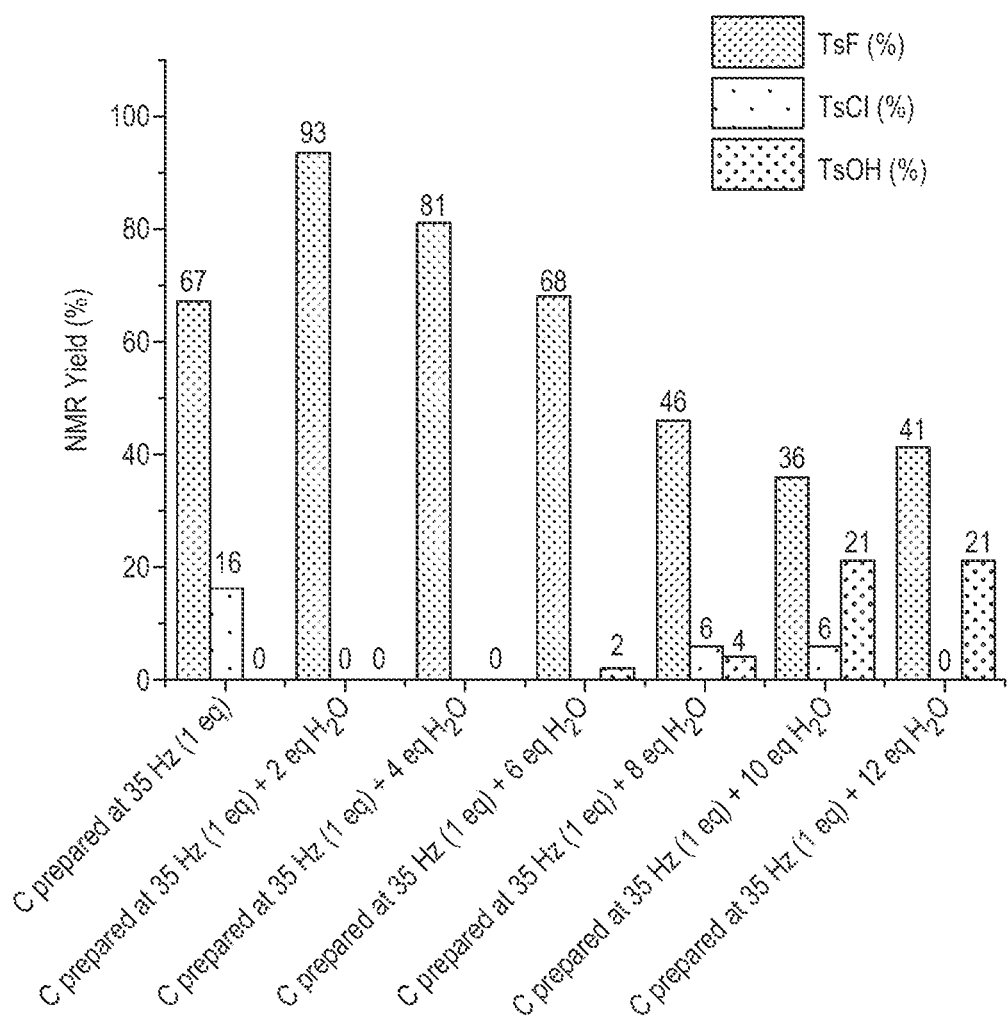
FIG. 20 shows the NMR yields of TsF from TsCl using fluorspar and $K_2HPO_4$ as an activator with different amounts of water added to the fluorination reaction.
Figure 95:
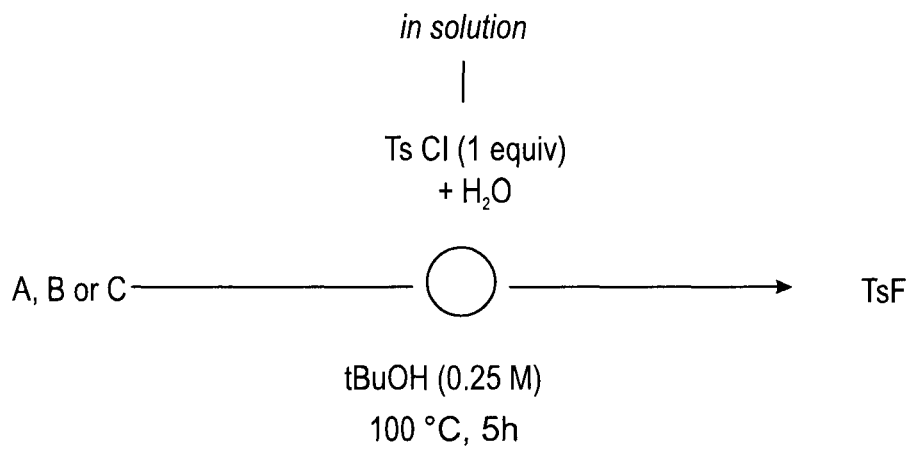
FIG. 95 illustrates a general scheme according to embodiments described herein.

FIG. 95 shows a reaction wherein the powder reagents of FIG. 93 were reacted with TsCl (1 equiv., 0.125-0.25 mmol) in a 0.25 M solution of tBuOH at 100° C. for 5 hours with the addition of water. The results (see FIG. 20) show that the addition of water to the reaction may be beneficial to achieving higher yields of organofluorine product (e.g., TsF).

Figure 21:
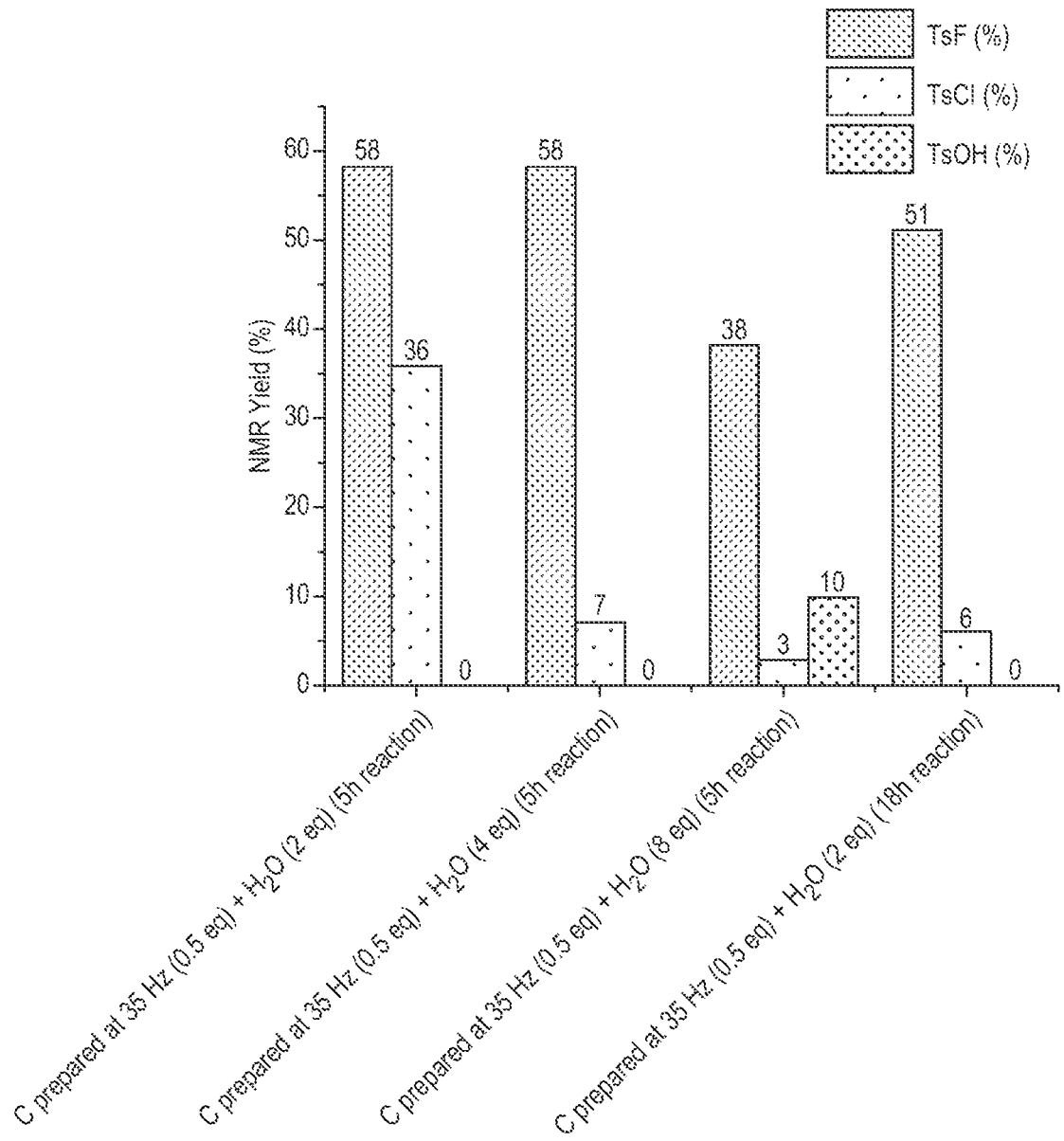
FIG. 21 shows the NMR yields of TsF from TsCl using fluorspar and $K_2HPO_4$ as an activator with different amounts of water added to the fluorination reaction and 5 hour or 18 hour reaction times.

Various experimental conditions were used using powder reagent C from FIG. 93 (containing 0.5 equivalents of CaF₂) as seen in FIG. 95 where C (0.5 equiv.) is reacted with TsCl (1 equiv., 0.125-0.25 mmol) in a solution of tBuOH (0.25 M) at 100° C. for 5 hours with the addition of varying amounts of water. FIG. 21 shows the results of these reactions. These results may indicate that larger amounts of added water may lower yields of fluorinated product but longer reaction times may increase product yield.

5.10. S—F Bond Scope

Figure 22:
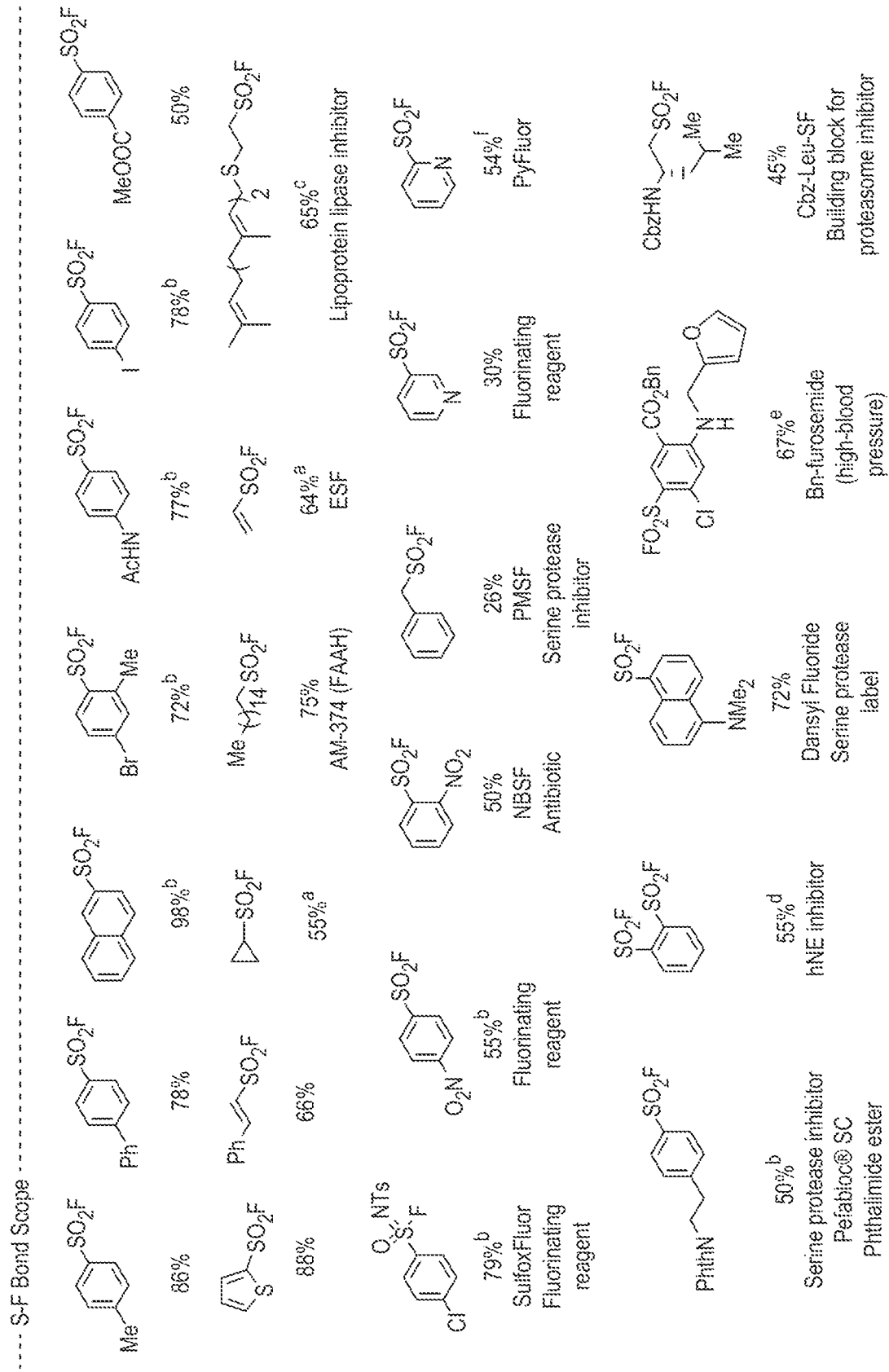
FIG. 22 shows the fluorination substrate scope of $R$—$SO_2Cl$ species.
Figure 96:
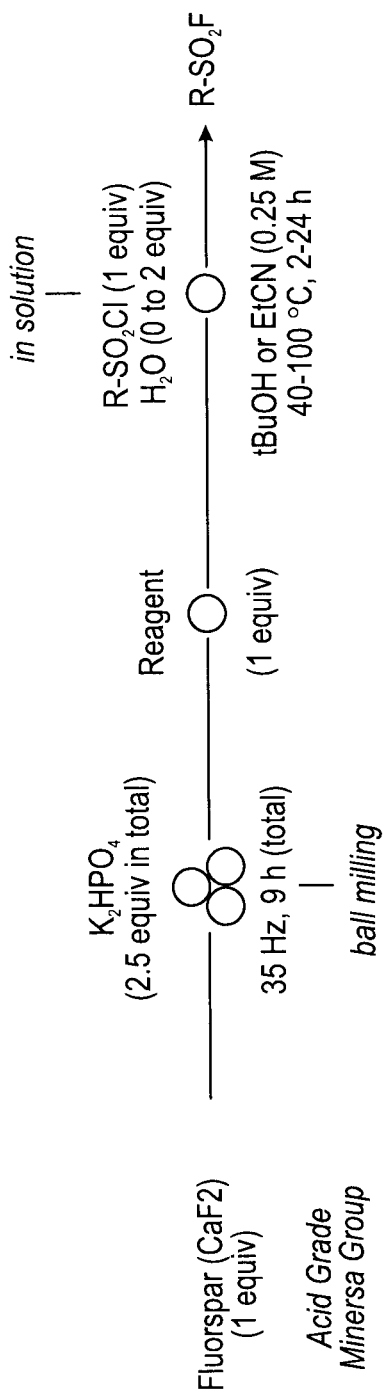
FIG. 96 illustrates a general scheme according to embodiments described herein.

A series of reactions were completed to assess the scope of SO₂—Cl substrates that could undergo fluorination, and the associated fluorination yields. All yields were isolated unless otherwise stated and all reactions were on 0.5 mmol scale unless otherwise stated $^{19}$F NMR yields were determined using 4-fluoroanisole as an internal standard. In FIG. 22, $^b$ indicates that EtCN was used instead of tBuOH (anhydrous), $^c$ indicates that the product was prepared via addition of all trans farnesyl-mercaptan to ESF, $^d$ indicates that the reaction was completed using 2.2 equivalents of "reagent", $^e$ indicates that the reaction was completed on 0.25 mmol scale, indicates that 1.25 mmol of "reagent" was used. In all instances, a INSOLIDO IST636 Ball Mill was used with stainless steel jars (15 mL) and ball (7 g) (316 SS grade). These reactions were carried out as detailed in FIG. 96 wherein Fluorspar (CaF₂) (1 equiv., acid grade) was milled with K₂HPO₄ (2.5 equiv. total) at 35 Hz for 9 hours total. The "reagent" (1 equiv.) was reacted with the R—SO₂Cl (1 equiv.) and H₂O (0-2 equiv) in tBuOH or EtCN (0.25 M) at 40-100° C. for 2-24 hours to achieve the fluorinated product. FIG. 22 shows all of the fluorinated products and their fluorinated yields. The results indicate that a wide range of substrates may undergo fluorination using the fluorination agents described herein.

5.11. C—F Bond Scope

Figure 23:
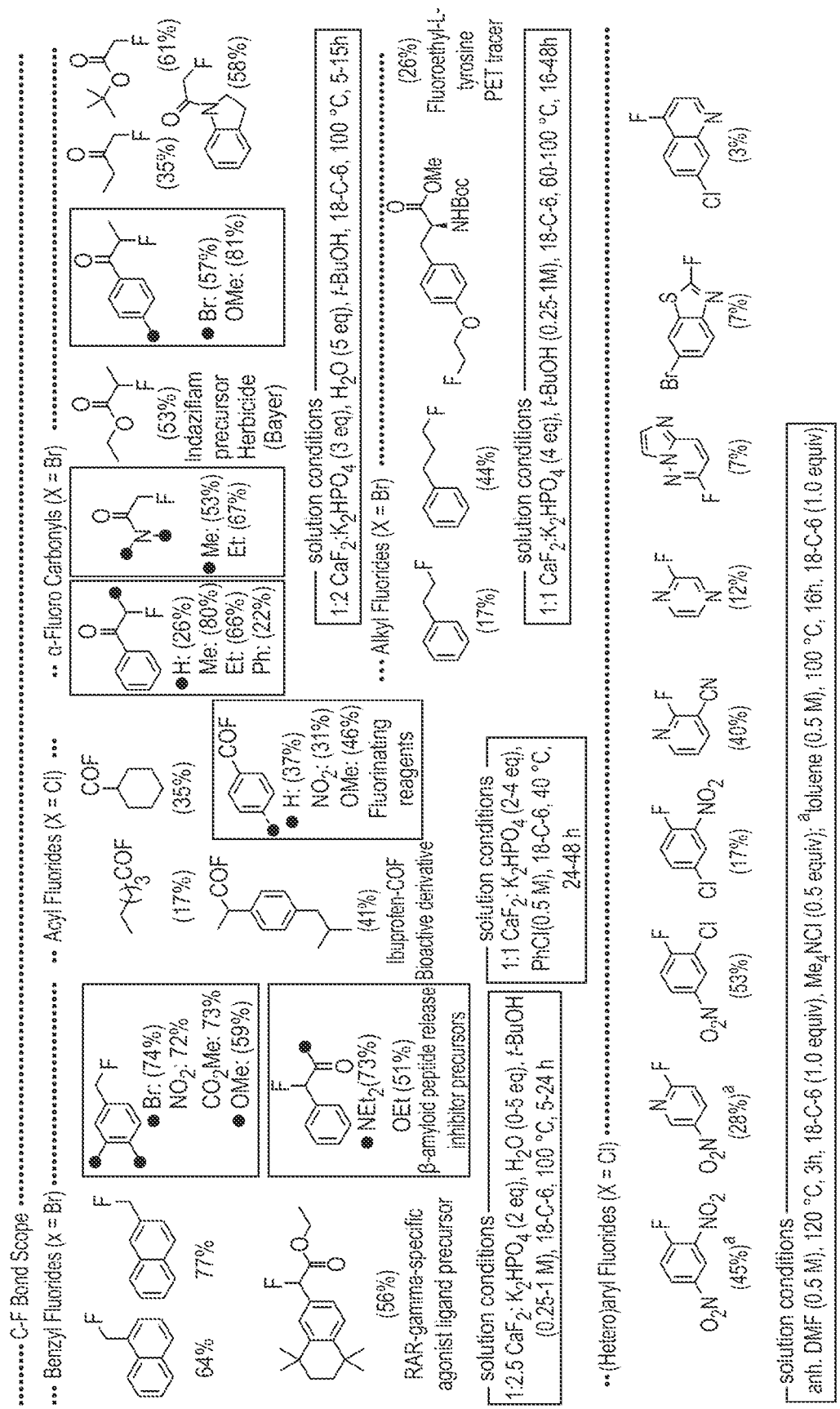
FIG. 23 shows the fluorination substrate scope of R—X species.
Figure 97:
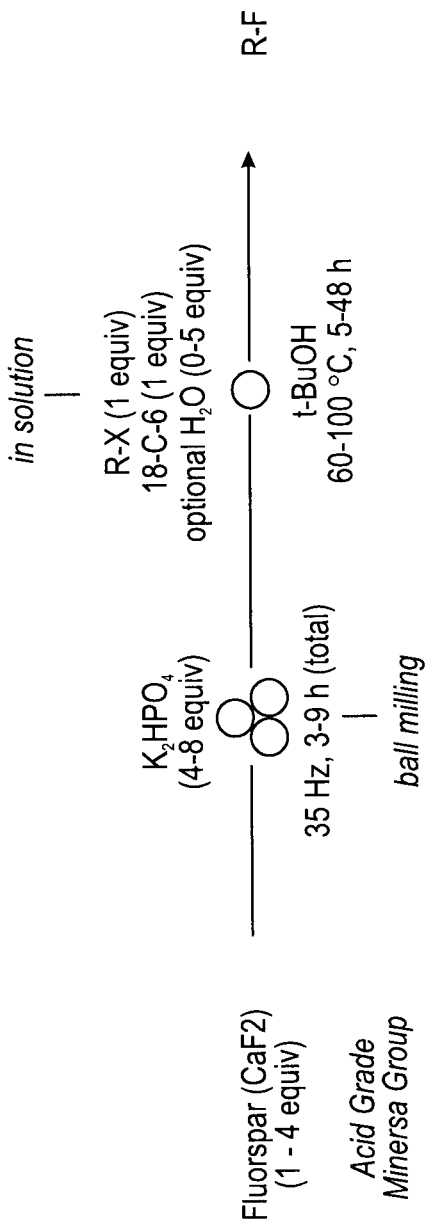
FIG. 97 illustrates a general scheme according to embodiments described herein.

A series of reactions were completed to assess the scope of R—X substrates that could undergo fluorination, wherein X indicates a halogen (Br or Cl) and the associated fluorination yields. Benzyl fluorides, acyl fluorides, alpha-fluoro carbonyls, alkyl fluorides, and (hetero)aryl fluorides were of those C—F bonds investigated as seen in FIG. 23. The fluorination reagent was created via ball milling as shown in FIG. 97 wherein CaF₂ (FluorSpar) (1-4 equiv.) was milled with K₂HPO₄ (4-8 equiv.) at 35 Hz for 3-9 hours total. This solid reagent was reacted with the R—X substrate (1 equiv.), 18-C-6 (1 equiv.) and optionally H₂O (0-5 equiv.) in a solution of tBuOH at 60-100° C. for 5-48 hours to achieve the desired product, the yields and specific solution conditions of which can be seen in FIG. 23. All isolated yields are not in parentheses and were conducted on a 0.5 mmol scale. All yields in parentheses are NMR yields. All reactions were completed using an INSOLIDO IST636 Ball Mill and using stainless steel jars (15 mL) with a 7 g ball (316 SS grade). The results indicate a range of different halogenated functionalities can undergo fluorination using the aforementioned fluorination reagents.

5.12 Solution State NMR and Powder X-Ray Diffraction

Figure 24A:
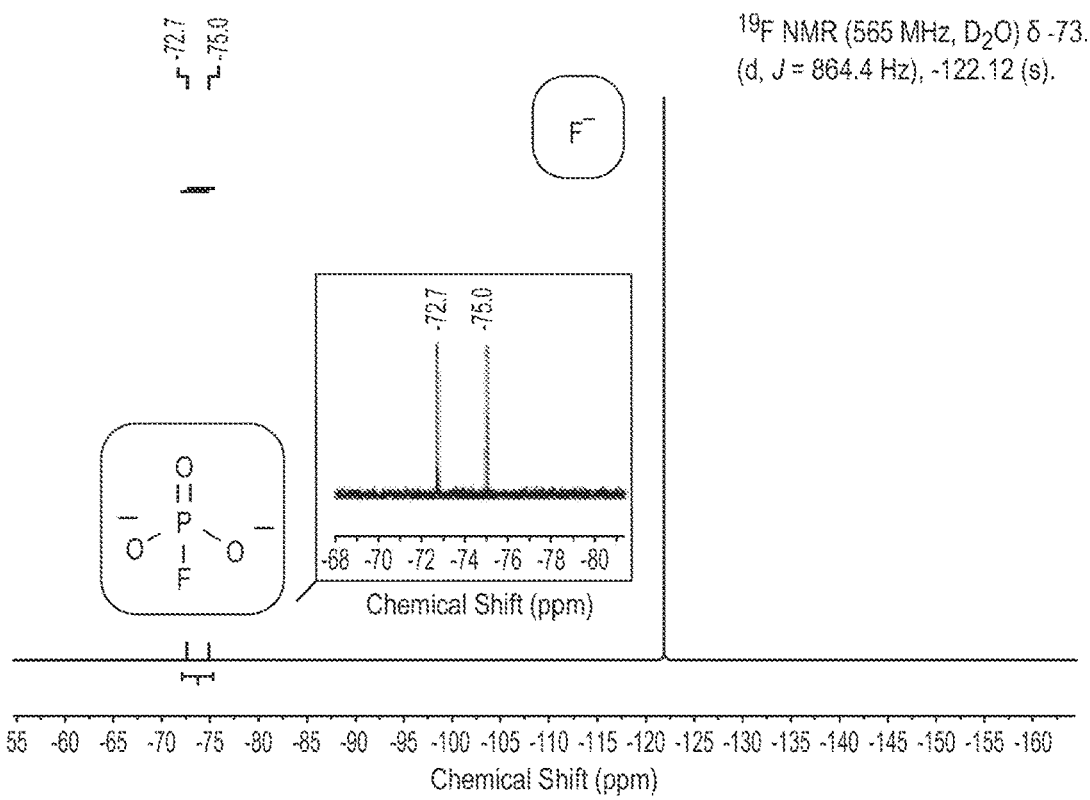
FIG. 24 shows $^{19}$F NMR (24A) and $^{31}$P NMR (24B) of the soluble product of milling of fluorspar and $K_2HPO_4$.
Figure 24B:
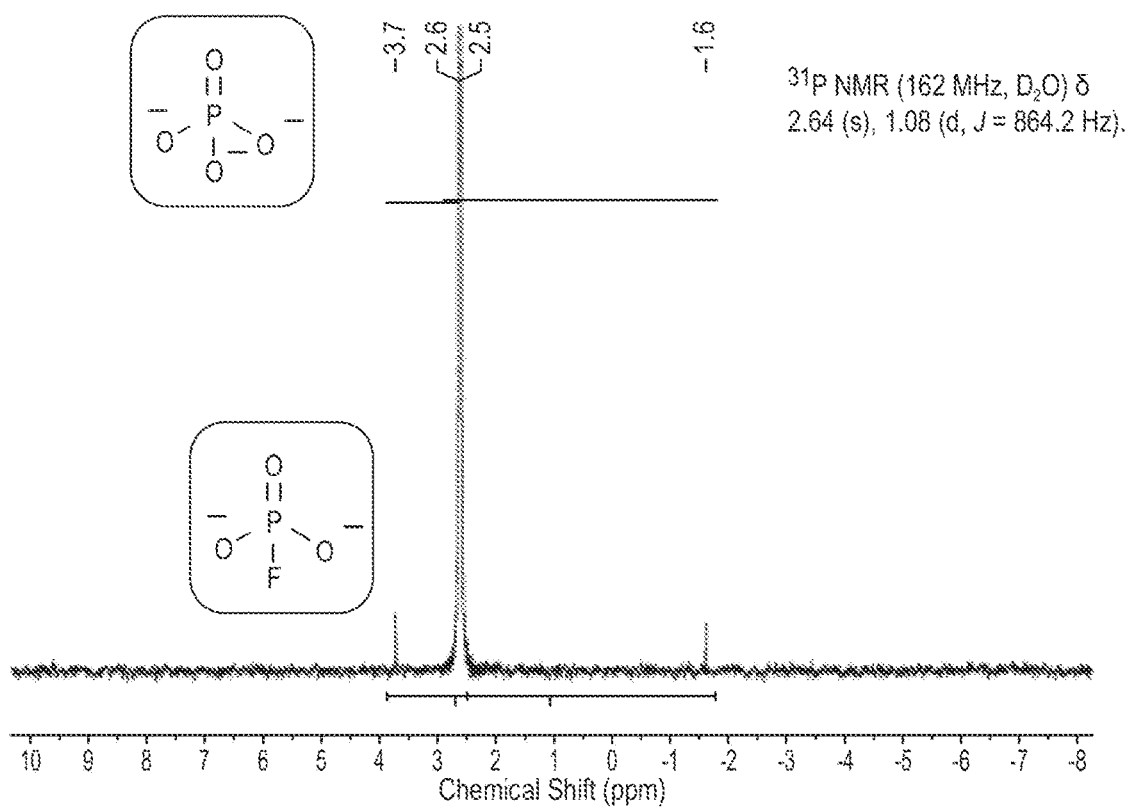
Figure 98:
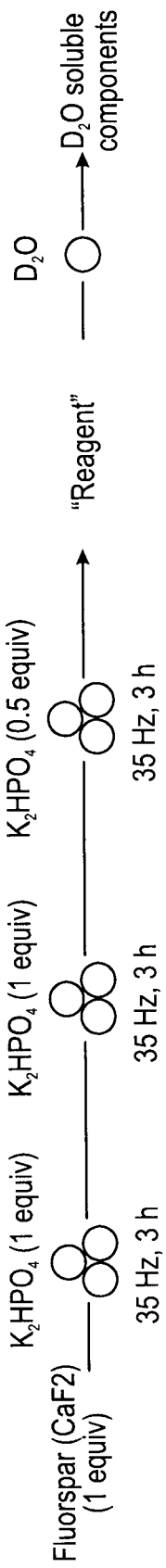
FIG. 98 illustrates a general scheme according to embodiments described herein.

Fluorspar (CaF₂) was milled with K₂HPO₄ (2.5 equiv. total) as seen in FIG. 98 to form a "reagent". The reagent was dissolved in D₂O to form D₂O soluble components for study via solution state NMR. FIG. 24A shows $^{19}$F NMR indicating the presence of F⁻ ion and PO₃F²⁻ ion in solution upon dissolution. FIG. 24B shows $^{31}$P NMR indicating the presence of PO₄³⁻ and PO₃F²⁻.

Figure 25:
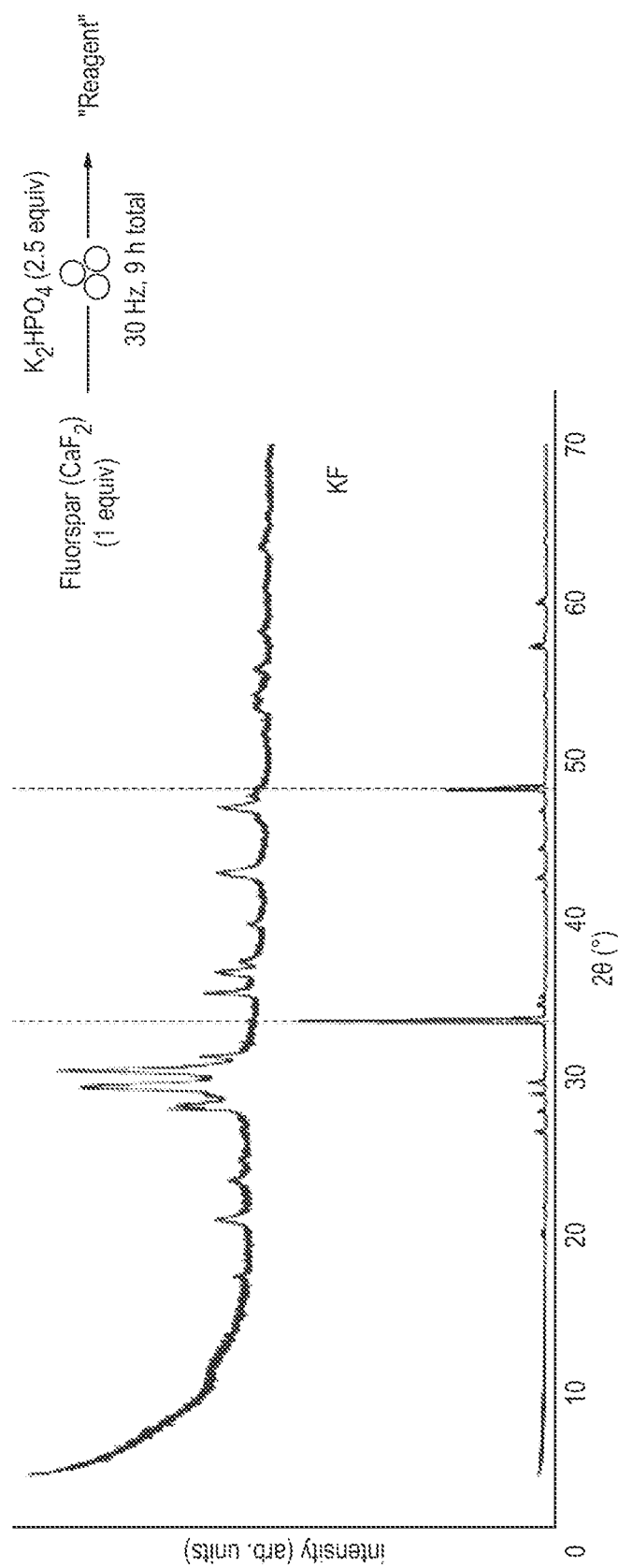
FIG. 25 shows the PXRD diffractogram of the milling product of fluorspar with $K_2HPO_4$ after 9 hours at 30 Hz referenced to crystalline KF (bottom).
Figure 27:
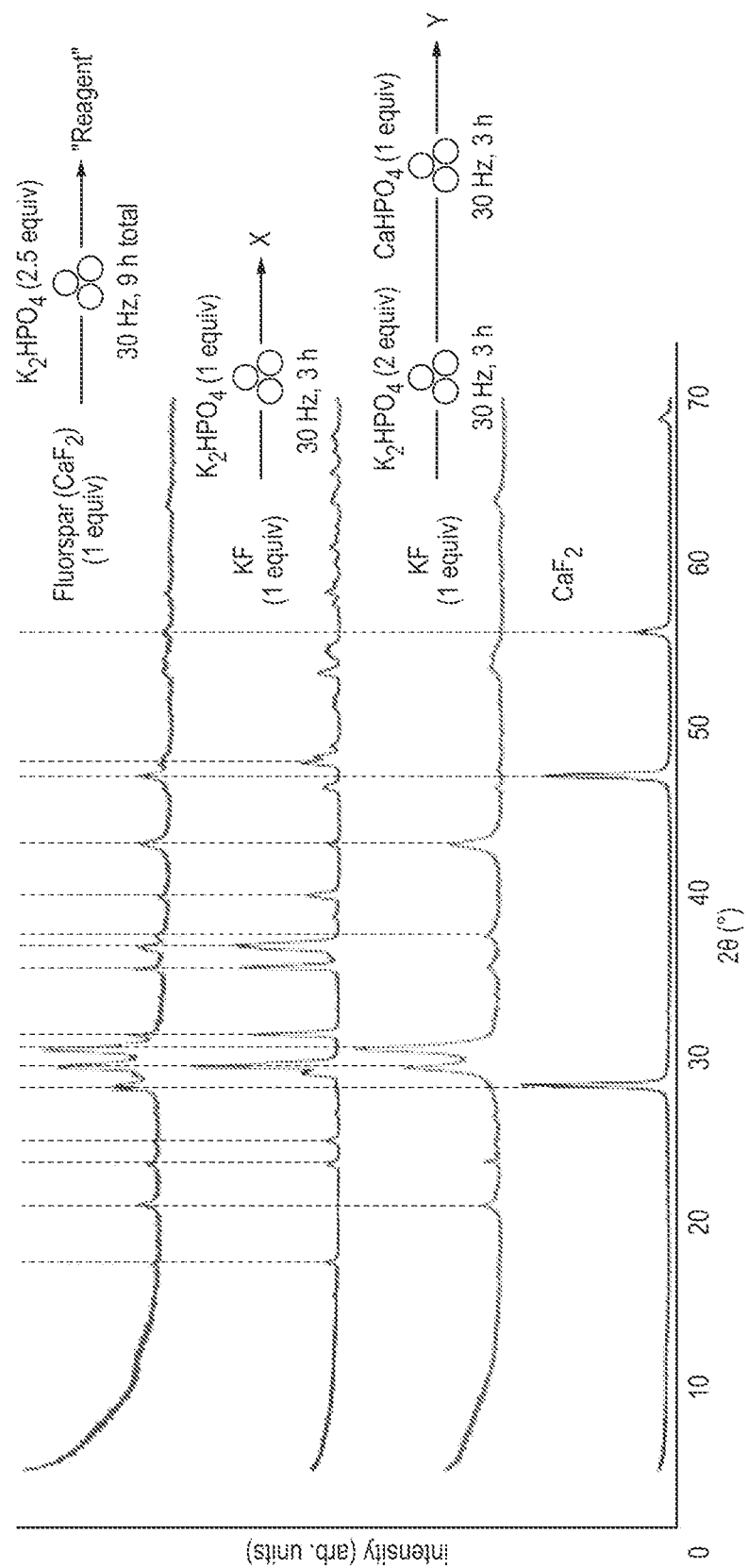
FIG. 27 shows stacked PXRD diffractograms of (from top to bottom), fluorspar milled with $K_2HPO_4$ for 9 hours at 30 Hz, KF milled with $K_2HPO_4$ for 3 hours at 30 Hz, KF milled with $K_2HPO_4$ for 3 hours at 30 Hz followed by $CaHPO_4$ for 3 hours at 30 Hz, and crystalline $CaF_2$.
Figure 99:
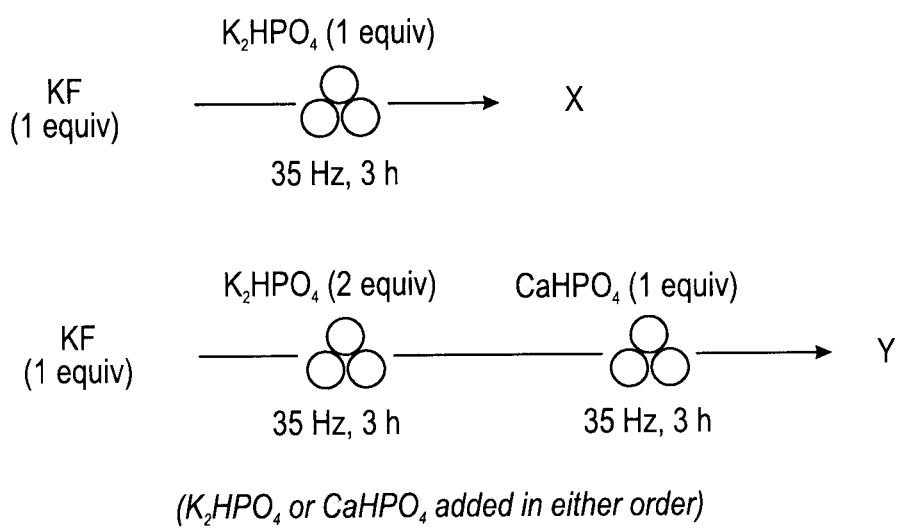
FIG. 99 illustrates a general scheme according to embodiments described herein.

FIG. 25 shows a powder x-ray diffraction pattern (PXRD) of the "reagent" with a reference PXRD pattern for potassium fluoride (KF). The PXRD pattern indicated no presence of KF upon completion of the ball milling reaction. FIG. 26 and Table 5.12.1 show PXRD data of the fluorinating reagent, "Fluoromix" that results from the "reagent" formation depicted in FIG. 98 when fluorspar is milled with 2.5 total equivalents of K₂HPO₄. FIG. 27 shows the crystalline components of "reagent" consistent with X (KF (1 equiv.) milled with K₂HPO₄ (1 equiv.) at 30 Hz for 3 hours), Y (KF (1 equiv.) milled with K₂HPO₄ (1 equiv.) at 30 Hz for 3 hours followed by the addition of CaHPO₄ (1 equiv.)), and crystalline CaF₂ as a reference PXRD pattern. X and Y could be synthesized independently via FIG. 99.

Figure 28A:
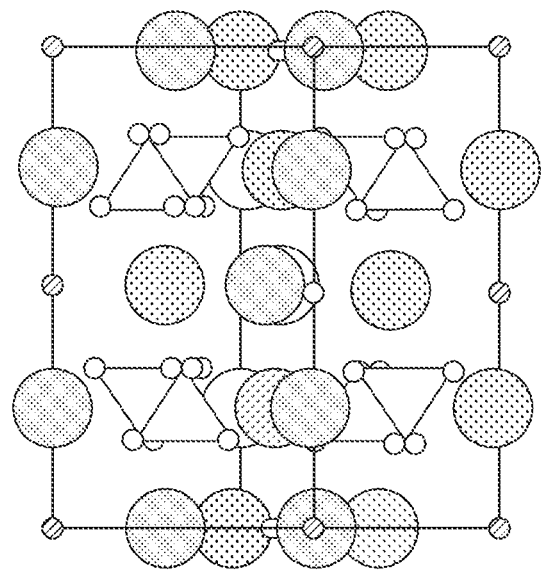
FIG. 28 shows the simulated crystal structure of the product of KF milled with $K_2HPO_4$ for 3 hours at 30 Hz (A) and KF milled with $K_2HPO_4$ for 3 hours at 30 Hz followed by $CaHPO_4$ for 3 hours at 30 Hz, and crystalline $CaF_2$ (B).
Figure 28B:
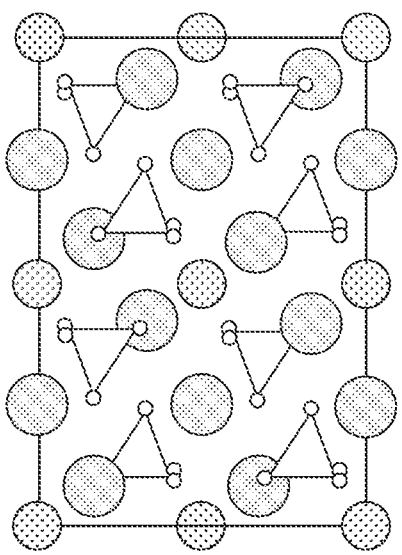
Figure 29:
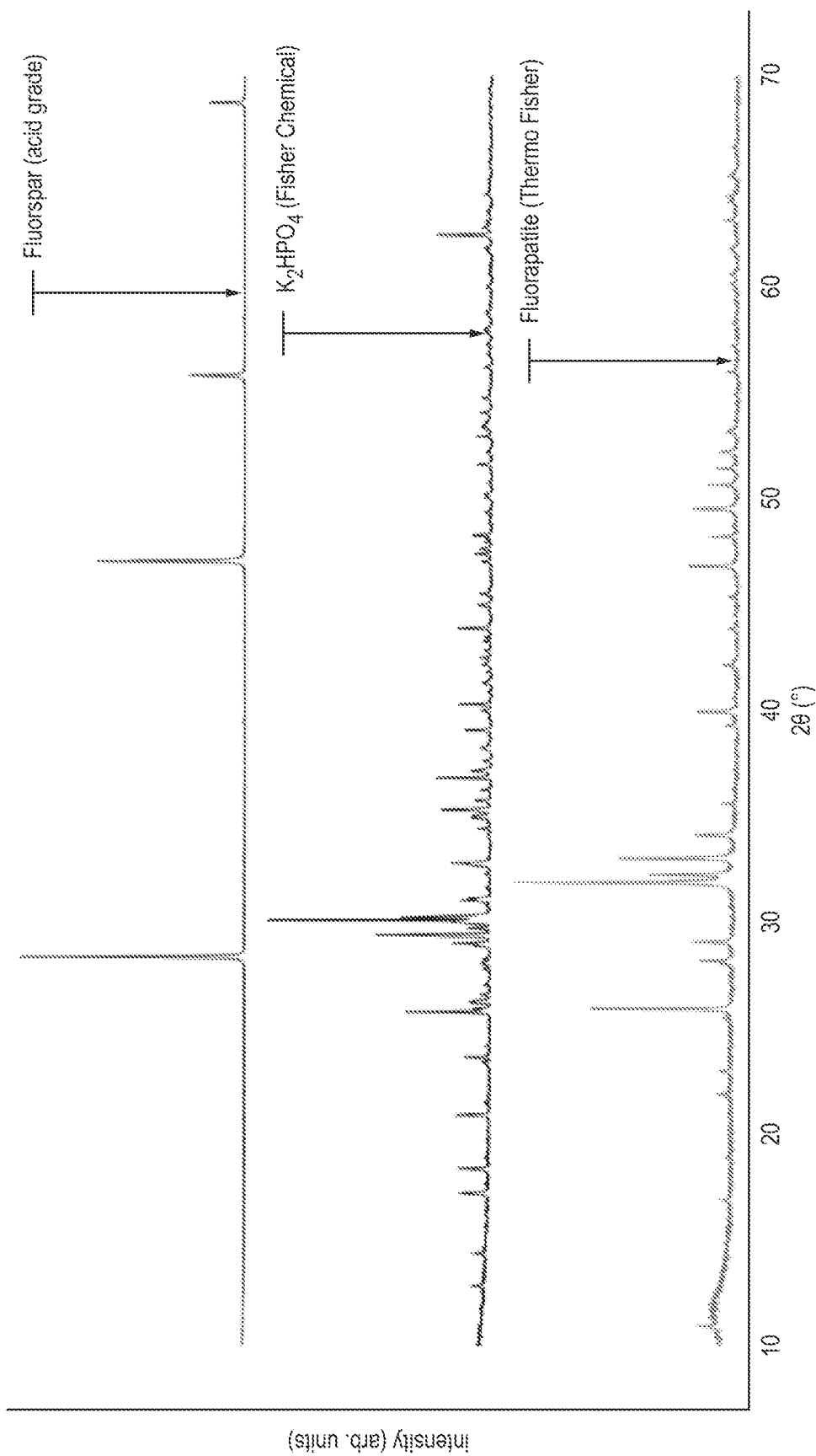
FIG. 29 shows stacked PXRD diffractograms of fluorspar, $K_2HPO_4$, and fluorapatite.
Figure 30:
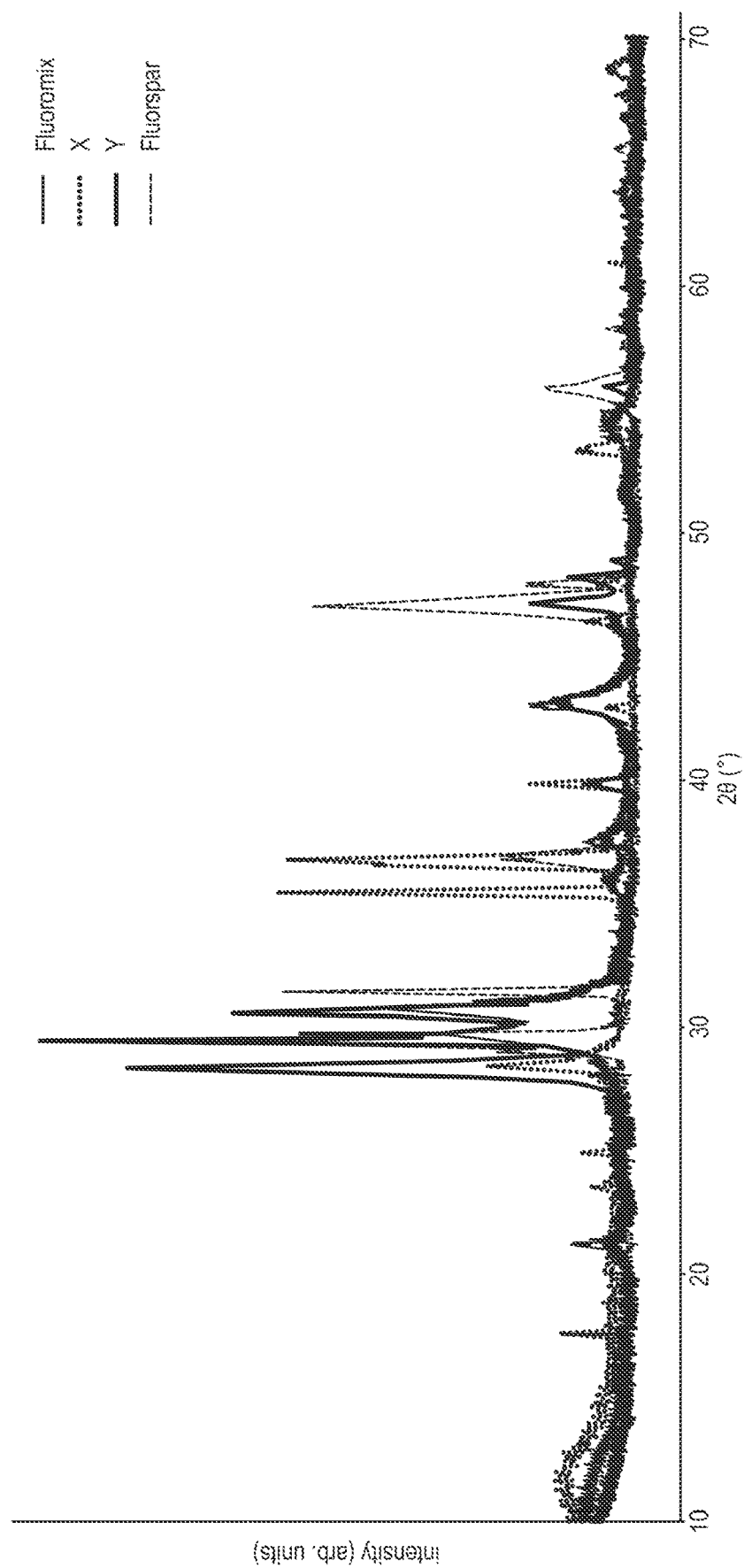
FIG. 30 shows overlayed PXRD diffractograms of fluoromix, KF milled with $K_2HPO_4$ for 3 hours at 30 Hz, KF milled with $K_2HPO_4$ for 3 hours at 30 Hz followed by $CaHPO_4$ for 3 hours at 30 Hz, and crystalline $CaF_2$, and fluorspar.

This PXRD may indirectly support the formation and involvement of KF and CaHPO₄ species in the solid state reaction. The structures of X and Y were simulated based upon their PXRD patterns. FIG. 28A shows the simulated structure of X which may be K₃(HPO₄)F, which is a related structure to K₃(PO₃F)F. FIG. 28B shows the simulated structure of Y which may be $K_{2-x}Ca_y(PO_3F)_a(PO_4)_bF_c$, which is a related structure to K₂PO₃F. FIG. 29 shows PXRD experiments for Fluorspar (acid grade), K₂HPO₄ (Fisher Chemical), and Fluorapatite (Thermo Fisher). FIG. 30 shows an overlay of PXRD diffractograms of fluoromix, fluorspar, X, and Y. Residual CaF₂ is also observed in the diffractogram of fluoromix. Table 5.12.2 shows PXRD data of the crystalline components of X which has a proposed structure of K₃(HPO₄)F. Table 5.12.3 shows PXRD data of the crystalline components of Y, which has a proposed structure of $K_{2-x}Ca_y(PO_3F)_a(PO_4)_bF_c$.

TABLE 5.12.1.

| Pos. [°2Th.] | Height [cts] | FWHM [°2Th.] | d-spacing [Å] | Rel. Int. [%] |
|---|---|---|---|---|
| X 17.5396 | 65.74 | 0.1515 | 5.05648 | 6.01 |
| Y 21.1279 | 153.67 | 0.3031 | 4.20512 | 14.06 |
| X 23.5473 | 63.33 | 0.3031 | 3.77826 | 5.79 |
| X 24.8414 | 38.29 | 0.2165 | 3.58428 | 3.50 |
| CaF$_2$ 28.3270 | 387.64 | 0.1732 | 3.15067 | 35.46 |
| X 29.3567 | 889.96 | 0.1515 | 3.04246 | 81.42 |
| Y 29.6240 | 919.11 | 0.1299 | 3.01562 | 84.08 |
| Y 30.5396 | 1093.11 | 0.1948 | 2.92727 | 100.00 |
| X 31.5267 | 226.92 | 0.3031 | 2.83783 | 20.76 |
| X 35.3807 | 392.48 | 0.0758 | 2.53704 | 35.91 |
| X 36.7453 | 327.57 | 0.3897 | 2.44590 | 29.97 |
| Y 37.3937 | 109.61 | 0.2165 | 2.40496 | 10.03 |
| X 39.8065 | 109.97 | 0.3031 | 2.26458 | 10.06 |
| Y 42.9495 | 272.27 | 0.4330 | 2.10586 | 24.91 |
| X 47.1639 | 263.14 | 0.2381 | 1.92705 | 24.07 |
| CaF$_2$ 47.8144 | 104.83 | 0.1732 | 1.90234 | 9.59 |
| X 48.0882 | 90.13 | 0.3464 | 1.89215 | 8.24 |
| X 51.4329 | 21.62 | 0.6927 | 1.77669 | 1.98 |
| X 53.1839 | 95.20 | 0.2598 | 1.72225 | 8.71 |
| Y 54.2330 | 105.76 | 0.2598 | 1.69139 | 9.68 |
| CaF$_2$ 55.8995 | 80.81 | 0.1732 | 1.64485 | 7.39 |
| Y 58.2038 | 53.48 | 0.2598 | 1.58510 | 4.89 |
| Y 60.9230 | 31.01 | 0.2598 | 1.52071 | 2.84 |
| X 63.4275 | 54.12 | 0.6061 | 1.46656 | 4.95 |
| CaF$_2$ 68.7124 | 26.36 | 0.4224 | 1.36496 | 2.41 |

TABLE 5.12.2.

| Pos. [°2Th.] | Height [cts] | FWHM [°2Th.] | d-spacing [Å] | Rel. Int. [%] |
|---|---|---|---|---|
| 15.5985 | 40.81 | 0.1299 | 5.68107 | 2.34 |
| 17.5367 | 177.21 | 0.1082 | 5.05732 | 10.16 |
| 23.3979 | 99.97 | 0.1082 | 3.80204 | 5.73 |
| 24.8981 | 123.18 | 0.2165 | 3.57625 | 7.06 |
| 26.5567 | 27.17 | 0.5196 | 3.35654 | 1.56 |
| 28.0843 | 158.50 | 0.0325 | 3.17734 | 9.09 |
| 28.8933 | 359.19 | 0.0974 | 3.09019 | 20.60 |
| 29.3501 | 1540.63 | 0.0660 | 3.04062 | 88.34 |
| 29.4006 | 1743.95 | 0.0433 | 3.03802 | 100.00 |
| 29.6670 | 626.50 | 0.1082 | 3.01134 | 35.92 |
| 31.3455 | 918.24 | 0.0758 | 2.85381 | 52.65 |
| 35.3783 | 844.95 | 0.0974 | 2.53721 | 48.45 |
| 36.4954 | 710.20 | 0.0866 | 2.46207 | 40.72 |
| 36.7261 | 985.15 | 0.1299 | 2.44713 | 56.49 |
| 38.4075 | 43.66 | 0.1732 | 2.34379 | 2.50 |
| 39.8011 | 290.42 | 0.1299 | 2.26487 | 16.65 |
| 42.8332 | 73.55 | 0.2598 | 2.11131 | 4.22 |
| 46.2683 | 122.18 | 0.2598 | 1.96224 | 7.01 |
| 47.7691 | 316.46 | 0.1299 | 1.90404 | 18.15 |
| 48.1576 | 199.11 | 0.1299 | 1.88959 | 11.42 |
| 48.7914 | 68.65 | 0.1299 | 1.86651 | 3.94 |
| 51.3864 | 36.92 | 0.6927 | 1.77819 | 2.12 |
| 53.1696 | 153.70 | 0.3031 | 1.72268 | 8.81 |
| 54.3855 | 72.83 | 0.4330 | 1.68701 | 4.18 |
| 54.8541 | 100.27 | 0.1299 | 1.67370 | 5.75 |
| 57.5120 | 39.39 | 0.3464 | 1.60251 | 2.26 |
| 58.1605 | 89.36 | 0.3031 | 1.58618 | 5.12 |
| 59.8088 | 33.81 | 0.3464 | 1.54635 | 1.94 |
| 60.8554 | 73.32 | 0.2165 | 1.52223 | 4.20 |
| 62.1974 | 28.45 | 0.2598 | 1.49258 | 1.63 |
| 63.7003 | 56.77 | 0.3031 | 1.46094 | 3.26 |
| 65.4523 | 51.25 | 0.3464 | 1.42601 | 2.94 |
| 66.7273 | 39.38 | 0.3464 | 1.40183 | 2.26 |
| 67.6556 | 48.24 | 0.4224 | 1.38369 | 2.77 |

TABLE 5.12.3.

| Pos. [°2Th.] | Height [cts] | FWHM [°2Th.] | d-spacing [Å] | Rel. Int. [%] |
|---|---|---|---|---|
| 21.2490 | 76.30 | 0.2598 | 4.18143 | 12.32 |
| 29.5875 | 473.30 | 0.3464 | 3.01925 | 76.40 |
| 30.7329 | 619.48 | 0.3897 | 2.90929 | 100.00 |
| 35.9522 | 41.32 | 0.6927 | 2.49801 | 6.67 |
| 37.5864 | 65.52 | 0.3464 | 2.39308 | 10.58 |
| 43.1662 | 208.62 | 0.2598 | 2.09579 | 33.68 |
| 63.7377 | 27.33 | 0.7392 | 1.45896 | 4.41 |

Figure 31:
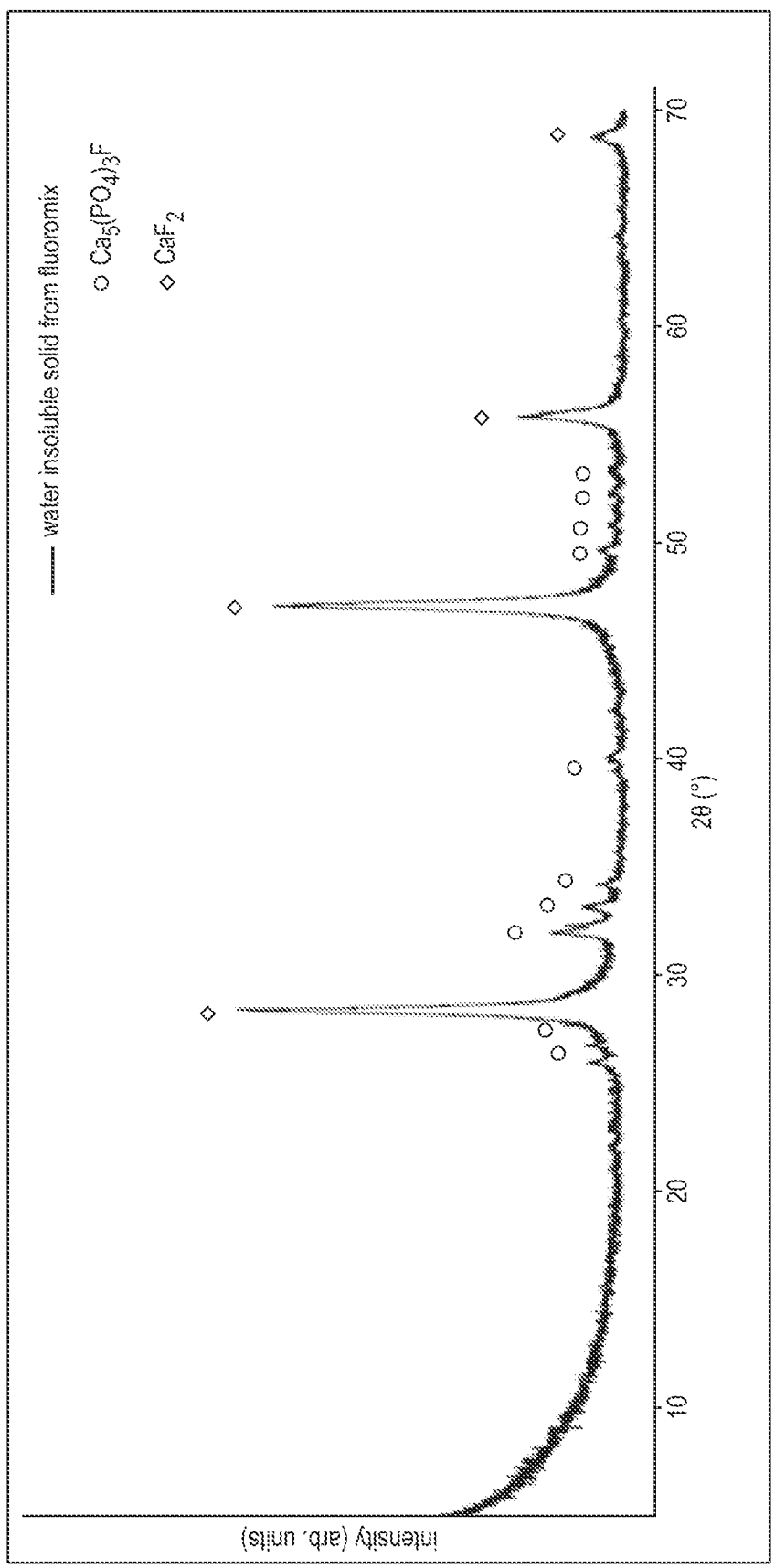
FIG. 31 shows the PXRD diffractogram of the water insoluble solid formed from the milling reaction of $CaF_2$ (fluorspar) and $K_2HPO_4$.
Figure 100:
FIG. 100 illustrates a general scheme according to embodiments described herein.

Fluorspar (CaF$_2$) (1 equiv.) was milled with K$_2$HPO$_4$ (2.5 equiv.) at 35 Hz for 9 hours total to form a "reagent" as seen in FIG. 100. This reagent ("Fluoromix") was washed with H$_2$O resulting in a water insoluble solid (84.5 mg from 500 mg of reagent, 17% yield). The resulting insoluble solid was examined via PXRD. FIG. 31 shows this PXRD with peaks labelled showing formation of Ca$_5$(PO$_4$)$_3$F or Ca$_5$(PO$_4$)$_3$OH (diamonds) and CaF$_2$ (circles). The PXRD data can also be found in Table 5.12.4.

TABLE 5.12.4.

| Pos. [°2Th.] | Height [cts] | FWHM [°2Th.] | d-spacing [Å] | Rel. Int. [%] |
|---|---|---|---|---|
| 25.9666 | 64.58 | 0.2165 | 3.43147 | 5.97 |
| 26.7534 | 64.57 | 0.1299 | 3.33231 | 5.97 |
| CaF$_2$ 28.4315 | 1080.91 | 0.2598 | 3.13933 | 100.00 |
| 31.9708 | 174.80 | 0.1515 | 2.79941 | 16.17 |
| 32.3361 | 113.01 | 0.1299 | 2.76862 | 10.45 |
| 33.1708 | 97.67 | 0.2598 | 2.70084 | 9.04 |
| 34.1856 | 47.24 | 0.1732 | 2.62295 | 4.37 |
| 40.1111 | 44.33 | 0.2598 | 2.24808 | 4.10 |
| 42.3659 | 13.44 | 0.5196 | 2.13351 | 1.24 |
| CaF$_2$ 47.0602 | 1011.70 | 0.1584 | 1.92946 | 93.60 |
| 47.1777 | 927.10 | 0.1515 | 1.92652 | 85.77 |
| 49.6779 | 42.95 | 0.2598 | 1.83526 | 3.97 |
| 50.8430 | 17.12 | 0.2598 | 1.79591 | 1.58 |
| 52.3671 | 13.80 | 0.2598 | 1.74717 | 1.28 |
| 53.3150 | 27.45 | 0.3464 | 1.71832 | 2.54 |
| CaF$_2$ 55.8298 | 292.84 | 0.1948 | 1.64674 | 27.09 |
| 64.2404 | 13.33 | 0.5196 | 1.44996 | 1.23 |
| CaF$_2$ 68.7885 | 84.35 | 0.5280 | 1.36364 | 7.80 |

Figure 32A:
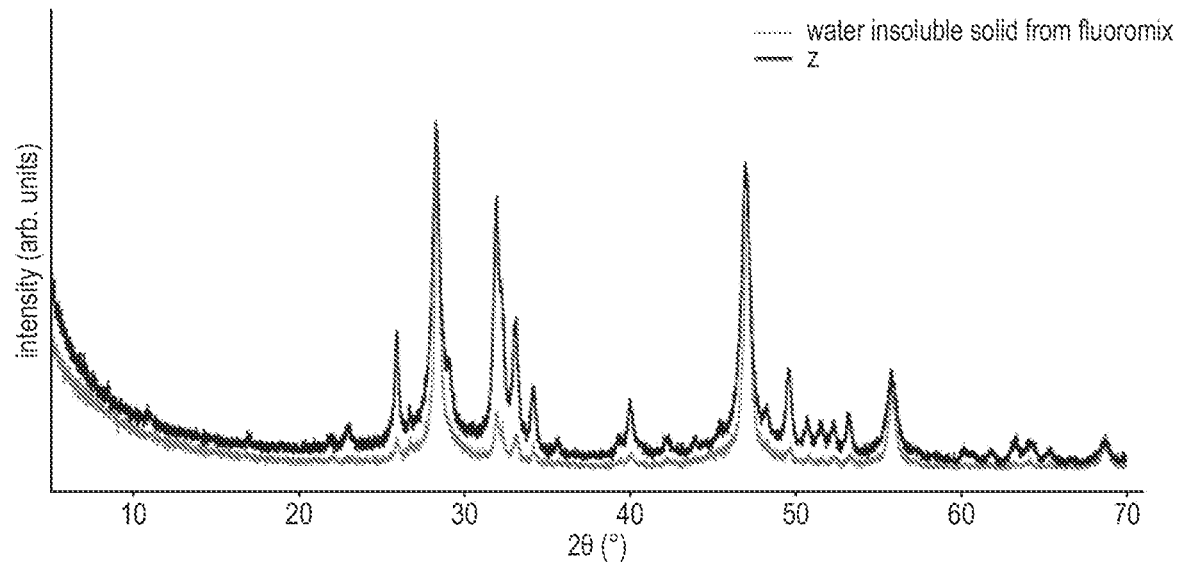
FIG. 32 shows the PXRD diffractogram of water insoluble solid formed from the milling reaction of $CaF_2$ (fluorspar) and $K_2HPO_4$ overlayed with the PXRD diffractogram of the milling product of fluorspar and $CaHPO_4$ (32A) and the PXRD diffractogram of the product formed from the milling reaction of fluorspar and CaHPO$_4$ after 3 hours at 30 Hz (32B).
Figure 32B:
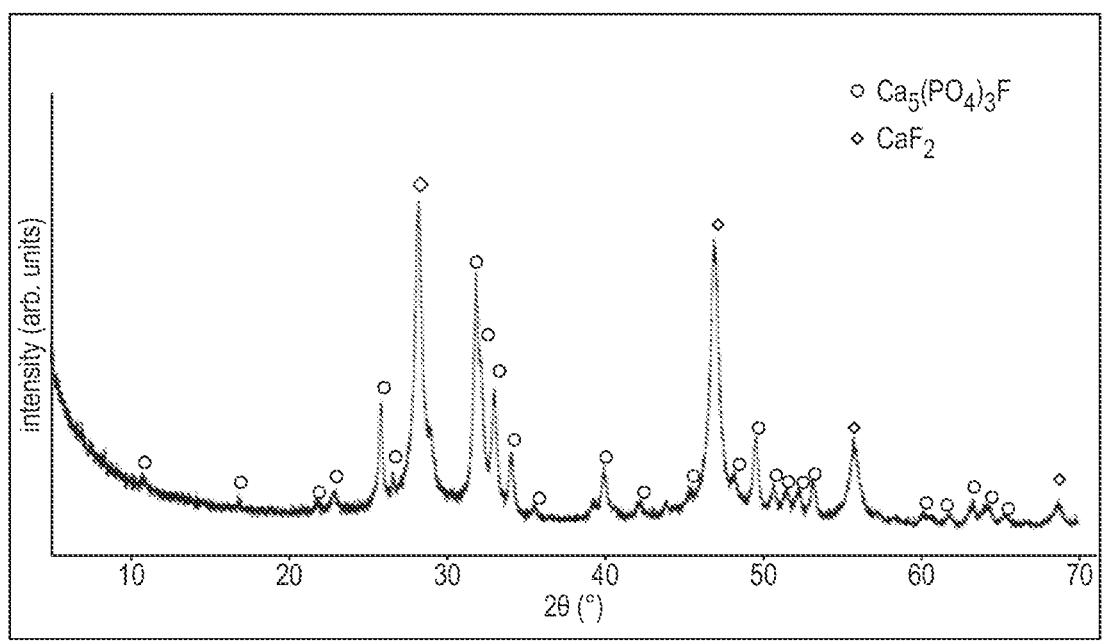
Figure 101:
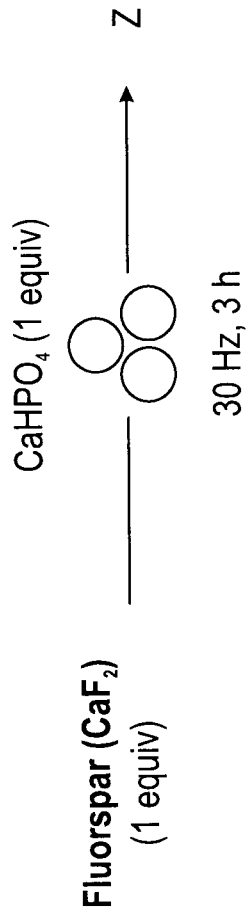
FIG. 101 illustrates a general scheme according to embodiments described herein.

In another instance, Fluorspar (CaF$_2$) was milled with equimolar CaHPO$_4$ to produce Z as seen in FIG. 101. This milling was completed at 30 Hz for 3 hours; FIG. 32A shows PXRD of Z as well as the water insoluble solid resulting from the reaction forming Z. FIG. 32B shows the PXRD of Z with crystalline phases of Ca$_5$(PO$_4$)$_3$F and CaF$_2$ highlighted. The PXRD data of Z can be found in Table 5.12.5. The milling of CaF$_2$ with equimolar anhydrous CaHPO$_4$ produces Z consistent Ca$_5$(PO$_4$)$_3$F (or Ca$_5$(PO$_4$)$_3$OH) and CaF$_2$.

TABLE 5.12.5.

| Pos. [°2Th.] | Height [cts] | FWHM [°2Th.] | d-spacing [Å] | Rel. Int. [%] |
|---|---|---|---|---|
| 10.8159 | 22.19 | 0.3464 | 8.18003 | 1.71 |
| 16.9988 | 27.36 | 0.3464 | 5.21612 | 2.11 |
| 21.9471 | 44.50 | 0.3031 | 4.04997 | 3.43 |
| 22.9223 | 87.66 | 0.3031 | 3.87984 | 6.76 |
| 25.9108 | 464.01 | 0.1515 | 3.43873 | 35.79 |
| 26.7231 | 164.61 | 0.1299 | 3.33602 | 12.70 |
| CaF$_2$ 28.3972 | 1296.45 | 0.2165 | 3.14305 | 100.00 |
| 29.1216 | 365.28 | 0.1732 | 3.06649 | 28.18 |

TABLE 5.12.5.-continued

| Pos. [°2Th.] | Height [cts] | FWHM [°2Th.] | d-spacing [Å] | Rel. Int. [%] |
|---|---|---|---|---|
| 31.9522 | 1014.39 | 0.1515 | 2.80100 | 78.24 |
| 32.3833 | 548.05 | 0.1948 | 2.76469 | 42.27 |
| 33.1624 | 541.34 | 0.0866 | 2.70150 | 41.76 |
| 34.1845 | 268.43 | 0.2598 | 2.62303 | 20.71 |
| 35.6375 | 53.32 | 0.1732 | 2.51934 | 4.11 |
| 39.3033 | 78.45 | 0.1732 | 2.29241 | 6.05 |
| 40.0474 | 226.94 | 0.1515 | 2.25151 | 17.50 |
| 42.2195 | 64.59 | 0.3031 | 2.14056 | 4.98 |
| 43.9611 | 61.89 | 0.2598 | 2.05972 | 4.77 |
| 45.4737 | 106.84 | 0.2598 | 1.99467 | 8.24 |
| $CaF_2$ 46.9114 | 1075.26 | 0.1515 | 1.93683 | 82.94 |
| 49.6178 | 342.27 | 0.3031 | 1.83734 | 26.40 |
| 50.7543 | 131.19 | 0.2165 | 1.79884 | 10.12 |
| 51.5785 | 118.41 | 0.2598 | 1.77201 | 9.13 |
| 52.3593 | 105.86 | 0.2598 | 1.74741 | 8.17 |
| 53.2237 | 143.52 | 0.1732 | 1.72106 | 11.07 |
| $CaF_2$ 55.7559 | 291.37 | 0.4330 | 1.64875 | 22.47 |
| 60.1404 | 30.48 | 0.3464 | 1.53861 | 2.35 |
| 61.8997 | 32.01 | 0.3897 | 1.49904 | 2.47 |
| 63.2828 | 70.58 | 0.3464 | 1.46957 | 5.44 |
| 64.2073 | 72.79 | 0.6061 | 1.45062 | 5.61 |
| 65.5460 | 30.47 | 0.5196 | 1.42420 | 2.35 |
| $CaF_2$ 68.7224 | 84.83 | 0.6336 | 1.36479 | 6.54 |

5.13. Polyfluorination Using Fluorspar Activated with $K_2HPO_4$

Figure 102:
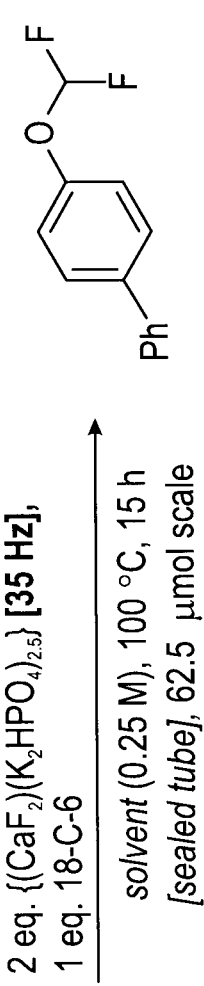
FIG. 102 illustrates a general scheme according to embodiments described herein.
Figure 102:
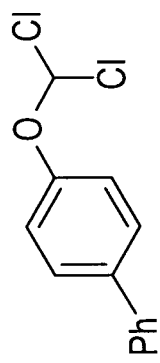

Gem-Difluorination was tested using fluorspar and $K_2HPO_4$ as an activating agent as described in FIG. 102.

Briefly, the substrate was reacted with 2 equiv. of $\{(CaF_2)(K_2HPO_4)_{2.5}\}$ which was obtained via milling at 35 Hz and 1 equivalent of 18-C-6 in 0.25 M solvent (described in Table 5.13.1) and reacted at 100° C. for 15 hours in a sealed tube. The yields of fluorinated products and side products can be seen in Table 5.13.1. The results indicate that difluorination may be achieved from dihalogenated starting materials using the fluorinating agents described herein, with low yields of monofluorinated product.

TABLE 5.13.1.

| Entry | Solvent | $ArOCHCl_2$[a] | $ArOCHClF$[b] | $ArOCHF_2$[b] | $ArOCHO$[a] |
|---|---|---|---|---|---|
| 1 | AcOH | n.d. | 0% | 0% | 65% |
| 2 | DMSO | n.d. | 0% | 0% | <1% |
| 3 | tAmOH | n.d. | 0% | 18% | <1% |
| 4 | PhCl | n.d. | 11% | 19% | <1% |
| 5[c] | PhCl | n.d. | 9% | 17% | <1% |
| 6 | MeCN | n.d. | 4% | 30% | 0% |

Figure 103:
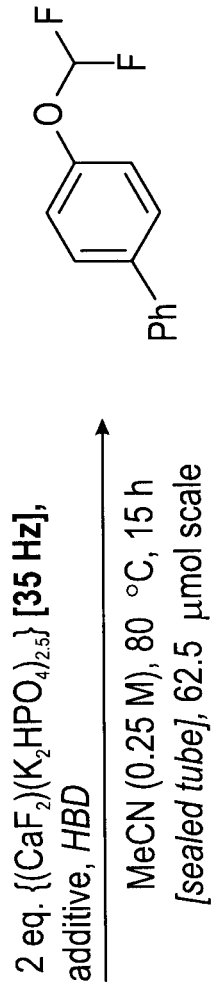
FIG. 103 illustrates a general scheme according to embodiments described herein.
Figure 103:
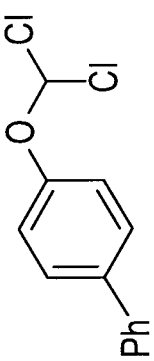

[a]quantified by $^1$H-NMR;
[b]quantified by $^{19}$F-NMR;
[c]entry from previous screening (30 Hz ball milling);
n.d. = not determined due to overlapping signal In some instances, the gem-difluorination was tested as described in FIG. 103.

Briefly, the substrate was reacted with 2 equiv. of $\{(CaF_2)(K_2HPO_4)_{2.5}\}$ which was obtained via milling at 35 Hz and 1 equivalent of an additive (see Table 5.13.2), HBD, and reacted in a solvent (0.25 M) at 100° C. for 15 hours in a sealed tube. The yields of fluorinated product and side products as determined from NMR can be seen in Table 5.13.2. Similarly to above, the results indicate that difluorination may be achieved from dihalogenated starting materials using the fluorinating agents described herein, with low yields of monofluorinated product.

TABLE 5.13.2

| Entry | Additive | HBD | $ArOCHCl_2$[a] | $ArOCHClF$[b] | $ArOCHF_2$[b] | $ArOCHO$[a] |
|---|---|---|---|---|---|---|
| 1 | 1 eq. 18-C-6 | — | n.d. | 18% | 36% | 0% |
| 2[c] | 1 eq. 18-C-6 | — | n.d. | 13% | 32% | 0% |
| 3[d] | 1 eq. 18-C-6 | — | n.d. | 8% | 24% | 0% |
| 4 | 1 eq. [2.2.2]Cryptand | — | n.d. | 5% | 21% | 0% |
| 5 | 1 eq. 18-C-6 | 1 eq. Schreiner's urea[e] | n.d. | 1% | 5% | n.d. |
| 6 | 1 eq. 18-C-6 | 0.2 eq. Science cat.[e] | n.d. | 9% | 34% | n.d. |

Figure 104:
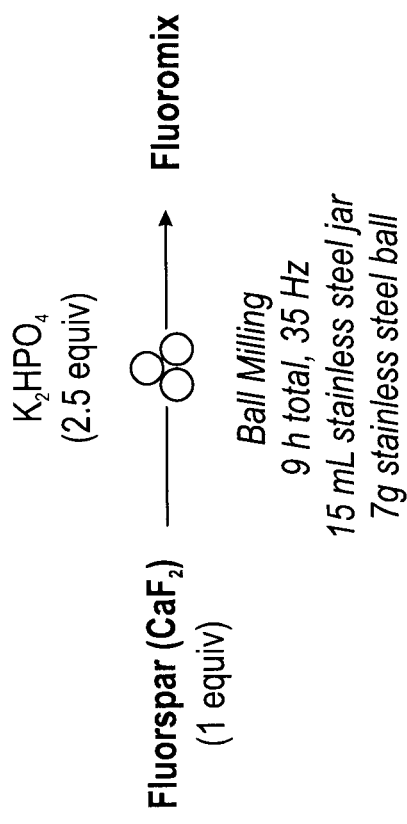
FIG. 104 illustrates a general scheme according to embodiments described herein.

5.14. Mechanistic Understanding of Mechanochemical Activation of Fluorpsar with $K_2HPO_4$ Fluorspar ($CaF_2$) is ball milled with anhydrous $K_2HPO_4$ to afford a fluorinating reagent (Fluoromix) (FIG. 104) which is comprised of crystalline phases (X, Y) and residual crystalline $CaF_2$. Powder X-Ray Diffraction (PXRD) patterns of species X and Y match the reflection (peaks) positions and peak intensities observed in Fluoromix. Calcium hydrogen phosphate ($CaHPO_4$) and potassium fluoride (KF) may be products of the reaction between $CaF_2$ and $K_2HPO_4$. X is the product of ball milled KF with $K_2HPO_4$, and X has the proposed structure $K_3(HPO_4)F$ and is isostructural to $K_3(PO_3F)F$. Y has the proposed structure $K_{2-x}Ca_y(PO_3)F_a(PO_4)_bF_c$ and is isostructural to $K_2PO_3F$. The formation of X and Y from ball milling fluorspar and $K_2HPO_4$ may indirectly support the formation of KF and $CaHPO_4$ as intermediates in this reaction en route to X and Y. A PXRD diffractogram of the water insoluble component of fluoromix was measured and contains reflections that are consistent with $CaF_2$ and $Ca_5(PO_4)_3F$ (fluorapatite) as a mixture (mixture Z). Z may be independently prepared by ball milling $CaHPO_4$ with $CaF_2$.

Figure 33:
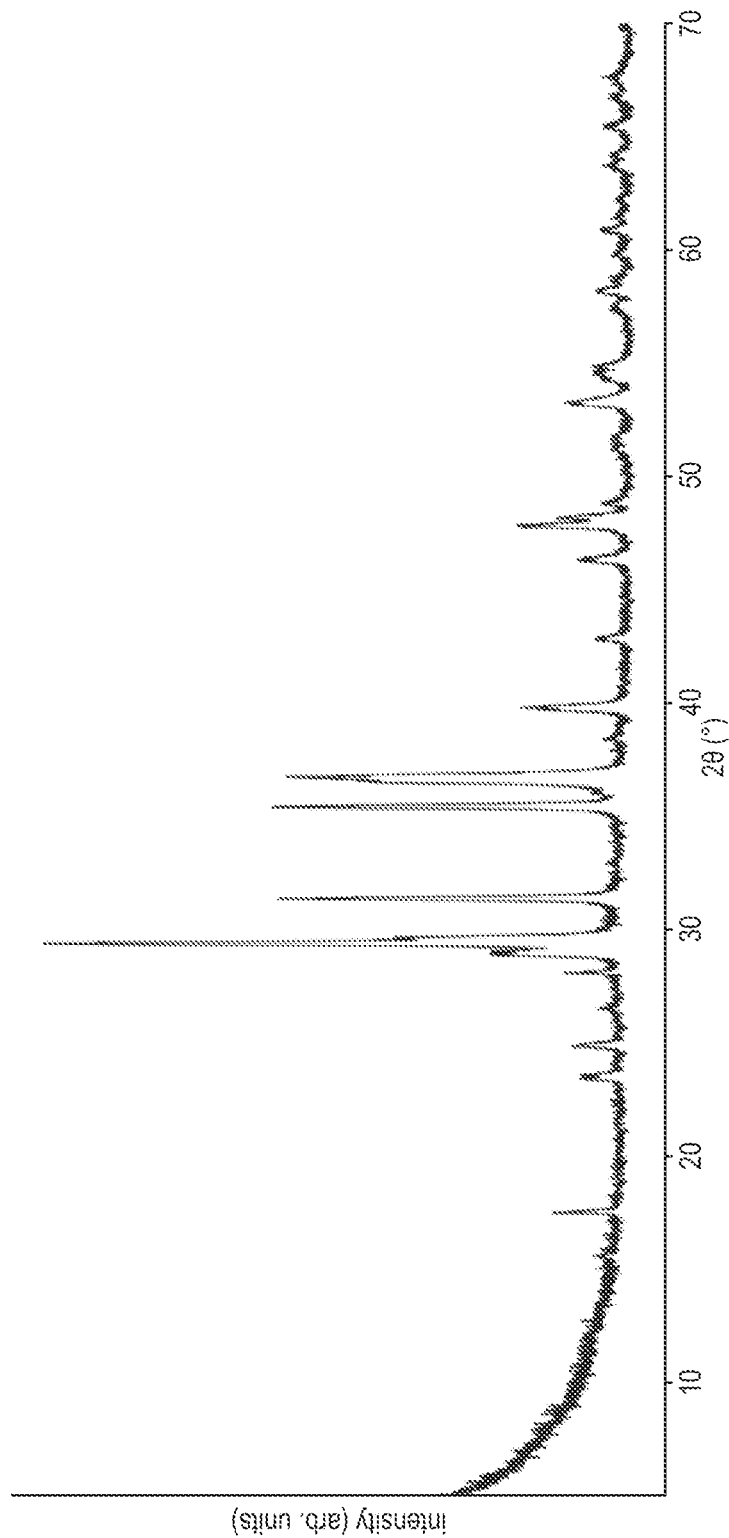
FIG. 33 shows the PXRD diffractogram of X (KF milled with K$_2$HPO$_4$ for 3 hours at 35 Hz).
Figure 34:
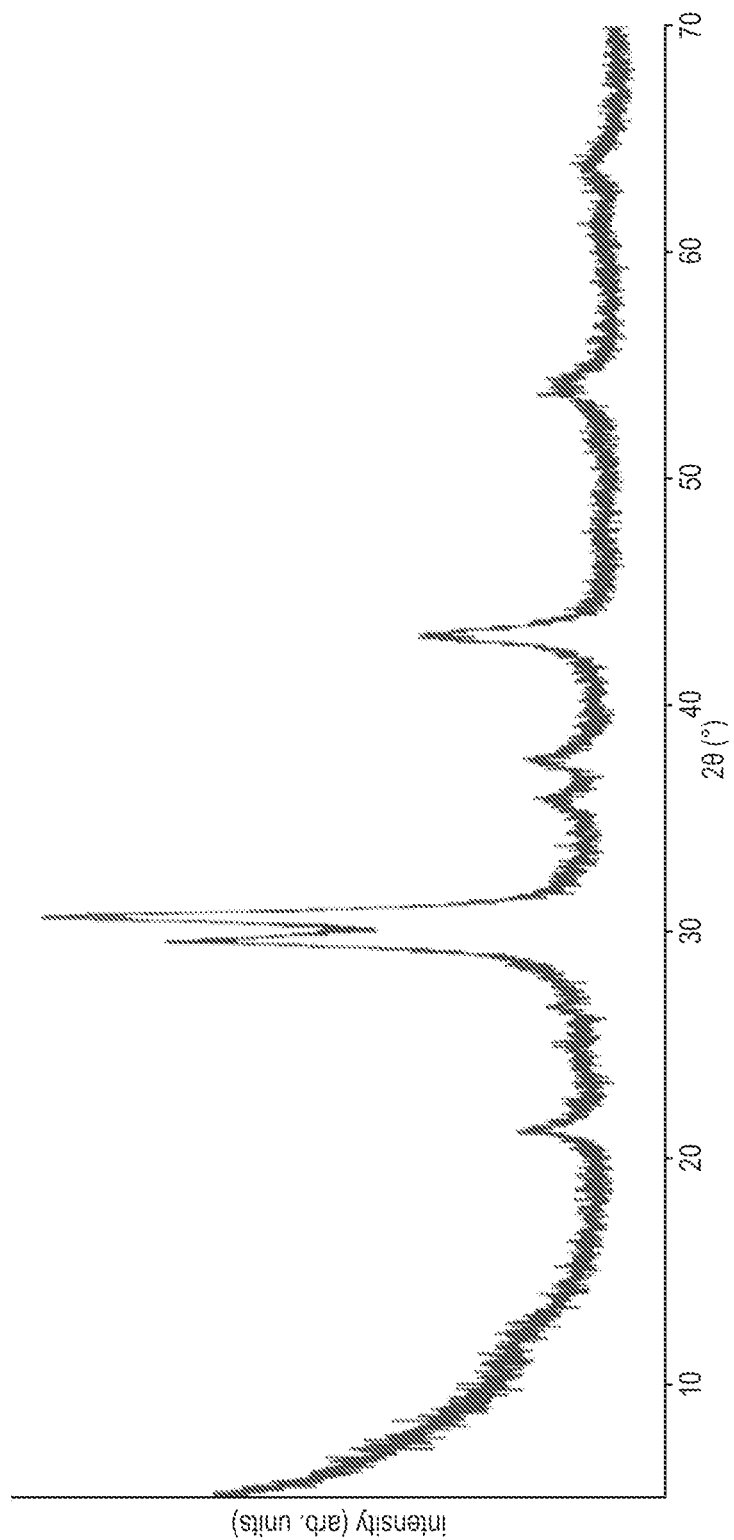
FIG. 34 shows the PXRD diffractogram of Y (KF milled with K$_2$HPO$_4$ for 3 hours at 35 Hz followed by CaHPO$_4$ for 3 hours at 35 Hz).

Table 5.14.1 shows the PXRD data of starting material, Fluorspar ($CaF_2$). Table 5.14.2 and FIG. 33 show PXRD data of X, consistent with $K_3(HPO_4)F$ (related structure to $K_3(PO_3F)F$). Table 5.14.3 and FIG. 34 show PXRD data of Y, consistent with $K_2—XCa_y(PO_3F)_a(PO_4)_bF_c$ (related to $K_2PO_3F$). Table 5.14.4 shows PXRD data of Z, consistent with $Ca_5(PO_4)_3F$ and unreacted $CaF_2$.

TABLE 5.14.1.

| Pos. [°2Th.] | d-spacing [Å] | Rel. Int. [%] |
|---|---|---|
| 28.2976 | 3.15126 | 100.00 |
| 47.0169 | 1.93113 | 66.30 |
| 55.8035 | 1.64609 | 18.60 |
| 68.6839 | 1.36546 | 5.08 |

TABLE 5.14.2.

| Pos. [°2Th.] | Rel. Int. [%] |
|---|---|
| 15.5985 | 2.34 |
| 17.5367 | 10.16 |
| 23.3979 | 5.73 |
| 24.8981 | 7.06 |
| 26.5567 | 1.56 |
| 28.0843 | 9.09 |
| 28.8933 | 20.60 |
| 29.3501 | 88.34 |
| 29.4006 | 100.00 |
| 29.6670 | 35.92 |
| 31.3455 | 52.65 |
| 35.3783 | 48.45 |
| 36.4954 | 40.72 |
| 36.7261 | 56.49 |
| 38.4075 | 2.50 |

TABLE 5.14.3.

| Pos. [°2Th.] | Rel. Int. [%] |
|---|---|
| 21.2490 | 12.32 |
| 29.5875 | 76.40 |
| 30.7329 | 100.00 |
| 35.9522 | 6.67 |
| 37.5864 | 10.58 |
| 43.1662 | 33.68 |
| 63.7377 | 4.41 |

TABLE 5.14.4.

| Pos. [°2Th.] | Rel. Int. [%] |
|---|---|
| 22.0434 | 3.25 |
| 26.0518 | 38.31 |
| 28.3091 | 44.28 |
| 29.2225 | 29.05 |
| 32.0450 | 100.00 |
| 33.1785 | 47.59 |
| 34.2570 | 23.21 |
| 40.1975 | 18.16 |
| 42.3548 | 3.49 |
| 43.9319 | 3.24 |
| 46.9721 | 35.95 |
| 48.4374 | 11.16 |
| 49.6795 | 27.56 |
| 50.9224 | 11.78 |
| 53.3052 | 12.49 |
| 56.2117 | 7.20 |
| 61.9102 | 2.77 |
| 64.2938 | 4.97 |

Figure 35:
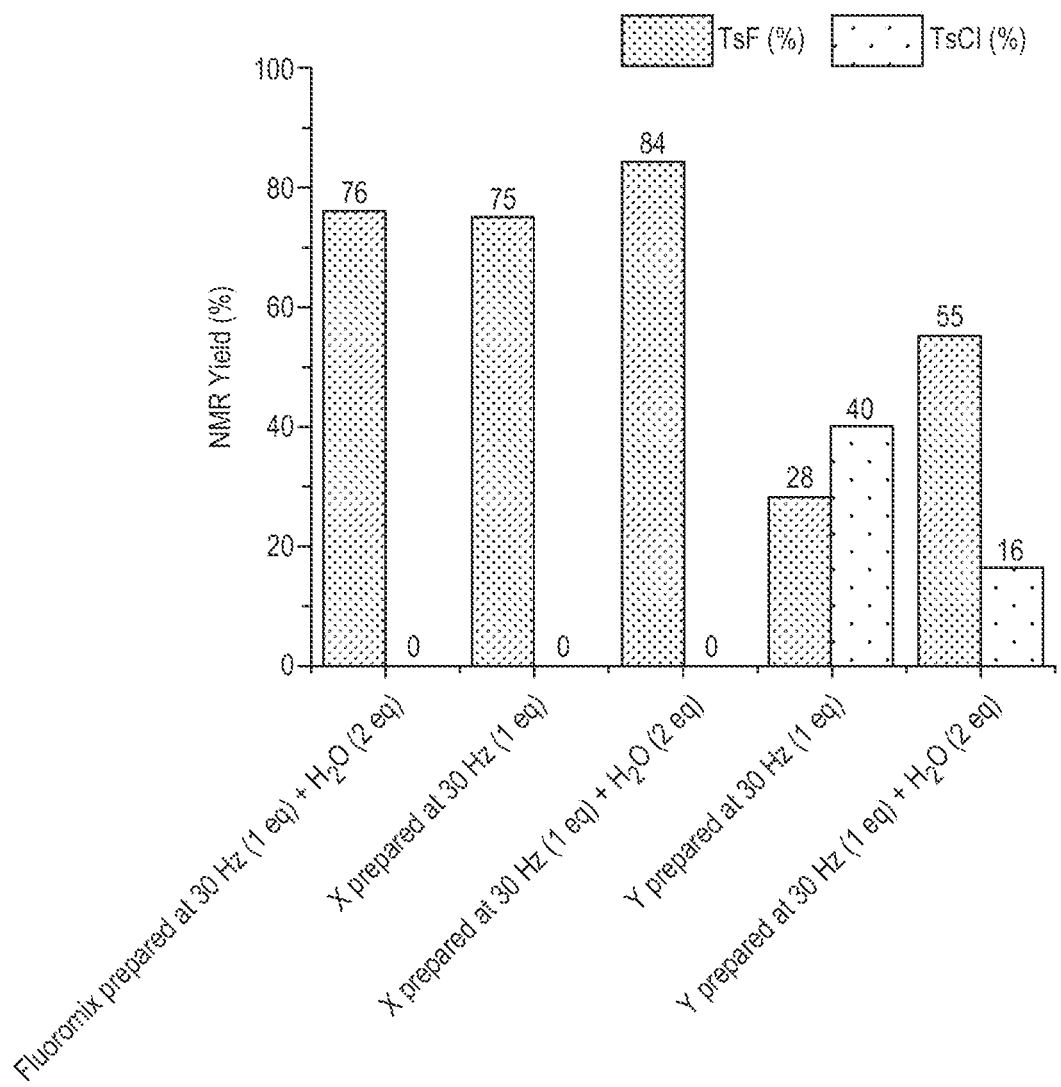
FIG. 35 shows the NMR yield of TsF from TsCl upon reaction with fluoromix or X (KF milled with K$_2$HPO$_4$ for 3 hours at 35 Hz) or Y (KF milled with K$_2$HPO$_4$ for 3 hours at 35 Hz followed by CaHPO$_4$ for 3 hours at 35 Hz) independently.
Figure 105:
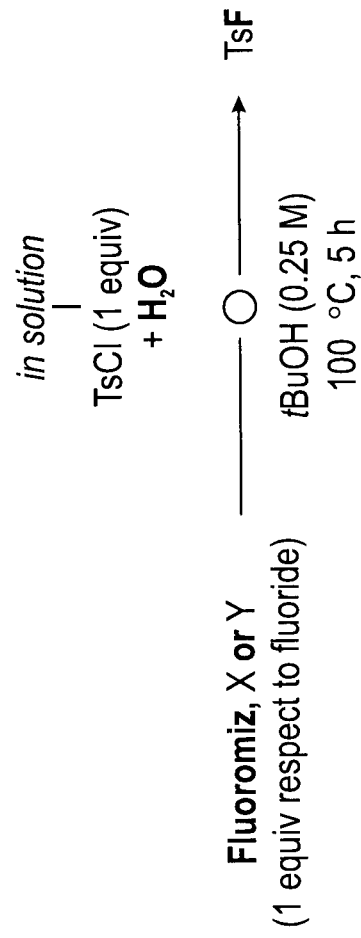
FIG. 105 illustrates a general scheme according to embodiments described herein.

Each crystalline species of the Fluoromix (X or Y) was prepared independently and tested in the fluorination of tosyl chloride (TsCl). X or Y can be used to convert S(VI)-Cl bonds into an S(VI)-F bond whilst $CaF_2$ or Z ("apatite structure" consistent with $Ca_5(PO_4)_3F$) do not afford any fluorinated product. The fluorination using X or Y was carried out as described in FIG. 105, X or Y (1 equiv. with respect to fluoride) was reacted in a tBuOH solution with the TsCl (1 equiv.) with $H_2O$ at 100° C. for 5 hours to afford the fluorinated product. The resulting yields when Fluoromix was used, or when X or Y were used independently are seen in FIG. 35 for fluorinated product yield TsF and starting material yield TsCl. Fluoromix and X (ball milled KF with $K_2HPO_4$) afford toslyl fluoride (TsF) in high yield. Fluorination yield is decreased when Y (ball milled KF, $K_2HPO_4$ and $CaHPO_4$) is used, indicative of reduced fluorinating ability when $CaHPO_4$ is incorporated into product X, which may be ameliorated through the addition of water (2 equiv.).

6. Alternative Activators of Fluorspar ($CaF_2$)

6.1. Formation of $KCaF_3$ and NaF Using Hydroxide Activators

Figure 36:
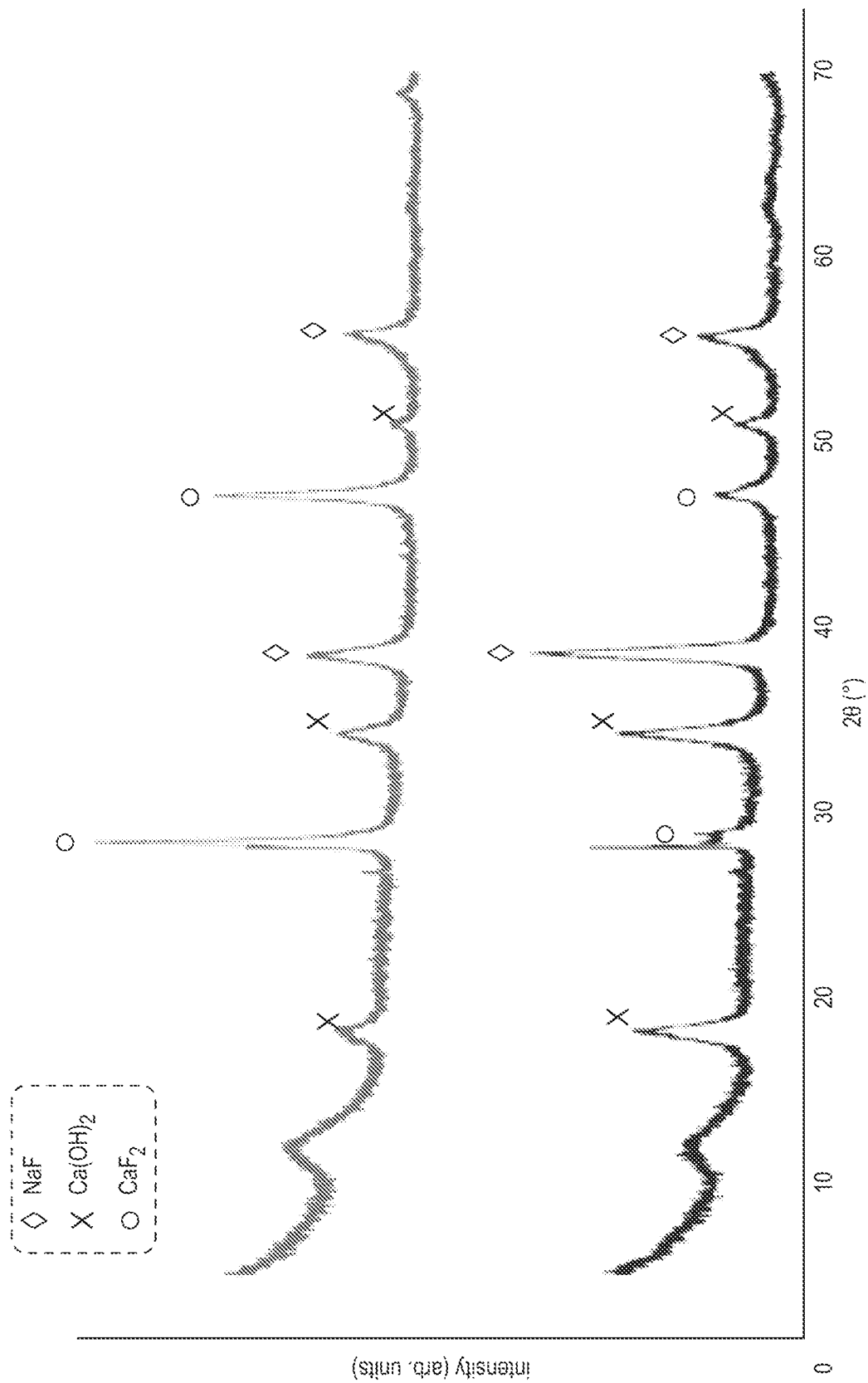
FIG. 36 shows the PXRD diffractogram of fluorspar with NaOH.
Figure 106:
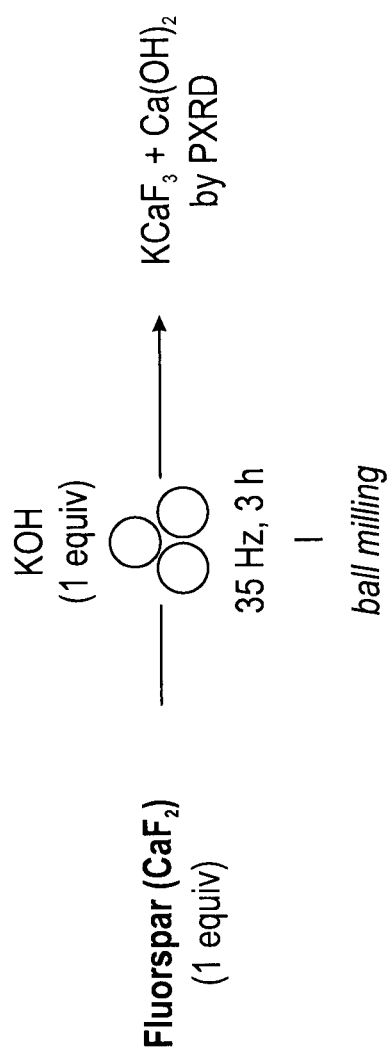
FIG. 106 illustrates a general scheme according to embodiments described herein.
Figure 107:
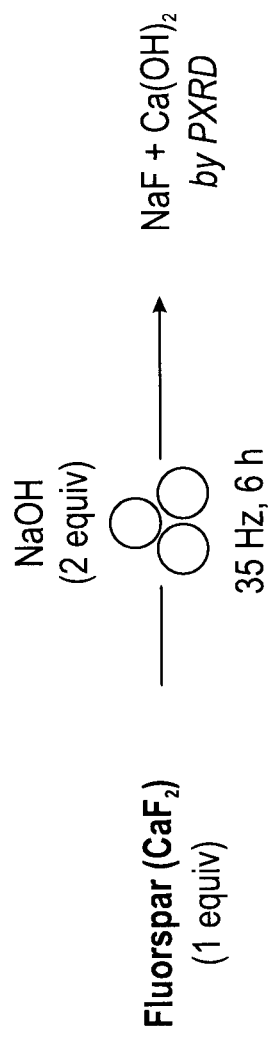
FIG. 107 illustrates a general scheme according to embodiments described herein.

Hydroxide activators (KOH and NaOH) were probed as alternative activators as described in FIGS. 106 and 107. Briefly, Fluorspar ($CaF_2$, 1 equiv.) was added to a stainless steel jar with KOH (1 equiv.) and milled for 3 hours at 35 Hz. Based on PXRD data, this reaction resulted in the formation of $KCaF_3$ and $Ca(OH)_2$. Alternatively, Fluorspar ($CaF_2$, 1 equiv.) was milled with NaOH (2 equiv.) for 6 hours at 35 Hz. As determined by PXRD, this reaction led to the formation of NaF and $Ca(OH)_2$. FIG. 36 shows the PXRD of products from the reaction shown in FIG. 107 between Fluorspar and NaOH.

6.2. Fluorination of TsCl Using Hydroxide Activators

Figure 108:
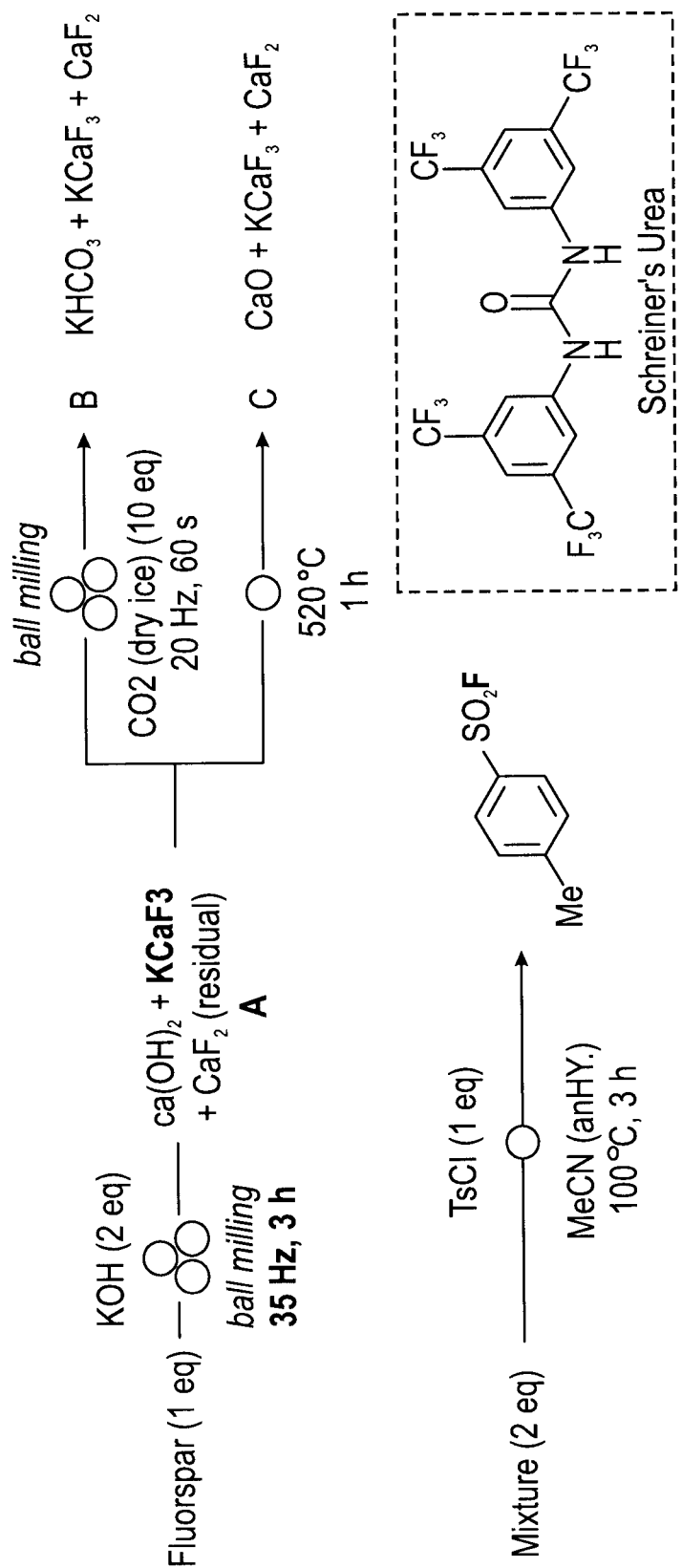
FIG. 108 illustrates a general scheme according to embodiments described herein.

Fluorspar (1 equiv.) was milled with KOH (2 equiv.) at 35 Hz for 3 hours as depicted in FIG. 108 to form $Ca(OH)_2$, $KCaF_3$, and residual $CaF_2$ (A). This mixture was milled with dry ice (10 equiv.) at 20 Hz for 60 seconds to form (B) consisting of $KHCO_3$, $KCaF_3$, and $CaF_3$. The mixture (A) was also heated at 520° C. for 1 hour to form (C), CaO, $KCaF_3$, and $CaF_2$. These mixtures (2 equiv.) were reacted in solution with TsCl (1 equiv., 0.125 mmol) according to FIG. 108 in acetonitrile (anhydrous) at 100° C. for 3 hours to form the fluorinated product. In some case, an additive such as Schreiner's Urea or 18-crown-6 was added (see Table 6.2). Fluorination of TsCl using either the treated or untreated $KCaF_3/Ca(OH)_2$ mixture was achieved. The results indicate that using hydroxide activators with Fluorspar, fluorination can occur. Exemplary conditions include the addition of additives such as crown ethers or Schreiner's urea.

TABLE 6.2.

| Entry | Mixture (2 eq) | Additive (1 eq) | TsF (%) | TsCl (%) | TsOH (%) |
|---|---|---|---|---|---|
| 1 | A | — | 0 | 0 | 100 |
| 2 | B | — | 12 | 37 | 51 |
| 3 | C | — | 11 | 36 | 53 |
| 4 | A | 18-crown-6 | 17 | 0 | 70 |
| 5 | B | 18-crown-6 | 17 | 0 | 70 |
| 6 | C | 18-crown-6 | 36 | 34 | 30 |
| 7 | A | Schreiner's urea | 31 | 52 | 17 |

6.3. Fluorination of TsCl Using Alternative Non-Phosphate Activators

Figure 37:
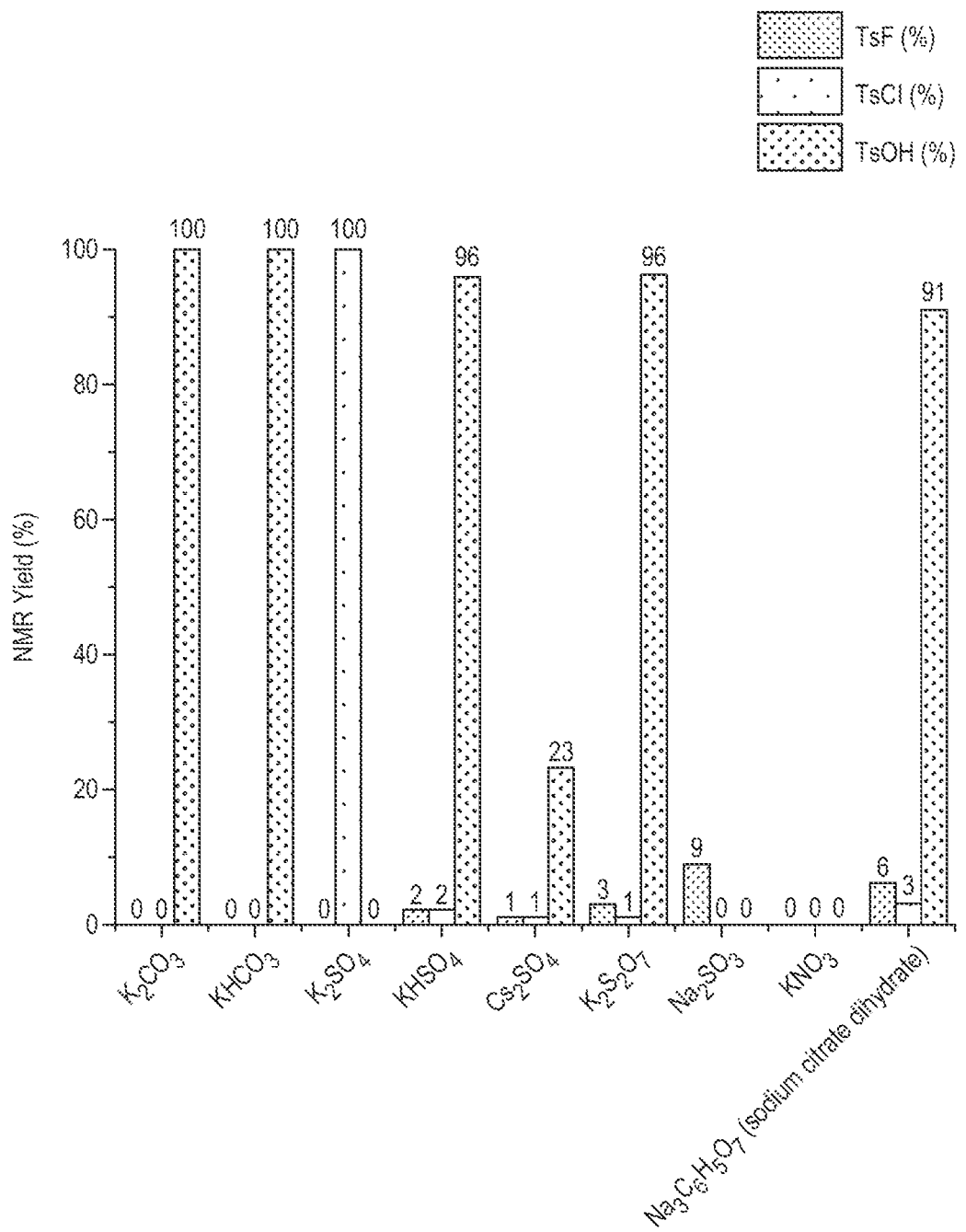
FIG. 37 shows NMR yields of TsF from TsCl using fluorspar and various non-phosphate activators.
Figure 109:
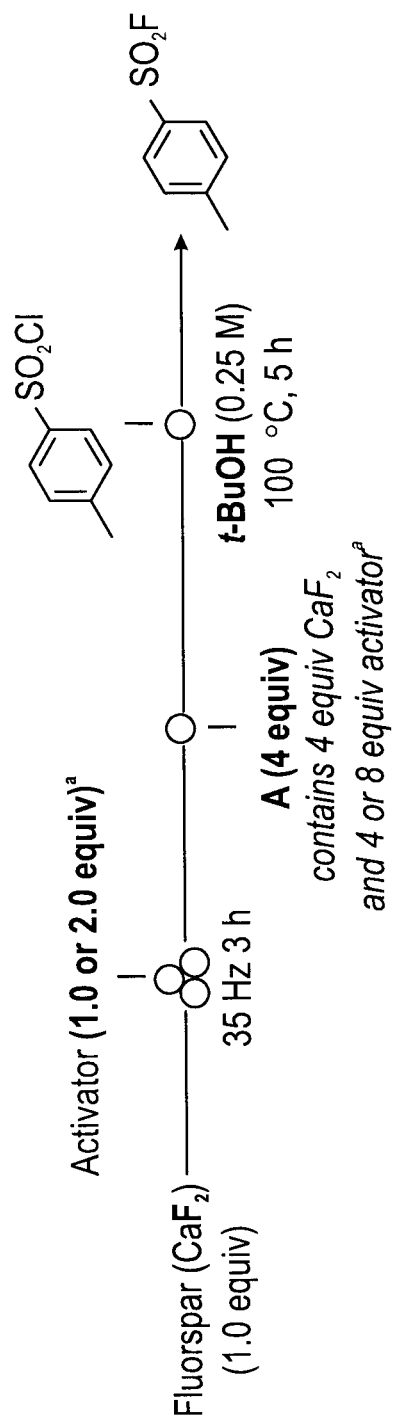
FIG. 109 illustrates a general scheme according to embodiments described herein.

Alternative non-phosphate activators were investigated and fluorination of TsCl was investigated via the scheme depicted in FIG. 109. Fluorspar ($CaF_2$, 1 equiv.) was milled with the activator (1.0 or 2.0 equiv., see FIG. 37) for 3 hours at 35 Hz to form A. A was used as the fluorinating reagent with TsCl in a tBuOH (0.25 M) solution and reacted at 100° C. for 5 hours to from a fluorinated product. The NMR yields of the reactions using various activators are shown in FIG. 37. The reaction using sodium sulfite ($Na_2SO_3$) as an activator resulted in an itractable mixture of products in the solution phase. The non-phosphate activators included $K_2CO_3$, $KHCO_3$, $K_2SO_4$, $KHSO_4$, $Cs_2SO_4$, $K_2S_2O_7$, $Na_2SO_3$, $KNO_3$, and sodium citrate dihydrate. The fluorination yields indicate that exemplary non-phosphate activators may include $Na_2SO_3$ and sodium citrate dihydrate. The resulting activated fluorspar reagent (A) was analyzed with PXRD.

Figure 38:
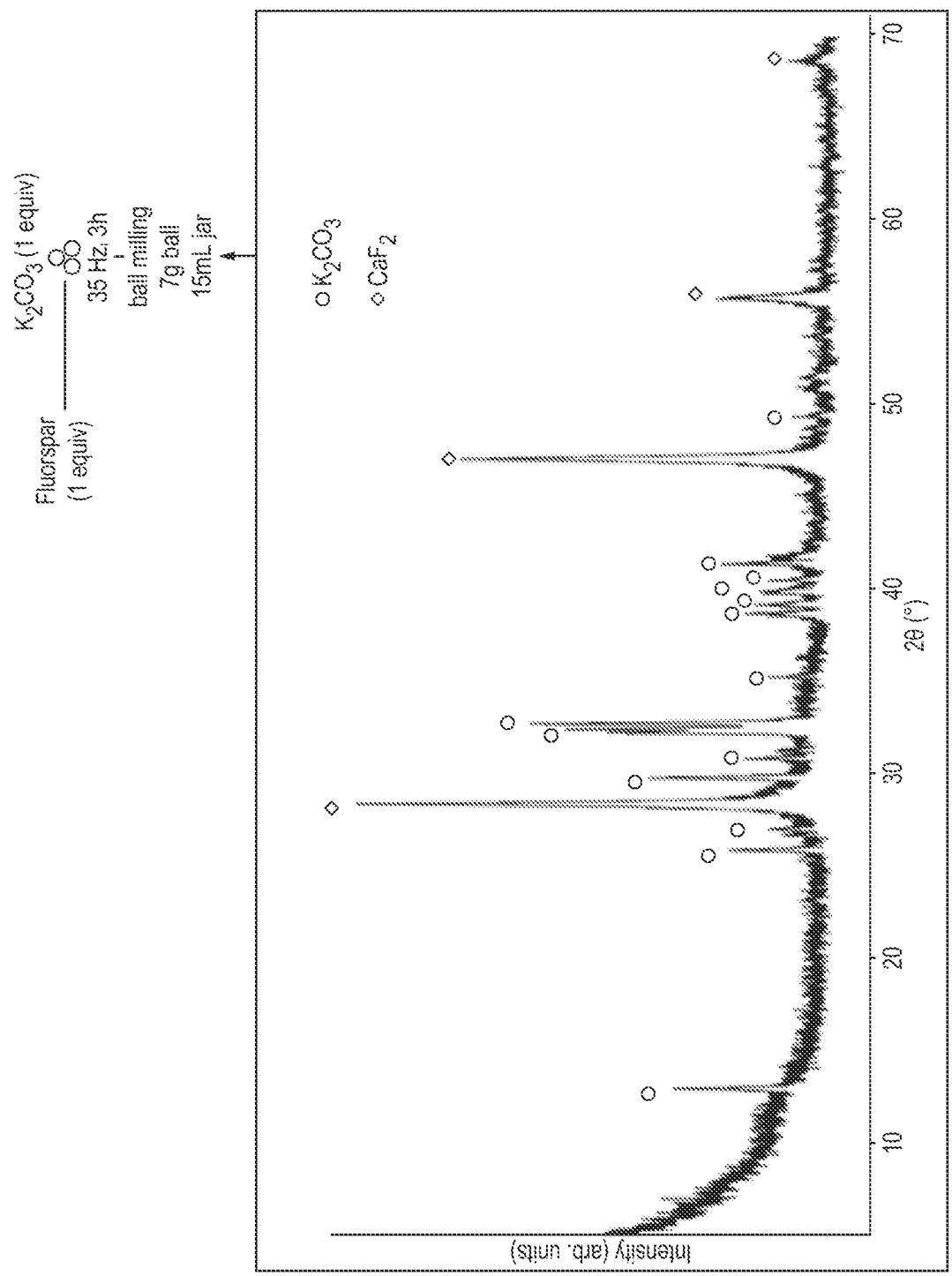
FIG. 38 shows the PXRD diffractogram of the product of the fluorspar milling reaction with K$_2$CO$_3$ for 3 hours at 35 Hz.

FIG. 38 shows the PXRD pattern resulting from milling of Fluorspar with $K_2CO_3$ at 35 Hz for 3 hours. Table 6.3.1 shows the PXRD data from the milling of Fluorspar with $K_2CO_3$ represented in FIG. 38. Labels in FIG. 38 indicates a crystalline phase of $K_2CO_3$ and $CaF_2$.

TABLE 6.3.1

| Pos. [°2Th.] | Height [cts] | FWHM [°2Th.] | d-spacing [Å] | Rel. Int. [%] |
|---|---|---|---|---|
| 12.9106 | 144.72 | 0.0866 | 6.85716 | 24.98 |
| 25.8539 | 101.94 | 0.1299 | 3.44616 | 17.59 |
| 26.6959 | 31.71 | 0.1299 | 3.33935 | 5.47 |
| 26.9959 | 49.07 | 0.1515 | 3.30292 | 8.47 |
| 28.3703 | 579.44 | 0.1515 | 3.14597 | 100.00 |
| 29.7826 | 196.84 | 0.1299 | 2.99991 | 33.97 |
| 30.8164 | 76.76 | 0.1082 | 2.90160 | 13.25 |
| 32.2202 | 235.71 | 0.0758 | 2.77831 | 40.68 |
| 32.4335 | 324.62 | 0.0758 | 2.76053 | 56.00 |
| 32.7123 | 347.33 | 0.0649 | 2.73764 | 59.94 |
| 35.2790 | 40.41 | 0.1299 | 2.54412 | 6.97 |
| 38.7430 | 65.59 | 0.2165 | 2.32425 | 11.32 |
| 39.1613 | 57.38 | 0.2165 | 2.30039 | 9.90 |
| 39.8516 | 57.63 | 0.2165 | 2.26212 | 9.95 |
| 40.5478 | 39.16 | 0.1299 | 2.22488 | 6.76 |
| 41.4026 | 122.91 | 0.0866 | 2.18089 | 21.21 |
| 47.0989 | 443.53 | 0.1082 | 1.92956 | 76.55 |
| 49.4343 | 20.97 | 0.2598 | 1.84373 | 3.62 |
| 50.9012 | 18.98 | 0.2598 | 1.79399 | 3.28 |
| 51.3471 | 15.41 | 0.6927 | 1.77946 | 2.66 |
| 53.7815 | 18.31 | 0.2598 | 1.70452 | 3.16 |
| 55.8616 | 121.34 | 0.2598 | 1.64588 | 20.94 |
| 68.7508 | 30.46 | 0.4224 | 1.36430 | 5.26 |

Figure 39:
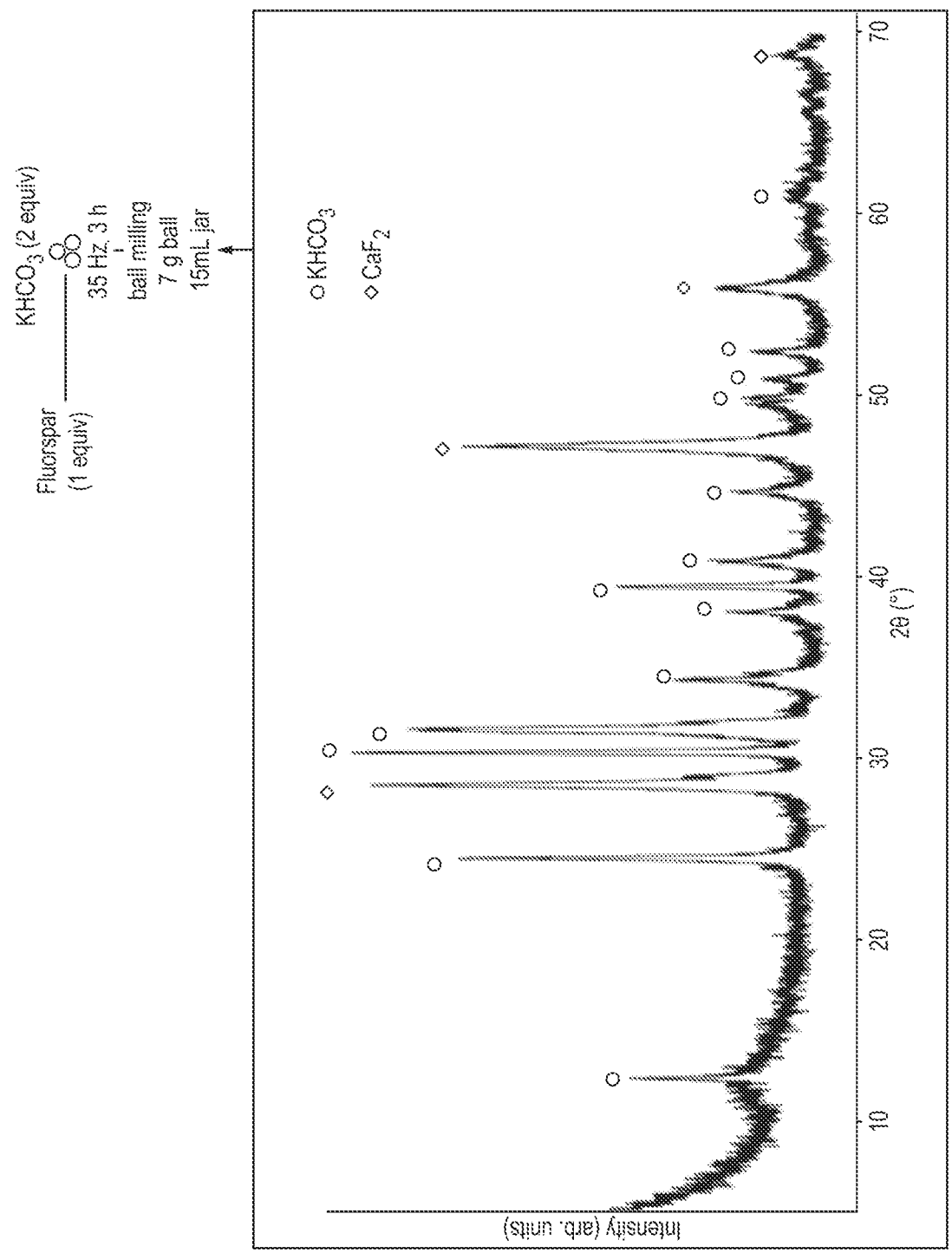
FIG. 39 shows the PXRD diffractogram of the product of the fluorspar milling reaction with KHCO$_3$ for 3 hours at 35 Hz.

FIG. 39 shows the PXRD pattern resulting from milling of Fluorspar with $KHCO_3$ at 35 Hz for 3 hours. Table 6.3.2 shows the PXRD data from the milling of Fluorspar with $KHCO_3$ represented in FIG. 39. Labels in FIG. 39 indicates a crystalline phase of $KHCO_3$ and $CaF_2$.

TABLE 6.3.2

| Pos. [°2Th.] | Height [cts] | FWHM [°2Th.] | d-spacing [Å] | Rel. Int. [%] |
|---|---|---|---|---|
| 12.2501 | 123.64 | 0.1299 | 7.22535 | 27.19 |
| 24.4342 | 359.63 | 0.1732 | 3.64308 | 79.09 |
| 28.4554 | 435.01 | 0.2165 | 3.13675 | 95.67 |
| 28.9876 | 115.83 | 0.1299 | 3.08036 | 25.47 |
| 30.2433 | 454.69 | 0.0758 | 2.95526 | 100.00 |
| 31.4423 | 373.37 | 0.1948 | 2.84525 | 82.11 |
| 31.6259 | 389.58 | 0.1299 | 2.82915 | 85.68 |
| 31.9991 | 116.90 | 0.1299 | 2.79700 | 25.71 |
| 34.2459 | 130.85 | 0.1082 | 2.61846 | 28.78 |
| 38.0312 | 76.88 | 0.1732 | 2.36610 | 16.91 |
| 39.4041 | 196.56 | 0.1948 | 2.28677 | 43.23 |
| 40.8305 | 89.69 | 0.1732 | 2.21012 | 19.72 |
| 44.6882 | 80.08 | 0.1732 | 2.02789 | 17.61 |
| 47.1870 | 351.72 | 0.2381 | 1.92616 | 77.35 |
| 49.8903 | 69.65 | 0.2165 | 1.82795 | 15.32 |
| 50.9410 | 47.90 | 0.3464 | 1.79268 | 10.54 |
| 52.5013 | 55.63 | 0.2598 | 1.74302 | 12.23 |
| 56.0264 | 96.82 | 0.3031 | 1.64143 | 21.29 |
| 60.9589 | 15.94 | 0.6927 | 1.51990 | 3.51 |
| 65.6349 | 9.80 | 0.5196 | 1.42249 | 2.16 |
| 68.8465 | 32.51 | 0.4224 | 1.36263 | 7.15 |

Figure 40:
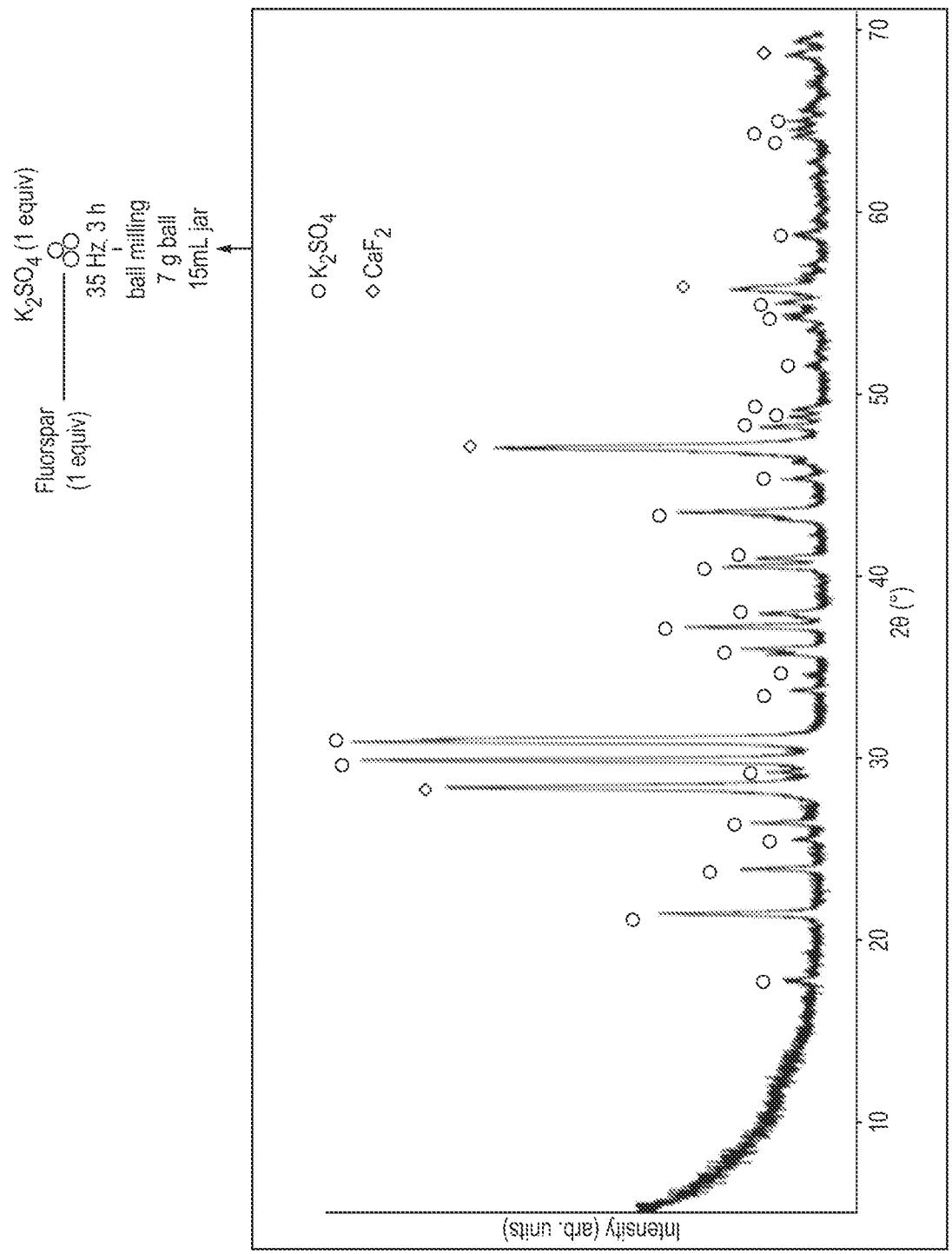
FIG. 40 shows the PXRD diffractogram of the product of the fluorspar milling reaction with K$_2$SO$_4$ for 3 hours at 35 Hz.

FIG. 40 shows the PXRD pattern resulting from milling of Fluorspar with $K_2SO_4$ at 35 Hz for 3 hours. Table 6.3.3 shows the PXRD data from the milling of Fluorspar with $K_2SO_4$ represented in FIG. 40. Labels in FIG. 40 indicates a crystalline phase of $K_2SO_4$ and $CaF_2$.

TABLE 6.3.3

| Pos. [°2Th.] | Height [cts] | FWHM [°2Th.] | d-spacing [Å] | Rel. Int. [%] |
|---|---|---|---|---|
| 5.1556 | 100.92 | 0.5196 | 17.14099 | 11.33 |
| 17.7779 | 36.96 | 0.2598 | 4.98925 | 4.15 |
| 21.4518 | 292.38 | 0.1948 | 4.14236 | 32.83 |
| 23.8955 | 141.47 | 0.1299 | 3.72398 | 15.88 |
| 25.5175 | 46.92 | 0.1732 | 3.49084 | 5.27 |
| 26.4249 | 109.07 | 0.1299 | 3.37299 | 12.25 |
| 28.4008 | 706.53 | 0.2381 | 3.14265 | 79.33 |
| 29.2377 | 76.72 | 0.1299 | 3.05458 | 8.61 |
| 29.8670 | 833.06 | 0.0792 | 2.98916 | 93.54 |
| 29.9401 | 809.94 | 0.0528 | 2.98943 | 90.94 |
| 30.8750 | 890.60 | 0.1056 | 2.89383 | 100.00 |
| 31.1020 | 655.56 | 0.1584 | 2.87322 | 73.61 |
| 33.7120 | 49.11 | 0.1848 | 2.65650 | 5.51 |
| 34.5815 | 14.87 | 0.3168 | 2.59168 | 1.67 |
| 35.7248 | 83.91 | 0.1584 | 2.51131 | 9.42 |
| 36.0391 | 128.92 | 0.1848 | 2.49013 | 14.48 |
| 37.2299 | 267.29 | 0.1056 | 2.41317 | 30.01 |
| 37.9967 | 105.23 | 0.2112 | 2.36621 | 11.82 |
| 40.5344 | 186.48 | 0.1320 | 2.22374 | 20.94 |
| 40.9781 | 123.32 | 0.1320 | 2.20068 | 13.85 |
| 43.1380 | 77.39 | 0.1584 | 2.09536 | 8.69 |
| 43.5430 | 254.60 | 0.1584 | 2.07680 | 28.59 |
| 45.4011 | 59.57 | 0.2112 | 1.99603 | 6.69 |
| 47.0925 | 613.94 | 0.2112 | 1.92821 | 68.94 |
| 48.2283 | 114.70 | 0.1056 | 1.88542 | 12.88 |
| 48.8066 | 52.18 | 0.2112 | 1.86442 | 5.86 |
| 49.2157 | 47.15 | 0.2640 | 1.84988 | 5.29 |
| 51.6379 | 21.04 | 0.4224 | 1.76865 | 2.36 |
| 53.6603 | 17.56 | 0.3168 | 1.70667 | 1.97 |
| 54.1987 | 54.01 | 0.1584 | 1.69098 | 6.06 |
| 55.0831 | 70.70 | 0.1584 | 1.66590 | 7.94 |
| 55.7987 | 159.66 | 0.1584 | 1.64622 | 17.93 |
| 58.8748 | 48.50 | 0.3696 | 1.56733 | 5.45 |
| 62.8418 | 18.13 | 0.4224 | 1.47759 | 2.04 |
| 64.2204 | 50.41 | 0.2640 | 1.44916 | 5.66 |
| 64.6329 | 57.18 | 0.1056 | 1.44090 | 6.42 |

TABLE 6.3.3-continued

| Pos. [°2Th.] | Height [cts] | FWHM [°2Th.] | d-spacing [Å] | Rel. Int. [%] |
|---|---|---|---|---|
| 65.1681 | 35.16 | 0.3168 | 1.43036 | 3.95 |
| 68.7906 | 49.87 | 0.4224 | 1.36360 | 5.60 |
| 69.4698 | 51.79 | 0.1584 | 1.35192 | 5.82 |

Figure 41:
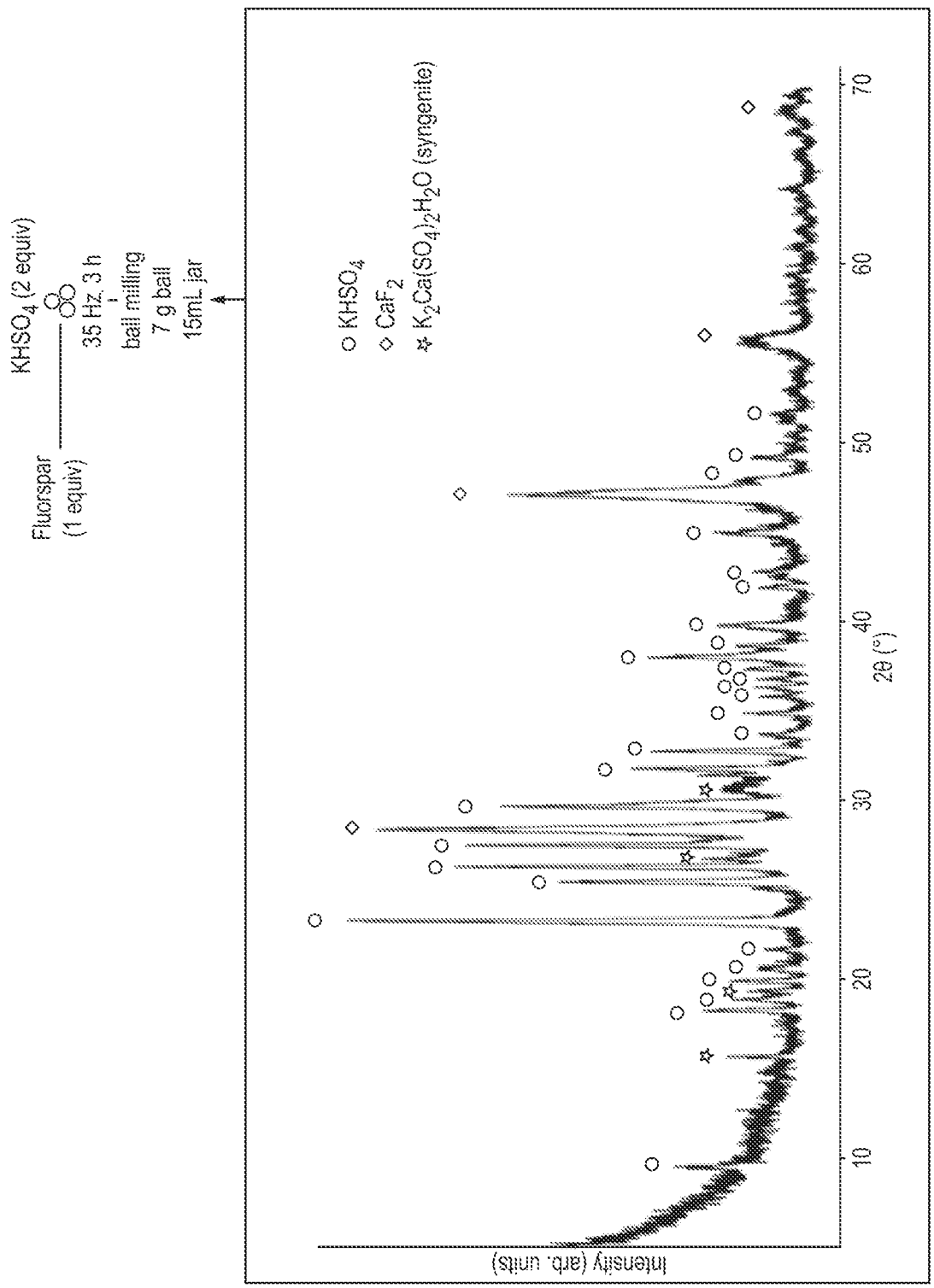
FIG. 41 shows the PXRD diffractogram of the product of the fluorspar milling reaction with KHSO$_4$ for 3 hours at 35 Hz.

FIG. 41 shows the PXRD pattern resulting from milling of Fluorspar with $KHSO_4$ at 35 Hz for 3 hours. Table 6.3.4 shows the PXRD data from the milling of Fluorspar with $KHSO_4$ represented in FIG. 41. Labels in FIG. 41 indicates a crystalline phase of $KHSO_4$, $K_2Ca(SO-4)_2H_2O_2$(syngenite), and $CaF_2$.

TABLE 6.3.4

| Pos. [°2Th.] | Height [cts] | FWHM [°2Th.] | d-spacing [Å] | Rel. Int. [%] |
|---|---|---|---|---|
| 9.4797 | 62.07 | 0.1732 | 9.32980 | 10.47 |
| Syngenite 15.6743 | 57.87 | 0.1299 | 5.65376 | 9.76 |
| 18.2434 | 113.03 | 0.1732 | 4.86298 | 19.06 |
| 18.8952 | 64.59 | 0.1732 | 4.69668 | 10.89 |
| Syngenite 19.4234 | 42.96 | 0.1515 | 4.57012 | 7.24 |
| 19.9139 | 83.23 | 0.1515 | 4.45866 | 14.03 |
| 20.5445 | 43.12 | 0.1299 | 4.32320 | 7.27 |
| 21.6718 | 30.63 | 0.1732 | 4.10080 | 5.17 |
| 23.3210 | 593.11 | 0.0541 | 3.81439 | 100.00 |
| 25.4818 | 325.95 | 0.1948 | 3.49564 | 54.96 |
| Syngenite 26.3384 | 453.30 | 0.1515 | 3.38386 | 76.43 |
| 26.7634 | 121.85 | 0.1299 | 3.33109 | 20.54 |
| 27.5127 | 464.84 | 0.0866 | 3.24204 | 78.37 |
| 28.4297 | 569.90 | 0.1948 | 3.13953 | 96.09 |
| 29.6910 | 393.27 | 0.1515 | 3.00896 | 66.31 |
| Syngenite 30.6219 | 98.75 | 0.2598 | 2.91958 | 16.65 |
| 31.5012 | 126.68 | 0.1299 | 2.84006 | 21.36 |
| 31.8374 | 218.30 | 0.1948 | 2.81084 | 36.81 |
| 32.7922 | 180.11 | 0.1732 | 2.73115 | 30.37 |
| 33.6933 | 46.12 | 0.1515 | 2.66014 | 7.78 |
| 34.9230 | 58.91 | 0.1299 | 2.56924 | 9.93 |
| 35.8691 | 45.63 | 0.1299 | 2.50361 | 7.69 |
| 36.4744 | 33.67 | 0.1732 | 2.46344 | 5.68 |
| 36.8389 | 48.58 | 0.1732 | 2.43990 | 8.19 |
| 37.3834 | 75.15 | 0.1948 | 2.40560 | 12.67 |
| 38.0312 | 189.76 | 0.1082 | 2.36610 | 31.99 |
| 38.6991 | 85.51 | 0.1515 | 2.32679 | 14.42 |
| 39.8702 | 103.10 | 0.2165 | 2.26111 | 17.38 |
| 41.9603 | 48.09 | 0.1299 | 2.15319 | 8.11 |
| 42.8908 | 55.71 | 0.1299 | 2.10861 | 9.39 |
| 45.0074 | 102.01 | 0.2598 | 2.01424 | 17.20 |
| 47.2173 | 385.29 | 0.1948 | 1.92500 | 64.96 |
| 48.1065 | 74.23 | 0.2165 | 1.89147 | 12.52 |
| 49.2473 | 55.11 | 0.1732 | 1.85030 | 9.29 |
| 51.7741 | 33.44 | 0.2598 | 1.76578 | 5.64 |
| 52.9853 | 18.43 | 0.4330 | 1.72824 | 3.11 |
| 55.5297 | 67.74 | 0.3464 | 1.65493 | 11.42 |
| 56.0099 | 72.11 | 0.3464 | 1.64187 | 12.16 |
| 59.4932 | 19.67 | 0.2598 | 1.55379 | 3.32 |
| 61.0679 | 11.65 | 0.3464 | 1.51745 | 1.96 |
| 62.0966 | 12.94 | 0.2598 | 1.49476 | 2.18 |
| 64.3255 | 26.65 | 0.2598 | 1.44824 | 4.49 |
| 66.4721 | 11.96 | 0.6061 | 1.40659 | 2.02 |
| 67.5187 | 17.00 | 0.2598 | 1.38731 | 2.87 |
| 68.5917 | 21.96 | 0.7392 | 1.36707 | 3.70 |

Figure 42:
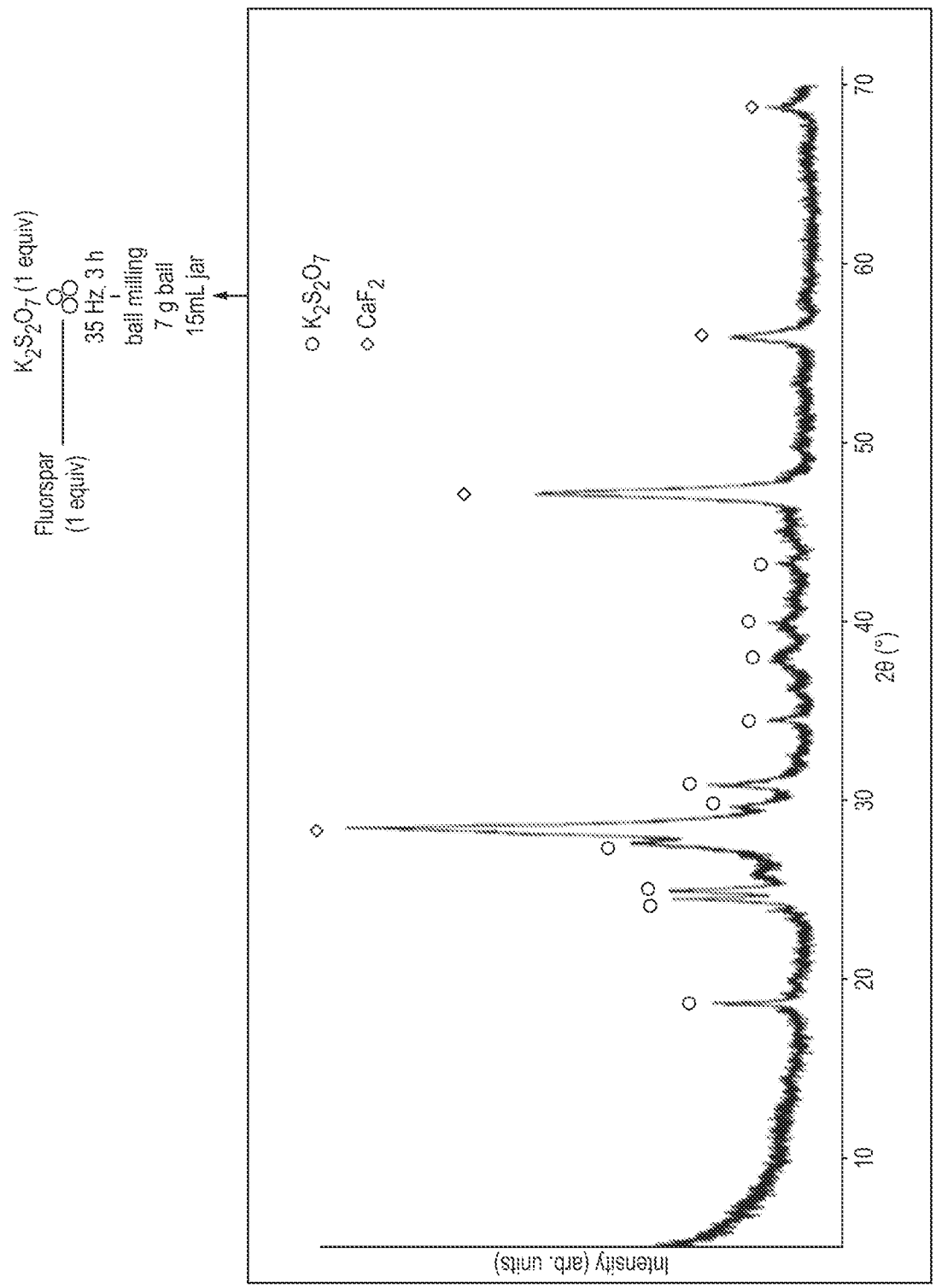
FIG. 42 shows the PXRD diffractogram of the product of the fluorspar milling reaction with K$_2$S$_2$O$_7$ for 3 hours at 35 Hz.

FIG. 42 shows the PXRD pattern resulting from milling of Fluorspar with $K_2S_2O_7$ at 35 Hz for 3 hours. Table 6.3.5 shows the PXRD data from the milling of Fluorspar with $K_2S_2O_7$ represented in FIG. 42. Labels in FIG. 42 indicates a crystalline phase of $K_2S_2O_7$ and $CaF_2$.

TABLE 6.3.5

| Pos. [°2Th.] | Height [cts] | FWHM [°2Th.] | d-spacing [Å] | Rel. Int. [%] |
|---|---|---|---|---|
| 18.6759 | 158.99 | 0.1515 | 4.75132 | 19.51 |
| 24.5269 | 213.14 | 0.1515 | 3.62953 | 26.15 |
| 24.9651 | 223.94 | 0.2598 | 3.56681 | 27.48 |
| 25.8936 | 81.49 | 0.4330 | 3.44098 | 10.00 |
| 27.6051 | 292.05 | 0.2598 | 3.23141 | 35.83 |
| 28.1502 | 512.13 | 0.1299 | 3.17005 | 62.83 |
| 28.4887 | 815.05 | 0.1082 | 3.13315 | 100.00 |
| 29.6651 | 116.36 | 0.2165 | 3.01153 | 14.28 |
| 30.8497 | 134.66 | 0.2165 | 2.89854 | 16.52 |
| 34.5076 | 53.64 | 0.2165 | 2.59921 | 6.58 |
| 36.1930 | 16.57 | 0.5196 | 2.48194 | 2.03 |
| 37.8307 | 47.81 | 0.8659 | 2.37818 | 5.87 |
| 39.8507 | 39.48 | 0.6927 | 2.26217 | 4.84 |
| 41.3817 | 17.93 | 0.5196 | 2.18195 | 2.20 |
| 43.2539 | 26.00 | 0.5196 | 2.09174 | 3.19 |
| 44.9790 | 24.93 | 0.6927 | 2.01545 | 3.06 |
| 47.1481 | 476.17 | 0.1948 | 1.92766 | 58.42 |
| 55.9592 | 126.70 | 0.4330 | 1.64324 | 15.54 |
| 58.2197 | 8.73 | 0.6927 | 1.58471 | 1.07 |
| 68.7851 | 52.76 | 0.4224 | 1.36370 | 6.47 |

Figure 43:
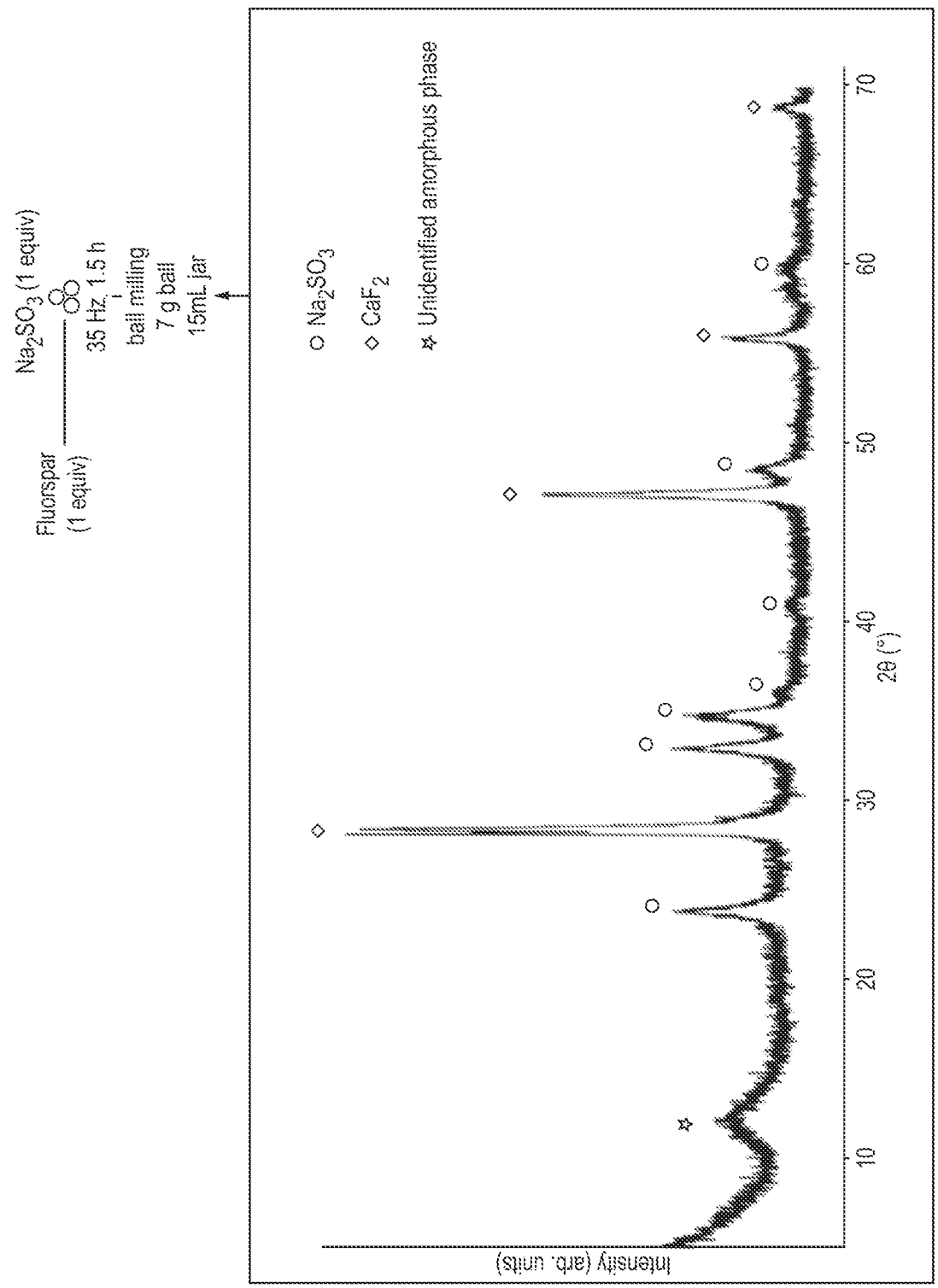
FIG. 43 shows the PXRD diffractogram of the product of the fluorspar milling reaction with Na$_2$SO$_3$ for 1.5 hours at 35 Hz.

FIG. 43 shows the PXRD pattern resulting from milling of Fluorspar with $Na_2SO_3$ at 35 Hz for 3 hours. Table 6.3.6 shows the PXRD data from the milling of Fluorspar with $Na_2SO_3$ represented in FIG. 43. Labels in FIG. 43 indicates a crystalline phase of $Na_2SO_3$, $CaF_2$, and an unidentified amorphous phase.

TABLE 6.3.6

| Pos. [°2Th.] | Height [cts] | FWHM [°2Th.] | d-spacing [Å] | Rel. Int. [%] |
|---|---|---|---|---|
| 23.8355 | 155.83 | 0.1732 | 3.73321 | 21.77 |
| 28.1608 | 715.75 | 0.0433 | 3.16889 | 100.00 |
| 28.4753 | 622.31 | 0.1948 | 3.13460 | 86.95 |
| 32.9735 | 156.27 | 0.2165 | 2.71654 | 21.83 |
| 34.8502 | 131.51 | 0.2598 | 2.57444 | 18.37 |
| 41.0281 | 13.76 | 0.8659 | 2.19993 | 1.92 |
| 47.1164 | 387.85 | 0.1082 | 1.92888 | 54.19 |
| 48.6067 | 69.26 | 0.3464 | 1.87317 | 9.68 |
| 55.9232 | 109.79 | 0.3031 | 1.64421 | 15.34 |
| 59.8245 | 19.50 | 0.6927 | 1.54598 | 2.72 |
| 68.8731 | 43.89 | 0.4224 | 1.36217 | 6.13 |

Figure 44:
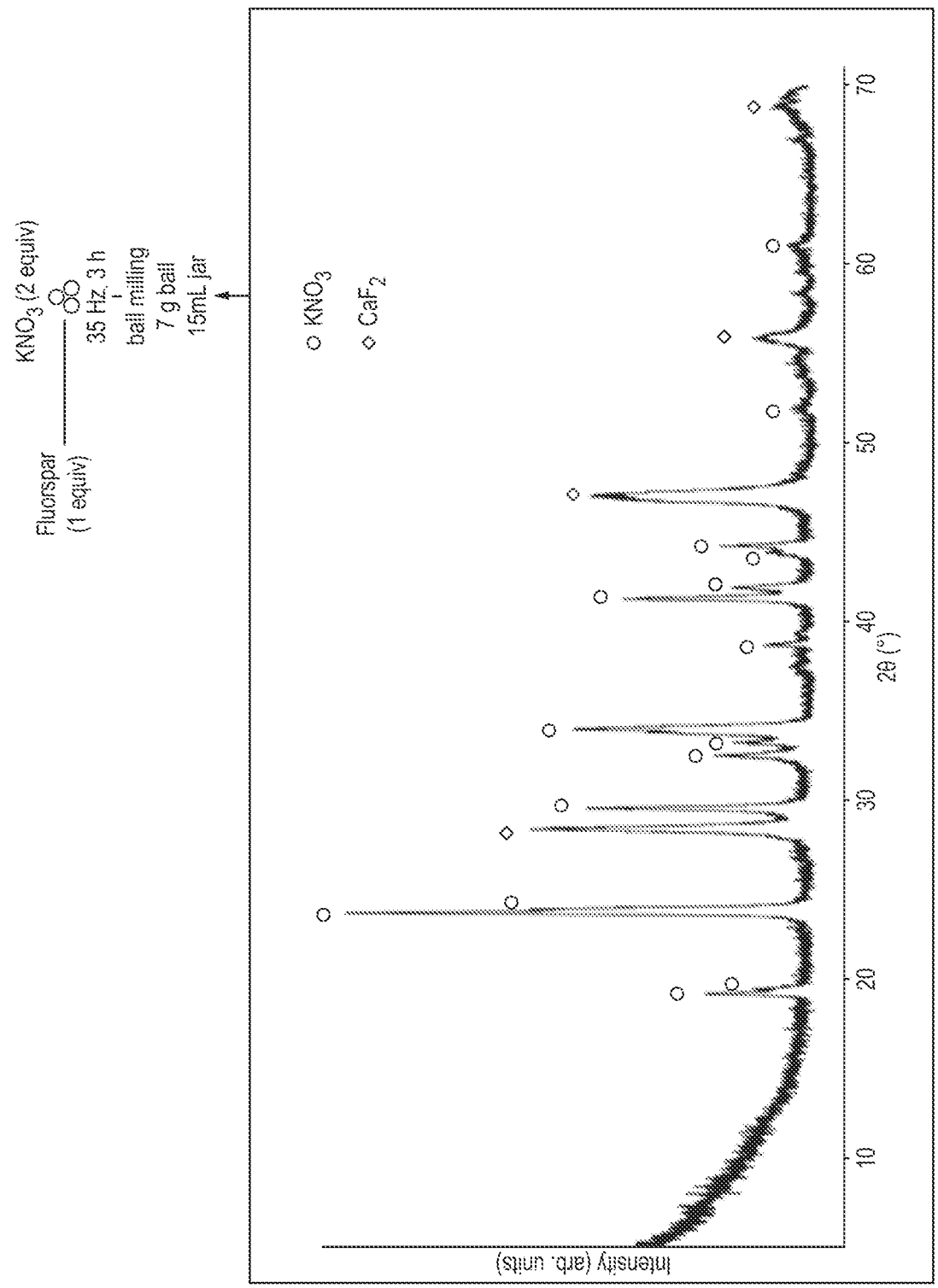
FIG. 44 shows the PXRD diffractogram of the product of the fluorspar milling reaction with KNO$_3$ for 3 hours 35 Hz.

FIG. 44 shows the PXRD pattern resulting from milling of Fluorspar with $KNO_3$ at 35 Hz for 3 hours. Table 6.3.7 shows the PXRD data from the milling of Fluorspar with $KNO_3$ represented in FIG. 44. Labels in FIG. 44 indicates a crystalline phase of $KNO_3$ and $CaF_2$.

TABLE 6.3.7

| Pos. [°2Th.] | Height [cts] | FWHM [°2Th.] | d-spacing [Å] | Rel. Int. [%] |
|---|---|---|---|---|
| 19.0933 | 166.39 | 0.1515 | 4.64838 | 22.78 |
| 23.6201 | 730.32 | 0.0758 | 3.76677 | 100.00 |
| 23.8949 | 426.50 | 0.1515 | 3.72408 | 58.40 |
| 28.3673 | 462.76 | 0.1732 | 3.14629 | 63.36 |
| 29.5161 | 370.32 | 0.1948 | 3.02640 | 50.71 |
| 32.4746 | 143.69 | 0.1948 | 2.75712 | 19.68 |
| 33.1816 | 102.66 | 0.1299 | 2.69998 | 14.06 |
| 33.9155 | 403.95 | 0.0866 | 2.64321 | 55.31 |
| 37.4570 | 21.26 | 0.2598 | 2.40105 | 2.91 |
| 38.6730 | 61.71 | 0.1732 | 2.32830 | 8.45 |
| 41.2213 | 299.90 | 0.1082 | 2.19006 | 41.07 |
| 41.8893 | 124.68 | 0.2165 | 2.15667 | 17.07 |
| 44.1951 | 129.97 | 0.1082 | 2.04936 | 17.80 |
| 46.7107 | 259.71 | 0.2598 | 1.94468 | 35.56 |
| 47.0655 | 348.31 | 0.3897 | 1.93085 | 47.69 |
| 51.8589 | 16.72 | 0.3464 | 1.76309 | 2.29 |

TABLE 6.3.7-continued

| Pos. [°2Th.] | Height [cts] | FWHM [°2Th.] | d-spacing [Å] | Rel. Int. [%] |
|---|---|---|---|---|
| 55.8970 | 78.75 | 0.6061 | 1.64492 | 10.78 |
| 58.3619 | 15.97 | 0.2598 | 1.58118 | 2.19 |
| 61.0249 | 22.10 | 0.5196 | 1.51841 | 3.03 |
| 66.9806 | 17.43 | 0.2598 | 1.39714 | 2.39 |
| 68.9193 | 53.99 | 0.3696 | 1.36137 | 7.39 |

Figure 45:
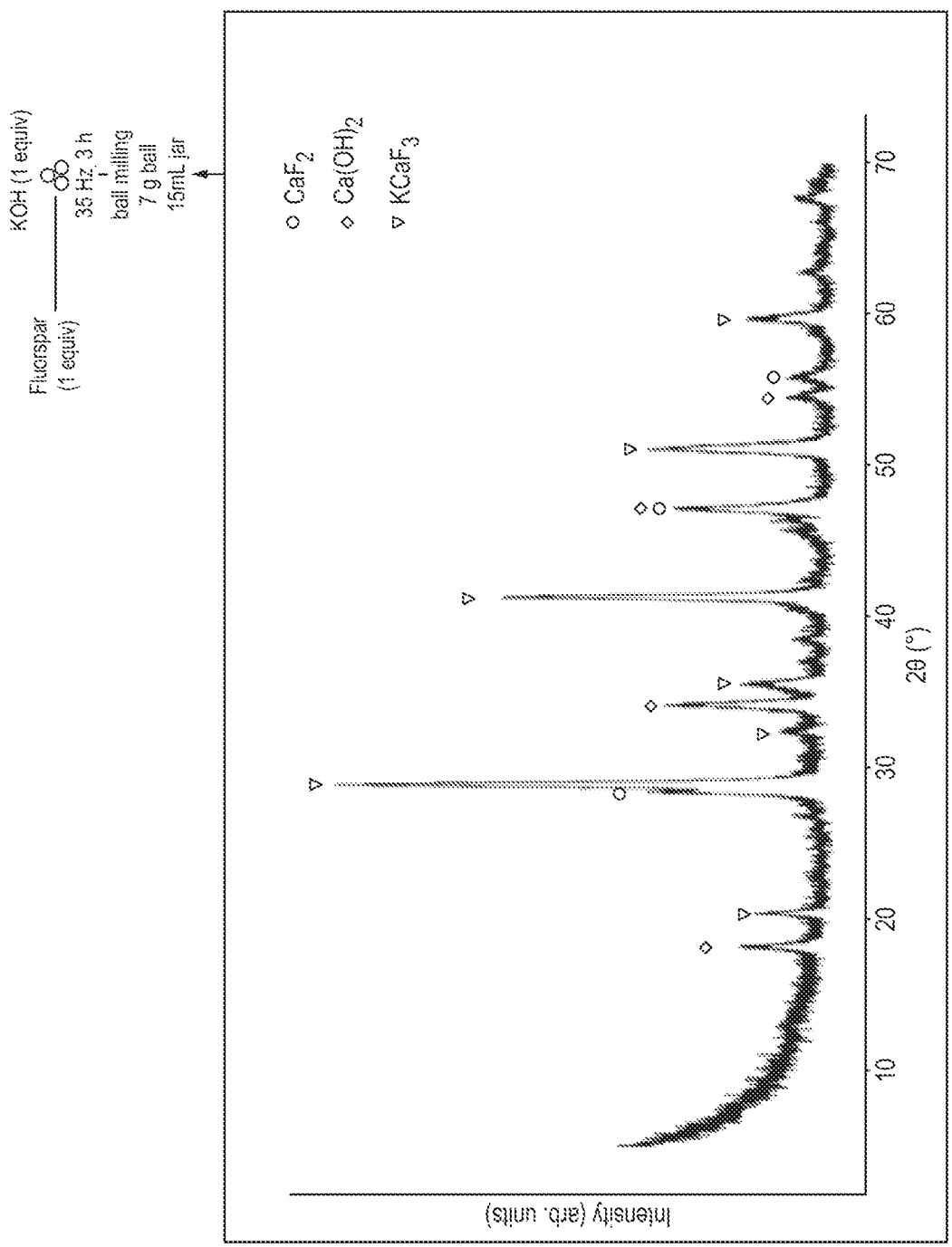
FIG. 45 shows the PXRD diffractogram of the product of the fluorspar milling reaction with KOH for 3 hours 35 Hz.

FIG. 45 shows the PXRD pattern resulting from milling of Fluorspar with KOH at 35 Hz for 3 hours. Table 6.3.8 shows the PXRD data from the milling of Fluorspar with KOH represented in FIG. 45. Labels in FIG. 45 indicates a crystalline phase of $Ca(OH)_2$, $KCaF_2$, and $CaF_2$.

TABLE 6.3.8

| Pos. [°2Th.] | Height [cts] | FWHM [°2Th.] | d-spacing [Å] | Rel. Int. [%] |
|---|---|---|---|---|
| $Ca(OH)_2$ 18.3059 | 55.74 | 0.3031 | 4.84651 | 11.78 |
| $KCaF_3$ 20.4243 | 53.12 | 0.2165 | 4.34838 | 11.22 |
| 26.8143 | 11.39 | 0.2598 | 3.32487 | 2.41 |
| $CaF_2$ 28.3800 | 144.77 | 0.1732 | 3.14491 | 30.58 |
| $KCaF_3$ 28.9043 | 473.34 | 0.2165 | 3.08905 | 100.00 |
| $KCaF_3$ 32.4309 | 19.70 | 0.3464 | 2.76074 | 4.16 |
| $Ca(OH)_2$ 34.1756 | 142.38 | 0.3897 | 2.62369 | 30.08 |
| $KCaF_3$ 35.6082 | 66.30 | 0.3464 | 2.52135 | 14.01 |
| $KCaF_3$ 38.5478 | 17.24 | 0.2598 | 2.33558 | 3.64 |
| $KCaF_3$ 41.3008 | 308.88 | 0.1299 | 2.18604 | 65.26 |
| $Ca(OH)_2$ 47.2316 | 123.86 | 0.4330 | 1.92445 | 26.17 |
| $KCaF_3$ 51.1272 | 175.11 | 0.3897 | 1.78659 | 36.99 |
| $Ca(OH)_2$ 54.5376 | 32.39 | 0.4330 | 1.68266 | 6.84 |
| $CaF_2$ 55.7686 | 27.72 | 0.3031 | 1.64840 | 5.86 |
| $KCaF_3$ 59.7330 | 68.83 | 0.4330 | 1.54813 | 14.54 |
| $Ca(OH)_2$ 62.8171 | 18.65 | 0.3464 | 1.47934 | 3.94 |
| $CaF_2$ 67.6726 | 26.77 | 0.6336 | 1.38338 | 5.65 |

Figure 46:
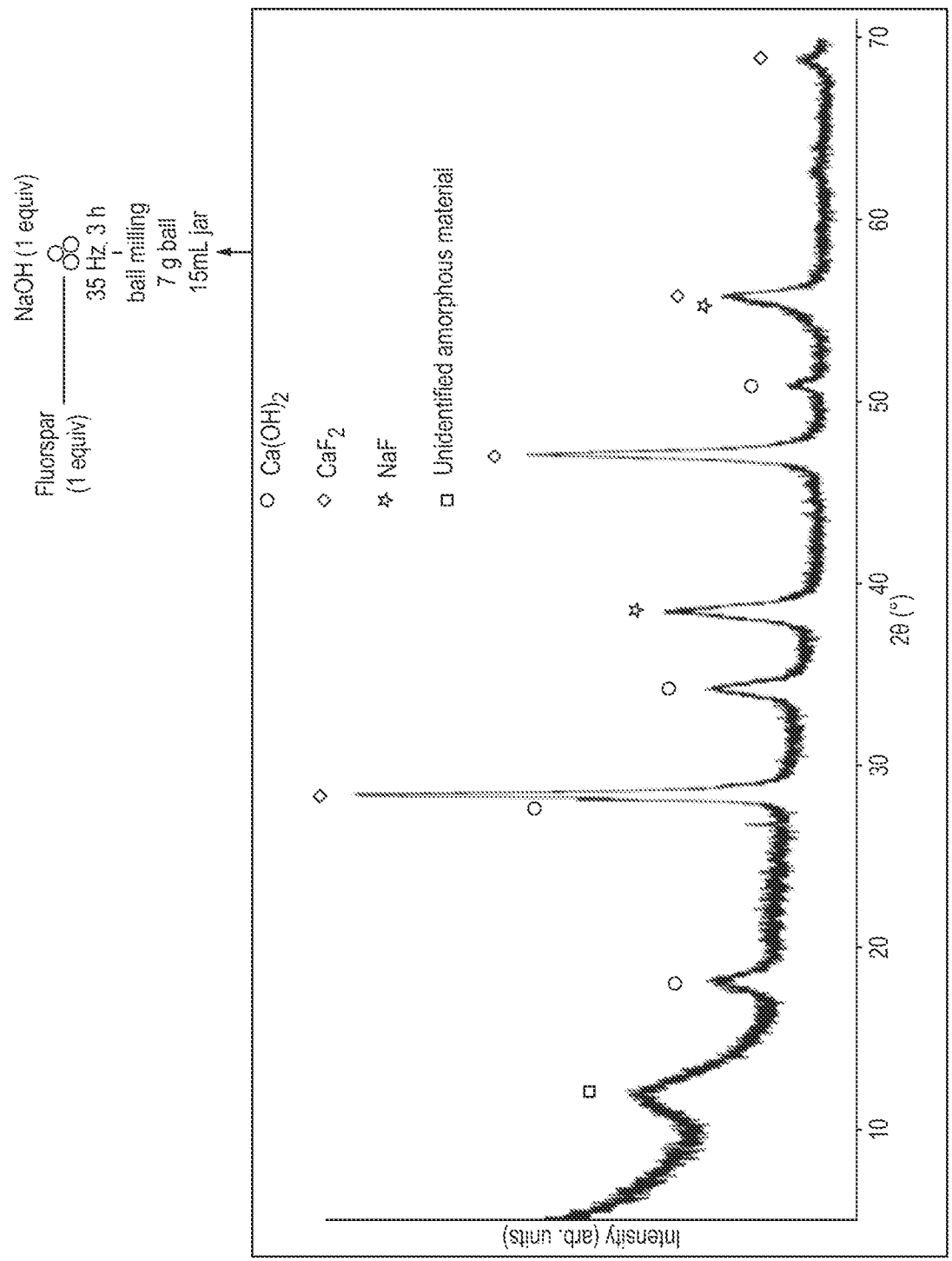
FIG. 46 shows the PXRD diffractogram of the product of the fluorspar milling reaction with NaOH for 3 hours 35 Hz.

FIG. 46 shows the PXRD pattern resulting from milling of Fluorspar with NaOH at 35 Hz for 3 hours. Table 6.3.9 shows the PXRD data from the milling of Fluorspar with NaOH represented in FIG. 46. Labels in FIG. 46 indicates a crystalline phase of $Ca(OH)_2$, NaF, $CaF_2$, and an unidentified amorphous material.

TABLE 6.3.9

| Pos. [°2Th.] | Height [cts] | FWHM [°2Th.] | d-spacing[Å] | Rel. Int. [%] |
|---|---|---|---|---|
| $Ca(OH)_2$ 18.0813 | 122.86 | 0.6061 | 4.90620 | 13.13 |
| $Ca(OH)_2$ 28.0362 | 493.55 | 0.0325 | 3.18268 | 52.73 |
| $CaF_2$ 28.2772 | 936.03 | 0.2165 | 3.15610 | 100.00 |
| $Ca(OH)_2$ 34.2959 | 199.53 | 0.3464 | 2.61477 | 21.32 |
| NaF 38.4222 | 319.14 | 0.4763 | 2.34292 | 34.09 |
| $CaF_2$ 47.0805 | 700.67 | 0.1732 | 1.93027 | 74.84 |
| $Ca(OH)_2$ 50.9401 | 63.28 | 0.3464 | 1.79271 | 6.76 |
| NaF 55.8343 | 213.37 | 0.3031 | 1.64662 | 22.80 |
| $CaF_2$ 68.7807 | 53.36 | 0.5280 | 1.36378 | 5.70 |

Figure 110:
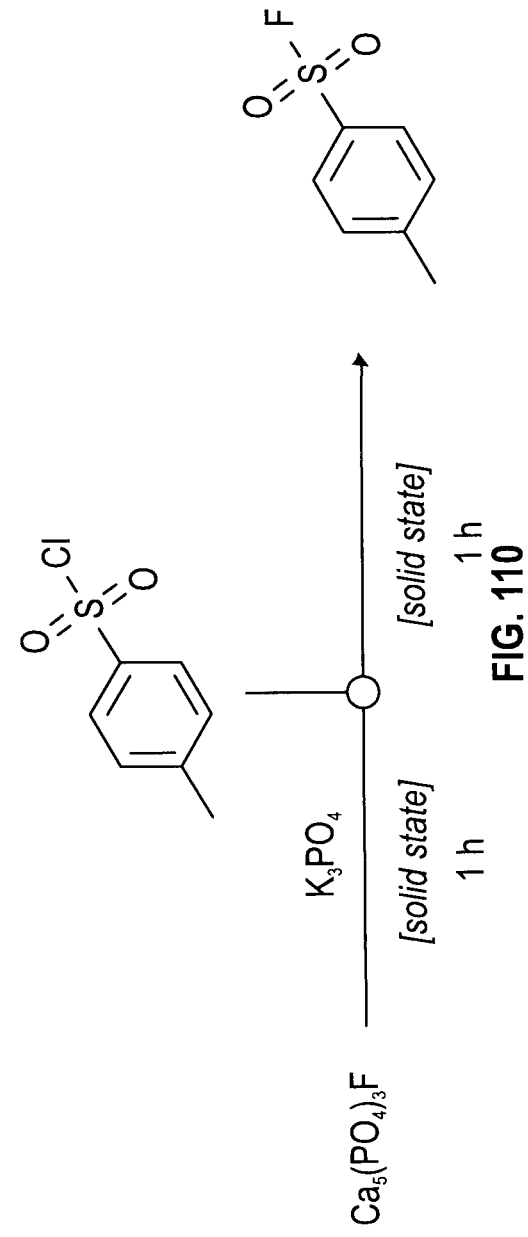
FIG. 110 illustrates a general scheme according to embodiments described herein.

7. Fluorination Using Fluorapatite 7.1. S—F Bond Formation Using Fluorapatite in the Solid State In some instances, fluorapatite was used in combination with $K_3PO_4$ to fluorinate TsCl in the solid state via ball milling as described in FIG. 110, the results of which can be found in Table 7.1. Briefly, fluorapatite ($Ca_5(PO_4)_3F$, 5 equiv.) and $K_3PO_4$ in varying ratios were milled at 30 Hz for 1 hour in 15 mL stainless steel jars using a 7 g ball. TsCl was added and milled for 1 hour longer at 30 Hz to obtain a fluorinated product (see Table 7.1 for yields). The grains of fluorapatite used were approximately 0.06-0.19 inches. The solid state reactions resulted in yields of organo-fluorine product (TsF) of 5% or less.

TABLE 7.1

| Entry | $Ca_5(PO_4)_3F/K_3PO_4$ ratio | $Ca_5(PO_4)_3F$ (equiv) | TsF | TsCl | Mass Balance |
|---|---|---|---|---|---|
| 1 | 2.5:1 | 5 | 5% | trace | 5% |
| 2 | 10:1 | 5 | <1% | 35% | <36% |

Figure 111:
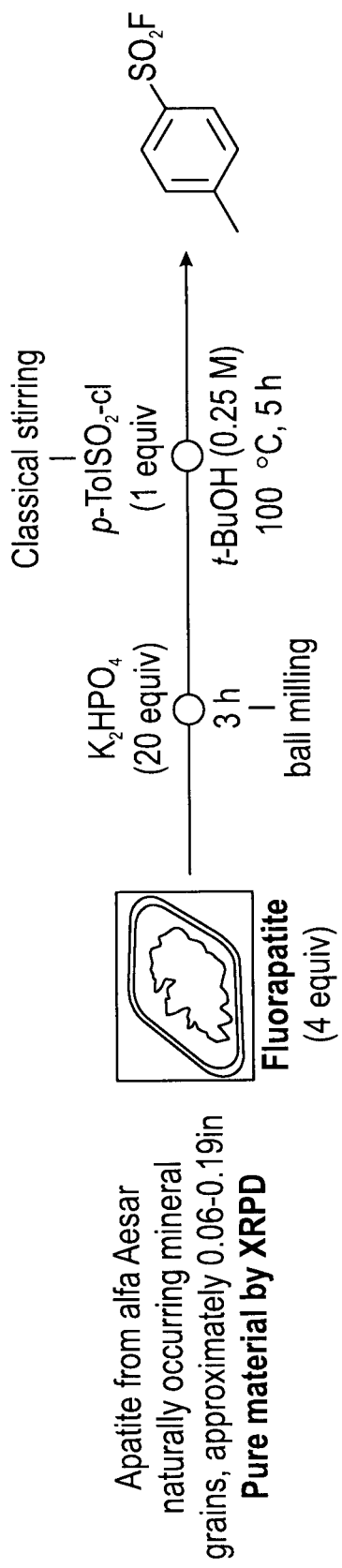
FIG. 111 illustrates a general scheme according to embodiments described herein.

0.25 mmol scale; $^{19}F$ NMR yields (4-fluoroanisole) in $CDCl_3$ 7.2. S—F Bond Formation Using Fluorapatite in the Solid State and Solution State Fluorapatite ($Ca_5(PO_4)_3F$) (approximately 0.06-0.19 in) was used in combination with $K_2HPO_4$ as described in FIG. 111 to create a fluorination reagent via ball milling under varying conditions as seen in Table 7.2. Specifically, fluorapatite (4 equiv.) was milled with $K_2HPO_4$ (20 equiv.) for 3 hours at varying frequencies, jar loading (mg/mL), and jar sizes (mL). The resulting powder reagent was reacted with p-TolSO$_2$—CI (TsCl) (1 equiv.) in a tBuOH (0.25 M) solution at 100° C. for 5 hours resulting in a fluorinated product, TsF. The yield of the fluorinated product and starting material, TsCl can be found in Table 7.2. The results indicate that jar loading may affect ball milling/fluorination yield and higher frequencies may be beneficial to yield. The results also highlight that, the solution reaction of the fluorapatite-$K_2HPO_4$ fluorination reagent with the TsCl can result in higher fluorinated product (TsF) yields than seen in the solid state reaction of Example 7.1.

TABLE 7.2

| Entry | Frequency (Hz) | Jar Loading (mg/mL) | Jar Size (mL) | Powder Loading (g) | TsF | TsCl |
|---|---|---|---|---|---|---|
| 1 | 30 | 17 | 30 | 0.5 | 15% | 0% |
| 2 | 30 | 33 | 30 | 1 | 21% | 0% |
| 3 | 30 | 33 | 15 | 0.5 | 28% | 0% |
| 4 | 30 | 67 | 15 | 1 | 23% | 0% |
| 5 | 30 | 133 | 15 | 2 | 15% | 0% |
| 6 | 35 | 33 | 15 | 0.5 | 36% | 0% |

7.3. Activator Screening Using Fluorapatite

Figure 112:
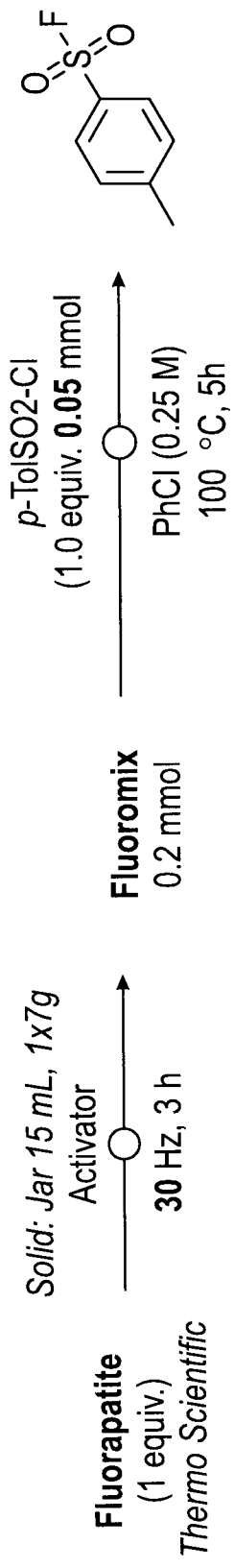
FIG. 112 illustrates a general scheme according to embodiments described herein.

Various activators were used in combination with fluorapatite to test their efficacy in forming a fluorinating reagent. The resulting fluorinating reagents, "Fluoromix", were probed as fluorinating reagents via reaction with p-TolSO$_2$—CI (TsCl) and yields of TsF were determined via $^{19}F$ NMR using 4-fluoroanisole as an internal standard. The reactions were carried out as described in FIG. 112.

Briefly, fluorapatite (1 equiv.) was milled with an activator (see Table 7.3) at 30 Hz for 3 hours in a 15 mL stainless steel jar with a 7 g ball to create Fluoromix. Fluoromix (0.2 mmol) was added to a PhCl solution (0.25 M) with p-TolSO$_2$—CI (1.0 equiv., 0.05 mmol) and reacted at 100° C. for 5 hours to form the fluorinated product, TsF. The yields of TsF and the side product yields can be found in Table 7.3. Successful fluorination may be possible with exemplary activators KCl+$K_2HPO_4$ or potassium pyrophosphate, although the success of fluorinating the TsCl starting material may be dependent on the activator used.

TABLE 7.3

| Entry | Activator | Total Mass | $PO_3F^{2-}$ | $F^-$ | TsF | TsCl |
|---|---|---|---|---|---|---|
| 1 | KCl (9 equiv.) | 1000 mg | 0% | 0% | 0% | 87% |
| 2 | $K_2CO_3$ (4.5 equiv.) | 1000 mg | 0% | 0% | 0% | 0% |
| 3 | KCl (9 equiv.) + $K_2HPO_4$ (1 equiv.) | 600 mg | 0% | 2% | 9% | 0% |
| 4 | $K_2CO_3$ (4.5 equiv.) + $K_2HPO_4$ (1 equiv.) | 600 mg | 0% | 15% | 0% | 0% |
| 5 | $K_2CO_3$ (4.5 equiv.) + $K_2HPO_4$ (2 equiv.) | 600 mg | 0% | 17% | 0% | 0% |
| 6 | $KHCO_3$ (5 equiv.) | 600 mg | 0% | 5% | 0% | 0% |
| 7 | $KHCO_3$ (5 equiv.) + $K_2HPO_4$ (2 equiv.) | 600 mg | 0% | 3% | trace | 0% |
| 8 | $KH_2PO_4$ (5 equiv.) | 500 mg | 0% | 1% | 0% | 85% |
| 9 | $K_3PO_4$ (5 equiv.) | 500 mg | 0% | 14% | | |
| 10 | Potassium pyrophosphate (2.5 equiv.) | 500 mg | 0% | 25% | 4% | 26% |
| 11 | Potassium triphosphate (1.67 equiv.) | 500 mg | 6% | 3% | trace | 51% |

7.4. Varying Stoichiometry of Fluorapatite Fluorination

Figure 113:
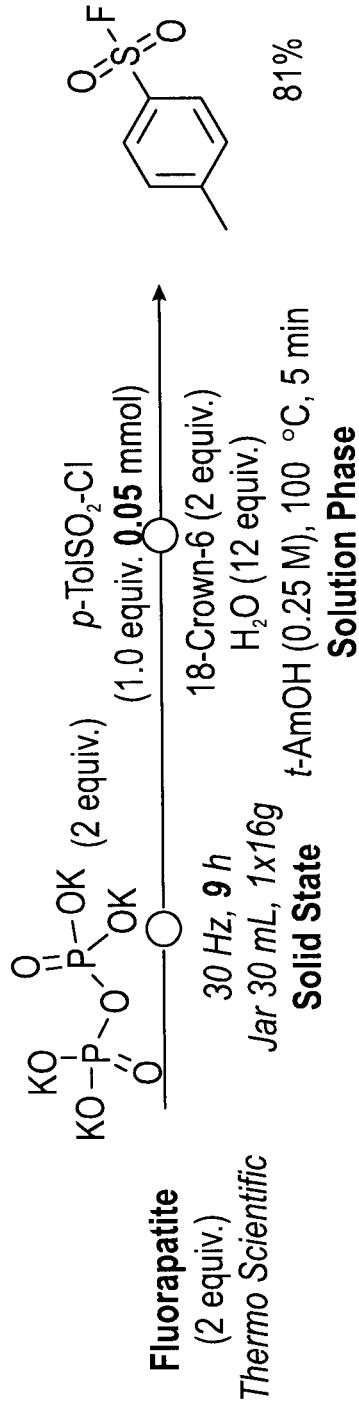
FIG. 113 illustrates a general scheme according to embodiments described herein.
Figure 114:
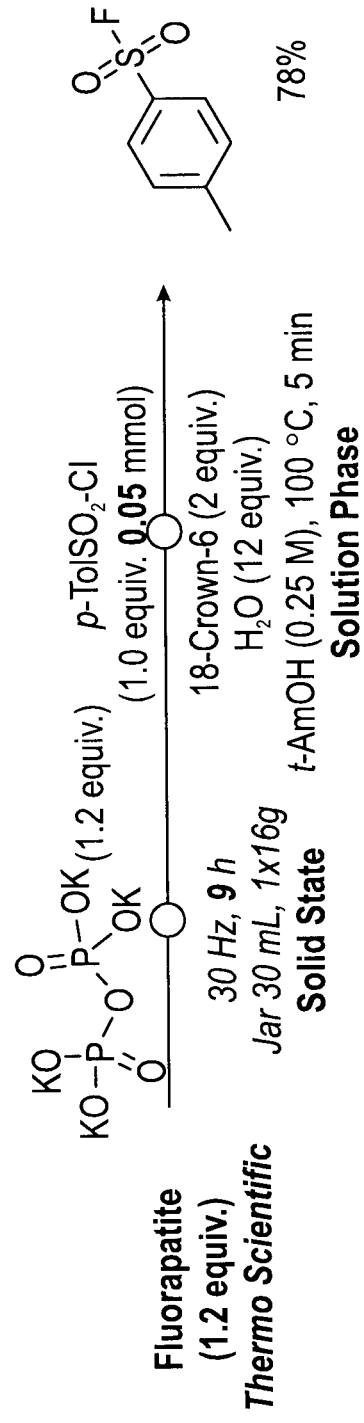
FIG. 114 illustrates a general scheme according to embodiments described herein.
Figure 115:
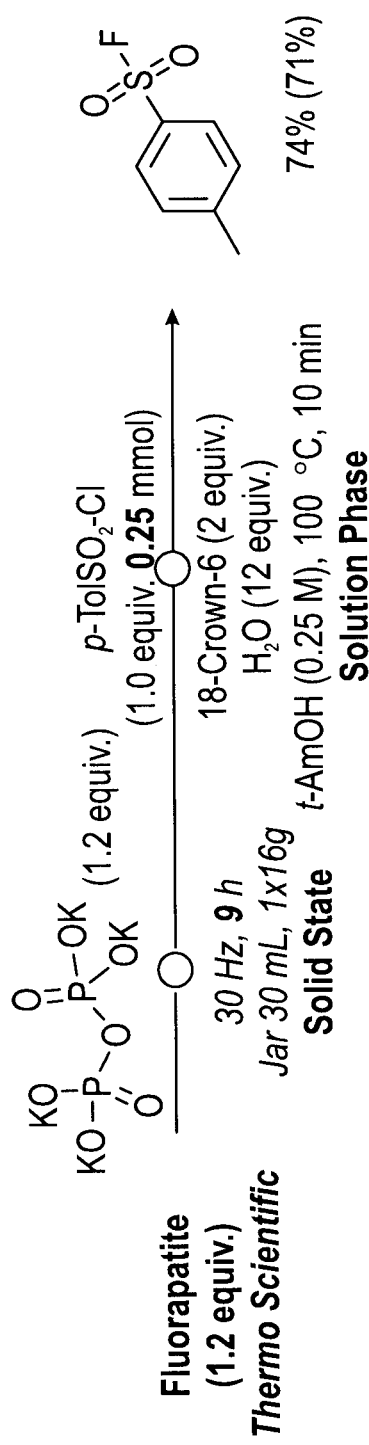
FIG. 115 illustrates a general scheme according to embodiments described herein.

Various conditions were probed in order to examine changes in fluorination yield using fluoroapatite. This included changing the stoichiometry between fluorapatite, the phosphate activator, the TsCl, as well as changing the reaction time, as seen in FIGS. 113-115.

In all conditions, the fluorapatite was milled first with the phosphate activator before being reacted in the solution phase with the TsCl (p-$TolSO_2$—Cl). When fluorapatite (2 equiv.) was milled with 2 equiv. of the phosphate activator followed by solution phase reaction with 0.05 mmol of TsCl as described in FIG. 113, the TsF yield was 81%. When 1.2 equiv. of fluorapatite was milled with 1.2 equiv. of phosphate activator followed by solution phase reaction with TsCl (0.05 mmol), the TsF yield was 78%. Finally, when fluorapatite (1.2 equiv.) was milled with 1.2 equiv. of phosphate followed by solution phase reaction for 10 minutes with 0.25 mmol of TsCl, the yield of TsF was 74%. The yields of the organo-fluorine product indicate that pyrophosphate activator along with 18-crown-6 may be an exemplary combination to achieve high organo-fluorination yields.

7.5. Reaction Scope of Fluorapatite Fluorination

Figure 47:
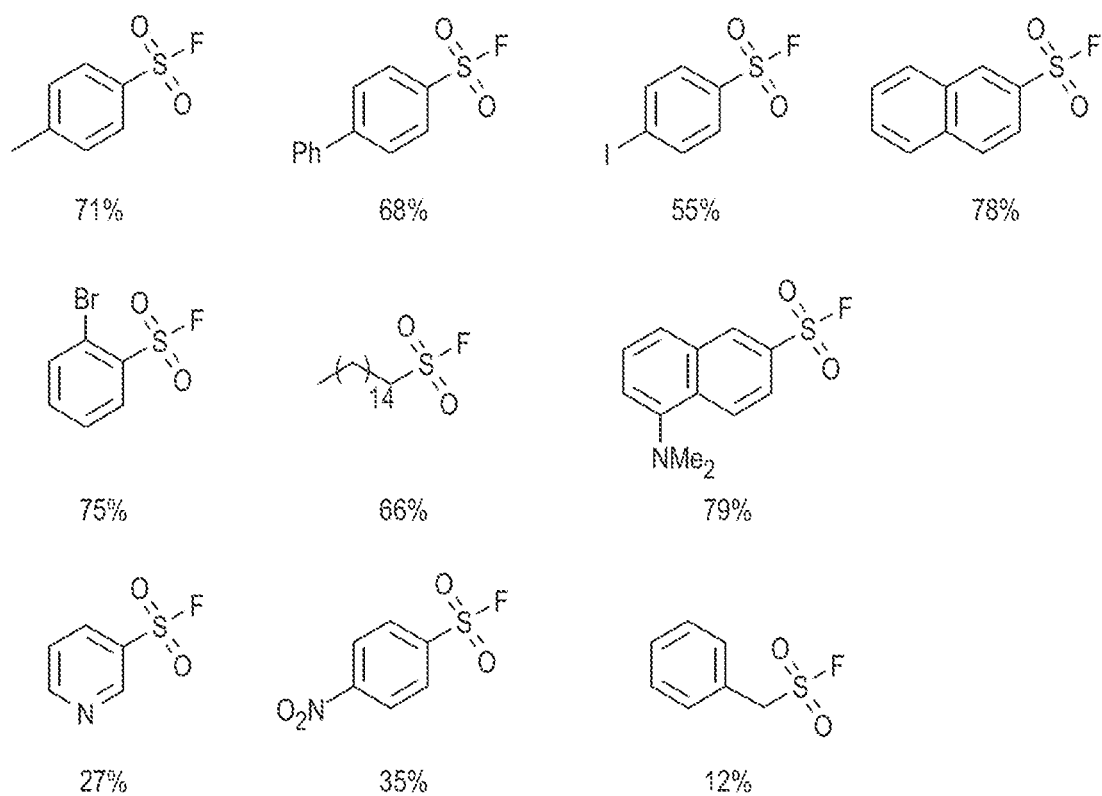
FIG. 47 shows the reaction scope of R—SO$_2$Cl species with fluorapatite using a phosphate activator and associated yields.
Figure 116:
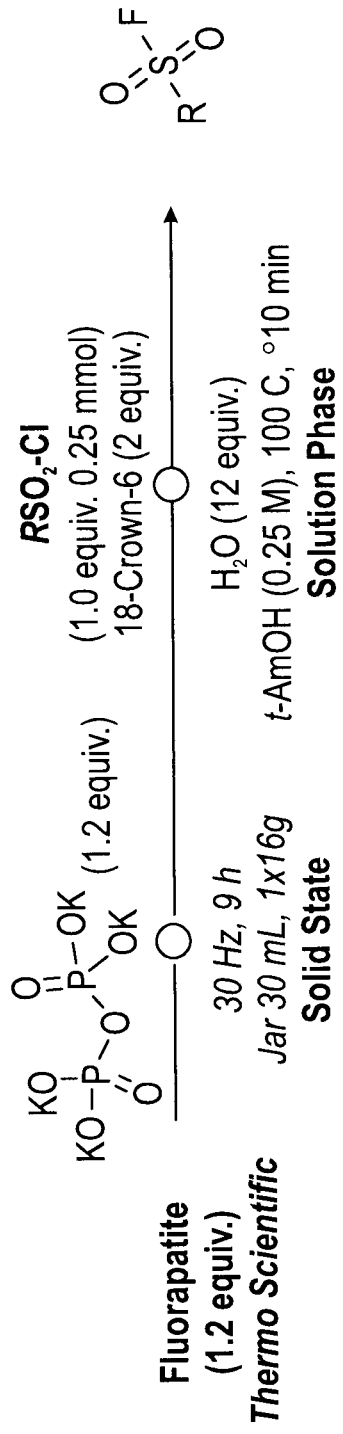
FIG. 116 illustrates a general scheme according to embodiments described herein.

As described in FIG. 116, fluorapatite was milled with a phosphate activator to form the fluorination agent and reacted in the solution phase with a range of $RSO_2$—Cl substrates to form $RSO_2$—F (see FIG. 47). FIG. 47 shows the yields of the resulting reactions and fluorinated products which range from 12% to 79%. The reactions were carried out as follows. Fluorapatite (1.2 equiv.) was milled with the phosphate activator (1.2 equiv) at 30 Hz for 9 hours in a 30 mL stainless steel jar with 1 16 g ball. The resulting powder reagent was reacted with the $RSO_2$—Cl substrate (1.0 equiv., 0.25 mmol) in the solution phase in t-AmOH (0.25 M) at 100° C. for 10 minutes with 18-crown-6 and 12 equiv. of $H_2O$ resulting in the fluorinated product. The results show that the pyrophosphate activator in addition to 18-crown-6 may be used with fluorapatite as a fluorinating reagent to fluorinate a wide variety of substrates including aliphatic and aromatic substrates.

7.6. Mechanistic Insiqht of Fluorapatite Mechanochemical Reaction by PXRD

Figure 117:
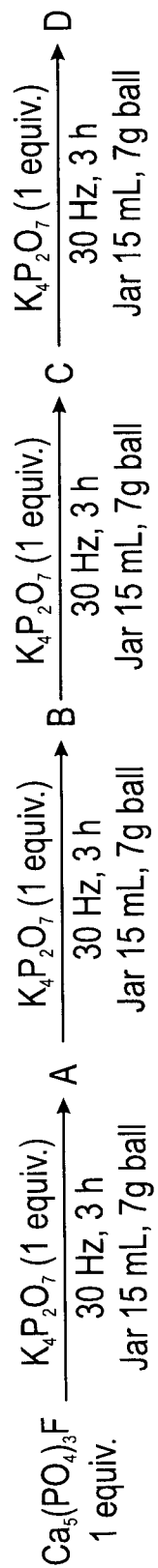
FIG. 117 illustrates a general scheme according to embodiments described herein.

The mechanism of the mechanochemical reaction between fluorapatite ($Ca_5(PO_4)_3F$) and $K_4P_2O_7$ was investigated via subsequent additions and milling as described in FIG. 117 via the formation and analysis of products A-D.

Figure 48:
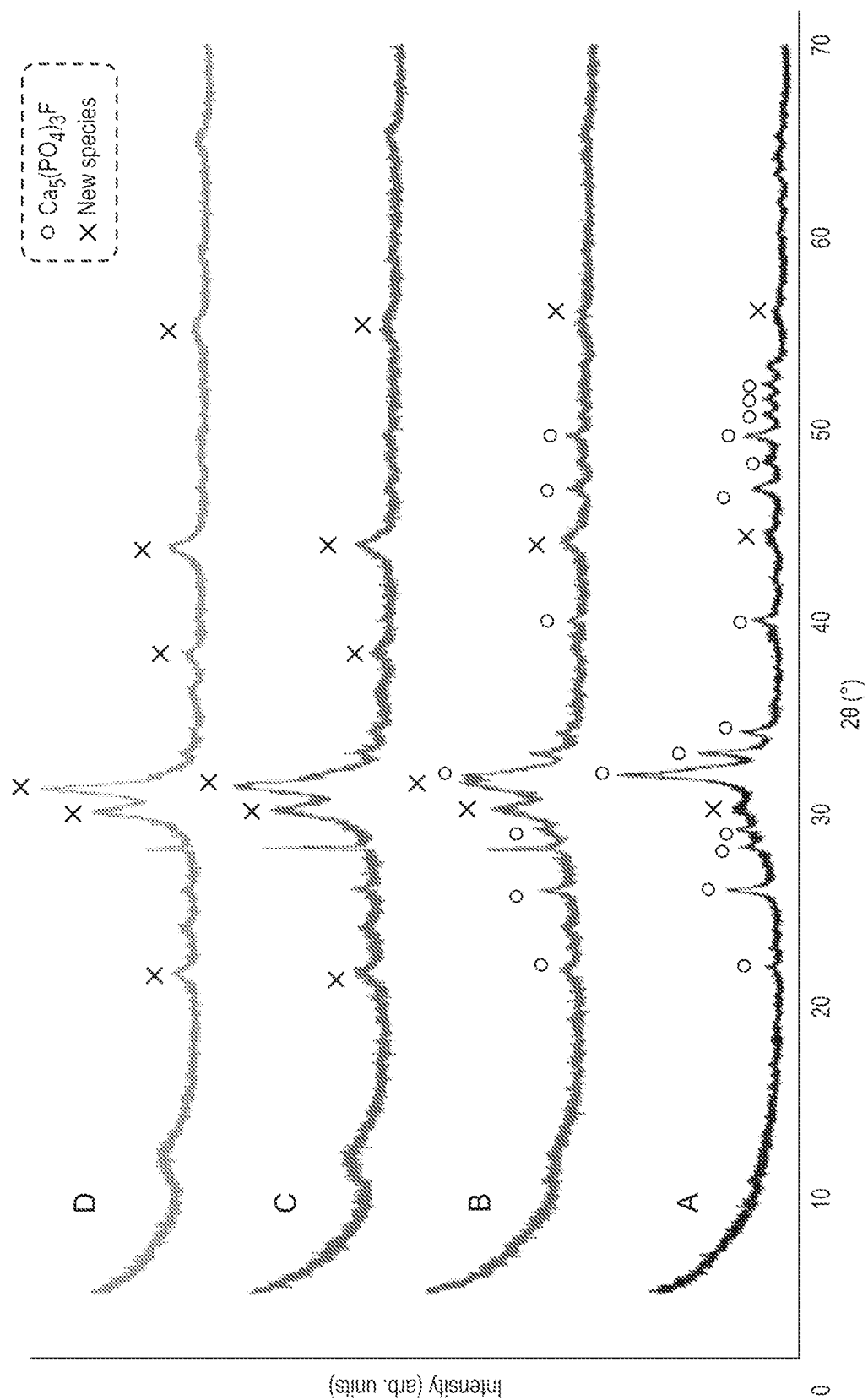
FIG. 48 shows stacked PXRD diffractograms of the products of the fluorapatite milling reaction upon subsequent additions of K$_4$P$_2$O$_7$ (4 separate additions of 1 equivalent).

FIG. 48 shows the stacked PXRD patterns of products A, B, C, and D where circles indicate fluorapatite starting material and x indicate a new species. This data shows the consumption of crystalline fluorapatite by mechanochemical reaction with potassium pyrophosphate and a new crystalline species forming over the course of the reaction. Products C and D may be indicative of no fluorapatite starting material, whereas $Ca_5(PO_4)_3F$ starting material is present in samples A and B.

Figure 49:
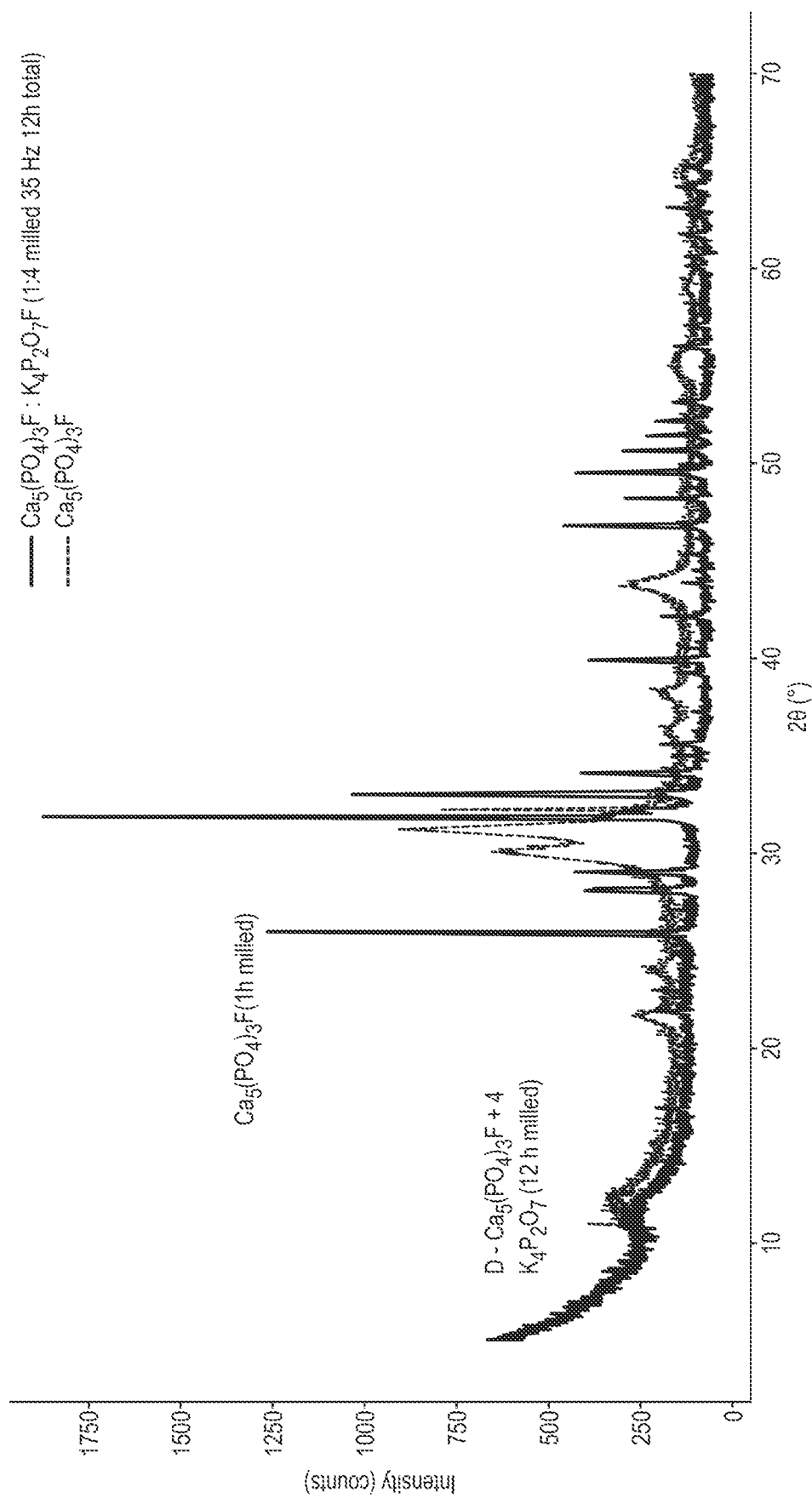
FIG. 49 shows the PXRD diffractogram of pure fluorapatite after 1 hour of milling overlayed with a fluorapatite sample (1 equiv.) that was milled for 12 hours total at 35 Hz with K$_4$P$_2$O$_7$ (4 equiv.).

FIG. 49 shows a PXRD pattern of pure fluorapatite after 1 hour of milling overlayed with a fluorapatite sample (1 equiv.) that was milled for 12 hours total at 35 Hz with $K_4P_2O_7$ (4 equiv.). The result indicates consumption of the fluorapatite by mechanochemical reaction with potassium pyrophosphate.

Figure 50:
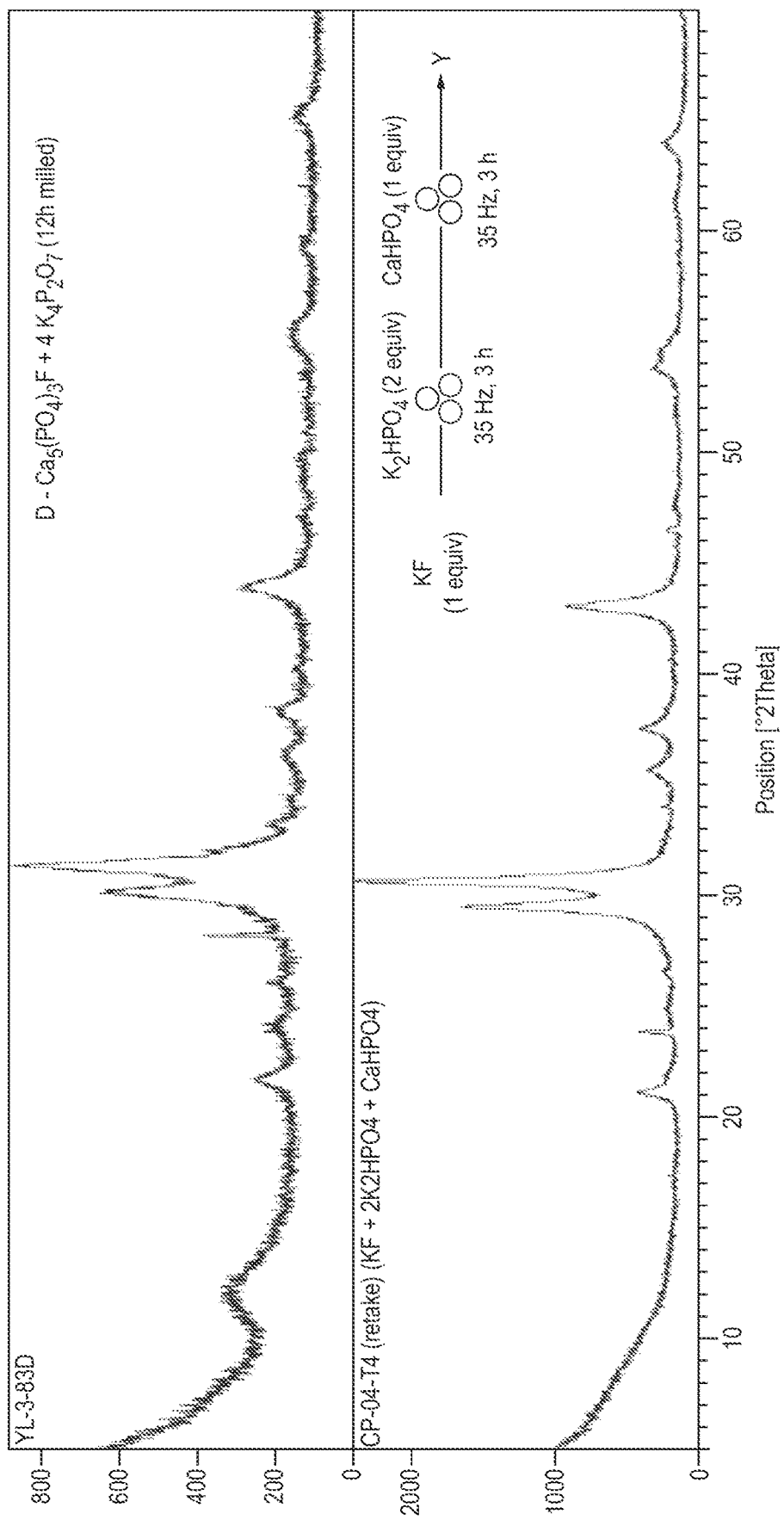
FIG. 50 shows stacked PXRD diffractograms of the reaction 1:4 equiv. milling reaction (D) between fluorapatite (Ca$_5$(PO$_4$)$_3$F) and K$_4$P$_2$O$_7$, and the milling reaction between potassium fluoride (KF, 1 equiv.) and K$_2$HPO$_4$ (2 equiv., 35 Hz, 3 hours) followed by CaHPO$_4$ (1 equiv., 35 Hz, 3 hours).
Figure 118:
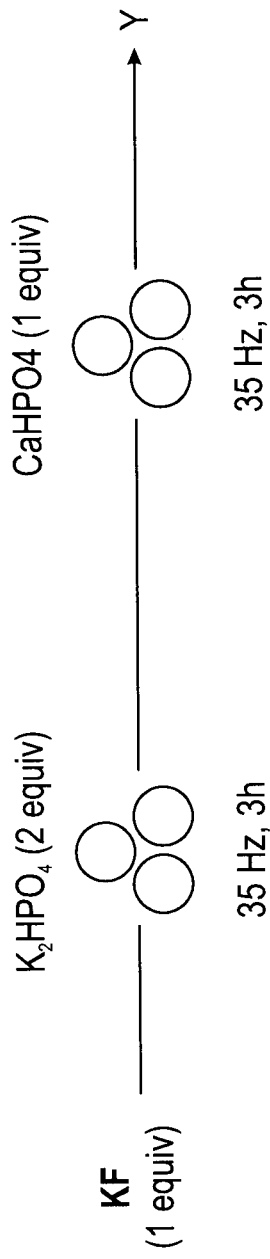
FIG. 118 illustrates a general scheme according to embodiments described herein.

FIG. 50 shows a comparison of the PXRD pattern of the reaction 1:4 equiv. milling reaction (D) between fluorapatite ($Ca_5(PO_4)_3F$) and $K_4P_2O_7$, and the milling reaction between potassium fluoride (KF, 1 equiv.) and $K_2HPO_4$ (2 equiv., 35 Hz, 3 hours) followed by $CaHPO_4$ (1 equiv., 35 Hz, 3 hours) as seen in FIG. 118. The resulting patterns may indicate a similar structure of D to one of the components in the Y (Y=$K_{2-x}Ca_y(PO_3F)_a(PO_4)_bF_c$). The peaks at higher degrees 2-theta value than those observed in the PXRD of the crystalline phase of Y are consistent with a closely related structure to Y with different ratios of $Ca^{2+}$, $K^+$, $F^-$, or $PO_4^{3-}$.

Figure 51:
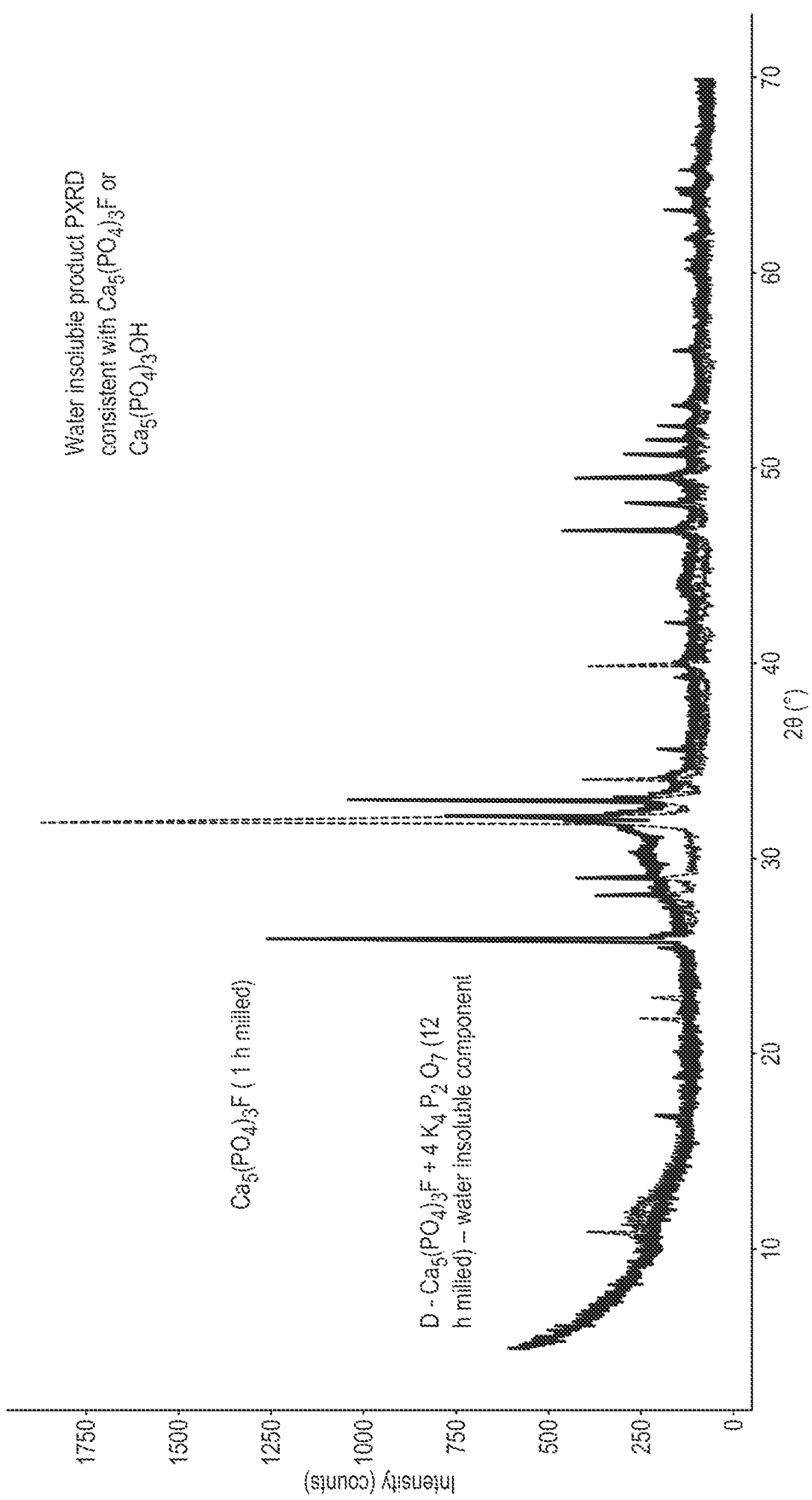
FIG. 51 shows the PXRD diffractogram of the water insoluble product of the reaction between fluorapatite and potassium pyrophosphate overlayed with the PXRD diffractogram of fluorapatite.

Product D from FIG. 117 was washed with water and separated into an $H_2O$ insoluble component and an $H_2O$ soluble component. FIG. 51 shows the PXRD data of the water insoluble component and is compared to a crystalline reference pattern, in this case, pure milled, $Ca_5(PO_4)_3F$ (fluorapatite). The water insoluble product's PXRD pattern may be consistent with $Ca_5(PO_4)_3F$ or $Ca_5(PO_4)_3OH$.

7.7. Fluorapatite Activation Using Potassium Pyrophosphate

Figure 52:
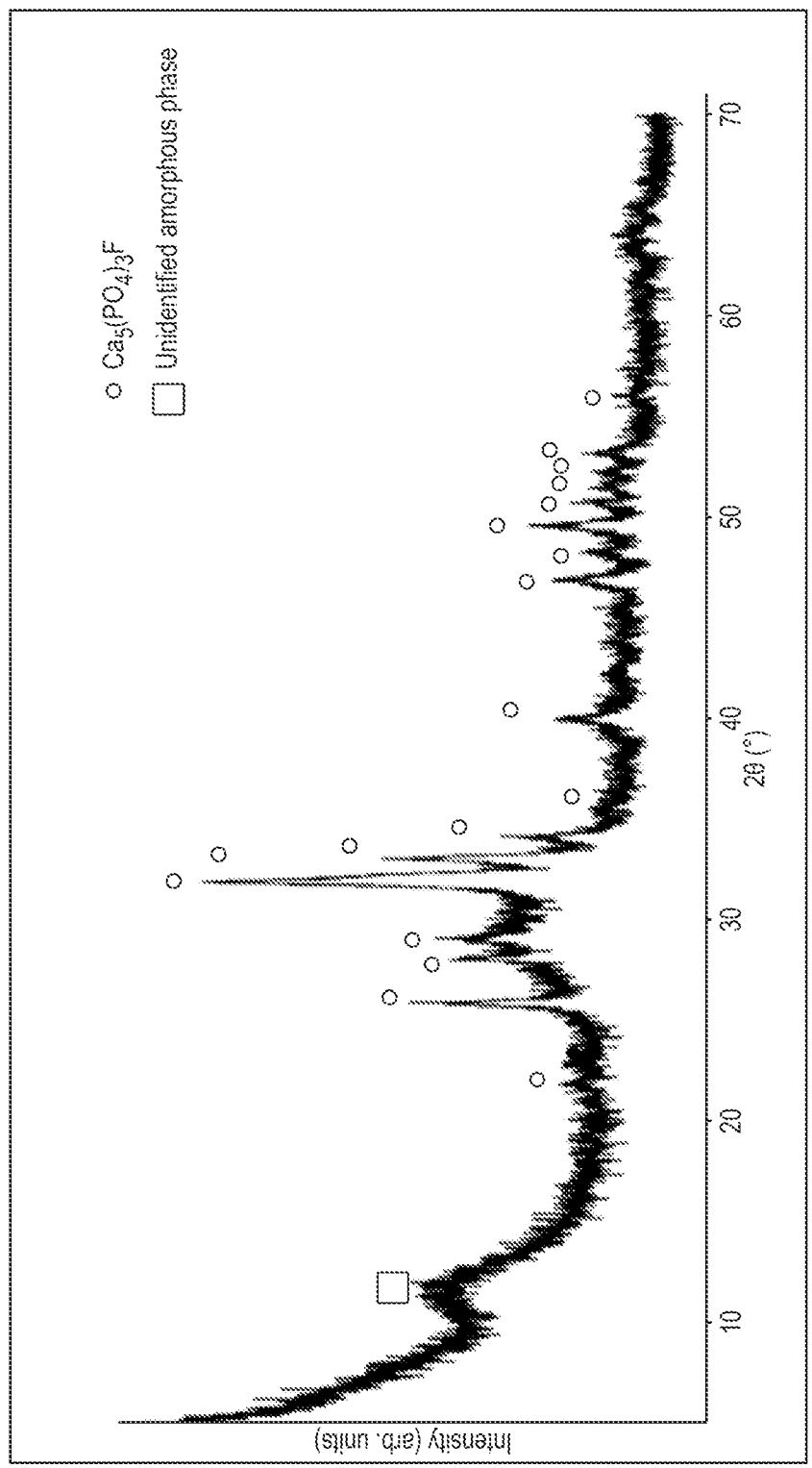
FIG. 52 shows the PXRD diffractogram of the milling reaction of fluorapatite and 1 equivalent of K$_4$P$_2$O$_7$ for 9 hours at 30 Hz.
Figure 119:
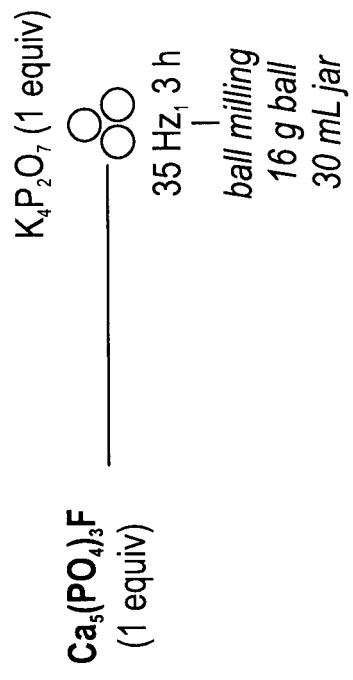

Fluorapatite activation was tested using 1 equivalent of potassium pyrophosphate ($K_4P_2O_7$) and the milling reaction was monitored via PXRD. The milling reaction proceeded as described in FIG. 119 wherein 1 equivalent of fluorapatite ($Ca_5(PO_4)_3F$ was milled with 1 equivalent of $K_4P_2O_7$ at 30 Hz for 9 hours using a 16 g ball in a 30 mL stainless steel jar. FIG. 52 and Table 7.7.1 show the PXRD data indicating presence of crystalline phases of $Ca_5(PO_4)_3F$ and an unidentified amorphous phase. No crystalline potassium pyrophosphate was observed by PXRD.

TABLE 7.7.1

| Pos. [°2Th.] | Height [cts] | FWHM [°2Th.] | d-spacing [Å] | Rel. Int. [%] |
|---|---|---|---|---|
| 25.9458 | 189.47 | 0.1732 | 3.43417 | 42.12 |
| 28.0927 | 147.16 | 0.1732 | 3.17642 | 32.71 |
| 29.0831 | 149.29 | 0.2598 | 3.07046 | 33.19 |
| 31.8944 | 449.86 | 0.1515 | 2.80595 | 100.00 |
| 33.0730 | 230.80 | 0.2165 | 2.70860 | 51.30 |
| 34.1646 | 94.18 | 0.2598 | 2.62451 | 20.94 |
| 39.9834 | 64.49 | 0.2598 | 2.25497 | 14.34 |
| 46.8705 | 71.79 | 0.2598 | 1.93843 | 15.96 |
| 48.2530 | 37.20 | 0.3464 | 1.88607 | 8.27 |
| 49.5507 | 96.86 | 0.3464 | 1.83967 | 21.53 |

TABLE 7.7.1-continued

| Pos. [°2Th.] | Height [cts] | FWHM [°2Th.] | d-spacing [Å] | Rel. Int. [%] |
|---|---|---|---|---|
| 50.7233 | 43.60 | 0.2598 | 1.79986 | 9.69 |
| 52.2369 | 41.11 | 0.2598 | 1.75122 | 9.14 |
| 53.1801 | 43.37 | 0.3464 | 1.72236 | 9.64 |
| 63.3126 | 19.73 | 0.6336 | 1.46773 | 4.39 |

Figure 53:
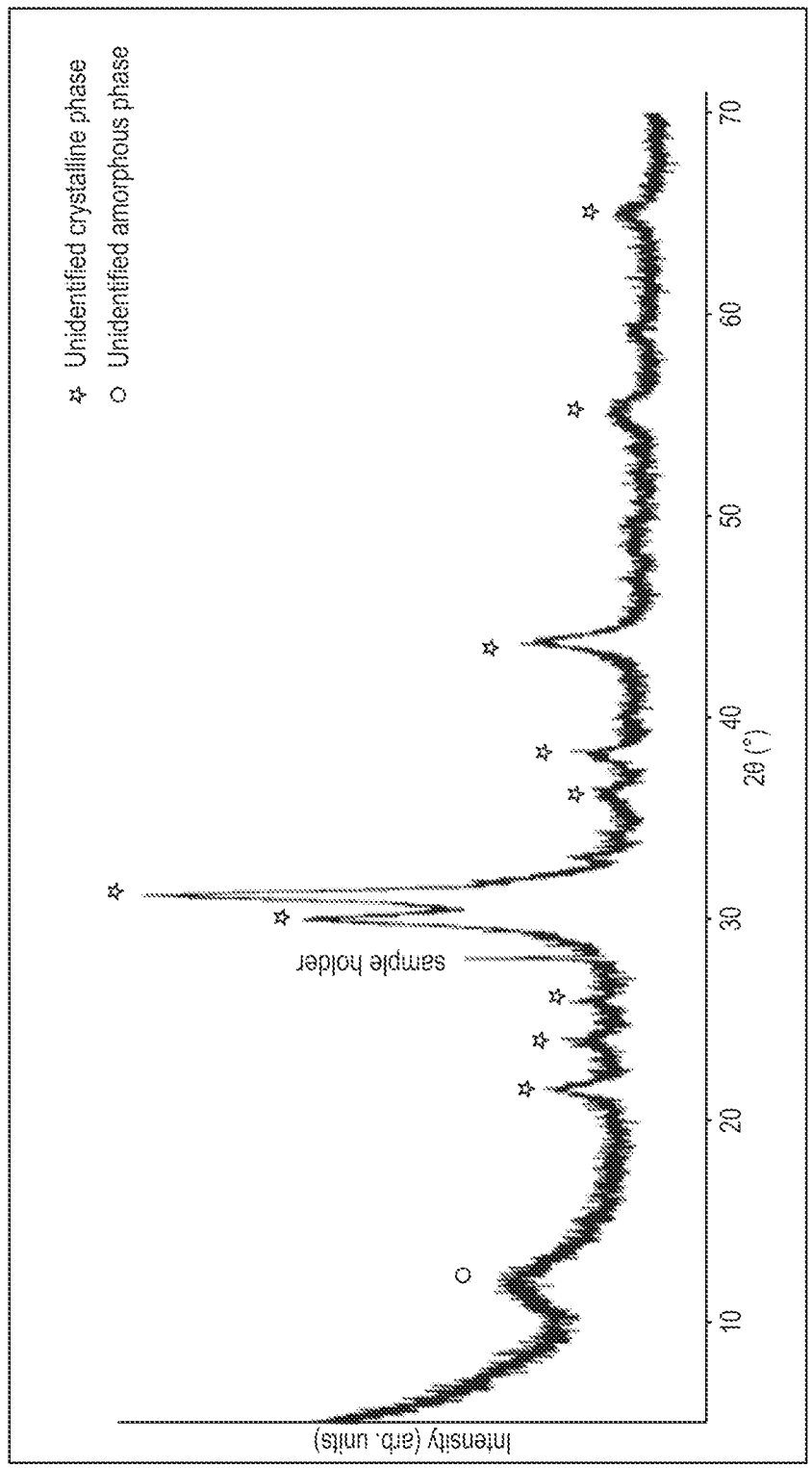
FIG. 53 shows the PXRD diffractogram of the milling reaction of 4 subsequent additions of 1 equivalent of K$_4$P$_2$O$_7$ to 1 equivalent of fluorapatite with 3 hours of milling at 35 Hz after each addition.
Figure 120:
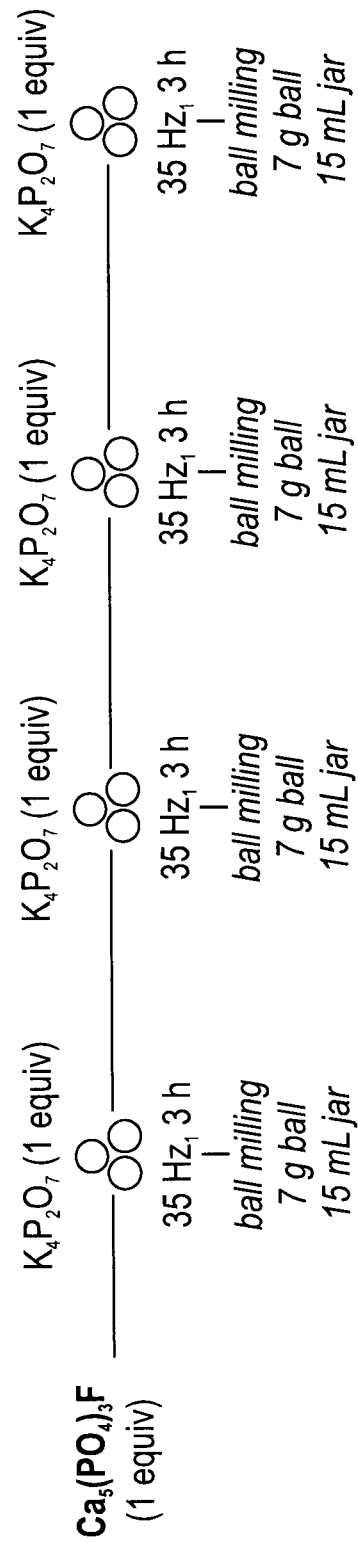

In another instance, fluorapatite (1 equiv.) was milled with 4 equivalents of potassium pyrophosphate to consume the crystalline fluorapatite as described in FIG. 120. Briefly, the fluorapatite was milled with 1 equivalent of potassium pyrophosphate for 3 hours at 35 Hz before the addition of a second equivalent and subsequent milling for 3 hours at 35 Hz, and this was repeated until 4 total equivalents of potassium pyrophosphate had been added and milled with the fluorapatite. The resulting product was analyzed by PXRD as seen in FIG. 53 and Table 7.7.2. The PXRD was consistent with an unidentified crystalline phase which is isostructural to $K_{2-x}Ca_y(PO_3F)_a(PO_4)_bF_c$.

TABLE 7.7.2

| Pos. [°2Th.] | Height [cts] | FWHM [°2Th.] | d-spacing [Å] | Rel. Int. [%] |
|---|---|---|---|---|
| 21.5831 | 92.10 | 0.3464 | 4.11746 | 13.29 |
| 24.1496 | 48.92 | 0.6061 | 3.68537 | 7.06 |
| 26.0036 | 45.04 | 0.2598 | 3.42666 | 6.50 |
| 28.0998 | 238.05 | 0.0433 | 3.17562 | 34.35 |
| 30.0617 | 479.63 | 0.3897 | 2.97270 | 69.20 |
| 31.2880 | 693.08 | 0.2381 | 2.85893 | 100.00 |
| 33.1727 | 63.32 | 0.3464 | 2.70068 | 9.14 |
| 36.4610 | 31.20 | 0.6061 | 2.46431 | 4.50 |
| 38.3505 | 58.81 | 0.6061 | 2.34714 | 8.48 |
| 43.7833 | 141.57 | 0.5196 | 2.06767 | 20.43 |
| 46.9843 | 14.31 | 0.6927 | 1.93400 | 2.06 |
| 59.1913 | 20.45 | 0.6927 | 1.56099 | 2.95 |
| 65.1133 | 39.12 | 0.8448 | 1.43143 | 5.64 |

7.8. Fluorapatite and Fluorspar Activation

Figure 121:
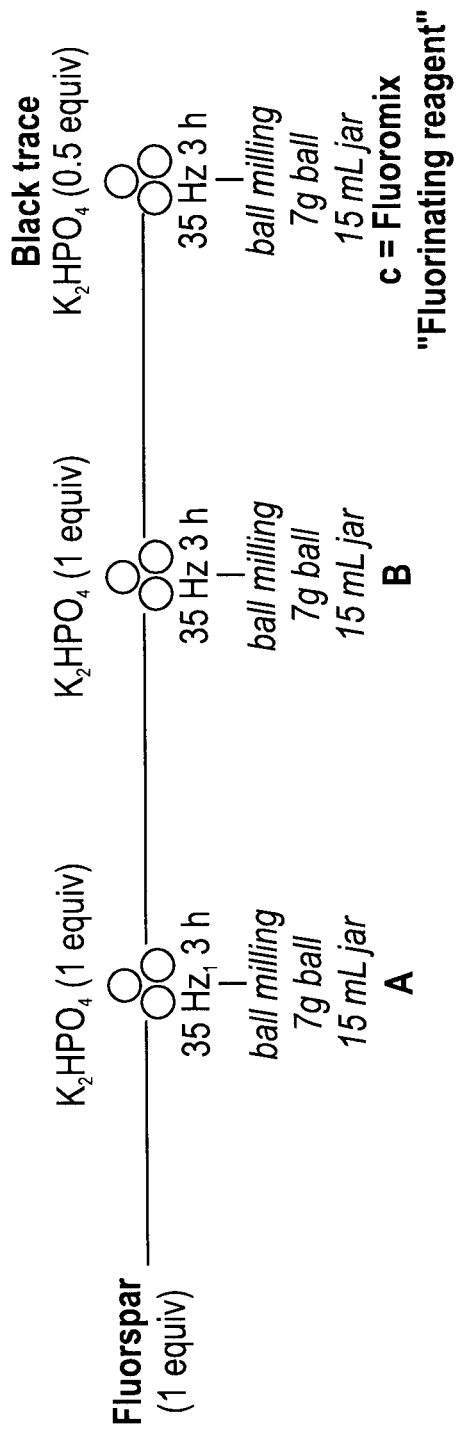
Figure 122:
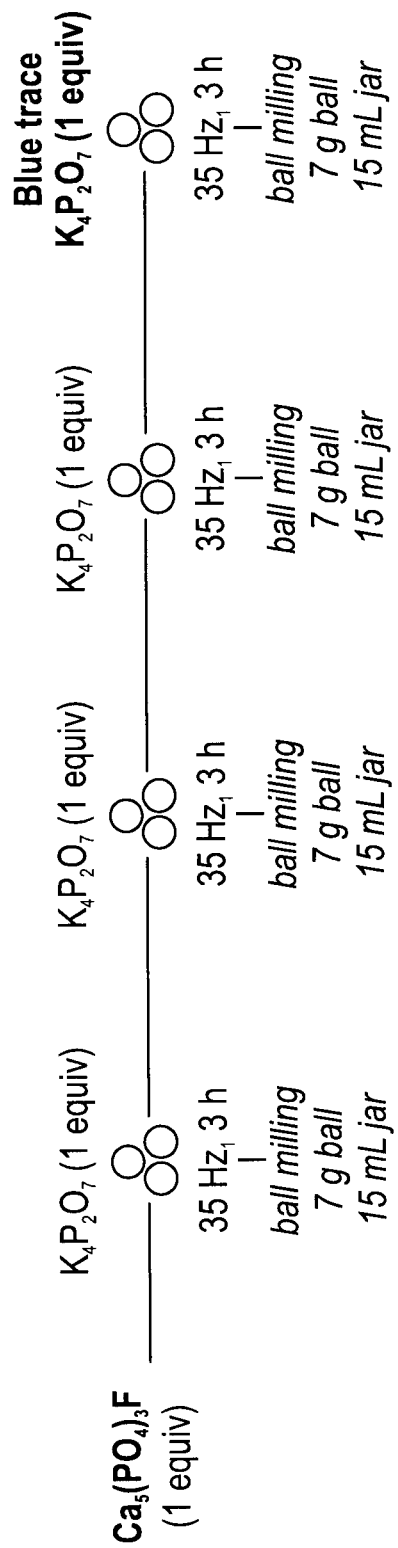

Fluorapatite and Fluorspar activation with $K_4P_2O_7$ (4 equiv.) and $K_2HPO_4$ (2.5 equiv.) respectively were compared via PXRD. The activations reactions were completed as described in FIGS. 121 and 122.

8. Alternative Mechanochemical Procedures: Twin-Screw Extruder & Planetary Ball Mill 8.1. Materials and Abbreviations Thermofisher Process 11 Twin Screw Extruder was fixed with a gravimetric single screw feeder (hopper) for programmed addition of solids. The pressurized die was not fixed to the twin-screw extruder for these experiments. Extrudite refers to the processed material that comes out the end of the extruder. $CaF_2$ (97% reagent grade purchased from Alfa Aesar and used as received. $K_2HPO_4$ (anhydrous, 98%) purchased from Acros Organics and used as received. Screw configurations are shown in each graphics and are made up of conveying "C", kneading "K", and reverse "R" elements. Multiple individual elements make up a "section". Furthermore, kneading sections can be subdivided by rotation from previous element, these can be at 30°, 60° or 90°. $F_R$=feed rate of solids into the extruder. $S_s$=screw speed at which the stainless-steel screws co-rotate. $S_T$=screw temperature, each of the six segments can be heated to an individual temperature and these are specified if used. $T_R$=residence time which is measured by the first time solids fall into the twin-screw extruder to the first time solids are observed at the exit.

8.2. General Procedure for Twin-Screw Extrusion

To a 100 mL conical flask was charged $CaF_2$ (3.12 g, 40 mmol) and $K_2HPO_4$ (6.97 g, 40 mmol). The solids were loosely mixed with a spatula and then charged into the single screw feeder. At this point the relevant feed rate ($F_R$), screw speed ($S_s$), and screw temperature ($S_T$) were programmed on the twin-screw extruder. The extruder was turned on, followed swiftly by the hopper. A 50 mL collection beaker was placed at the exit of the screw. After observation of the first appearance of solids coming out the exit, the beaker was used to collect the first ~200 mg. Following this the collection beakers were exchanged and the "fluoromix" extrudite collected. This was continued until amount collected slows down significantly. At this point the beaker is exchanged back again for the first beaker to collect any residual extrudite. The "fluoromix" is then weighed (usually about 7 grams). The material is decanted into a vial and kept under vacuum overnight.

8.3. Variation of Screw Temperature on Generation of Active Fluorination Material Following the general procedure outlined above (Example 8.2), the effect of screw temperature ($S_T$) was investigated. FIG. 54 shows a general scheme for which $CaF_2$ (40 mmol) and $K_2HPO_4$ (40 mmol) are reacted to form the active fluorinated material. The temperature, $S_T$, was varied between 25° C. and 200° C. and the screw speed was 50 rpm. The residence time was 100 seconds. The resulting "fluoromix" was reacted with TsCl in the solution state in tBuOH (0.25 M) at 100° C. for 5 hours to form the fluorinated product, TsF. The screw temperatures, resulting fluorinated product, TsF, yields, and starting material yields, TsCl can be seen in Table 8.3. The results may indicate that lower screw temperatures may be helpful in achieving higher yields of organo-fluorine product (e.g., TsF) and lower yields of starting material (e.g., TsCl).

TABLE 8.3

| $S_T$ (° C.) | TsF (%) | TsCl (%) |
|---|---|---|
| 25 | 7 | 68 |
| 50 | 6 | 77 |
| 100 | 6 | 79 |
| 150 | 5 | 78 |
| 200 | 3 | 85 |

8.4. Variation of Screw Speed on Generation of Active Fluorination Material

Figure 55:
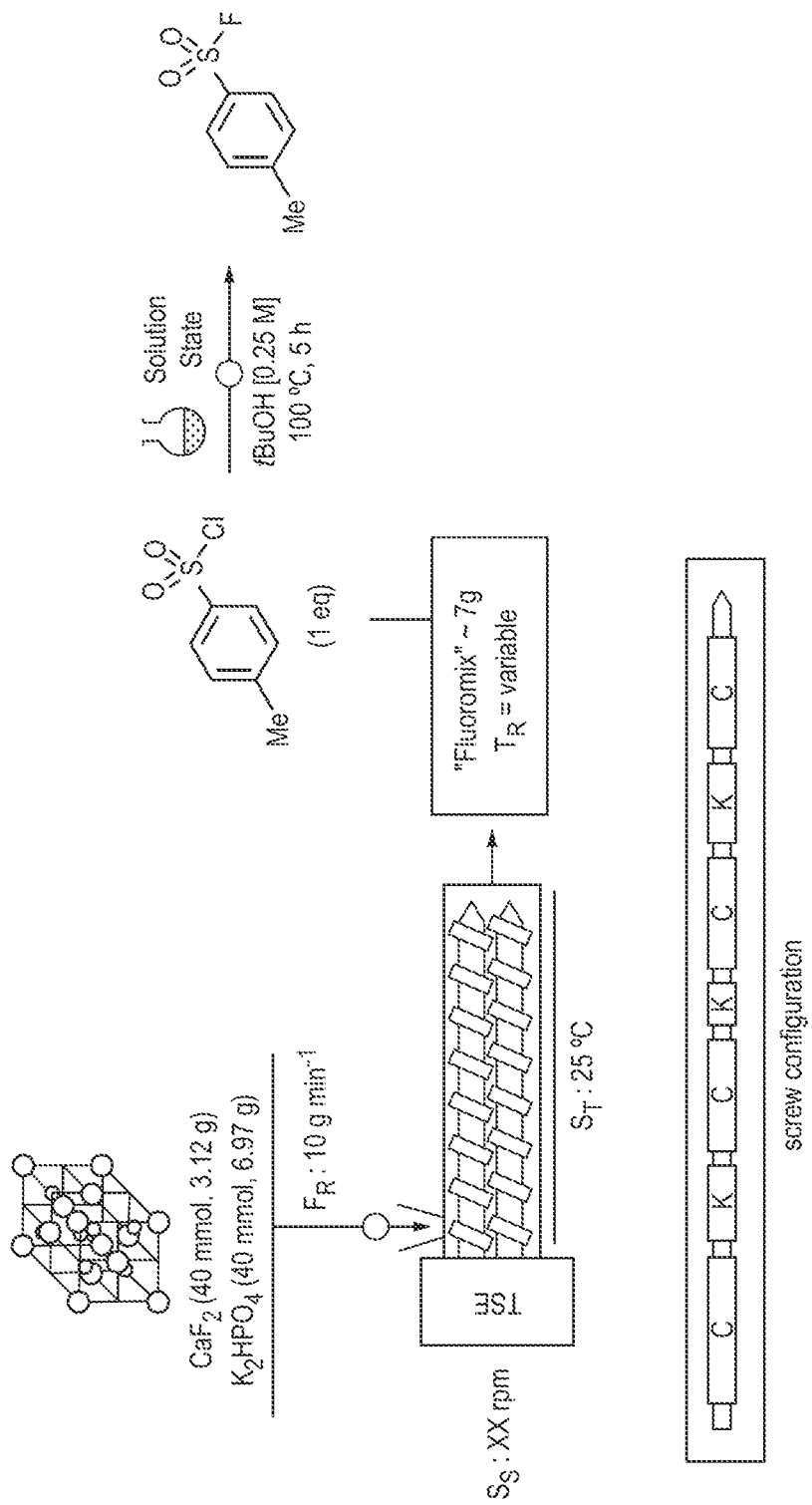
FIG. 55 shows a general scheme for which the effect of the variation of screw speed on the generation of active fluorination material was tested.

Following the general procedure outlined above (Example 8.2), the effect of screw speed ($S_r$) on generation of active fluorination material was investigated. FIG. 55 shows a general scheme for which $CaF_2$ (40 mmol) and $K_2HPO_4$ (40 mmol) are reacted to form the active fluorinated material. The spin speed was varied between 10 rpm and 75 rpm and the residence time ($T_R$) was varied as shown in Table 8.4. The screw temperature was 25° C. and feed rate was 10 g/min. The resulting active fluorinated material, "Fluoromix" was reacted with TsCl in a tBuOH solution (0.25 M) at 100° C. for 5 hours to form the fluorinated product. The spin speed ($S_s$), residence time ($T_R$), product yield (TsF), and starting material yield (TsCl) can be seen in Table 8.4. The results may indicate that the screw speed and residence time may not significantly impact the resulting yield of organo-fluorine product (e.g., TsF).

TABLE 8.4

| $S_S$ (rpm) | $T_R$ (secs) | TsF (%) | TsCl (%) |
|---|---|---|---|
| 10 | torqued | — | — |
| 10* | 420 | 6 | 68 |
| 25 | 165 | 6 | 77 |
| 75 | 80 | 6 | 67 |

Figure 56:
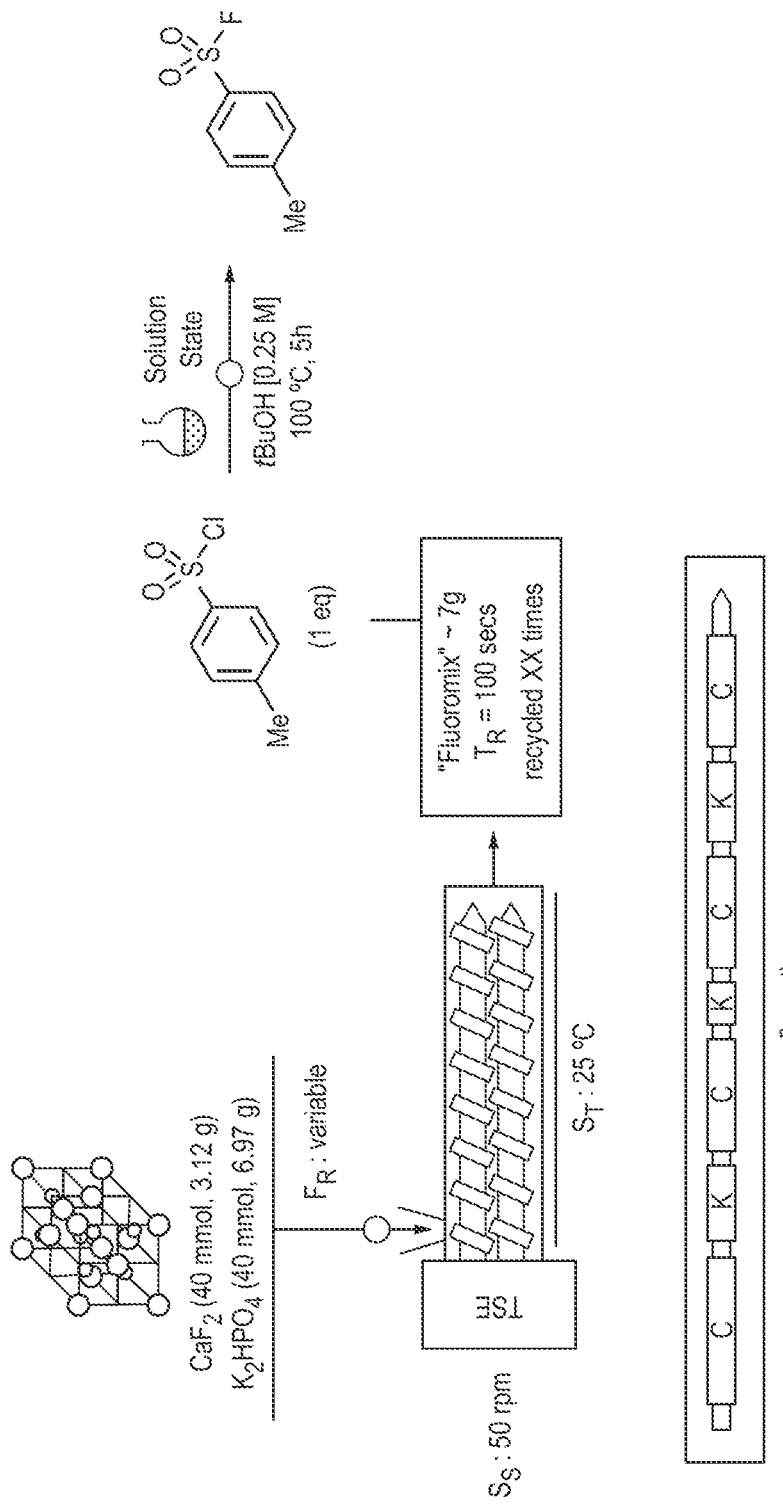
FIG. 56 shows a general scheme for which the effect of the variation of the number of recycling times on the generation of active fluorination material was tested.

*$F_R$ = 5 g min$^{-1}$ 8.5. Variation of Amount of Times Recycled Through Extruder on Generation of Active Fluorination Species Following the general procedure outlined above (Example 8.2), in this instance the solids were fed by spatula into the twin-screw extruder (without the use of a hopper), and at the end of the screwing process, the extrudite was added back into the extruder for a further number of runs (e.g., recycled). This serves to impar the same amount of mechanical force but increase the residence time. The effect of extrudite recycling was investigated via the Scheme seen in FIG. 56. FIG. 56 shows the general scheme for which CaF$_2$ (40 mmol) and K$_2$HPO$_4$ (40 mmol) can be reacted to form the active fluorinated species. In this instance, the feed rate is variable, the screw speed is 50 rpm, the screw temperature is 25° C., and the residence time is 100 seconds, but the resulting material is recycled back into the extruder 1, 2, or 3 times the results of which can be seen in Table 8.5. The resulting "Fluoromix" was reacted with 1 equiv. of TsCl in the solution state (0.25 M tBuOH) at 100° C. for 5 hours to form the fluorinated product. The resulting fluorinated product yield, TsF, and starting material yield, TsCl, can also be seen in Table 8.5. These results indicate that increased recycling times may result in higher yield of organo-fluorine product (e.g., TsF) and lower yields of starting material (e.g., TsCl).

TABLE 8.5

| Recycled | TsF (%) | TsCl (%) |
|---|---|---|
| 1 | 7 | 67 |
| 2 | 9 | 58 |
| 3 | 9 | 54 |

8.6. Extruding CaF$_2$ without the Presence of K$_2$HPO$_4$

Figure 57:
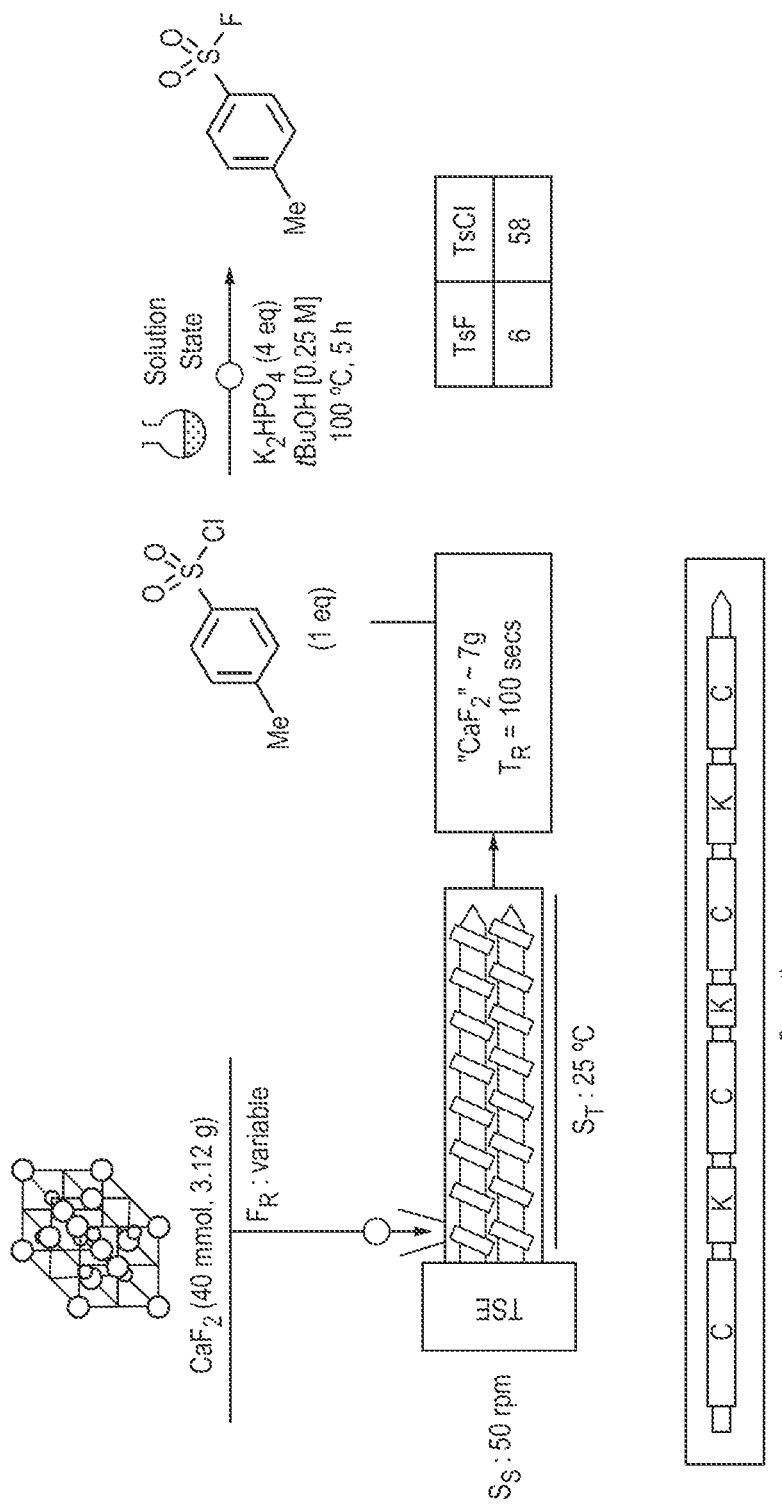
FIG. 57 shows a general scheme for which only CaF$_2$ is added into the twin-screw extruder without the K$_2$HPO$_4$.

Following the general procedure outlined above (Example 8.2), in this instance, CaF$_2$ fed into the twin-screw extruder without the presence of K$_2$HPO$_4$. FIG. 57 shows the general scheme for which CaF$_2$ (40 mmol) is added into the twin-screw extruder with variable feed rates, at a screw speed of 50 rpm, a screw temperature of 25° C., and a residence time of 100 seconds. The resulting "CaF$_2$" that has been extruded was reacted with TsCl (1 equiv.) in a 0.25 M tBuOH solution with added K$_2$HPO$_4$ (4 equiv.) and reacted at 100° C. for 5 hours to form a fluorinated product, TsF. The result was a TsF yield of 6% and a TsCl yield of 58% when the CaF$_2$ was not extruded in the presence of K$_2$HPO$_4$. Under mechanical forces, and without the presence of an ionic salt in the mechanochemical process, CaF$_2$ may be activated to provide fluoride in the conversion of p-toluenesulfonyl chloride to p-toluenesulfonyl fluoride.

8.7. Investigations into Altering the Screw Configuration

Figure 58:
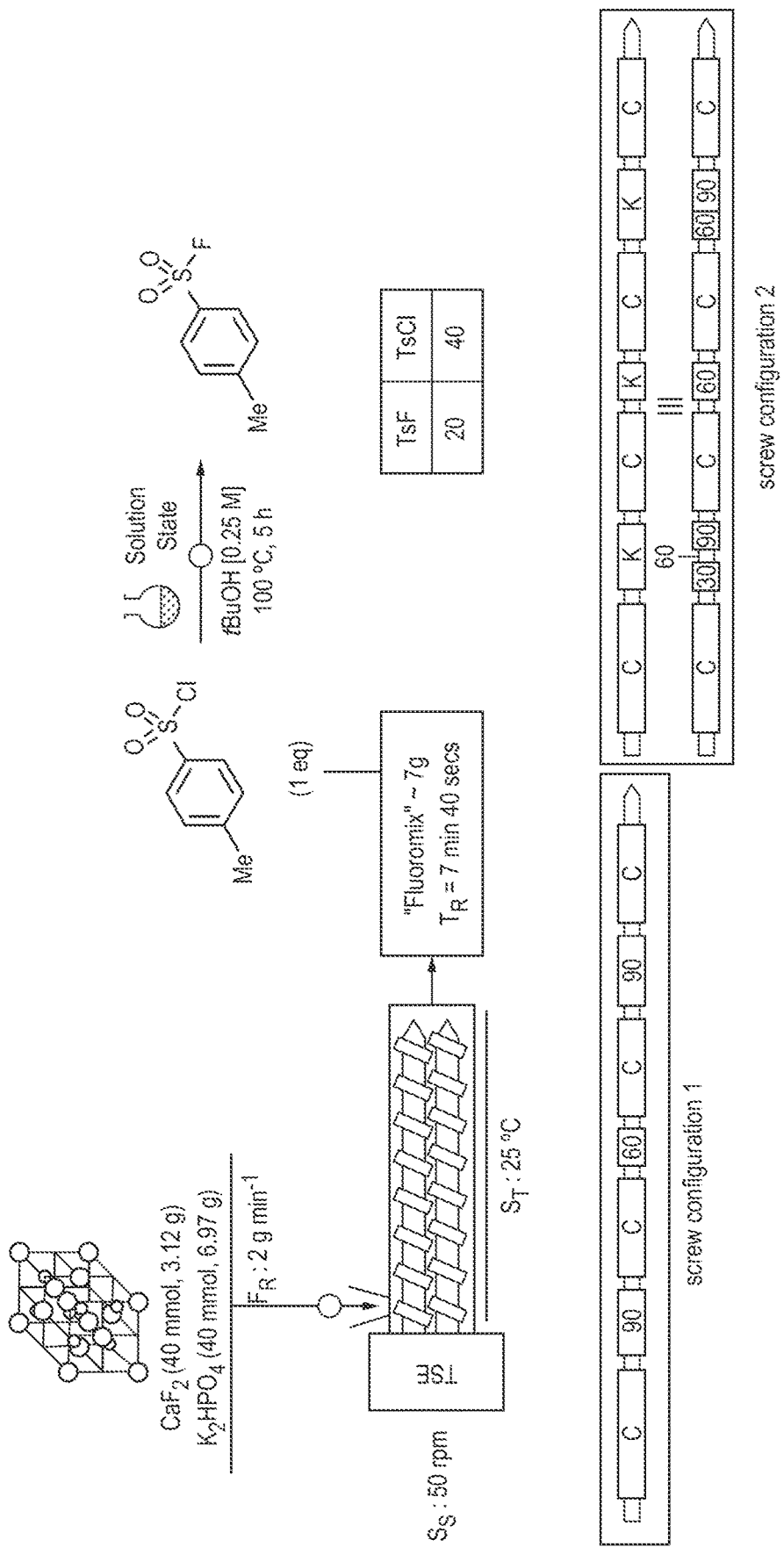
FIG. 58 shows a general scheme for which the effect of varying screw configuration on generation of active fluorination material was tested.

Following the general procedure outlined above (Example 8.2), in this instance, a screw configuration (configuration 1) is outlined as seen in FIG. 58. The effect of screw configuration 1 was analyzed. FIG. 58 shows a general scheme for which CaF$_2$ (40 mmol) and K$_2$HPO$_4$ (40 mmol) are added to the twin-screw extruder with a feed rate of 2 g min$^{-1}$, a screw speed of 50 rpm, a screw temperature of 25° C., and a residence time of 40 seconds. An alternate configuration was also examined (screw configuration 2). Screw configuration 2 was "C-(30-60-90)-C-(60)-C-(60-90)-C", whereas screw configuration 1 was "C-90-C-60-C-90-C". The resulting "fluoromix" was reacted with TsCl (1 equiv.) in a solution of tBuOH (0.25 M) at 100° C. for 5 hours to form the resulting fluorinated product, TsF. The yield of fluorinated, TsF was 20% and yield of starting material, TsCl, was 40% upon utilization of screw configuration 1. The utilization of additional alternative screw configurations may be useful in increasing and/or tuning the yield of organo-fluorine products (e.g., TsF).

8.8. Planetary Mills

Figure 123:
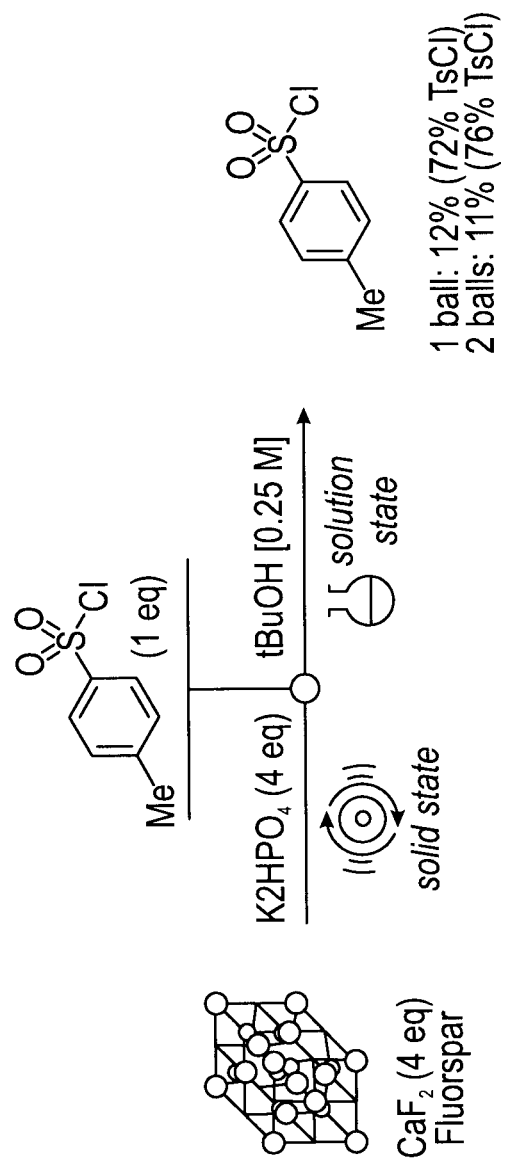

The Fritsch Pulverisette planetary mill was used. Zirconia jars (12 mL) and zirconia balls (3.4 g) were used in milling experiments. To a zirconia jar, added was charged fluorspar (312 mg, 4 mmol) and K$_2$HPO$_4$ (697 mg, 4 mmol) and either one or two 3.4 g zirconia balls. The jars were sealed and attached to the planetary mill. The mill was set to 800 rpm, 15-minute milling session, 11 repeats (12 in total), with a 2 minute gap between each one, and reverse in direction of milling after each session. After this time the material was scraped out of the vial and added to a vial which was kept under vacuum overnight before use. FIG. 123 shows a general scheme for which CaF$_2$ (4 equiv.) is milled via a planetary mill with 4 equiv. of K$_2$HPO$_4$. The resulting powder was reacted with TsCl (1 equiv.) in a solution of tBuOH (0.25 M) at 100° C. for 5 hours. The resulting yield when 1 ball was used in the milling was 12% TsF (72% TsCl starting material). The resulting yield when 2 balls were used in the milling was 11% TsF (76% TsCl starting material). Thus, planetary mills may be useful in creating fluorinating reagents comprising CaF$_2$ and an activator (e.g., K$_2$HPO$_4$).

While specific embodiments of the invention have been described herein for the purpose of reference and illustration, various modifications will be apparent to a person skilled in the art without departing from the scope of the invention as defined by the appended claims.

The project leading to this application has received funding from the European Research Council (ERC) under the European Union's Horizon 2020 research and innovation programme (grant agreement No 832994).

The invention claimed is:

1. A method of manufacturing an activated fluorination reagent, the method comprising:
    combining a first salt, the first salt comprising calcium and fluorine, with a second salt, the second salt comprising an anion, which said anion when combined with Ca$^{2+}$ to form a third salt has a lattice energy greater than 2450 KJ/mol, to form a salt mixture; and
    applying mechanical force to the salt mixture to yield the activated fluorination reagent.

2. The method of claim 1, wherein the first salt is CaF$_2$ or Ca$_5$(PO$_4$)$_3$F.

3. The method of claim 1, wherein the second salt is a metal hydroxide, a metal sulphite, a metal sulphate, a carbonate, or an inorganic phosphate.

4. The method of claim 3, wherein the inorganic phosphate is a pyrophosphate.

5. The method of claim 1, wherein a ratio of the first salt to the second salt is about 1:0.5 to 1:100.

6. The method of claim 5, wherein the mechanical force is applied using a ball mill, a mortar and pestle, a twin-screw extruder, using an ultrasonic bath, a resonant acoustic mixer, and/or a mechanical press.

7. The method of claim 6, wherein the mechanical press comprises a jaw crusher.

8. The method of claim 6, wherein the ball mill comprises a vibratory mill, a planetary mill, a drum mill, and/or an attritor mill.

9. The method of claim 6, wherein the method does not comprise reacting a strong acid with the first salt to form hydrofluoric acid.

10. The method of claim 9, wherein <1 ppm of HF is produced at any point during the reaction.

11. The method of any of claim 10, wherein the mechanical force is applied at a frequency of about 0.5 Hz-60 kHz.

12. The method of claim 11, wherein the mechanical force is applied at a temperature of about −20-100° C.

13. The method of claim 1, further comprising combining the activated fluorination reagent,
with a reactant; and fluorinating the reactant to produce a fluorinated compound.

14. The method of claim 13, wherein the fluorinated compound is an organo-fluorine compound.

15. The method of claim 13, wherein the activated fluorination reagent comprises characteristic 2θ reflections at about 21.9°, 30.3°, 31.6°, and/or 43.4°.

16. The method of claim 13, wherein the reactant is an aromatic or aliphatic compound comprising at least one leaving group located at a site to be fluorinated.

17. The method of claim 16, wherein the leaving group is a halogen.

18. The method of claim 17, wherein a fluorination reaction yield of the organofluorine compound is at least about 10% measured based on a starting amount of the reactant.

19. The method of claim 18, wherein the fluorination reaction is a mono-fluorination reaction.

20. The method of claim 18, wherein the fluorination reaction is a di-fluorination reaction.

* * * * *